US006685617B1

(12) United States Patent
Blinn et al.

(10) Patent No.: US 6,685,617 B1
(45) Date of Patent: Feb. 3, 2004

(54) INHIBITORS OF $\alpha_4\beta_1$ MEDIATED CELL ADHESION

(75) Inventors: James Blinn, Lawton, MI (US); Robert Chrusciel, Portage, MI (US); Jed Fisher, Kalamazoo, MI (US); Steven Tanis, Kalamazoo, MI (US); Edward Thomas, Kalamazoo, MI (US); Thomas Lobl, Foster City, CA (US); Bradley Teegarden, San Diego, CA (US)

(73) Assignees: Pharmacia & Upjohn Company, Kalamazoo, MI (US); Tanabe Seiyaku Co., Ltd., Osaka (JP)

( * ) Notice: Subject to any disclaimer, the term of this patent is extended or adjusted under 35 U.S.C. 154(b) by 0 days.

(21) Appl. No.: 09/720,088
(22) PCT Filed: Jun. 23, 1999
(86) PCT No.: PCT/US99/14233
§ 371 (c)(1),
(2), (4) Date: Mar. 9, 2001
(87) PCT Pub. No.: WO99/67230
PCT Pub. Date: Dec. 29, 1999

Related U.S. Application Data

(60) Provisional application No. 60/090,421, filed on Jun. 23, 1998.

(51) Int. Cl.[7] ............... A61K 31/425; A61K 31/54; C07D 277/06; C07D 279/12
(52) U.S. Cl. ............... 514/227.5; 514/227.8; 514/365; 514/371; 544/58.4; 548/200
(58) Field of Search ............... 548/200; 514/365, 514/227.5, 227.8, 371; 544/58.4

(56) References Cited

U.S. PATENT DOCUMENTS

| | | | |
|---|---|---|---|
| 4,517,686 A | 5/1985 | Ruoslahti et al. ............... 3/1 |
| 4,578,079 A | 3/1986 | Ruoslahti et al. ............... 623/11 |
| 4,589,881 A | 5/1986 | Pierschbacher et al. ......... 623/11 |
| 4,614,517 A | 9/1986 | Ruoslahti et al. ............... 623/11 |
| 4,661,111 A | 4/1987 | Ruoslahti et al. ............... 623/11 |
| 4,683,291 A | 7/1987 | Zimmerman et al. ........... 530/324 |
| 4,792,525 A | 12/1988 | Ruoslahti et al. ...... 435/240.243 |
| 4,816,484 A | 3/1989 | Tovoshima et al. ........... 514/563 |
| 5,688,913 A | 11/1997 | Arrhenius et al. ........... 530/330 |
| 6,093,696 A * | 7/2000 | Head et al. ............... 514/19 |
| 6,197,794 B1 * | 3/2001 | Head et al. ............... 514/342 |

FOREIGN PATENT DOCUMENTS

| | | |
|---|---|---|
| WO | 9622966 | 8/1996 |
| WO | WO9622966 | 8/1996 |
| WO | WO9853814 | 12/1998 |
| WO | WO9853817 | 12/1998 |
| WO | WO9853818 | 12/1998 |
| WO | WO9854207 | 12/1998 |
| WO | WO 9906390 | 2/1999 |
| WO | WO 9906431 | 2/1999 |
| WO | WO 9906432 | 2/1999 |
| WO | WO 9906433 | 2/1999 |
| WO | WO 9906434 | 2/1999 |
| WO | WO 9906435 | 2/1999 |
| WO | WO 9906436 | 2/1999 |
| WO | WO 9906437 | 2/1999 |
| WO | WO 9910312 | 3/1999 |
| WO | WO 9910313 | 3/1999 |
| WO | WO9926615 | 6/1999 |
| WO | WO9926921 | 6/1999 |
| WO | WO9926922 | 6/1999 |
| WO | WO9935163 | 7/1999 |
| WO | WO9937618 | 7/1999 |
| WO | WO9943642 | 9/1999 |
| WO | WO9948879 | 9/1999 |
| WO | WO9961465 | 12/1999 |
| WO | WO9964390 | 12/1999 |
| WO | WO9964395 | 12/1999 |

OTHER PUBLICATIONS

CAS printout for Head et al. (US 6,197,794) 2001.*
M.D. Pierschbacher et al., Proc. Natl. Acad. Sci., 81:5985–5988 (Oct. 1984).
K. T. Wanner et al., Liebigs Annalen Der Chemie, 5:477–484 (1993).
J.L. Guan et al., Cell, 60:53–61(Jan. 1990).
R.O. Hynes, Cell, 48:549–554 (Feb. 1987).
M.E. Hemler, Annu. Rev. Immunol., 8:365–400(1990).
R. Pytela et al., Cell, 40:191–198 (Jan. 1985).
C. Rüegg et al., J. Cell Biol., 117(1):179–189(Apr. 1992).
D.P. Andrew et al., J. Immunol., 153:3847–3861(1994).
M.J. Briskin et al., Nature, 363:461–464(Jun. 1993).

(List continued on next page.)

Primary Examiner—Richard L. Raymond
(74) Attorney, Agent, or Firm—Browdy and Neimark, P.L.L.C.

(57) ABSTRACT

The present invention relates to compound of formula (I), that are potent inhibitors of $\alpha_4\beta_1$ mediated adhesion to either VCAM or CS-1 and which could be useful for the treatment of inflammatory diseases. Specifically, the molecules of the present invention can be used for treating or preventing $\alpha_4\beta_1$ adhesion mediated conditions in a mammal such as a human. This method may comprise administering to a mammal or a human patient an effective amount of the compound or composition as explained in the present specification.

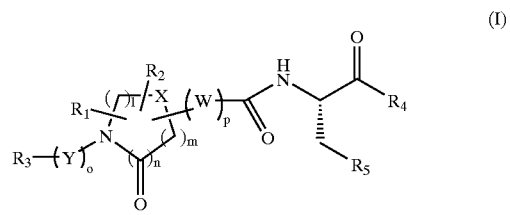

9 Claims, No Drawings

OTHER PUBLICATIONS

A.M. Shyjan et al., J. Immunol., 156:2851–2857(1996).
T.M. Carlos et al., Immunol. Rev., 114:5–28(1990).
L. Osborn, Cell, 62:3–6(Jul. 1990).
T.A. Springer, Nature, 346:425–434(Aug. 1990).
J.G. Geng et al., Nature, 343:757–760 (Feb. 1990).
L.M. Stoolman, Cell, 56:907–910 (Mar. 1989).
A.C.H.M. Van Dinther–Janssen et al., J. Immunol., 147:4207–4210 (Dec. 1991).
A. Laffón et al., J. Clin. Invest., 88:546–552 (Aug. 1991).
J. Morales–Ducret et al., J. Immunol. 149:1424–1431 (Aug. 1992).
G. M. Walsh et al., J. Immunol., 146:3419–342 (May 1990).
B.S. Bochner et al., J. Exp. Med., 173:1553–1556 (Jun. 1991).
W. M. Abraham et al., J. Clin. Invest., 93:776–787 (Feb. 1994).
V. B. Weg et al., J. Exp. Med., 177:561–566 (Feb. 1993).
D.K. Podolsky et al., J. Clin. Invest., 92:372–380 (Jul. 1993).
R.G. Bell et al., J. Immunol. 151(9):4790–4802 (Nov. 1993).
T.A. Yednock et al., Nature, 356:63–66 (Mar. 1993).
J.L. Baron et al., J. Exp. Med., 177:57–68 (Jan. 1993).
J.L. Baron et al., J. Clin. Invest., 93:1700–1708 (Apr. 1994).
X.D. Yang et al., Proc. Natl. Acad. Sci., 90:10494–10498 (1993).
L.C. Burkly et al., Diabetes, 43:529–534 (Apr. 1994).
E.A. Wayner et al., J. Cell Biol., 109:1321–1330 (Sep. 1989).
M.I. Cybulsky et al., Science, 251:788–791 (Feb. 1991).

* cited by examiner

INHIBITORS OF $\alpha_4\beta_1$ MEDIATED CELL ADHESION

This application is the national phase under 35 U.S.C. §371 of PCT International Application No. PCT/US99/14233 which has an International filing date of Jun. 23, 1999, which designated the United States of America.

BACKGROUND OF THE INVENTION

1. Field of the Invention

The present invention relates to small molecules that are potent inhibitors of $\alpha_4\beta_1$ mediated adhesion to either VCAM or CS-1 and which are useful for the treatment of inflammatory diseases.

2. Description of Related Art

The extracellular matrix (ECM) is the major component of connective tissue which provides structural integrity, and promotes cell migration and differentiation. As part of these functions, extracellular matrix molecules such as fibronectin, collagen, laminin, von Willebrand factor, thrombospondin, fibrinogen, and tenascin have been shown to support adhesion of cells in vitro. This adhesive interaction is critical for a number of biological processes including hemostasis, thrombosis, wound bealing, tumor metastasis, immunity and inflammation.

Fibronectin (FN) is the prototype ECM molecule. The major cell attachment site in the fibronectin molecule has been reproduced synthetically with the amino acid sequence arginine-glycine-aspartic acid, or RGD using single letter nomenclature. Peptides containing the RGD sequence which either inhibit or promote cell adhesion have been described (U.S. Pat. Nos. 4,589,881; 4,661,111; 4,517,686; 4,683,291; 4,578,079; 4,614,517; and 4,792,525). Changes in the peptide as small as the exchange of alanine for glycine or glutamic acid for aspartic acid, which constitute the addition of a single methyl or methylene group to the tripeptide, eliminates these activities (Pierschbacher et al., *Proc. Natl. Acad. Sci. USA* 81:5985 (1984)). Recently, a second FN cell binding domain has been identified within the alternatively spliced region of the A chain of the molecule, known as the connecting segment 1 (CS-1). The most active cell-binding site within this alternatively spliced region is composed of 25 amino acids where the carboxy terminus contains the sequence EILDVPST. The amino acid sequence EILDVPST forms a recognition motif on FN for cell surface receptors. (Wayner et al., *J. Cell Biol.* 109:1321 (1989); Guan et al., *Cell* 60:53 (1990)).

The receptors which recognize these sites on FN belong to a gene superfamily called integrins which consist of heterodimeric complexes of non-covalently associated alpha and beta subunits. A common β subunit combines with unique I subunits to form an adhesion receptor of defined specificity. To date, 8 β subunits have been identified which can dimerize with 16 distinct I subunits forming 22 distinct integrins. The β subfamily, also known as the VLA family (Very Late Activation Antigens), binds to ECM molecules such as FN, collagen and laminin. For reviews, see, Hynes. *Cell* 48:549 (1987); Hemler, *Annu. Rev. Immunol.* 8:365 (1990). Leukocyte interaction with FN at the two spatially separate binding domains is mediated by two distinct integrins. The RGD site is recognized by the integrin $\alpha_5\beta_1$, while, EILDV is recognized by $\alpha_4\beta_1$ (Pytela et al., *Cell* 40:191 (1985); Wayner et al., *J. Cell Biol.* 109:1321 (1989); Guan et al, *Cell* 60:53 (1990)).

Vascular endothelial cells form the interface between blood and tissues and control the passage of leukocytes as well as plasma fluid into tissues. A variety of signals generated at the site of inflammation can activate both endothelial cells as well as circulating leukocytes so that they become more adhesive to one another. Following this initial adhesion the leukocytes migrate into the tissues to perform host defense functions. Several adhesion molecules have been identified which are involved in leukocyte-endothelial interactions.

In the $\beta_1$, subfamily, in addition to binding to fibronectin, $\alpha_4\beta_1$ interacts with a cytokine inducible protein on endothelial cells termed vascular cell adhesion molecule (VCAM). Further involved in the leukocyte-endothelial adhesion process is the $\beta_2$ integrin subfamily. $\beta_2$ integrins include CD11a/CD18, CD11b/CD18, and CD11c/CD18. In addition, the $\beta_7$ subunit associates with $\alpha_4$ to form a unique $\alpha_4\beta_7$ heterodimer which binds to FN, to VCAM, and to Mucosal Addressin Cell Adhesion Molecule-I (MAdCAM) (Ruegg et al, *J. Cell. Biol.* 117:179 (1992); Andrew et al., *J. Immunol.* 153:3847 (1994); Briskin et al., *Nature* 363:461 (1993); Shyjan et al, *J. Immunol.* 156:2851 (1996)). $\alpha_4$ integrins are widely expressed on different cell types including hematopoietic progenitors, lymphocytes, natural killer cells, monocytes, eosinophils, basophils, and mast cells (Helmer, M. E., *Annu. Rev. Immunol.* 8:365 (1990)). Other molecules on endothelial cells which bind to the leukocytes include ICAM-1, ICAM-2, E-selectin and P-selectin (Carlos and Harlan, *Immunol. Rev.* 114:1 (1990); Osborn, L., *Cell* 62:3 (1990); Springer T., *Nature* 346:425 (1990); Geng et al., *Nature* 347:757 (1990); Stoolman, *Cell* 56:907 (1989)).

A number of in vitro and in vivo studies indicate that $\alpha_4\beta_1$ plays a critical role in the pathogenesis of a variety of diseases. Monoclonal antibodies directed against $\alpha_4$ have been tested in a variety of disease models. Anti-$\alpha_4$ antibodies block adhesion of lymphocytes to synovial endothelial cells; this adhesion plays a potential role in rheumatoid arthritis (van Dinther-Janssen et al, *J. Immunol.* 147:4207 (1991)). $\alpha_4$ has also been implicated with respect to rheumatoid arthritis in separate studies (Laffon et al, *J. Clin. Invest.* 88:546 (1991); Morales-Ducret et al, *J. Immunol.* 149:1424 (1992)). A significant number of studies have evaluated the role of $\alpha_4$ in allergy and asthma. For example, monoclonal antibodies to $\alpha_4$ block adhesion of basophils and eosinophils to cytokine activated endothelial cells (Walsh et al, *J. Immunol.* 146:3419 (1991); Bochner et al, *J. Exp. Med.* 173:1553 (1991)). Monoclonal antibodies to $\alpha_4$ were also effective in several lung antigen challenge models (Abraham et al, *J. Clin. Invest.* 93:776 (1994); Weg et al, *J. Exp. Med.* 177:561 (1993)). The cotton-top tamarin, which experiences spontaneous chronic colitis, showed a significant attenuation of their colitis when anti-$\alpha_4$ antibody was administered (Podolsky et al, *J. Clin. Invest.* 92:372 (1993); Bell et al, *J. Immunol.* 151:4790 (1993)). In a rat and mouse model, autoimmune encephalomyelitis was blocked by anti-$\alpha_4$ antibody (Yednock et al, *Nature* 356:63 (1992); Baron et al, *J. Exp. Med.* 177:57 (1993)). Anti-$\alpha_4$ monoclonal antibodies also inhibit insulitis and delay the onset of diabetes in the non-obese diabetic mouse (Baron et al, *J. Clin. Invest.* 93:1700 (1994); Yang et al, *Proc. Natl. Acad. Sci. USA* 90:10494 (1993); Burkly et al, *Diabetes* 43:529 (1994)). $\alpha_4$ is also implicated in atherosclerosis due to its endothelial expression during atherogenesis (Cybulsky et al, *Science* 251:788 (1991)). The migration of leukocytes to an inflammatory site can also be blocked by anti-$\alpha_4$ antibodies. In addition to the blocking of migration, inhibitors of leukocyte endothelial adhesion may block the costimulatory signals mediated by integrins and thus inhibit overproduction of inflammatory cytokines. In a separate set of experiments not using anti-α₄ antibodies, the peptides GRDGSP or EILDV were tested against contact hypersensitivity response. The contact hypersensitivity response was found to be blocked by GRDGSP or EILDV suggesting that both $\alpha_4\beta_1$ and $\alpha_5\beta_1$ are involved in this inflammatory response.

Other ailments which may involve $\alpha_4\beta_1$-mediated conditions include the inflammatory disorders rheumatoid arthritis, allergic disorders, asthma, spontaneous chronic colitis, insulitis, contact hypersensitivity response, atherosclerosis and autoimmune encephalomyelitis. These studies illustrate that small molecules that are potent inhibitors of $\alpha_4\beta_1$ mediated adhesion to either VCAM-1 or CS-1 may be used as a form of treatment in numerous inflammatory diseases. However, these inflammatory conditions could be expanded to include adult respiratory distress syndrome. AIDS, cardiovascular diseases, thrombosis or harmful platelet aggregation, reocclusion following thrombolysis, allograft rejection, reperfusion injury, psoriasis, eczema, contact dermatitis and other skin inflammatory diseases, osteoporosis, osteoarthritis, atherosclerosis, neoplastic diseases including metastasis of neoplastic or cancerous growth, wound healing enhancement, treatment of certain eye diseases such as detaching retina, Type I diabetes, multiple sclerosis, systemic lupus erythematosus (SLE), inflammatory and immunoinflammatory conditions including ophthalmic inflammatory conditions and inflammatory bowel diseases, ulcerative colitis, regional enteritis and other autoimmune diseases. Accordingly, a compound which could inhibit these conditions is desirable.

SUMMARY OF THE INVENTION

The present invention particularly provides:

A compound of the formula:

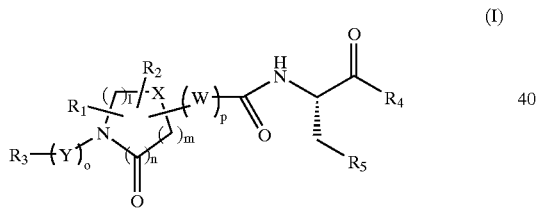

(I)

In the above formula (I), $R_1$ may occur one to four times and each occurrence is independently hydrogen or $C_{1-6}$ alkyl. Also in the above formula (I), $R_2$ is hydrogen, pyridyl, $C_{1-6}$ alkyl, ($C_{1-6}$ alkyl)—$CO_2$—$R_{11}$, or —$CO_2$—$R_{11}$. In addition, $R_1$ and $R_2$ may be attached to the same carbon atom and form a carbocyclic ring of 5–8 atoms together with the carbon atom to which they are attached, or they may be attached to the same carbon atom and form a ring of 5–8 atoms of the formula:

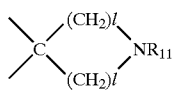

together with the carbon atom to which they are attached.

In the above formula (I), $R_3$ is hydrogen, phenyl, $C_{1-6}$ alkyl, $C_{3-6}$ alkenyl, $C_{7-17}$ arylalkyl, ($C_{1-6}$ alkyl)—$CO_2$—$R_{11}$, ($C_{2-6}$ alkenyl)—$CO_2$—$R_{11}$, ($C_{1-6}$ alkyl)—CO—$C_{1-6}$ alkyl, ($C_{1-6}$ alkyl)—O—$C_{1-6}$ alkyl, ($C_{1-6}$ alkyl)—OH, ($C_{1-6}$ alkyl)—CN, adamantyl or one of the following:

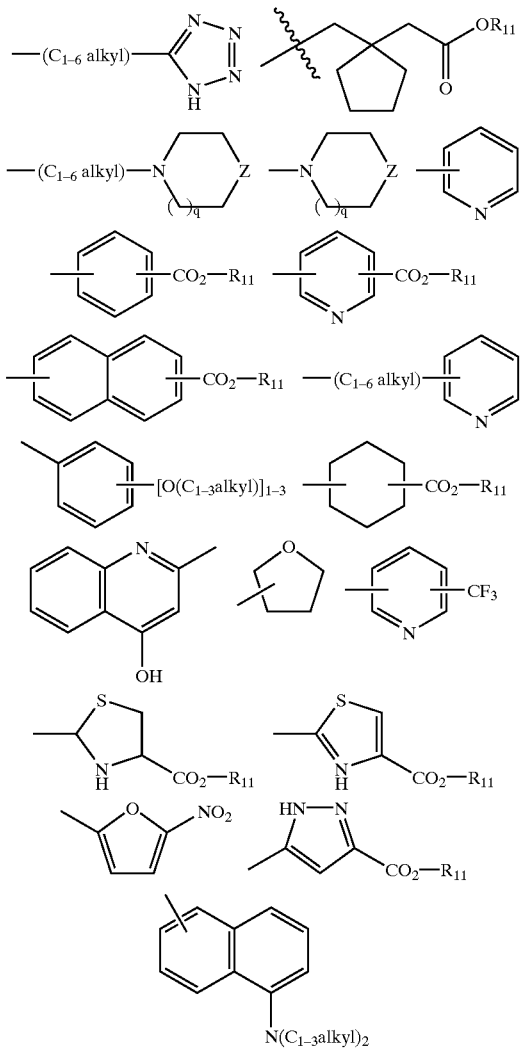

In addition, $R_2$ and $R_3$—$(Y)_o$— may combine with each other at the terminal thereof to form a ring of the following formula together with the carbon atom and the nitrogen atom to which they are attached:

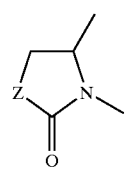

In the above formula (I), $R_4$ is —O—$R_{11}$, $NH_2$, NHOH, —O—($C_{7-10}$ arylalkyl), or is of the formula:

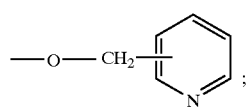

In the above formula (I), $R_5$ is a formula of the following:

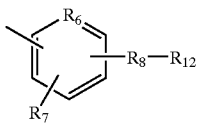

In the above, $R_6$ is N or CH, $R_7$ is hydrogen or halogen, $R_8$ is —NH—$Y_1$—, —OCH$_2$—, or —CONH—, $R_9$ may occur one to three times and is a halogen, $C_{1-6}$ alkoxy, $C_{1-6}$ alkyl or trifluoromethyl, $R_{10}$ is $C_{1-6}$ alkyl, or $(C_{1-6}$ alkyl)—OH, or hydrogen, $R_{11}$ is hydrogen or $C_{1-6}$ alkyl, $R_{12}$ is $C_{1-6}$ alkyl or the following formula:

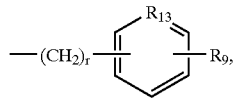

and $R_{13}$ is N or CH.

In the above formula (I), W is $(C_{1-6}$ alkyl), X is S, O, or CH$_2$, Y and $Y_1$ are independently —CO—, —C(=O)O—, —SO$_2$—, or —C(=O)N(R$_{10}$)— and Z is O, CH$_2$, or N—R$_{11}$.

In the above, l is 1, 2, or 3, m is 1 or 2, n is 0 or 1, o is 0 or 1, p is 0 or 1, q is 0 or 1, and r is 0, 1, 2 or 3.

The above formula (I) has the provisos that:

(1) when Y is —C(=O)O—, $R_3$ cannot be hydrogen;

(2) when $R_4$ is equal to O—$(C_4$ alkyl), $C_4$ alkyl is not equal to tert-butyl;

(3) in those pyrrolidine structures (l is 1; m is 2; n is 0; o is 0; p is 1; X is CH$_2$), W is equal to CH$_2$; and (4) the compound is not

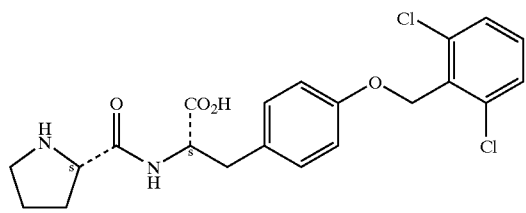

In another embodiment of the present invention, $R_5$ is a formula of the following:

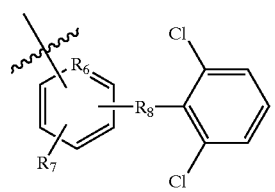

wherein $R_7$ is hydrogen or Cl.

In another embodiment of the present invention, $R_2$ is hydrogen or $C_{1-6}$ alkyl. Additionally, $R_1$ and $R_2$ may be attached to the same carbon atom and may form a carbocyclic ring of 5–8 atoms together with the carbon atom to which they are attached or be attached to the same carbon atom and form a ring of 5–8 atoms of the formula:

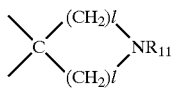

together with the carbon atom to which they are attached. Also, in this embodiment, n is 0, m is 2 and p is 0.

In yet another embodiment of the present invention, $R_1$ is hydrogen or $C_{1-3}$ alkyl, and $R_2$ is hydrogen or $C_{1-4}$ alkyl. Additionally, $R_1$ and $R_2$ may be attached to the same carbon atom and may form a carbocyclic ring of 5–8 atoms together with the carbon atom to which they are attached or be attached to the same atom and form a ring of 5–8 atoms of the formula:

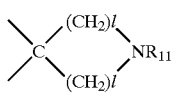

together with the carbon atom to which they are attached. Also in this embodiment, $R_3$ is hydrogen, $C_{1-6}$ alkyl, $C_{7-17}$ arylalkyl, $(C_{1-6}$ alkyl)—OH, $(C_{1-6}$ alkyl)—CO—R$_{11}$, $(C_{1-6}$ alkyl)—CN, adamantyl, phenyl, or one of the following:

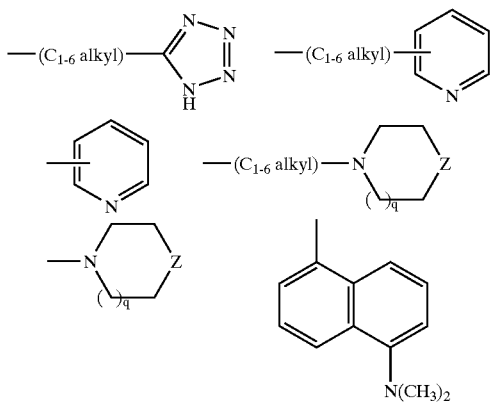

Additionally, in this embodiment, $R_4$ is —O—$R_{11}$, NH$_2$, NHOH, or $R_4$ is of the formula:

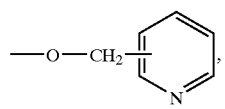

$R_{11}$ is hydrogen or CH$_3$, and X is S or O.

In another embodiment, $R_1$ and $R_2$ are hydrogen, and $R_3$ is $(C_{2-6}$ alkenyl)—CO$_2$—R$_{11}$, $(C_{1-6}$ alkyl)—O—C$_{1-3}$ alkyl, $(C_{1-6}$ alkyl)—CO$_2$R$_{11}$, or one of the following:

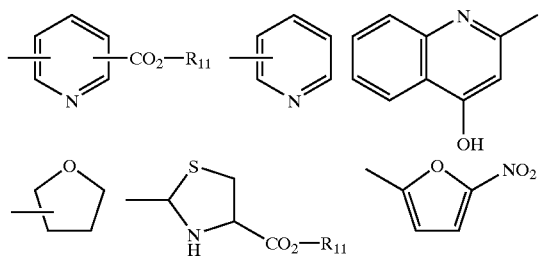

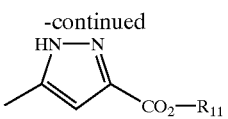

Also, in this embodiment, $R_4$ is $O-R_{11}$, $R_6$ is CH, $R_{11}$ is hydrogen, and $R_7$ is hydrogen. Additionally, X is S, Y is —CO—, and l is 1.

In another embodiment of the present invention, $R_1$ and $R_2$ are hydrogen, and $R_3$ is $C_{1-6}$ alkyl, ($C_{1-6}$ alkyl)—$CO_2$—$R_{11}$, ($C_{2-6}$ alkenyl)—$CO_2$—$R_{11}$, ($C_{1-6}$ alkyl)—CO—$C_{1-6}$ alkyl, ($C_{1-6}$ alkyl)—O—$C_{1-3}$ alkyl, ($C_{1-6}$ alkyl)—CN, or one of the following:

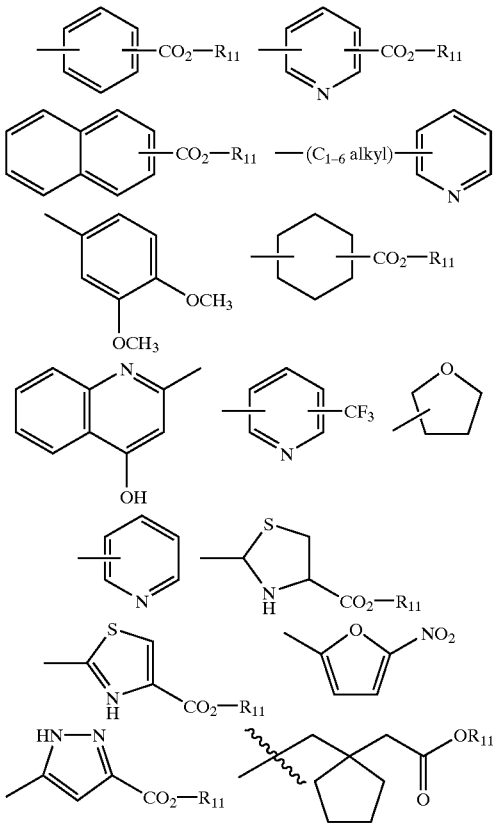

Additionally, $R_4$ is OH, $R_6$ is CH, $R_{11}$ is hydrogen, $R_7$ is hydrogen, X is $CH_2$, and Y is —CO— or —C(=O)NH—.

In another embodiment of the present invention. W is ($C_{1-3}$ alkyl), X is $CH_2$, Y is —C(=O)O—, $R_1$ is hydrogen, $R_2$ is hydrogen, ($C_{1-3}$ alkyl)—$CO_2$—$R_{11}$, or —$CO_2$—$R_{11}$, $R_3$ is hydrogen, $C_{7-10}$ arylalkyl, $C_{1-6}$ alkyl, or ($C_{1-6}$ alkyl)—$CO_2$—$R_{11}$, $R_4$ is OH, $R_6$ is CH, $R_{11}$ is hydrogen, $R_7$ is hydrogen, l is 1 or 3, and n is 0.

In another embodiment of the present invention, W is $C_{1-3}$ alkyl, X is $CH_2$, $R_1$ is hydrogen, $R_2$ is ($C_{1-4}$ alkyl)—$CO_2$—$R_{11}$, or $CO_2$—$R_{11}$, $R_3$ is hydrogen, $C_{1-3}$ alky, or $C_{2-7}$ alkenyl, $R_4$ is OH, $R_6$ is CH, $R_{11}$ is hydrogen, $R_7$ is hydrogen, l is 1, m is 1, n is 1, o is 0, and p is 1.

In another embodiment, the compound of the present invention is represented by the following formula

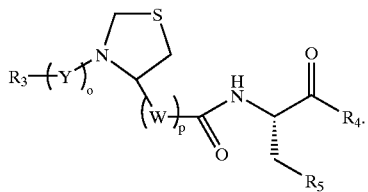

In another embodiment of the present invention, $R_1$ and $R_2$ are hydrogen, and $R_3$ is $C_{1-6}$ alkyl, ($C_{1-6}$ alkyl)—$CO_2R_{11}$, ($C_{2-6}$ alkenyl)—$CO_2R_{11}$, ($C_{1-6}$ alkyl)—O—$C_{1-3}$ alkyl, or one of the following:

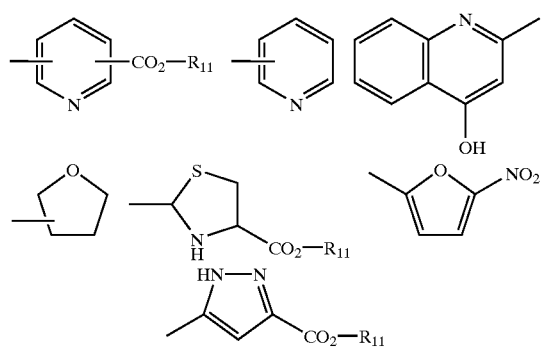

Additionally, in this embodiment, $R_4$ is $O-R_{11}$, $R_6$ is CH, $R_{11}$ is hydrogen or $C_{1-6}$ alkyl, $R_7$ is hydrogen, X is S, Y is —C(=O)O—, and l is 1.

In another embodiment of the present invention, $R_1$ is hydrogen or $C_{1-3}$ alkyl and $R_2$ is hydrogen or $C_{1-4}$ alkyl. Additionally, $R_1$ and $R_2$ may be attached to the same carbon atom and may form a carbocyclic ring of 5–8 atoms, or be attached to the same atom and form a ring of 5–8 atoms of the formula:

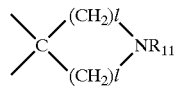

together with the carbon atom to which they are attached. In this embodiment, $R_3$ is hydrogen, $C_{1-6}$ alkyl, $C_{7-17}$ arylalkyl, ($C_{1-6}$ alkyl)—OH, ($C_{1-6}$ alkyl)—$CO_2$—$R_{11}$, ($C_{1-6}$ alkyl)—CN, adamantyl, phenyl, or one of the following:

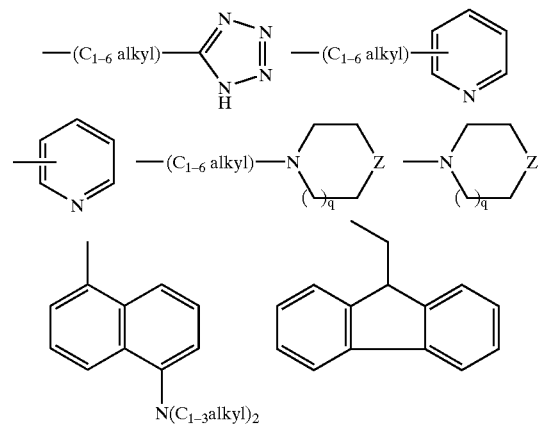

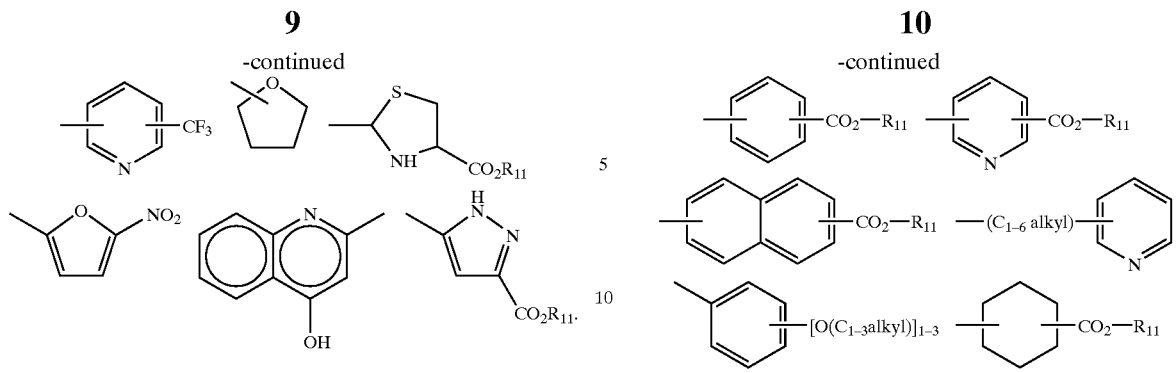

Additionally, in this embodiment, $R_4$ is $-O-R_{11}$, $NH_2$, NHOH, or $R_4$ is of the formula

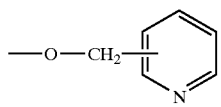

Also, $R_{11}$ is hydrogen or $C_{1-6}$ alkyl, and X is S or O.

In yet another embodiment, the compound of the present invention is represented by the following formula (I-a):

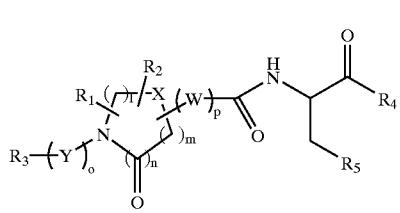

(I-a)

In the above formula (I-a), $R_1$ may occur one to four times and each occurrence is independently hydrogen or $C_{1-6}$ alky, and $R_2$ is hydrogen, pyridyl, $C_{1-6}$ alkyl, $(C_{1-6}$ alkyl)—$CO_2$—$R_{11}$, or —$CO_2$—$R_{11}$. Additionally, $R_1$ and $R_2$ may be attached to the same carbon atom and form a carbocyclic ring of 5–8 atoms together with the carbon atom to which they are attached, or they may be attached to the same carbon atom and form a ring of 5–8 atoms of the formula:

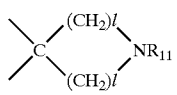

together with the carbon atom to which they are attached. Additionally, in this embodiment, $R_3$ is hydrogen, phenyl, $C_{1-6}$ alkyl, $C_{3-6}$ alkenyl, $C_{7-17}$ arylalkyl, $(C_{1-6}$ alkyl)—$CO_2$—$R_{11}$, $(C_{2-6}$ alkenyl)—$CO_2$—$R_{11}$, $(C_{1-6}$ alkyl)—$CO$—$C_{1-6}$ alkyl, $(C_{1-6}$ alkyl)—$O$—$C_{1-6}$ alkyl, $(C_{1-6}$ alkyl)—OH, $(C_{1-6}$ alkyl)—CN, adamantyl or one of the following:

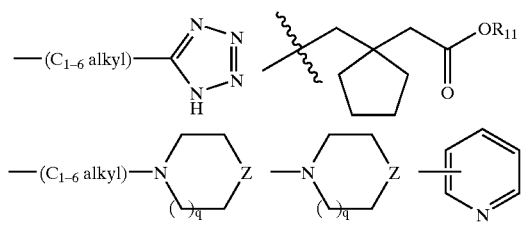

In addition, $R_2$ and $R_{3-(Y)_o}$— may combine with each other at the terminal thereof to form a ring of the following formula together with the carbon atom and the nitrogen atom to which they are attached:

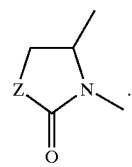

Additionally, $R_4$ is $-O-R_{11}$, $NH_2$, NHOH, $-O-(C_{7-10}$ arylalkyl), or is of the formula

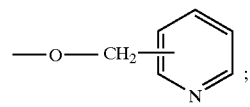

;

Also, in this embodiment, $R_5$ is a formula of the following:

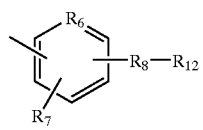

Additionally, in this embodiment, $R_6$ is N or CH, $R_7$ is hydrogen or halogen, $R_8$ is —NH—$Y_1$—, —$OCH_2$—, or —CONH—, $R_9$ may occur one to three times and is a halogen, $C_{1-6}$ alkoxy, $C_{1-6}$ alkyl or trifluoromethyl, $R_{10}$ is $C_{1-6}$ alkyl, or $(C_{1-6}$ alkyl)—OH, or hydrogen, $R_{11}$ is hydrogen or $C_{1-6}$ alkyl, $R_{12}$ is $C_{1-6}$ alkyl or the following formula:

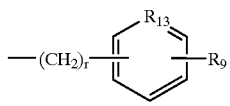

$R_{13}$ is N or CH, W is ($C_{1-6}$ alkyl), X is S, O, or $CH_2$, Y and $Y_1$ are independently —CO—, —C(=O)O—, —$SO_2$—, or —C(=O)N($R_{10}$)—, Z is O, $CH_2$, or N—$R_{11}$, l is 1, 2, or 3, m is 1 or 2, n is 0 or 1, o is 0 or 1, p is 0 or 1, q is 0 or 1 and r is 0, 1, 2 or 3. This particular embodiment of the present invention has the provisos that (1) when Y is —C(=O)O—, $R_3$ cannot be hydrogen;
(2) when $R_4$ is equal to O—($C_4$ alkyl), $C_4$ alkyl is not equal to tert-butyl;
(3) in those pyrrolidine structures (l is 1; m is 2; n is 0; o is 0; p is 1; X is $CH_2$), W is equal to $CH_2$;
(4) the compound has an $IC_{50}$ value of less than 5 μM in a Jurkat CS-1 assay and/or an $IC_{50}$ value of less than 50 μM in a Jurkat EC assay; and
(5) the compound is not

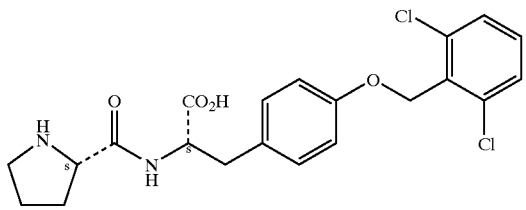

In yet another embodiment of the compound of formula (I), $R_1$ may occur one to four times and each occurrence is independently hydrogen or $C_{1-6}$ alkyl. Also, $R_2$ is hydrogen, pyridyl, $C_{1-6}$ alkyl, ($C_{1-6}$ alkyl)—$CO_2$—$R_{11}$, or —$CO_2$—$R_{11}$. Additionally, $R_1$ and $R_2$ may be attached to the same carbon atom and form a carbocyclic ring of 5–8 atoms together with the carbon atom to which they are attached, or they may be attached to the same carbon atom and form a ring of 5–8 atoms of the formula:

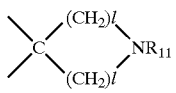

together with the carbon atom to which they are attached. In this embodiment, $R_3$ is hydrogen, phenyl, $C_{1-6}$ alkyl, $C_{3-6}$ alkenyl, $C_{7-17}$ arylalkyl, ($C_{1-6}$ alkyl)—$CO_2$—$R_{11}$, ($C_{2-6}$ alkenyl)—$CO_2$—$R_{11}$, ($C_{1-6}$ alkyl)—CO—$C_{1-6}$ alkyl, ($C_{1-6}$ alkyl)—O—$C_{1-6}$ alkyl, ($C_{1-6}$ alkyl)—OH, ($C_{1-6}$ alkyl)—CN, adamantyl or one of the following:

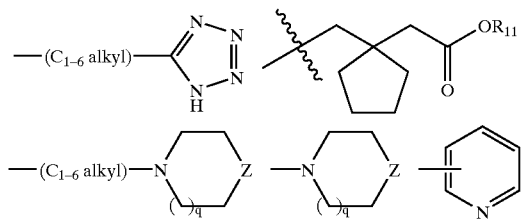

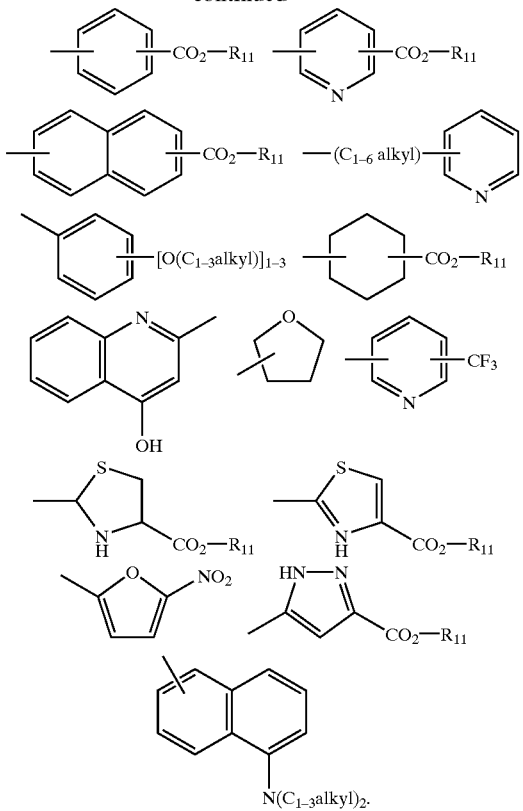

In addition, $R_2$ and $R_3$—(Y)$_o$— may combine with each other at the terminal thereof to form a ring of the following formula together with the carbon atom and the nitrogen atom to which they are attached:

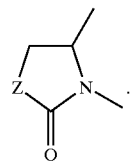

In this embodiment, $R_4$ is —O—$R_{11}$, $NH_2$, NHOH, —O—($C_{7-10}$ arylalkyl), or $R_4$ is of the formula:

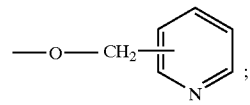

Also, in this embodiment, $R_5$ is a formula of the following:

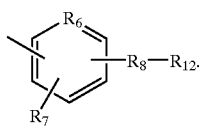

Additionally, in this embodiment, $R_6$ is N or CH, $R_7$ is hydrogen or halogen, $R_8$ is —NHCO—, $R_9$ may occur one to three times and is a halogen, $C_{1-6}$ alkoxy, $C_{1-6}$ alkyl or trifluoromethyl, $R_{10}$ is $C_{1-6}$ alkyl, or ($C_{1-6}$ alkyl)—OH, or hydrogen, $R_{11}$ is hydrogen or $C_{1-6}$ alkyl, $R_{12}$ is $C_{1-6}$ alkyl or the following formula:

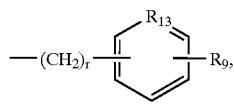

$R_{13}$ is N or CH, W is ($C_{1-6}$ alkyl), X is S, O, or $CH_2$, Y is —CO—, —C(=O)O—, —C(=O)N($R_{10}$)—, Z is O, $CH_2$, or N—$R_{11}$, l is 1, 2, or 3, m is 1 or 2, n is 0 or 1, o is 0 or 1, p is 0 or 1, q is 0 or 1, and r is 0, 1, 2 or 3. In this embodiment, the following provisos apply:

(1) when Y is —C(=O)O—, $R_3$ cannot be hydrogen;
(2) when $R_4$ is equal to O—($C_4$ alkyl), $C_4$ alkyl is not equal to tert-butyl; and
(3) in those pyrrolidine structures (l is 1; m is 2; n is 0; o is 0; p is 1; X is $CH_2$), W is equal to $CH_2$.

In yet another embodiment of the compound of formula (I-a), $R_1$ may occur one to four times and each occurrence is independently hydrogen or $C_{1-6}$ alkyl, and $R_2$ is hydrogen, pyridyl, $C_{1-6}$ alkyl, ($C_{1-6}$ alkyl)—$CO_2$—$R_{11}$, or —$CO_2$—$R_{11}$. Additionally, $R_1$ and $R_2$ may be attached to the same carbon atom and form a carbocyclic ring of 5–8 atoms together with the carbon atom to which they are attached, or they may be attached to the same carbon atom and form a ring of 5–8 atoms of the formula:

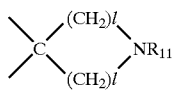

together with the carbon atom to which they are attached. Additionally, in this embodiment, $R_3$ is hydrogen, phenyl, $C_{1-6}$ alkyl, $C_{3-6}$ alkenyl, $C_{7-17}$ arylalkyl, ($C_{1-6}$ alkyl)—$CO_2$—$R_{11}$, ($C_{2-6}$ alkenyl)—$CO_2$—$R_{11}$, ($C_{1-6}$ alkyl)—CO—$C_{1-6}$ alkyl, ($C_{1-6}$ alkyl)—O—$C_{1-6}$ alkyl, ($C_{1-6}$ alkyl)—OH, ($C_{1-6}$ alkyl)—CN, adamantyl or one of following:

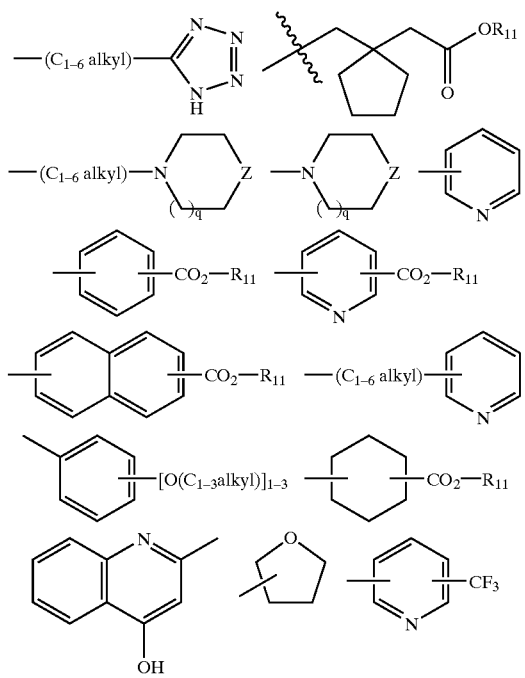

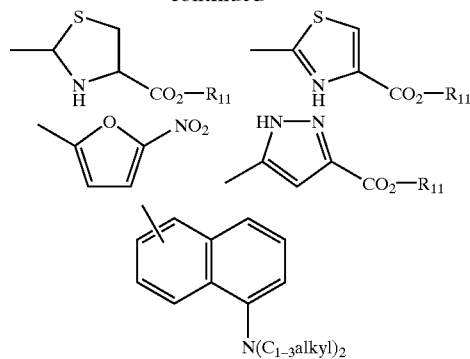

In addition, $R_2$ and $R_3$—(Y)$_o$— may combine with each other at the terminal thereof to form a ring of the following formula together with the carbon atom and the nitrogen atom to which they are attached:

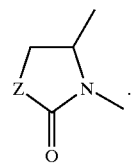

Additionally, $R_4$ is —O—$R_{11}$, $NH_2$, NHOH, —O—($C_{7-10}$ arylalkyl), or is of the formula

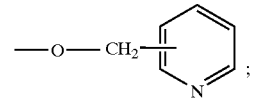

Also, in this embodiment, $R_5$ is a formula of the following:

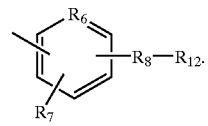

Additionally, in this embodiment, $R_6$ is N or CH, $R_7$ is hydrogen or halogen, $R_8$ is —NHCO—, $R_9$ may occur one to three times and is a halogen, $C_{1-6}$ alkoxy, $C_{1-6}$ alkyl or trifluoromethyl, $R_{10}$ is $C_{1-6}$ alkyl, or ($C_{1-6}$ alkyl)—OH, or hydrogen, $R_{11}$ is hydrogen or $C_{1-6}$ alkyl, $R_{12}$ is $C_{1-6}$ alkyl or the following formula:

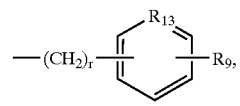

$R_{13}$ is N or CH, W is ($C_{1-6}$ alkyl), X is S, O, or $CH_2$, Y is —CO—, —C(=O)O— or —C(=O)N($R_{10}$)—, Z is O, $CH_2$, or N—$R_{11}$, l is 1, 2, or 3, m is 1 or 2, n is 0 or 1, o is 0 or 1, p is 0 or 1, q is 0 or 1, and r is 0, 1, 2 or 3. This particular embodiment of the present invention has the provisos that (1) when Y is —C(=O)O—, $R_3$ cannot be hydrogen;
(2) when $R_1$ is equal to O—($C_4$ alkyl), $C_4$ alkyl is not equal to tert-butyl;
(3) in those pyrrolidine structures (l is 1; m is 2; n is 0; o is 0; p is 1; X is $CH_2$), W is equal to $CH_2$; and (4) the compound has an $IC_{50}$ value of less than 5 μM in a Jurkat CS-1 assay and/or an $IC_{50}$ value of less than 50 μM in a Jurkat EC assay.

In another embodiment of the compound of formula (I), $R_1$ may occur one to four times and each occurrence is independently hydrogen or $C_{1-6}$ alkyl, $R_2$ is hydrogen, pyridyl, $C_{1-6}$ alkyl, ($C_{1-6}$ alkyl)—$CO_2$—$R_{11}$, or —$CO_2$—$R_{11}$. Additionally, $R_1$ and $R_2$ may be attached to the same carbon atom and form a carbocyclic ring of 5–8 atoms together with the carbon atom to which they are attached, or they may be attached to the same carbon atom and form a ring of 5–8 atoms of the formula:

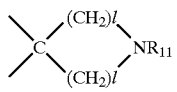

together with the carbon atom to which they are attached. Also, in this embodiment, $R_3$ is hydrogen, phenyl, $C_{1-6}$ alkyl, $C_{3-6}$ alkenyl, $C_{7-17}$ arylalkyl, ($C_{1-6}$ alkyl)—$CO_2$—$R_{11}$, ($C_{2-6}$ alkenyl)—$CO_2$—$R_{11}$, ($C_{1-6}$ alkyl)—$CO$—$C_{1-6}$ alkyl, ($C_{1-6}$ alkyl)—$O$—$C_{1-6}$ alkyl, ($C_{1-6}$ alkyl)—OH, ($C_{1-6}$ alkyl)—CN, adamantyl or one of the following:

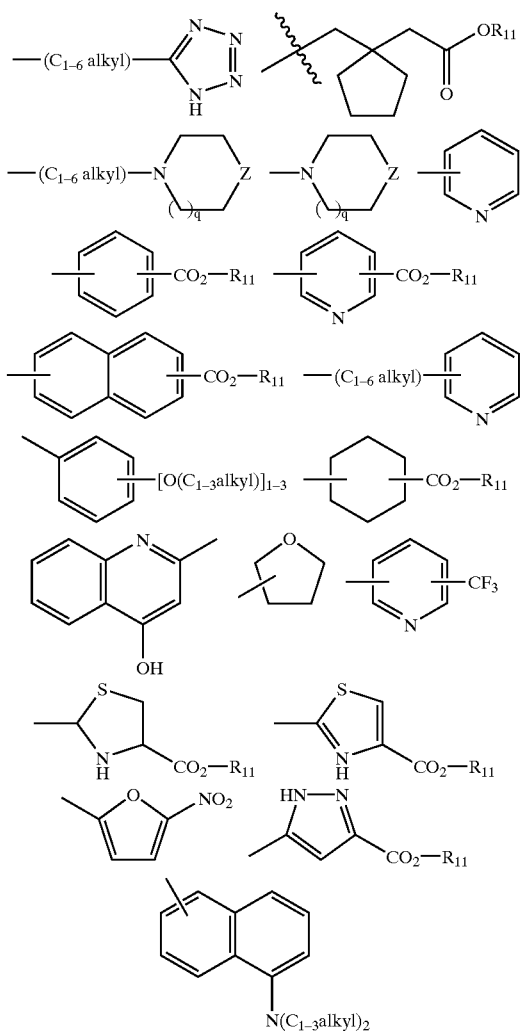

In addition, $R_2$ and $R_3$—$(Y)_o$— may combine with each other at the terminal thereof to form a ring of the following formula together with the carbon atom and the nitrogen atom to which they are attached:

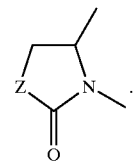

In this embodiment, $R_4$ is —O—$R_{11}$, $NH_2$, NHOH, —O—($C_{7-10}$ arylalkyl), or $R_4$ is of the formula:

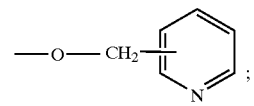

In this embodiment, $R_5$ is a formula of the following:

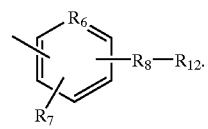

Also, in this particular embodiment, $R_6$ is N or CH, $R_7$ is hydrogen or halogen, $R_8$ is —$OCH_2$—, $R_9$ may occur one to three times and is a halogen, $C_{1-6}$ alkoxy, $C_{1-6}$ alkyl or trifluoromethyl, $R_{10}$ is $C_{1-6}$ alkyl, ($C_{1-6}$ alkyl)—OH, or hydrogen, $R_{11}$ is hydrogen or $C_{1-6}$ alkyl, $R_{12}$ is $C_{1-6}$ alkyl or the following formula:

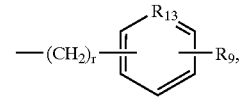

$R_{13}$ is N or CH, W is ($C_{1-6}$ alkyl), X is S, O, or $CH_2$, Y is —CO—, —C(=O)O— or —C(=O)N($R_{10}$)—, Z is O, $CH_2$, or N—$R_1$, l is 1, 2, or 3, m is 1 or 2, n is 0 or 1, o is 0 or 1, p is 0 or 1, q is 0 or 1, and r is 0, 1, 2 or 3. This particular embodiment has the following provisos:

(1) when Y is —C(=O)O—, $R_3$ cannot be hydrogen;
(2) when $R_4$ is equal to O—($C_4$ alkyl), $C_4$ alkyl is not equal to tert-butyl;
(3) in those pyrrolidine structures (l is 1; m is 2; n is 0; o is 0; p is 1; X is $CH_2$), W is equal to $CH_2$;
(4) when $R_3$ is phenyl, $C_{1-6}$ alkyl, $C_{7-17}$ arylalkyl, ($C_{1-6}$ alkyl)—$CO_2$—$R_{11}$, ($C_{1-6}$ alkyl)—O—$C_{1-6}$ alkyl or ($C_{1-6}$ alkyl)—OH, o is 0; and
(5) the compound is not

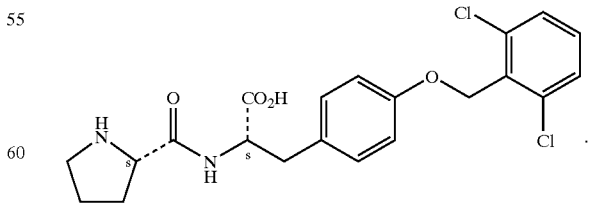

In yet another embodiment of the compound of formula (I-a), $R_1$ may occur one to four times and each occurrence is independently hydrogen or $C_{1-6}$ alkyl, and $R_2$ is hydrogen, pyridyl, $C_{1-6}$ alkyl, ($C_{1-6}$ alkyl)—$CO_2$—$R_{11}$, or —$CO_2$—

$R_{11}$. Additionally, $R_1$ and $R_2$ may be attached to the same carbon atom and form a carbocyclic ring of 5–8 atoms together with the carbon atom to which they are attached, or they may be attached to the same carbon atom and form a ring of 5–8 atoms of the formula:

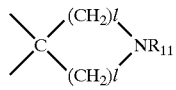

together with the carbon atom to which they are attached. Additionally, in this embodiment, $R_3$ is hydrogen, phenyl, $C_{1-6}$ alkyl, $C_{3-6}$ alkenyl, $C_{7-17}$ arylalkyl, $(C_{1-6}$ alkyl)—$CO_2$—$R_{11}$, $(C_{2-6}$ alkenyl)—$CO_2$—$R_{11}$, $(C_{1-6}$ alkyl)—CO—C, alkyl, $(C_{1-6}$ alkyl)—O—$C_{1-6}$ alkyl, $(C_{1-6}$ alkyl)—OH, $(C_{1-6}$ alkyl)—CN, adamantyl or one of the following:

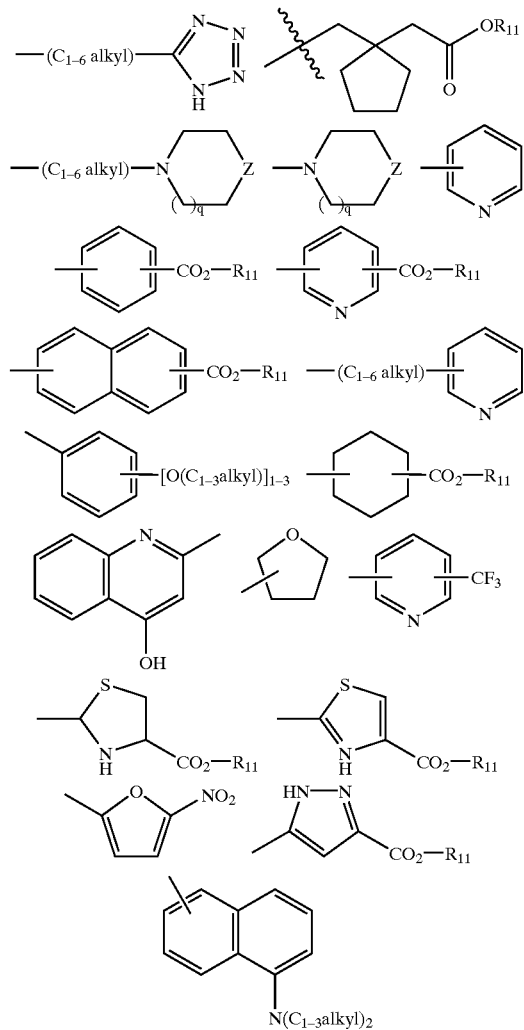

In addition, $R_2$ and $R_3$—$(Y)_o$— may combine with each other at the terminal thereof to form a ring of the following formula together with the carbon atom and the nitrogen atom to which they are attached:

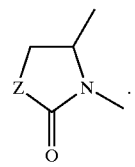

Additionally, $R_4$ is —O—$R_{11}$, $NH_2$, NHOH, —O—($C_{7-10}$ arylalkyl), or is of the formula

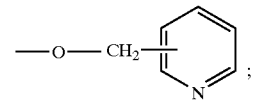

Also, in this embodiment, $R_5$ is a formula of the following:

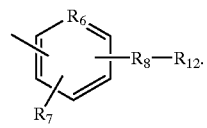

Additionally, in this embodiment, $R_6$ is N or CH, $R_7$ is hydrogen or halogen, $R_8$ is —$OCH_2$—, $R_9$ may occur one to three times and is a halogen, $C_{1-6}$ alkoxy, $C_{1-6}$ alkyl or trifluoromethyl, $R_{10}$ is $C_{1-6}$ alkyl, or $(C_{1-6}$ alkyl)—OH, or hydrogen, $R_{11}$ is hydrogen or $C_{1-6}$ alkyl, $R_{12}$ is $C_{1-6}$ alkyl or the following formula:

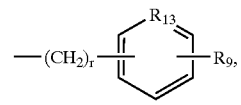

$R_{13}$ is N or CH, W is ($C_{1-6}$ alkyl), X is S, O, or $CH_2$, Y is —CO—, —C(=O)O— or —C(=O)N(R,O)—, Z is O, $CH_2$, or N—$R_{11}$, l is 1, 2, or 3, m is 1 or 2, n is 0 or 1, o is 0 or 1, p is 0 or 1, q is 0 or 1, and r is 0, 1, 2 or 3. This particular embodiment of the present invention has the provisos that:

(1) when Y is —C(=O)O—, $R_3$ cannot be hydrogen;

(2) when $R_4$ is equal to O—($C_4$ alkyl), $C_4$ alkyl is not equal to tert-butyl;

(3) in those pyrrolidine structures (l is 1; m is 2; n is 0; o is 0; p is 1; X is $CH_2$), W is equal to $CH_2$;

(4) the compound has an $IC_{50}$ value of less than 5 µM in a Jurkat CS-1 assay and/or an $IC_{50}$ value of less than 50 µM in a Jurkat EC assay;

(5) when $R_3$ is phenyl, $C_{1-6}$ alkyl, $C_{7-17}$ arylalkyl, $(C_{1-6}$ alkyl)—$CO_2$—$R_{11}$, $(C_{1-6}$ alkyl)—O—$C_{1-6}$ alkyl or $(C_{1-6}$ alkyl)—OH, o is 0; and (6) the compound is not

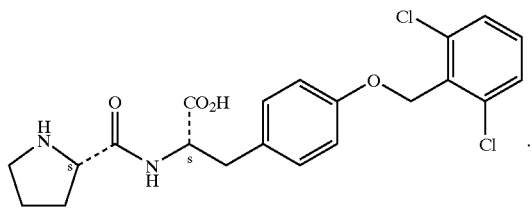

In the above formula (I) the absolute stereochemistry for the bond leading to $R_5$ is shown, however the absolute stereochemistry has not been shown for all examples which follow. It is understood that all other formulas also follow this type of absolute stereochemistry unless otherwise stated. Additionally, it is to be understood by those of skill in the art that the present invention embodies stereochemical configurations other than those shown. Specifically, the present invention embodies all configurations including the various stereoisomers. Compounds which do not meet the absolute stereochemistry in formula (I) should meet an activity threshold in various assays, to be explained below, which can ensure their efficacy as useful molecules. The present invention includes mixtures, such as racemic mixtures, which contain molecules having the claimed stereochemistry.

The desired compound of the present invention may be clinically used either in a free form or in the form of pharmaceutically acceptable salts thereof. Pharmaceutically acceptable salts include acid-addition salts with inorganic acid or organic acid (e.g., hydrochloride, sulfate, nitrate, hydrobromide, methanesulfonate, p-toluenesulfonate, acetate), salt with inorganic base, organic base or amino acid (e.g., triethylamine salt, a salt with tysine, an alkali metal salt, an alkali earth metal salt and the like).

The compound may also be formulated into a pharmaceutical composition comprising a therapeutically effective amount of the compound as defined above and a pharmaceutically acceptable carrier or diluent.

The compound can also be used for treating or preventing $\alpha_4\beta_1$ adhesion mediated conditions in a mammal such as a human. This method may comprise administering to a mammal or a human patient an effective amount of the compound or composition as explained above.

This method can be used to treat such inflammatory conditions as rheumatoid arthritis, asthma, allergy conditions, adult respiratory distress syndrome, AIDS, cardiovascular diseases, thrombosis or harmful platelet aggregation, reocclusion following thrombolysis, allograft rejection, reperfusion injury, psoriasis, eczema, contact dermatitis and other skin inflammatory diseases, osteoporosis, osteoarthritis, atherosclerosis. neoplastic diseases including metastasis of neoplastic or cancerous growth, wound healing enhancement, treatment of certain eye diseases such as detaching retina, Type I diabetes, multiple sclerosis, systemic lupus erythematosus (SLE), inflammatory and immunoinflammatory conditions including ophthalmic inflammatory conditions and inflammatory bowel diseases, ulcerative colitis, atherosclerosis, regional enteritis and other autoimmune diseases.

As mentioned above, the compounds and compositions containing the compounds according to the present invention are particularly useful in treating or preventing $\alpha_4\beta_1$ adhesion mediated conditions in a mammal such as a human. The present inventors have found that the compounds and compositions containing the compounds according to the present invention are most useful in the treatment of asthma.

The desired compound of the present invention or pharmaceutically acceptable salts thereof may be administered either orally or parenterally, and it may be used as a suitable pharmaceutical preparation, for example, a tablet, a granule, a capsule, a powder, an injection, and an inhalation by a conventional process.

The dose of the desired compound of the present invention or a pharmaceutically acceptable salt thereof varies depending on an administration method, age, body weight, and state of a patient, but, in general, the daily dose is preferably about 0.1 to 100 mg/kg/day, however, 1 to 100 mg/kg/day may also be suitable.

Preferred Routes of Administration for Asthma

It is preferred that the compound of the present invention be administered in the form of an Aerosol. However, other routes of administration include intravenous, oral, intramuscular, and subcutaneous.

In the case of aerosol administration, compositions containing the compounds of the present invention can be prepared to provide for an excellent means for administering in aerosol form for inhalation therapy. Accordingly, the present invention will provide for self-propelling compositions containing the compounds of the present invention.

Propellants employed should be non-toxic and have a vapor pressure suitable for the conditions under which administration occurs. These propellants can be fluorinated or fluorochlorinated lower saturated aliphatic hydrocarbons. The preferred propellants of this type are the halogenated alkanes containing not more than two carbon atoms and at least one fluorine atom. Illustrative of these are trichloromonofluoromethane, dichlorodifluoromethane, monochlorotrifluoromethane, dichloromonofluoromethane and 1,2-dichloro-1,1,2,2-tetrafluoroethane. These compounds are available from E.I. duPont de Nemours and Company under the trade name "Freon". These propellants may be employed singularly or in admixture.

In addition to the propellant, an organic solvent may also be employed. The organic solvent must be non-toxic and without undesirable effects on inhalation in the amount present in the aerosol produced. In addition, the solvent should be substantially anhydrous, completely miscible with the propellant or mixture of propellants employed and have a suitable boiling point. Examples of such solvents included non-toxic aliphatic alcohols such as ethanol; ethers such as ethyl ether and vinyl ether; ketones such as acetone; and suitable halogenated lower alkanes.

In addition to the organic solvent, the composition may also optionally contain a non-toxic hygroscopic glycol. The glycol must be substantially miscible with the organic solvent and the propellant employed. Satisfactory glycols include propylene glycol, triethylene glycol, glycerol, butylene glycol and hexylene glycol.

The above indicated methods of administration and formulation of aerosol compositions should not be viewed as limiting. The compounds of the present invention can be formulated in anyway deemed suitable to one of ordinary skill in the art so as to obtain the desired effects.

Pharmaceutical Compositions

As indicated previously, the compounds of formula (I) can be formulated into pharmaceutical compositions. In determining when a compound of formula (I) is indicated for the treatment of a given disease, the particular disease in question, its severity, as well as the age, sex, weight, and condition of the subject to be treated, must be taken into consideration and this perusal is to be determined by the skill of the attendant physician.

For medical use, the amount of a compound of formula (I) required to achieve a therapeutic effect will, of course, vary both with the particular compound, the route of administration, the patient under treatment, and the particular disorder or disease being treated. A suitable daily dose of a compound of Formula (I), or a pharmaceutically acceptable salt thereof, for a mammalian subject suffering from, or likely to suffer from, any condition as described hereinbefore is 0.1 mg to 100 mg of the compound of formula I, per kilogram body weight of the mammalian subject. In the case of systematic administration, the dose may be in the range of 0.5 to 500 mg of the compound per kilogram body weight, the most preferred dosage being 0.5 to 50 mg/kg of mammal body weight administered two to three times daily. In the case of topical administration, e.g., to the skin or eye, a suitable dose may be in the range of 0.1 μg to 100 μg of the compound per kilogram, typically about 0.1 μg/kg.

In the case of oral dosing, a suitable dose of a compound of Formula (I), or a physiologically acceptable salt thereof, may be as specified in the preceding paragraph, but most preferably is from 1 mg to 10 mg of the compound per kilogram, the most preferred dosage being from 1 mg to 5 mg/kg of mammal body weight, for example, from 1 to 2 mg/kg. Most preferably, a unit dosage of an orally administrable composition encompassed by the present invention contains less than about 1.0 g of a formula (I) compound.

It is understood that formulation, both for human and veterinary use, of the present invention may be presented to the mammal by inhalation. To achieve therapeutic effect, the dose may be in the range of 0.5 to 500 mg of the compound, per kg body weight. The most preferred dosage being 0.5 to 50 mg/kg of mammal body weight administered two to three times daily.

It is understood that the ordinarily skilled physician or veterinarian will readily determine and prescribe the effective amount of a compound of formula (I) to prevent or arrest the progress of the condition for which treatment is administered. In so proceeding, the physician or veterinarian could employ relatively low doses at first, subsequently increasing the dose until a maximum response is obtained.

The compounds and compositions of the present invention can be administered to patients suffering from a condition listed herein in an amount which is effective to fully or partially alleviate undesired symptoms of the condition. The symptoms may be caused by inappropriate cell adhesion mediated by $\alpha_4\beta_1$ integrins. Such inappropriate cell adhesion would typically be expected to occur as a result of increased VCAM-1 and/or CS-1 expression on the surface of endothelial cells. Increased VCAM-1 and/or CS-1 expression can be due to a normal inflammation response or due to abnormal inflammatory states. In either case, an effective dose of a compound of the invention may reduce the increased cell adhesion due to increased VCAM-1 expression by endothelial cells. Reducing the adhesion observed in the disease state by 50% can be considered an effective reduction in adhesion. More preferably, a reduction in adhesion by 90%, is achieved. Most preferably adhesion mediated by VCAM-1/$\alpha_4\beta_1$ and/or CS-1 interaction is abolished by an effective dose. Clinically, in some instances, effect of the compound can be observed or a decrease in white cell infiltration into tissues or a site of injury. To achieve a therapeutic effect, then, the compounds or compositions of the present invention are administered to provide a dose effective to reduce or eliminate inappropriate cell adhesion or to alleviate undesired symptoms.

While it is possible for an active ingredient to be administered alone, it is preferable to present it as a pharmaceutical formulation comprising a compound of formula (I) and a pharmaceutically acceptable carrier thereof. Such formulations constitute a further feature of the present invention.

The formulations, both for human and veterinary medical use, of the present invention comprise an active ingredient of formula (I), in association with a pharmaceutically acceptable carrier thereof and optionally other therapeutic ingredient(s), which are generally known to be effective in treating the disease or condition encountered. The carrier(s) must be "acceptable" in the sense of being compatible with the other ingredients of the formulations and not deleterious to the recipient thereof.

The formulations include those in a form suitable for oral, pulmonary, ophthalmic, rectal, parenteral (including subcutaneous, intramuscular, and intravenous), intraparticular, topical, nasal inhalation (e.g., with an aerosol) or buccal administration. Such formulation are understood to include long-acting formulations known in the art.

The formulations may conveniently be presented in unit dosage form and may be prepared by any of the methods well known in the art of pharmacy. All methods may include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired form.

Formulations of the present invention suitable for oral administration may be in the form of discrete units such as capsules, cachets, tablets, or lozenges, each containing a predetermined amount of the active ingredient in the form of a powder or granules; in the form of a solution or suspension in an aqueous liquid. Formulations for other uses could involve a nonaqueous liquid; in the form of an oil-in-water emulsion or a water-in-oil emulsion; in the form of an aerosol; or in the form of a cream or ointment or impregnated into a transdermal patch for use in administering the active ingredient transdermally, to a patient in need thereof. The active ingredient of the present inventive compositions may also be administered to a patient in need thereof in the form of a bolus, electuary, or paste.

The practitioner is referred to "Remington: The Science and Practice of Pharmacy," 19th Edition, c. 1995 by the Philadelphia College of Pharmacy and Science, as a comprehensive tome on pharmaceutical preparations.

Abbreviations $Ac_2O$: Acetic anhydride
EtOAc: Ethyl acetate
BCECF-AM: 2',7'-bis-(2-carboxyethyl)-5-(and 6-)carboxyfluorescein acetoxymethyl ester
BOP-Cl: Bis(2-oxo-3-oxazolidinyl)phosphinic chloride
BOP Reagent: Benzotriazol-1-yloxy-tris(dimethylamino)-phosphonium hexafluorophosphate
DMEM: Dulbecco's Minimal Eagle's Media
DMF: Dimethyl formamide
DIEA: Diisopropylethylamine
EDC: 1-(3-Dimethylaminopropyl)-3-ethylcarbodiimide hydrochloride
Et: Ethyl
EtOH: Ethanol HATU: N-[(Dimethylamino)-1H-1,2,3-triazolo[4,5-b]-pyridin-1-ylmethylene]-N-methylmethanaminium hexafluorophosphate N-oxide
HBSS: Hank's Balanced Salt Solution
HBTU: O-Benzotriazol-1-yl-N,N,N',N'-tetramethyluronium hexafluorophosphate
HOBT (HOBt): 1-Hydroxybenzotriazole
HSA: Human serum albumin
LDA: Lithium diisopropylamide
Me: Methyl
meq: milliequivalent
MeOH: Methanol
n-Bu: n-Butyl
NMP: 1-Methyl-2-pyrrolidinone
PBS: Phosphate buffered saline
Pd-C: Palladium on charcoal
Ph: Phenyl SPDP: 3-(2-pyridyldithio)propionic acid N-hydroxysuccinimide ester
t-Bu: t-butyl
THF: Tetrahydrofuran
TFA: Trifluoroacetic acid
DMSO: dimethyl sulfoxide
HOAt: 1-hydroxy-7-azabenzotriazole
DMAP: 4-dimethylaminopyridine
FMOC: 9-fluorenylmethoxycarbonyl
Bn: benzyl
PyBOP: (benzotriazol-1-yloxy)tripyrrolidinophosphonium hexafluorophosphate
BOC: tert-butoxycarbonyl The representative compounds according to the present invention are prepared as described below. The compounds of the present invention are prepared in a similar manner.

Scheme A

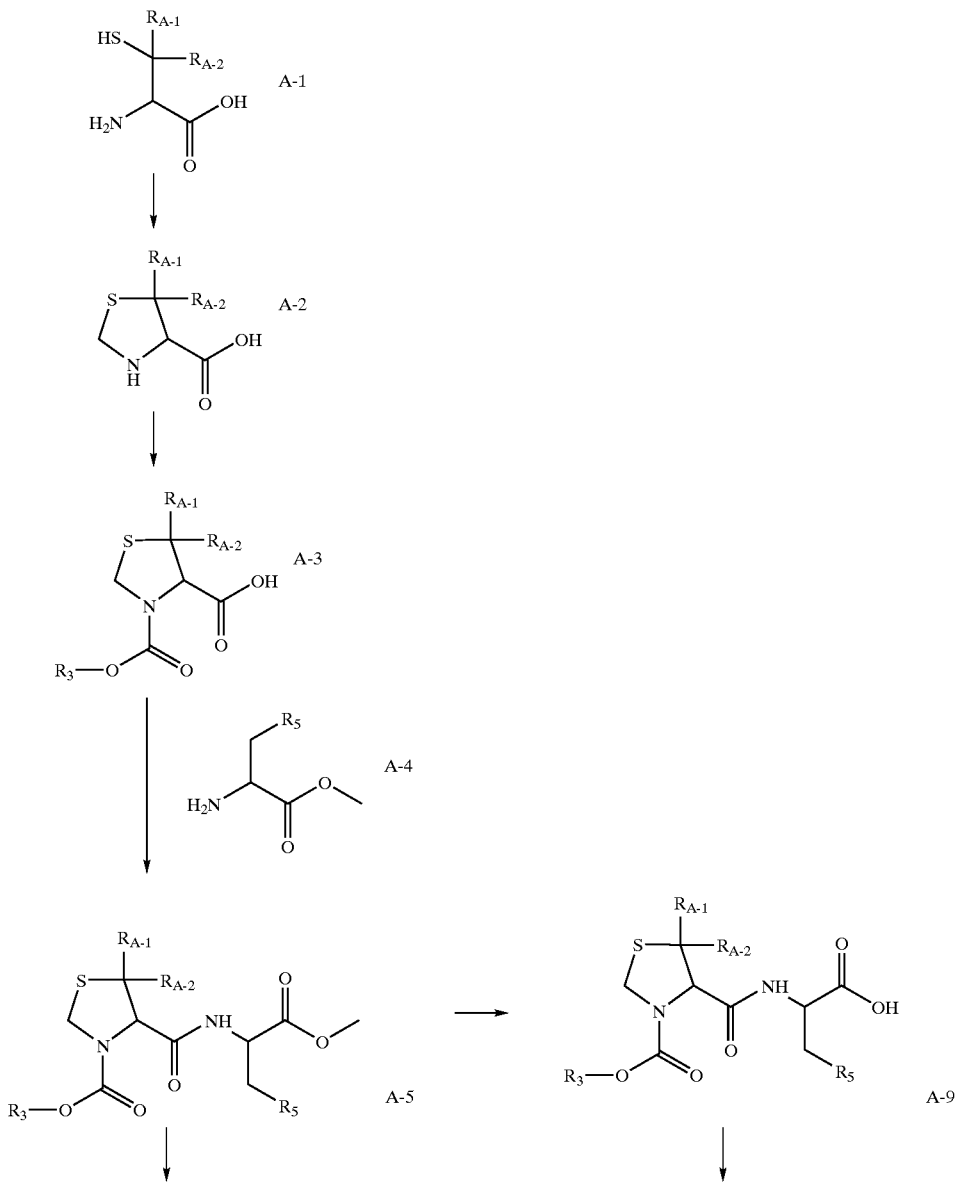

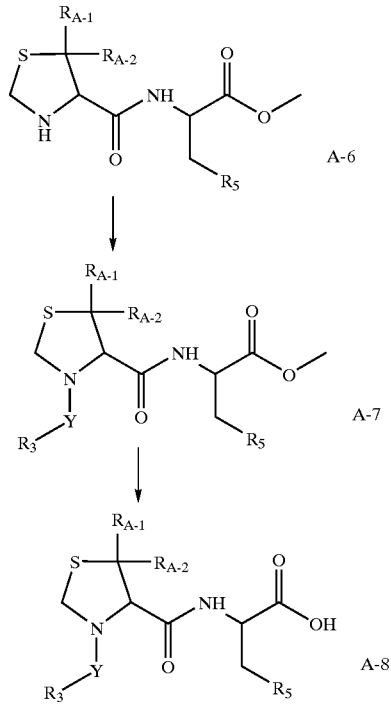

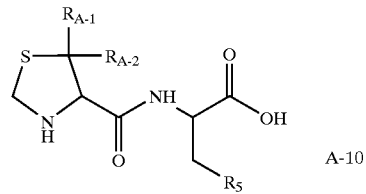

$R_{A-1}$ and $R_{A-2}$ are defined independently as $R_1$.

Scheme A describes a general method for the preparation of examples of the formula A-5, A-6, A-7, A-8, A-9 and A-10. A commercially available or readily prepared sulfur containing amino acid of structure A-1 (for the synthesis of β,β-disubstituted cysteine amino acids see: Stanfield, G. F.; Hruby, V. J. *Synth. Commun.* 1988, 18, 531 and references therein) is condensed with formaldehyde to afford the thiazolidine-4-carboxylic acid of general formula A-2 (for the condensation of aldehydes with cysteine or similar sulfur containing amino acids see for example: (a) Ratner, S.; Clark, H. T. *J. Am. Chem. Soc.* 1937, 59, 200. (b) Lewis, N. J.; Inloes, R. L.; Hes, J.; Matthews, R. H.; Milo, G. *J. Med. Chem.* 1978, 21, 1070. (c) Oya, M.; Baba, T.; Kato, E.; Kawashima, Y.; Watanbe, T. *Chem. Pharm. Bull.* 1982, 30, 440.). Standard protection affords carbamate A-3 which is readily condensed with amino acid derivative A-4 under standard peptide synthesis conditions to provide the psuedodipeptide A-5 (for a review of procedures of peptide synthesis see: Bodansky, M.; Bodansky, A. *The Practice of Peptide Synthesis*; Springer-Verlag: Berlin, 1984). Deprotection of the carbamate from A-5 provides the useful intermediate A-6. The amine group may be reacted with a variety of electrophilic reagents such as: (1) commercially available or readily prepared sulfonyl chlorides (for the synthesis of sulfonyl chlorides see for examples: (a) Roblin, R. O.; Clapp, J. W. *J. Am. Chem. Soc.* 1950, 72, 4890. (b) Gilbert, E. E. in *Sulfonation and Related Reactions* Olah, G. A., Ed. John Wiley and Sons, New York; 1965. (c) Park, Y. J.; Shin, H. H.; Kin, Y. H. *Chem Lett.* 1992, 1483. (d) Kim, D.; Ko, Y. K.; Kim, S. H. *Synthesis*, 1992, 1203.) to afford sulfonamides of general structure A-7 where Y is $SO_2$— (preparation 5); (2) carbonates or chloroformates to afford carbamates of general structure A-7 where Y is $CO_2$— (preparations 2, 7, 8); (3) isocyanates to afford ureas of general structure A-7 where Y is $CONHR_3$ (preparation 9); (4) phosgene or a suitable equivalent and an amine to afford ureas of general structure A-7 where Y is $CON(C_{1-6}$ alkyl) $R_3$— (preparation 10, also see for example: Nowick, J. S.; Homes, D. L.; Noronha, G.; Smith, E. M.; Tram, M. N.; Huang, S. *J. Org. Chem.* 1996, 61, 3929.); (5) acid chlorides and carboxylic anhydrides to provide amides of structure A-7 where Y is CO— (preparation 11). Mild base hydrolysis of monoesters of general structure A-7 (preparation 6) or diesters of general structure A-7 (preparation 12) affords the acids of general structure A-8. Mild base hydrolysis of the ester of general structure A-5 provides acid A-9 (preparation 6 or 13) which may be further deprotected to afford the amino acid A-10 (preparation 14).

PREPARATION 1

(Scheme A, A-2: where $R_{A-1}$ and $R_{A-2}$ are the same and equal to H and stereochemistry is (S)).

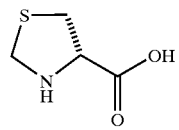

D-Cysteine hydrochloride monohydrate (A-1, where $R_{A-1}$ and $R_{A-2}$ are the same and equal to H and stereochemistry is (S)) (35.04 g, 0.19 mol) was dissolved in formaldehyde (40 wt % solution in water, 38 mL) and the reaction mixture allowed to stir for 18 h at ambient temperature. The mixture was cooled (0–5° C.) and absolute ethanol (93 mL) and pyridine (57 mL) were added. After one hour, the precipitate was collected by filtration, washed with cold absolute ethanol followed by diethyl ether and dried in vacuo to afford the title compound (24.6 g) as a white crystalline solid: mp 181–184° C. (Lit. 194–196° C.; Lewis, N. J.; Inoles, R. L.; Hes, J. *J. Med. Chem.* 1978, 21, 1070.); $^1$H NMR (DMSO-$d_6$) δ 4.22 (1H), 4.04 (1H), 3.86 (1H), 3.09 (1H), 2.24 (1H); MS (ESI+) for $C_4H_7NO_2S$ m/z 134.0 $(M+H)^+$.

PREPARATION 2

(Scheme A, A-3: where $R_{A-1}$ and $R_{A-2}$ are the same and equal to H, $R_3$ is 1-butyl and stereochemistry is (S)).

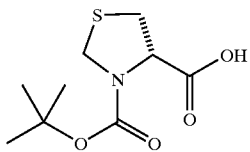

A solution of A-2 (Scheme A where $R_{A-1}$ and $R_{A-2}$ are the same and equal to H and stereochemistry is (S)) (24.6 g, 0.185 mol) and di-t-butyl dicarbonate (44.4 g, 0.2 mol) in THF (1 L) was heated to reflux for 18 h. Volatiles were removed in vacuo and the residue partitioned between ethyl acetate and 0.1 N NaOH. The aqueous layer was washed with ethyl acetate, made acidic with 1.0 N HCl (pH 3–4) and then extracted with ethyl acetate. The combined organic extracts were washed with brine, dried ($Na_2SO_4$), filtered and concentrated in vacuo. Crystallization of the white solid from hexane/methylene chloride provided the title compound (31.8 g) as white crystals: mp 132–134° C.; $[\alpha]^{25}_D =$ 117° (c 0.66, ethanol); IR (mull) 3002, 1747, 1635, 1421, 1404, 1393, 1310, 1215, 1198, 1166, 1144, 1122, 894, 862, 774 $cm^{-1}$; $^1$H NMR (DMSO-$d_6$) δ 4.57 (2H), 4.28 (1H), 3.09 (1H), 1.35 (9H); $^{13}$C NMR (DMSO-$d_6$) δ 171.8, 152.5, 79.8, 60.9, 48.4, 47.7, 33.8, 32.6, 27.7; MS (ESI+) for $C_9H_{15}NO_4S$ m/z 234.2 (M+H)$^+$; MS (ESI–) for $C_9H_{15}NO_4S$ m/z 232.1 (M–H)$^-$; Anal. Calcd for $C_9H_{15}NO_4S$: C, 46.34; H, 6.48; N, 6.00. Found: C, 46.27; H, 6.48; N, 6.03.

PREPARATION 3, EXAMPLE 1

[S-(R*,R*)]-4-[[[1-[[4-[(2,6-Dichlorobenzoyl)amino]phenyl]methyl]-2-methoxy-2-oxoethyl]amino]carbonyl]-3-thiazolidinecarboxylic Acid 3-(1,1-Dimethylethyl)ester (Scheme A, A-5: where $R_{A-1}$ and $R_{A-2}$ are the same and equal to H, $R_3$ is t-butyl, $R_5$ is 4-[(2,6-dichlorobenzoyl)amino]phenyl, and stereochemistry is (S,S)).

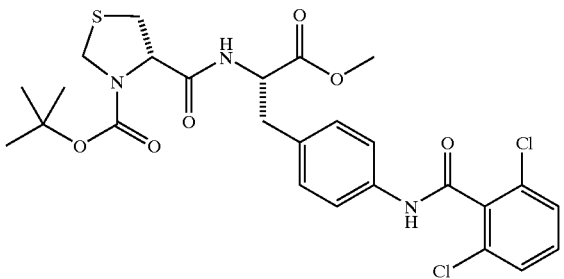

To a cooled (0–5° C.) suspension of A-3 (Scheme A where $R_{A-1}$ and $R_{A-2}$ are the same and equal to H, $R_3$ is 1-butyl and stereochemistry is (S)) (8.67 g, 37.2 mmol) and HOBT (5.69 g, 37.2 mmol) in $CH_2Cl_2$ (60 mL) was added a solution of EDC (7.12 g, 37.2 mmol) in $CH_2Cl_2$ (140 mL). After 30 min at 0–5° C., A-4 (where $R_5$ is 4-[(2,6-dichlorobenzoyl)amino]phenyl, and stereochemistry is (S)) (10 g, 24.8 mmol) was added followed by 4-methylmorpholine (2.72 mL, 24.8 mmol). The reaction mixture was gradually warmed to ambient temperature, stirred an additional 18 h and diluted with $CH_2Cl_2$ and 0.1 N HCl. The organic layer was separated and washed with 0.1 N HCl, sat. aqueous $NaHCO_3$, brine, dried ($Na_2SO_4$), filtered and concentrated in vacuo. Flash chromatography of the residue using hexane/ethyl acetate (50%) as eluant afforded the title compound (13.9 g) as a white solid. Recrystallization from acetone/hexane afforded a crystalline solid: mp 222–224° C.; IR (mull) 3282, 3254, 1738, 1714, 1707, 1678, 1662, 1610, 1562, 1545, 1431, 1414, 1287, 1256, 784 $cm^{-1}$; $^1$H NMR (CDCl$_3$) δ 7.57 (2H), 7.34 (5H), 7.14 (2H), 4.74 (3H), 4.30 (1H), 3.74 (3H), 3.37 (1H), 3.15 (3H), 1.45 (9H); $^{13}$C NMR (DMSO-$d_6$) δ 172.1, 162.3, 153.2, 137.6, 136.9, 133.2, 131.8, 131.7, 130.1, 128.7, 119.8, 80.4, 62.2, 53.7, 52.4, 36.7, 28.3; MS (ESI+) for $C_{26}H_{29}Cl_2N_3O_6S$ m/z 604.3 (M+Na)$^+$; Anal. Calcd for $C_{26}H_{29}Cl_3N_3O_6S$: C, 53.61; H, 5.02; N, 7.21. Found C, 53.82; H, 4.81; N, 7.22.

PREPARATION 4

(Scheme A, A-6: where $R_{A-1}$ and $R_{A-2}$ are the same and equal to H, $R_5$ is 4-[(2,6-dichlorobenzoyl)amino]phenyl, and stereochemistry is (S,S)).

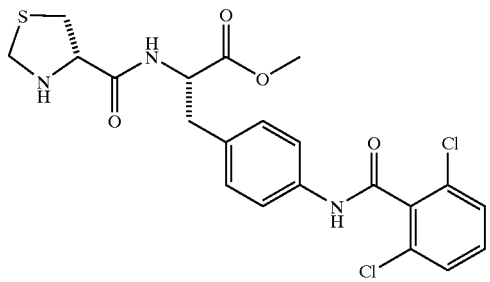

To a cooled (5–10° C.) solution of A-5 (Scheme A where $R_{A-1}$ and $R_{A-2}$ are the same and equal to H, $R_3$ is t-butyl, $R_5$ is 4-[(2,6-dichlorobenzoyl)amino]phenyl, and stereochemistry is (S,S)) (3.3 g, 5.67 mmol) in dioxane (34 mL) was added a solution of HCl in dioxane (4 M, 140 mL) in a dropwise manner over 30 min. After an additional 30 min at 0–5° C., the ice bath was removed and the reaction mixture stirred 1 h at ambient temperature. The volatiles were removed in vacuo to afford the title compound (2.94 g) as a light yellow solid: $^1$H NMR (DMSO-$d_6$) δ 10.70 (1H), 9.1 (1H), 7.52 (5H), 7.18 (2H), 4.64 (1H), 4.37 (1H), 4.21 (2H), 3.67 (3H), 3.10 (1H), 2.89 (1H), 2.70 (1H); $^{13}$C NMR (DMSO-$d_6$) δ 172.1, 162.3, 153.2, 137.6, 136.9, 133.2, 131.8, 131.7, 130.1, 128.7, 119.8, 80.4, 62.2, 53.7, 52.4, 36.7, 28.3; MS (ESI+) for $C_{21}H_{21}Cl_2N_3O_4S$ m/z 482.1 (M+H)$^+$.

PREPARATION 5 AND EXAMPLE 2

4-[(2,6-Dichlorobenzoyl)amino]-N-[[(4S)-3-(methylsulfonyl)-4-thiazolidinyl]carbonyl]-L-phenylalanine Methyl Ester (Scheme A, A-7: where $R_{A-1}$ and $R_{A-2}$ are the same and equal to H, $R_3$ is methyl, Y is $SO_2$, $R_5$ is 4-[(2,6-dichlorobenzoyl)amino]phenyl and stereochemistry is (S,S)).

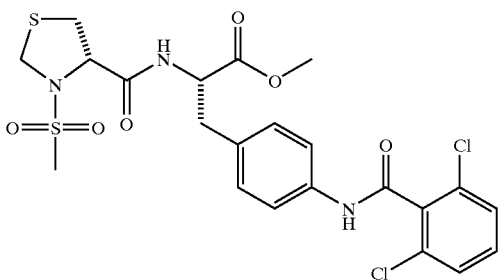

To a cooled (0–5° C.) solution of A-6 (Scheme A, where $R_{A-1}$ and $R_{A-2}$ are the same and equal to H, $R_5$ is 4-[(2,6-dichlorobenzoyl)amino]phenyl and stereochemistry is (S,S)) (2.0 g, 3.86 mmol) in anhydrous THF (50 mL) was added methanesulfonyl chloride (2.99 mL, 38.6 mmol) followed by pyridine (6.24 mL, 77.2 mmol). After 1 h at 0–5° C., the ice bath was removed and the solution stirred at ambient temperature for 2 h then diluted with ethyl acetate and 0.25 N HCl. The layers were separated and the organic layer washed with sat. aqueous $NaHCO_3$, brine, dried ($MgSO_4$), filtered and concentrated in vacuo. Purification of the residue by flash chromatography using ethyl acetate/methylene chloride/hexane (1:1:1) and isopropanol (0.1%) as eluant afforded the title compound (1.99 g) as an amorphous powder: IR (mull) 1742, 1666, 1605, 1562, 1534, 1515, 1432, 1413, 1344, 1327, 1269, 1218, 1195, 1156, 780 cm$^{-1}$; $^1$H NMR (300 MHz, CDCl$_3$) δ 7.55 (3H), 7.33 (3H), 7.12 (3H), 4.84 (1H), 4.69 (1H), 4.61 (1H), 4.29 (1H), 3.74 (3H), 3.50 (1H), 3.29 (1H), 3.14 (2H), 2.92 (3H); $^{13}$C NMR (75 MHz, CDCl$_3$) δ 171.2, 168.1, 162.4, 136.5, 135.9, 132.3, 132.2, 130.8, 130.0, 128.1, 120.6, 64.9, 53.2, 52.5, 51.8, 37.2, 34.1; MS (ESI+) for $C_{22}H_{23}Cl_2N_3O_6S_2$ m/z 559.8 (M+H)$^+$; HRMS (FAB) calcd for $C_{22}H_{23}Cl_2N_3O_6S_2+H_1$ 560.0483, found 560.0504; Anal. Calcd for $C_{22}H_{23}Cl_2N_3O_6S_2$: C, 47.15; H, 4.14; N, 7.50. Found: C, 46.88; H, 4.32; N, 7.16.

PREPARATION 6 AND EXAMPLE 3

4-[(2,6-Dichlorobenzoyl)amino]-N-[[(4S)-3-(methylsulfonyl)-4-thiazolidinyl]carbonyl]-L-phenylalanine (Scheme A, A-8: where $R_{A-1}$ and $R_{A-2}$ are the same and equal to H, $R_3$ is methyl, Y is $SO_2$, $R_5$ is 4-[(2,6-dichlorobenzoyl)amino]phenyl and stereochemistry is (S,S)).

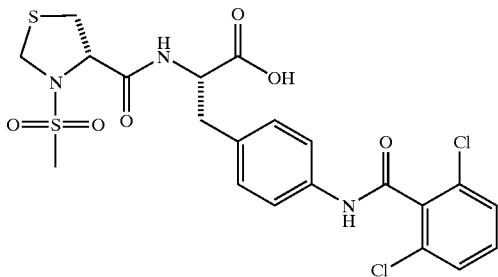

To a cooled (0–5° C.) solution of A-7 (Scheme A, where $R_{A-1}$ and $R_{A-2}$ are the same and equal to H, $R_3$ is methyl, Y is $SO_2$, $R_5$ is 4-[(2,6-dichlorobenzoyl)amino]phenyl and stereochemistry is (S,S)) (1.75 g, 3.12 mmol) in THF (100 mL) and water (10 mL) was added an 0.1 N aqueous solution of NaOH (34.3 mL, 3.43 mmol) via a syringe pump over 1 h. After an additional 45 min at 0–5° C., the reaction mixture was diluted with ethyl acetate and acidified with 0.25 N HCl to a pH of ca. 3. The organic layer was separated, washed with water and concentrated in vacuo. Purification of the residue by flash chromatography using methylene chloride and methanol (0–5%) as eluant provided a solid which was lyophilized from glacial acetic acid to provide the title compound (1.42 g) as an amorphous powder: $[\alpha]^{25}_D$=103° (c 0.97, ethanol); IR (mull) 3291, 1736, 1666, 1605, 1562, 1534, 1516, 1432, 1414, 1339, 1270, 1195, 1154, 799, 780 cm$^{-1}$. $^1$H NMR (300 MHz, CD$_3$OD) δ 7.58 (2H), 7.45 (3H), 7.25 (2H), 4.72 (2H), 4.37 (1H), 3.17 (5H), 2.99 (3H); $^{13}$C NMR (75 MHz, CD$_3$OD) δ 174.1, 171.6, 165.2, 138.3, 137.7, 134.8, 133.4, 132.4, 131.2, 129.4, 121.6, 66.2, 55.0, 52.9, 37.9, 37.5, 35.7; MS (ESI+) for $C_{21}H_{21}Cl_2N_3O_6S_2$ m/z 545.8 (M+H)$^+$; HRMS (FAB) calcd for $C_{21}H_{21}Cl_2N_3O_6S_2+H_1$ 546.0327, found 546.0358, Anal. Calcd for $C_{21}H_{21}Cl_2N_3O_6S_2$: C, 46.16; H, 3.87; N, 7.69. Found: C, 46.24; H, 4.04; N, 7.33.

PREPARATION 7 AND EXAMPLE 4

[S-(R*,R*)]-4-[[[1-[[4-[(2,6-Dichlorobenzoyl)amino]phenyl]methyl]-2-methoxy-2-oxoethyl]amino]carbonyl]-3-thiazolidinecarboxylic Acid 3-Ethyl Ester (Scheme A, A-7: where $R_{A-1}$ and $R_{A-2}$ are the same and equal to H, $R_3$ is ethyl, Y is $CO_2$—, $R_5$ is 4-[(2,6-dichlorobenzoyl)amino]phenyl and stereochemistry is (S,S)).

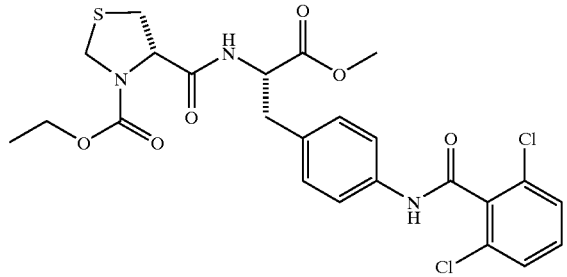

To a cooled (0–5° C.) solution of A-6 (where $R_{A-1}$ and $R_{A-2}$ are the same and equal to H, $R_5$ is 4-[(2,6-dichlorobenzoyl)amino]phenyl and stereochemistry is (S,S)) (1.25 g, 2.40 mmol) in anhydrous THF (30 mL) was added ethyl chloroformate (340 μL, 3.60 mmol) followed by triethylamine (810 μL, 5.79 mmol). After 1 h at 0–5° C., the ice bath was removed and the solution stirred a ambient temperature for 2 h then diluted with ethyl acetate and 0.25 N HCl. The layers were separated and the organic layer washed with sat. aqueous $NaHCO_3$, brine, dried ($MgSO_4$), filtered and concentrated in vacuo. Purification of the residue by flash chromatography using ethyl acetate/methylene chloride/hexane (1:1:1) and isopropanol (0.1%) as eluant afforded the title compound (1.10 g) as an amorphous powder: $^1$H NMR (300 MHz, CDCl$_3$) δ 7.59 (2H), 7.30 (3H), 7.10 (2H), 4.81 (1H), 4.72 (2H), 4.38 (1H), 4.11 (2H), 3.19 (4H), 1.25 (3H); $^{13}$C NMR (75 MHz, CDCl$_3$) δ 171.6, 163.0, 136.9, 136.2, 132.3, 132.1, 130.7, 129.8, 128.0, 120.3, 63.0, 62.8, 57.1, 53.2, 52.5, 37.0, 14.4; MS (ESI+) for $C_{24}H_{25}Cl_2N_3O_6S$ m/z 554.2 (M+H)$^+$; MS (FAB) m/z (rel. intensity) 554 (MH$^+$, 99), 557 (29), 556 (76), 555 (45), 554 (99), 349 (35), 245 (27), 175 (35), 173 (52), 160 (93), 88 (38); HRMS (FAB) calcd for $C_{24}H_{25}Cl_2N_3O_6S+H_1$ 554.0919, found 554.0908, Anal. Calcd for $C_{24}H_{25}Cl_2N_3O_6S$: C, 51.99; H, 4.55; N, 7.58. Found: C, 52.05; H, 4.67; N, 7.44.

PREPARATION 8 AND EXAMPLE 5

[S-(R*,R*)]-4-[[[1-[4-[(2,6-Dichlorophenyl)methoxy]phenyl)methyl]-2-methoxy-2-oxoethyl]amino]carbonyl]-3-thiazolidinecarboxylic Acid 3-[2-(1-piperidinyl)ethyl]ester (Scheme A, A-7: where $R_{A-1}$ and $R_{A-2}$ are the same and equal to H, $R_3$ is 2-(1-piperidinyl)ethyl, Y is $CO_2$—, $R_5$ is 4-[(2,6-dichlorophenyl)methoxy]phenyl and stereochemistry is (S,S)).

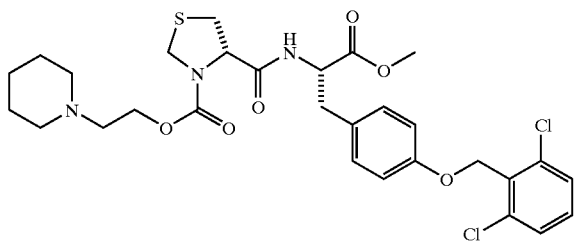

The title compound was prepared by a modification of the literature procedure of Ghosh, A. K.; Duong, T. T.; McKee, S. P.; Thompson, W. J. *Tetrahedron Lett.* 1992, 33, 2781. To a solution of 1-(2-hydroxyethyl)piperidine (5.11 g, 39.6 mmol) in $CH_3CN$ (220 mL) at ambient temperature was added N,N-disuccinimidyl carbonate (10.13 g, 39.6 mmol) and triethylamine (16.6 mL, 118.8 mmol). The solution was stirred at room temperature for 4 h and concentrated in vacuo to give a viscous oil. The oil was dissolved in a minimal amount of methylene chloride (50 mL) and added to a solution of A-6 (Scheme A, where $R_{A-1}$ and $R_{A-2}$ are the same and equal to H, $R_5$ is 4-[(2,6-dichlorophenyl)methoxy]phenyl and stereochemistry is (S,S)) (2.0 g, 3.96 mmol), triethylamine (0.60 mL) and DMAP (5 mg) in $CH_2Cl_2$ (10 mL). The solution was stirred overnight and an additional 5 equivalents of carbonate in methylene chloride (10 mL) [prepared as described above from N,N-disuccinimidyl carbonate (5.6 g, 19.8 mmol), triethylamine (8.3 mL, 59.4 mmol), and 1-(2-hydroxyethyl)piperidine (2.56 g, 19.8 mmol)] were added. After 3 h at room temperature, propylamine (30 mL, 0.71 mol) was slowly added (exothermic) and the solution diluted with $CH_2Cl_2$. The resulting solution was stirred vigorously for 15 min. and diluted with water. The organic layer was separated and washed with 0.1 M HCl, sat. aqueous $NaHCO_3$, dried ($MgSO_4$), filtered and concentrated in vacuo. Purification of the residue by flash chromatography using ethyl acetate/methylene chloride (3:1) as eluant followed by trituration in hexanes afforded the title compound (1.54 g, 62%) as an white powder: IR (mull) 1745, 1704, 1660, 1553, 1512, 1435, 1426, 1397, 1303, 1245, 1227, 1212, 1173, 1019, 765 cm$^{-1}$; $^1$H NMR (300 MHz, DMSO-$d_6$) δ 8.42 (1H), 7.54 (2H), 7.44 (1H), 7.13 (2H), 6.94 (2H), 5.17 (2H), 4.59 (2H), 4.48 (1H), 4.26 (1H), 4.02 (2H), 3.63 (3H), 3.19 (2H), 3.19 (1H), 2.82 (3H), 2.35 (4H), 1.36 (6H); $^{13}$C NMR (75 MHz, DMSO-$d_6$) δ 172.2, 170.0, 157.7, 153.9, 136.5, 132.2, 132.0, 130.8, 130.1, 129.2, 114.8, 65.3, 63.6, 57.3, 54.6, 53.9, 52.4, 36.4, 26.0, 24.3; MS (ESI+) for $C_{29}H_{35}Cl_2N_3O_6S$ m/z 623.9 (M+H)$^+$; Anal. Calcd for $C_{29}H_{35}Cl_2N_3O_6S$: C, 55.77; H, 5.65; N, 6.73. Found: C, 55.48; H, 5.73; N, 6.91.

PREPARATION 9 AND EXAMPLE 6

4-[(2,6-Dichlorobenzoyl)amino]-N-[[(4S)-3-[((1,1-dimethylethyl)amino)carbonyl]-4-thiazolidinyl]carbonyl]-L-phenylalanine Methyl Ester (Scheme A, A-7: where $R_{A-1}$ and $R_{A-2}$ are the same and equal to H, $R_3$ is t-butyl, Y is CONH—, $R_1$ is 4-[(2,6-dichlorobenzoyl)amino]phenyl and stereochemistry is (S,S)).

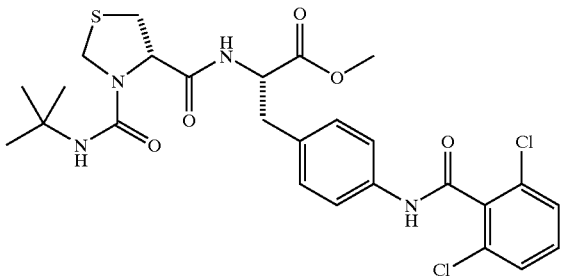

To a cooled (0–5° C.) solution of A-6 (Scheme A, where $R_{A-1}$ and $R_{A-2}$ are the same and equal to H, $R_5$ is 4-[(2,6-dichlorobenzoyl)amino]phenyl and stereochemistry is (S,S)) (140 mg, 0.27 mmol) in anhydrous THF (6 mL) was added tert-butyl isocyanate (0.62 mL, 5.4 mmol) followed by 4-dimethylaminopyridine (5 mg, 0.04 mmol). After 0.5 h at 0–5° C., the ice bath was removed and the solution stirred at ambient temperature for 16 h. Additional tert-butyl isocyanate (0.62 mL, 5.4 mmol) was added and the solution warmed to 50° C. for 4 h. The reaction mixture was cooled to room temperature and diluted with ethyl acetate and 0.25 N HCl. The layers separated and the organic layer washed with sat. aqueous $NaHCO_3$, brine, dried ($MgSO_4$), filtered and concentrated in vacuo. Purification of the residue by flash chromatography using ethyl acetate/methylene chloride (1:1:1) and isopropanol (0.1%) as eluant afforded the title compound (150 mg) as an amorphous powder: $^1$H NMR (300 MHz, CDCl$_3$) δ 7.93 (1H), 7.54 (2H), 7.26 (4H), 7.09 (2H), 4.74 (2H), 4.66 (1H), 4.41 (1H), 4.23 (1H), 3.70 (3H), 3.28 (1H), 3.09 (3H), 1.31 (9H); $^{13}$C NMR (75 MHz, CDCl$_3$) δ 171.4, 170.6, 162.4, 155.5, 136.3, 135.9, 132.5, 132.3, 130.8, 129.9, 128.1, 120.6, 62.7, 53.2, 52.4, 51.5, 49.0, 37.0, 32.9, 29.2; MS (ESI+) for $C_{26}H_{30}Cl_2N_4O_5S$ m/z 581.0 (M+H)$^+$, 603.0 (M+Na)$^+$; MS (FAB) m/z (rel. intensity) 581 (MH+, 23), 482 (50), 97 (36), 88 (36), 83 (45), 69 (99), 57 (81), 55 (79), 43 (50), 43 (69), 41 (50). HRMS (FAB) calcd for $C_{26}H_{30}Cl_2N_4O_5S$+H1 581.1392, found 581.1376.

PREPARATION 10 AND EXAMPLE 7

4-[(2,6-Dichlorobenzoyl)amino]-N-[[(4S)-3-[(diethylamino)carbonyl]-4-thiazolidinyl]carbonyl]-L-phenylalanine Methyl Ester (Scheme A, A-7: where $R_{A-1}$ and $R_{A-2}$ are the same and equal to H, $R_3$ is ethyl, Y is CON(CH$_2$CH$_3$)—, $R_5$ is 4-[(2,6-dichlorobenzoyl)amino]phenyl and stereochemistry is (S,S)).

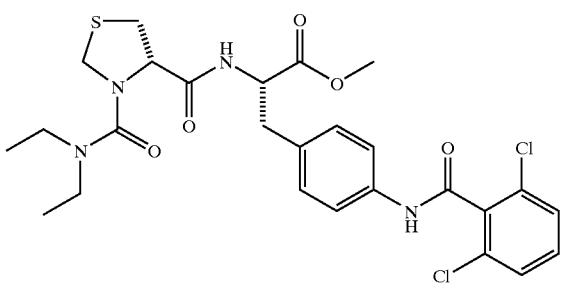

The title compound was prepared by a modification of the literature procedure of Majer, P.; Randad, R. S. *J. Org.*

*Chem.* 1994, 59, 1937. A cooled (0–5° C.) solution of A-6 (Scheme A, where $R_{A-1}$ and $R_{A-2}$ are the same and equal to H, $R_5$ is 4-[(2,6-dichlorobenzoyl)amino]phenyl and stereochemistry is (S,S)) (200 mg, 0.39 mmol) and triethylamine (56 μL, 0.40 mmol) in anhydrous methylene chloride (10 mL) was added to triphosgene (47 mg, 0.16 mmol) followed by additional triethylamine (56 μL, 0.40 mmol). After 0.5 h at 0–5° C., the ice bath was removed and the solution stirred at ambient temperature for 2 h. The solution was re-cooled (0–5° C.) and diethylamine (1.20 mL, 11.70 mmol) and 4-dimethylaminopyridine (5 mg, 0.04 mmol) were added. After 0.5 h at 0–5° C., the ice bath was removed and the solution stirred at ambient temperature for 16 h.

The solution was concentrated in vacuo and the residue partitioned between ethyl acetate and 0.25 N HCl. The layers were separated and the organic layer washed with sat. aqueous $NaHCO_3$, brine, dried ($MgSO_4$), filtered and concentrated in vacuo. Purification of the residue by flash chromatography using ethyl acetate/methylene chloride/hexane (1:1:1) and isopropanol (0.1%) as eluant afforded the title compound (200 mg) as an amorphous solid: $^1H$ NMR (300 MHz, $CDCl_3$) δ 7.86 (1H), 7.55 (2H), 7.30 (3H), 7.03 (2H), 6.90 (1H), 5.09 (1H), 4.83 (1H), 4.33 (2H), 3.76 (3H), 3.34 (3H), 3.11 (5H), 1.08 (6H); $^{13}C$ NMR ($CDCl_3$) δ 171.1, 169.6, 162.3. 162.2, 136.5, 135.9, 132.3, 132.1, 130.9, 129.9, 128.1, 120.3, 64.7, 53.4, 52.7, 52.5, 42.0, 37.0, 32.4, 13.1; MS (ESI+) for $C_{26}H_{30}N_4O_5S$ m/z 580.9 (M+H)$^+$; HRMS (EI) calcd for $C_{26}H_{30}Cl_2N_4O_5S$ 580.1314, found 580.1297, Anal. Calcd for $C_{26}H_{30}Cl_2N_4O_5S$: C, 53.70; H, 5.20; N, 9.63. Found: C, 53.63; H, 5.33; N, 9.36.

PREPARATION 11 AND EXAMPLE 8

[S-(R*,R*)]-4-[[[1-[[4-[(2,6-Dichlorobenzoyl)amino]phenyl]methyl]-2-methoxy-2-oxoethyl]amino]carbonyl]-γ-oxo-3-thiazolidinebutanoic Acid 3-Methyl Ester (Scheme A, A-7: where $R_{A-1}$ and $R_{A-2}$ are the same and equal to H, $R_3$ is $CH_2CH_2CO_2CH_3$, Y is CO, $R_5$ is 4-[(2,6-dichlorobenzoyl)amino]phenyl, and stereochemistry is (S,S)).

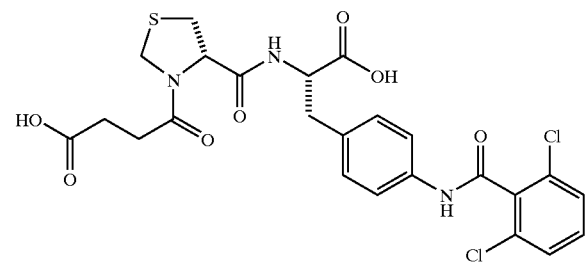

To a cooled (0–5° C.) solution of A-6 (Scheme A, where $R_{A-1}$ and $R_{A-2}$ are the same and equal to H, $R_5$ is 4-[(2,6-dichlorobenzoyl)amino]phenyl and stereochemistry is (S,S)) (1.03 g, 1.72 mmol) in anhydrous $CH_2Cl_2$ (25 mL) was added triethylamine (460 μL, 3.27 mmol) followed by methyl succinyl chloride (320 μL, 2.58 mmol). After 1 h at 0–5° C., the ice bath was removed and the solution stirred at ambient temperature for 2 h then diluted with 1 N HCl. The organic layer was separated, washed with sat. aqueous $NaHCO_3$, brine, dried ($Na_2SO_4$), filtered and concentrated in vacuo. Crystallization of the yellow solid from ethanol/water provided the title compound (824 mg) as a light yellow solid: mp 221–223° C.; IR (mull) 3275, 1748, 1731, 1687, 1626, 1610, 1561, 1542, 1517, 1430, 1416, 1326, 1268, 1224, 1193 cm$^{-1}$; $^1H$ NMR (DMSO-$d_6$) δ 10.64 (1H), 8.59 (1H), 8.24 (1H), 7.50 (5H), 7.16 (2H), 4.75 (2H), 4.51 (2H), 4.23 (1H), 3.63 (3H), 3.56 (3H), 2.87 (5H); $^{13}C$ NMR (DMSO-$d_6$) δ 172.9, 171.6, 169.9, 169.5, 161.9, 137.2, 136.5, 133.0, 132.8, 131.3, 129.8, 128.3, 119.4, 61.6, 53.6, 52.1, 51.4, 48.6, 36.4, 35.7, 35.2, 33.1, 29.0, 28.9, 28.5; MS (ESI+) for $C_{26}H_{27}Cl_2N_3O_7S$ m/z 596.0 (M+H)$^+$; MS (ESI−) for $C_{26}H_{27}Cl_2N_3O_7S$ m/z 593.9 (M−H)$^-$; Anal. Calcd for $C_{26}H_{27}Cl_2N_3O_7S$: C, 52.35; H, 4.56; N, 7.04. Found: C, 52.11; H, 4.47; N, 6.96.

PREPARATION 12 AND EXAMPLE 9

[S-(R*,R*)]-4-[[[1-Carboxy-2-[4-[(2,6-dichlorobenzoyl)amino]phenyl]ethyl]amino]carbonyl]-γ-oxo-3-thiazolidinebutanoic Acid (Scheme A, A-8: where $R_{A-1}$ and $R_{A-2}$ are the same and equal to H, $R_3$ is $CH_2CH_2CO_2CO_2H$, Y is CO, $R_5$ is 4-[(2,6-dichlorobenzoyl)amino]phenyl, and stereochemistry is (S,S)).

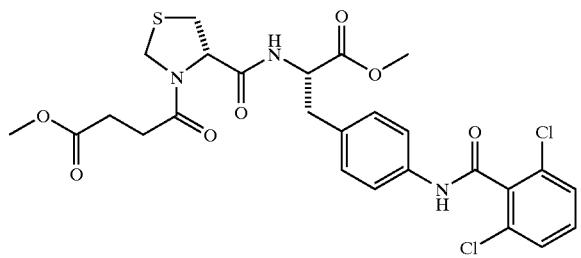

To a cooled (0–5° C.) solution of A-7 (Scheme A where $R_{A-1}$ and $R_{A-2}$ are the same and equal to H, $R_3$ is $CH_2CH_2CO_2CH_3$, Y is CO, $R_1$ is 4-[(2,6-dichlorobenzoyl)amino]phenyl, and stereochemistry is (S,S)) (130 mg, 0.22 mmol) in anhydrous THF (5 mL) and MeOH (1 mL) was added an aqueous (2 mL) solution of lithium hydroxide monohydrate (23 mg, 0.55 mmol) via a syringe pump over 1 h. After an additional 1 h at 0–5° C., the ice bath was removed and the solution stirred 2 h at ambient temperature. The reaction mixture was diluted with ethyl acetate and 0.1 N HCl and the organic layer was separated, washed with water, dried ($Na_2SO_4$), filtered and concentrated in vacuo. Lyophilization of the residue from glacial acetic acid afforded the title compound (101 mg) as a white amorphous powder: $^1H$ NMR ($CD_3CN$) δ 8.87 (1H), 7.55 (2H), 7.42 (3H), 7.22 (2H), 7.16 (1H), 4.95 (1H), 4.52 (3H), 3.12 (5H), 2.55 (5H); $^{13}C$ NMR ($CD_3CN$) δ 173.8, 171.7, 171.1, 169.8, 162.5, 136.7, 136.0, 133.5, 131.7, 131.3, 130.1, 129.2, 128.2, 119.7, 62.4, 53.6, 48.8, 36.2, 32.4, 29.1, 28.6; MS (ESI−) for $C_{24}H_{23}Cl_2N_3O_7S$ m/z 566.1 (M−H)$^-$; Anal. Calcd for $C_{24}H_{23}Cl_2N_3O_7S$: C, 50.31; H, 4.13; N, 7.33. Found: C, 50.13; H, 4.37; N, 6.93.

PREPARATION 13 AND EXAMPLE 10

[S-(R*,R*)]-4-[[[1-Carboxy-2-[4-[(2,6-dichlorobenzoyl)amino]phenyl]ethyl]amino]carbonyl]-3-thiazolidinecarboxylic Acid 3-(1,1-Dimethylethyl)ester (Scheme A, A-9: where $R_{A-1}$ and $R_{A-2}$ are the same and equal to H, $R_3$ is t-butyl, Y is $CO_2$—, $R_5$ is 4-[(2,6-dichlorobenzoyl)amino]phenyl, and stereochemistry is (S,S)).

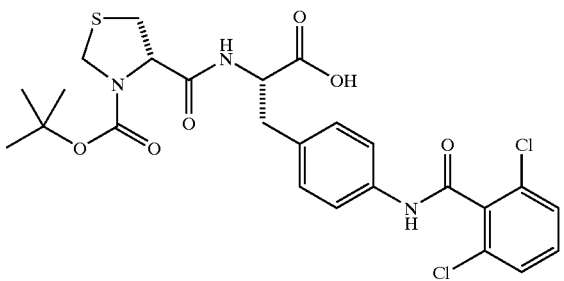

To a cooled (0–5° C.) of A-5 (Scheme A where $R_{A-1}$ and $R_{A-2}$ are the same and equal to H, $R_3$ is t-butyl, Y is $CO_2$—, $R_5$ is 4-[(2,6-dichlorobenzoyl)amino]phenyl, and stereochemistry is (S,S)) (150 mg, 0.26 mmol) in anhydrous THF (5 mL) and MeOH (1 mL) was added an aqueous (2 mL) solution of lithium hydroxide monohydrate (14 mg, 0.325 mmol) via syringe pump over 1 h. After an additional 1 h at 0–5° C., the ice bath was removed and the solution stirred 2 h at ambient temperature. The reaction mixture was diluted with ethyl acetate and 0.1 N HCl, the organic layer separated and washed with water, dried ($Na_2SO_4$), filtered and concentrated in vacuo. Lyophilization of the residue from glacial acetic acid afforded the title compound (142 mg) as an amorphous powder: IR (mull) 3285, 1735, 1666, 1606, 1562, 1539, 1516, 1432, 1413, 1394, 1326, 1259, 1219, 1195, 1161 $cm^{-1}$; $^1H$ NMR (DMF-$d_7$) δ 10.71 (1H), 8.36 (1H), 7.91 (2H), 7.72 (3H), 7.47 (2H), 4.88 (3H), 4.51 (1H), 3.40 (3H), 3.22 (2H), 1.57 (9H); $^{13}C$ NMR (DMF-$d_7$) δ 173.3, 163.1, 162.9, 162.7, 162.3, 154.0, 138.3, 137.5, 134.2, 132.3, 131.9, 130.6, 128.9, 120.0, 80.9, 63.1, 54.5, 49.9, 37.4, 28.3; MS (FAB) m/z (rel. intensity) 568 (MH+, 23), 570 (14), 568 (23), 471 (13), 470 (65), 469 (23), 468 (99), 466 (23), 175 (19), 88 (17), 57 (42); HRMS (FAB) calcd for $C_{25}H_{27}Cl_2N_3O_6S+H_1$ 568.1075, found 568.1071; MS (ESI−) for $C_{25}H_{27}Cl_2N_3O_6S$ m/z 565.8 (M−H)$^-$; Anal. Calcd for $C_{25}H_{27}Cl_2N_3O_6S \cdot 0.26H_2O$: C, 52.38; H, 4.84; N, 7.33. Found: C, 52.07; H, 5.12; N, 7.46; % Water (KF): 0.83.

PREPARATION 14 AND EXAMPLE 11

4-[(2,6-Dichlorobenzoyl)amino]-N-[[(4S)-4-thiazolidinyl]carbonyl]-L-phenylalanine Monohydrochloride Salt (Scheme A, A-10: where $R_{A-1}$ and $R_{A-2}$ are the same and equal to H, $R_5$ is 4-[(2,6-dichlorobenzoyl)amino]phenyl, and stereochemistry is (S,S)).

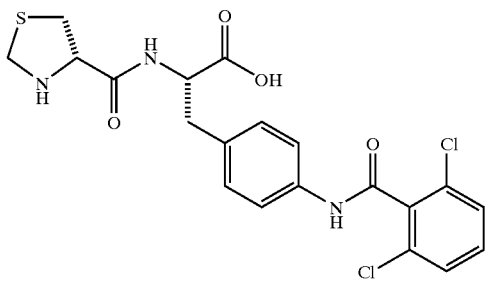

To a cooled (5–10° C.) solution of A-9 (Scheme A where $R_{A-1}$ and $R_{A-2}$ are the same and equal to H, $R_3$ is t-butyl, Y is $CO_2$—, $R_5$ is 4-[(2,6-dichlorobenzoyl)amino]phenyl, and stereochemistry is (S,S)) (193 mg, 0.34 mmol) in dioxane (2 mL) was added a solution of HCl in dioxane (4 M, 8 mL) in a dropwise manner over 30 min. After an additional 3.5 h at 0–5° C., the reaction mixture was concentrated in vacuo. Lyophilization of the residue from water afforded the title compound (158 mg) as an amorphous powder: IR (mull) 3248, 3191, 3048, 1731, 1664, 1605, 1577, 1562, 1541, 1516, 1431, 1414, 1327, 1195, 799 $cm^{-1}$; $^1H$ NMR (DMF-$d_7$) δ 9.11 (1H), 7.76 (2H), 7.60 (3H), 7.35 (2H), 4.66 (2H), 4.46 (2H), 3.55 (3H), 3.24 (2H), 3.10 (2H); $^{13}C$ NMR (DMF-$d_7$) δ 172.8, 167.6, 163.1, 162.9, 162.7, 162.3, 138.5, 137.5, 133.8, 132.3, 131.9, 130.6, 128.9, 120.0, 63.8, 54.8, 50.0, 37.3; MS (FAB) m/z (rel. intensity) 468 (MH+, 99), 544 (18), 528 (15), 472 (13), 471 (16), 470 (70), 469 (24), 468 (99), 175 (14), 173 (16), 88 (18); HRMS (FAB) calcd for $C_{20}H_{19}Cl_2N_3O_4S+H_1$ 468.0551, found 468.0556.

EXAMPLE 12

[S-(R*,R*)]-4-[[[1-Carboxy-2-[4-[(2,6-dichlorobenzoyl)amino]phenyl]ethyl]amino] carbonyl]-3-thiazolidinecarboxylic Acid 3-Ethyl Ester (Scheme A, A-8: where $R_{A-1}$ and $R_{A-2}$ are the same and equal to H, $R_3$ is ethyl, Y is $CO_2$, $R_5$ is 4-[(2,6-dichlorobenzoyl)amino]phenyl and stereochemistry is (S,S)).

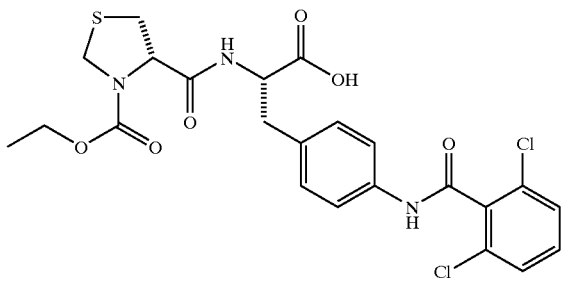

Example 12 was prepared from example 4 by the procedure described in preparation 6. Physical properties as follows: mp 118–121° C.; $[\alpha]^{25}_D$=106° (c 0.88, ethanol); IR (mull) 3283, 3196, 1665, 1606, 1561, 1539, 1516, 1431, 1414, 1345, 1327, 1271, 1219, 1195, 799 $cm^{-1}$; $^1H$ NMR (300 MHz, $CD_3OD$) δ 7.59 (2H), 7.44 (3H), 7.22 (2H), 4.69 (1H), 4.64 (1H), 4.41 (1H), 3.24 (3H), 2.95 (2H), 1.26 (3H); $^{13}C$ NMR (75 MHz, $CDCl_3$) δ 172.4, 171.5, 163.0, 154.8, 136.7, 136.6, 132.4, 132.1, 130.6, 129.9, 127.9, 120.3, 63.0, 62.7, 53.1, 36.7, 14.3; MS (FAB) m/z (rel. intensity) 540 (MH+, 59), 544 (12), 543 (17), 542 (53), 540 (59), 160 (32), 123 (15), 118 (20), 107 (99), 95 (11), 23 (21); HRMS (FAB) calcd for $C_{23}H_{23}Cl_2N_3O_6S+H_1$ 540.0762, found 540.0730, Anal. Calcd for $C_{23}H_{23}Cl_2N_3O_6S$: C, 51.12; H, 4.29; N, 7.78. Found: C, 50.77; H, 4.43; N, 7.68.

EXAMPLE 13

[R-(R*,S*)]-4-[[[1-[[4-[(2,6-Dichlorobenzoyl) amino]phenyl]methyl]-2-methoxy-2-oxoethyl] amino]carbonyl]-3-thiazolidinecarboxylic Acid 3-(1,1-Dimethylethyl)ester (Scheme A, A-7: where $R_{A-1}$ and $R_{A-2}$ are the same and equal to H, $R_3$ is t-butyl, Y is $CO_2$, $R_5$ is 4-[(2,6-dichlorobenzoyl)amino]phenyl and stereochemistry is (R,S)).

37

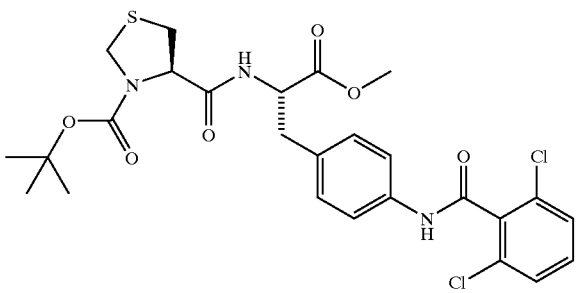

Example 13 was prepared as described in Scheme A from L-cysteine using di-t-butyl dicarbonate to form the requisite carbamate. Physical data as follows: IR (mull) 1746, 1666, 1606, 1562, 1538, 1516, 1432, 1413, 1324, 1267, 1260, 1216, 1195, 1162, 799 cm$^{-1}$; $^1$H NMR (CDCl$_3$) δ 7.56 (2H), 7.46 (1H), 7.33 (3H), 7.13 (2H), 6.94 (1H), 4.75 (3H), 4.25 (1H), 3.75 (3H), 3.39 (1H), 3.14 (3H), 1.43 (9H); $^{13}$C NMR (DMSO-d$_6$) δ 171.6, 171.5, 170.7, 170.1, 161.7, 152.6, 137.0, 136.9, 136.2, 132.6, 132.6, 131.2, 131.0, 129.3, 128.1, 119.1, 79.7, 78.2, 61.5, 53.4, 53.3, 51.8, 49.3, 49.1, 35.8, 27.6; MS (ESI+) for $C_{26}H_{29}Cl_2N_3O_6S$ m/z 604 (M+Na)$^+$; MS (ESI−) for $C_{26}H_{29}Cl_2N_3O_6S$ m/z 580 (M−H)$^-$; Anal. Calcd for $C_{26}H_{29}Cl_2N_3O_6S\cdot0.17H_2O$: C, 53.34; H, 5.05; N, 7.18. Found: C, 53.47; H, 5.14; N, 7.15. % Water (KF): 0.51.

EXAMPLE 14

[R-(R*,S*)]-4-[[[1-Carboxy-2-[4-[(2,6-dichlorobenzoyl)amino]phenyl]ethyl]amino]carbonyl]-3-thiazolidinecarboxylic Acid 3-(1,1-Dimethylethyl)ester (Scheme A, A-8: where $R_{A-1}$ and $R_{A-2}$ are the same and equal to H, $R_3$ is i-butyl, Y is $CO_2$, $R_5$ is 4-[(2,6-dichlorobenzoyl)amino]phenyl and stereochemistry is (R,S)).

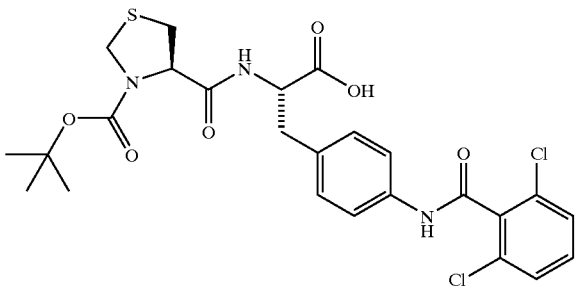

Example 14 was prepared from example 13 by the procedure described in preparation 6. Physical data as follows: IR (mull) 3285, 1665, 1607, 1562, 1538, 1516, 1432, 1413, 1394, 1327, 1259, 1217, 1195, 1162, 799 cm$^{-1}$; $^1$H NMR (DMSO-d$_6$) δ 12.70 (1H), 10.67 (1H), 8.14 (1H), 7.51 (5H), 7.20 (2H), 4.56 (1H), 4.35 (3H), 2.98 (3H), 1.22 (9H); $^{13}$C NMR (DMSO-d$_6$) δ 172.5, 170.1, 169.9, 161.6, 152.6, 136.9, 136.3, 133.0, 131.2, 131.0, 129.4, 128.1, 119.1, 79.8, 79.7, 61.6, 53.4, 49.2, 48.3, 35.9, 27.6, 20.9; HRMS (FAB) calcd for $C_{25}H_{27}Cl_2N_3O_6S+H_1$ 568.1075, found 568.1058; MS (ESI+) for $C_{25}H_{27}Cl_2N_3O_6S$ m/z 567.8 (M+H)$^+$; MS (ESI−) for $C_{25}H_{27}Cl_2N_3O_6S$ m/z 565.8 (M−H)$^-$; Anal. Calcd for $C_{25}H_{27}Cl_2N_3O_6S\cdot0.24H_2O$: C, 52.43; H, 4.84; N, 7.34. Found: C, 52.23; H, 4.76; N, 7.24. % Water (KF): 0.75.

38

EXAMPLE 15

[R-(R*,S*)]-4-[[[1-[[4-[(2,6-Dichlorobenzoyl)amino]phenyl]methyl]-2-methoxy-2-oxoethyl]amino]carbonyl]-3-thiazolidinecarboxylic Acid 3-Ethyl Ester (Scheme A, A-7: where $R_{A-1}$ and $R_{A-2}$ are the same and equal to H, $R_3$ is ethyl, Y is $CO_2$, $R_5$ is 4-[(2,6-dichlorobenzoyl)amino]phenyl and stereochemistry is (R,S)).

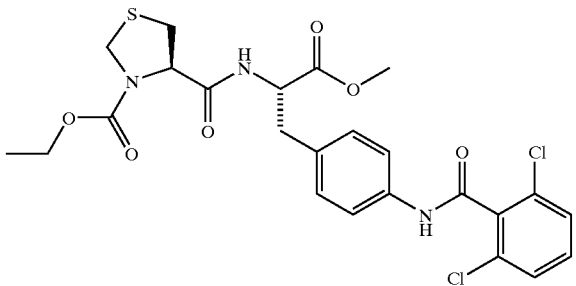

Example 15 was prepared as described in Scheme A from L-cysteine using ethyl chloroformate to form the requisite carbamate. Physical data as follows: IR (mull) 1744, 1666, 1606, 1561, 1538, 1515, 1445, 1431, 1414, 1345, 1325, 1270, 1216, 1194, 1184 cm$^{-1}$; $^1$H NMR (CDCl$_3$) δ 7.55 (2H), 7.36 (4H), 7.13 (2H), 6.95 (1H), 4.74 (3H), 4.21 (3H), 3.75 (3H), 3.40 (1H), 3.13 (3H), 1.26 (3H); $^{13}$C NMR (CDCl$_3$) δ 171.2, 169.4, 162.3, 136.2, 135.8, 132.4, 132.2, 131.0, 130.3, 130.1, 129.9, 128.2, 128.0, 127.9, 120.2, 62.9, 62.7, 53.2, 52.5, 37.1, 14.5, 14.3; MS (ESI+) for $C_{24}H_{25}Cl_2N_3O_6S$ m/z 553.8 (M+H)$^+$; MS (ESI−) for $C_{24}H_{25}Cl_2N_3O_6S$ m/z 551.8 (M−H)$^-$; Anal. Calcd for $C_{24}H_{25}Cl_2N_3O_6S\cdot0.24H_2O$: C, 51.59; H, 4.60; N, 7.52. Found: C, 51.89; H, 4.62; N, 7.51. % Water (KF): 0.77.

EXAMPLE 16

[R-(R*,S*)]-4-[[[1-Carboxy-2-[4-[(2,6-dichlorobenzoyl)amino]phenyl]ethyl]amino]carbonyl]-3-thiazolidinecarboxylic Acid 3-Ethyl Ester (Scheme A, A-8: where $R_{A-1}$ and $R_{A-2}$ are the same and equal to H, $R_3$ is ethyl, Y is $CO_2$, $R_5$ is 4-[(2,6-dichlorobenzoyl)amino]phenyl and stereochemistry is (R,S)).

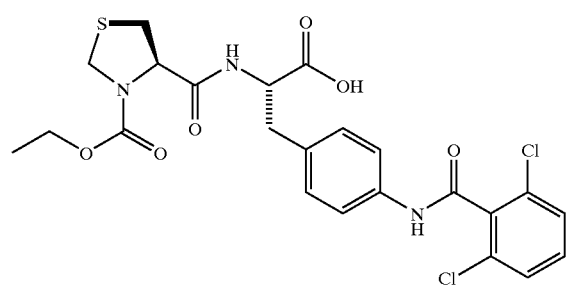

Example 16 was prepared from example 15 by the procedure described in preparation 6. Physical data as follows: IR (mull) 3287, 1664, 1606, 1561, 1539, 1516, 1445, 1431, 1414, 1346, 1327, 1271, 1217, 1195, 799 cm$^{-1}$; $^1$H NMR (DMSO-d$_6$) δ 12.80 (1H), 10.69 (1H), 8.26 (1H), 7.51 (5H), 7.19 (2H), 4.62 (2H), 4.37 (2H), 3.94 (2H), 2.96 (3H), 1.11 (3H); $^{13}$C NMR (DMSO-d$_6$) δ 172.5, 169.6, 161.7, 153.5, 136.9, 136.3, 133.0, 131.2, 131.0, 129.5, 128.1, 119.1, 61.2, 53.4, 52.5, 35.9, 22.3, 14.3; MS (ESI+) for C$_{23}$H$_{23}$Cl$_2$N$_3$O$_6$S m/z 540.0 (M+H)$^+$; MS (ESI−) for C$_{23}$H$_{23}$Cl$_2$N$_3$O$_6$S m/z 538.0 (M−H)$^-$; HRMS (FAB) calcd for C$_{23}$H$_{23}$Cl$_2$N$_3$O$_6$S+H$_1$ 540.0762, found 540.0775; Anal. Calcd for C$_{23}$H$_{23}$Cl$_2$N$_3$O$_6$S.0.34H$_2$O: C, 50.54; H, 4.37; N, 7.69. Found: C, 50.53; H, 4.48; N, 7.59. % Water (KF): 1.13.

EXAMPLE 17

[R-(R*,S*)]-4-[[[1-[[4-[(2,6-Dichlorobenzoyl) amino]phenyl]methyl]-2-methoxy-2-oxoethyl] amino]carbonyl]-5,5-dimethyl-3-thiazolidinecarboxylic Acid 3-(1,1-Dimethylethyl) ester (Scheme A, A-7: where R$_{A-1}$ and R$_{A-2}$ are the same and equal to CH$_3$, R$_3$ is t-butyl, Y is CO$_2$, R$_5$ is 4-[(2,6-dichlorobenzoyl)amino]phenyl and stereochemistry is (R,S)).

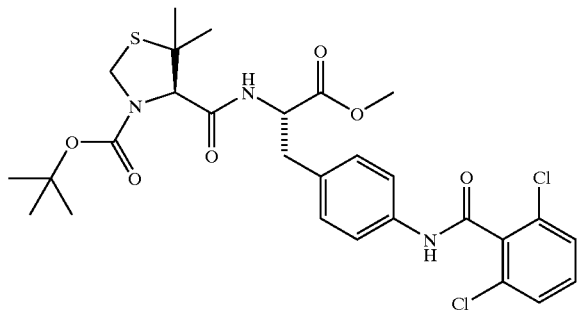

Example 17 was prepared as described in Scheme A from L-penicillamine using di-t-butyl dicarbonate to form the requisite carbamate. Physical data as follows: IR (mull) 1747, 1666, 1606, 1562, 1537, 1516, 1432, 1413, 1324, 1268, 1259, 1213, 1195, 1161, 1142 cm$^{-1}$; $^1$H NMR (CDCl$_3$) δ 7.56 (2H), 7.34 (4H), 7.21 (2H), 6.44 (1H), 4.94 (1H), 4.60 (2H), 4.08 (1H), 3.70 (3H), 3.10 (2H), 1.53 (3H), 1.42 (9H), 1.25 (3H); $^{13}$C NMR (DMSO-d$_6$) δ 171.4, 162.3, 136.3, 135.8, 132.6, 132.4, 131.0, 130.2, 130.0, 128.2, 120.5, 120.3, 120.2, 72.7, 63.9, 60.4, 52.9, 52.3, 48.3, 38.0, 30.3, 28.1, 23.9, 21.0, 14.2; MS (ESI+) for C$_{28}$H$_{33}$Cl$_2$N$_3$O$_6$S m/z 630.7 (M+Na)$^+$; Anal. Calcd for C$_{28}$H$_{33}$Cl$_2$N$_3$O$_6$S.0.13H$_2$O: C, 54.87; H, 5.47; N, 6.86. Found: C, 54.54; H, 5.55; N, 6.54. % Water (KF): 0.38.

EXAMPLE 18

[S-(R*,R*)]-4-[[[1-[[4-[(2,6-Dichlorobenzoyl) amino]phenyl]methyl]-2-methoxy-2-oxoethyl] amino]carbonyl]-3-thiazolidinecarboxylic Acid 3-[(9H-Fluoren-1-yl)methyl]ester (Scheme A, A-7: where R$_{A-1}$ and R$_{A-2}$ are the same and equal to H, R$_3$ is 9-fluorenylmethyl, Y is CO$_2$, R$_5$ is 4-[(2,6-dichlorobenzoyl)amino]phenyl and stereochemistry is (S,S)).

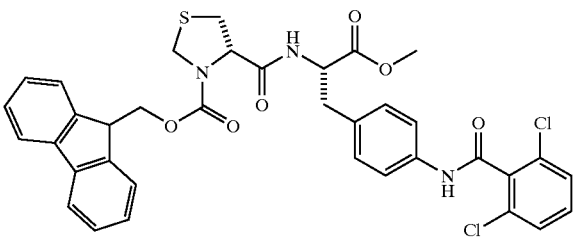

Example 18 was prepared as described in Scheme A from D-cysteine using 9-fluorenylmethyl chloroformate to form the requisite carbamate. Physical data as follows: IR (mull) 3280, 1750, 1692, 1671, 1604, 1560, 1538, 1515, 1441, 1430, 1422, 1346, 1320, 1222, 1118 cm$^{-1}$; $^1$H NMR (DMSO-d$_6$) δ 8.59 (1H), 7.87 (2H), 7.49 (12H), 4.65 (3H), 4.26 (4H), 3.52 (3H), 2.96 (3H); $^{13}$C NMR (DMSO-d$_6$) δ 171.4, 161.8, 143.5, 140.6, 137.0, 136.3, 132.5, 131.2, 131.1, 129.5, 128.1, 127.6, 127.1, 125.2, 125.1, 120.0, 119.2, 70.6, 70.0, 63.8, 63.2, 53.3, 53.1, 46.4, 36.2, 25.4; MS (ESI+) for C$_{36}$H$_{31}$Cl$_2$N$_3$O$_6$S m/z 703.9 (M+H)$^+$; Anal. Calcd for C$_{36}$H$_{31}$Cl$_2$N$_3$O$_6$S.0.1H$_2$O: C, 61.23; H, 4.45; N, 5.95. Found: C, 61.18; H, 4.56; N, 5.89. % Water (KF): 0.22.

EXAMPLE 19

[S-(R*,R*)]-4-[[[-Carboxy-2-[4-[(2,6-dichlorobenzoyl)amino]phenyl]ethyl]amino] carbonyl]-3-thiazolidinecarboxylic Acid 3-[(9H-Fluoren-1-yl)methyl]ester (Scheme A, A-8: where R$_{A-1}$ and R$_{A-2}$ are the same and equal to H, R$_3$ is 9-fluorenylmethyl, Y is CO$_2$, R$_5$ is 4-[(2,6-dichlorobenzoyl)amino]phenyl and stereochemistry is (S,S)).PNU-

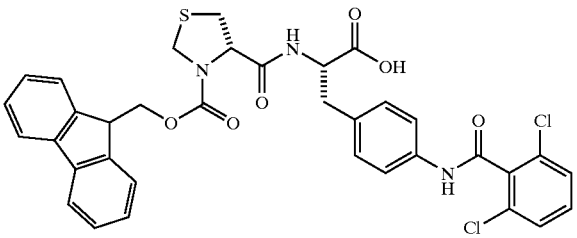

Example 19 was prepared from example 18 by the procedure described in preparation 6. Physical data as follows: IR (mull) 1672, 1606, 1561, 1533, 1517, 1431, 1413, 1347, 1324, 1269, 1218, 1195, 1116, 760, 742 cm$^{-1}$; $^1$H NMR (DMSO-d$_6$) δ 10.71 (1H), 8.32 (1H), 7.87 (2H), 7.47 (13H), 7.16 (2H), 4.62 (2H), 4.15 (5H), 2.90 (4H); $^{13}$C NMR (DMSO-d$_6$) δ 172.4, 169.2, 161.8, 143.6, 140.6, 137.0, 136.3, 133.0, 131.3, 131.1, 129.7, 129.6, 128.9, 128.2, 127.7, 127.1, 126.8, 125.2, 121.3, 120.1, 120.0, 119.2, 53.4, 48.4, 46.4, 36.4, 29.5, 20.0; MS (ESI+) for C$_{35}$H$_{29}$Cl$_2$N$_3$O$_6$S m/z 690.1 (M+H)$^+$; Anal. Calcd for C$_{35}$H$_{29}$Cl$_2$N$_3$O$_6$S.0.4H$_2$O: C, 60.25; H, 4.30; N, 6.02. Found: C, 59.88; H, 4.47; N, 5.75. % Water (KF): 1.02.

EXAMPLE 20

[S-(R*,R*)]-4-[[[1-[[4-[(2,6-Dichlorobenzoyl) amino]phenyl]methyl]-2-methoxy-2-oxoethyl] amino]carbonyl]-3-thiazolidinecarboxylic Acid 3-Phenylmethyl Ester (Scheme A, A-7: where R$_{A-1}$ and R$_{A-2}$ are the same and equal to H, R$_3$ is phenylmethyl, Y is CO$_2$, R$_5$ is 4-[(2,6- dichlorobenzoyl)amino]phenyl and stereochemistry is (S,S)).

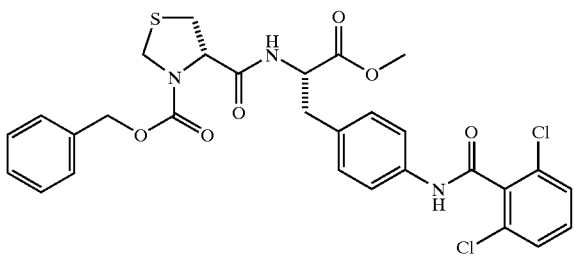

Example 20 was prepared as described in Scheme A from D-cysteine using benzyl chloroformate to form the requisite carbamate. Physical data as follows: IR (mull) 1748, 1694, 1690, 1673, 1610, 1561, 1542, 1517, 1441, 1430, 1408, 1355, 1324, 1269, 1217 cm$^{-1}$; $^1$H NMR (CDCl$_3$) δ 7.50 (2H), 7.33 (9H), 7.09 (2H), 6.75 (1H), 5.19 (2H), 4.78 (3H), 4.38 (3H), 3.73 (3H), 3.20 (3H); $^{13}$C NMR (DMSO-d$_6$) δ 171.4, 162.3, 136.3, 135.9, 135.7, 132.5, 132.4, 131.0, 130.0, 128.7, 128.4, 128.2, 128.1, 120.4, 68.2, 63.3, 53.2, 52.5, 37.2; MS (ESI+) for C$_{29}$H$_{27}$Cl$_2$N$_3$O$_6$S m/z 637.8 (M+Na)$^+$; MS (ESI−) for C$_{29}$H$_{27}$Cl$_2$N$_3$O$_6$S m/z 613.8 (M−H)$^-$; Anal. Calcd for C$_{29}$H$_{27}$Cl$_2$N$_3$O$_6$S.0.1H$_2$O: C, 56.39; H, 4.43; N, 6.80. Found: C, 56.31; H, 4.67; N, 6.71. % Water (KF): 0.19.

EXAMPLE 21

[S-(R*,R*)]-4-[[[1-Carboxy-2-[4-[(2,6-dichlorobenzoyl)amino]phenyl]ethyl]amino] carbonyl]-3-thiazolidinecarboxylic Acid 3-Phenylmethyl Ester (Scheme A, A-8: where R$_{A-1}$ and R$_{A-2}$ are the same and equal to H, R$_3$ is phenylmethyl, Y is CO$_2$, R$_5$ is 4-[(2,6-dichlorobenzoyl)amino phenyl and stereochemistry is (S,S)).

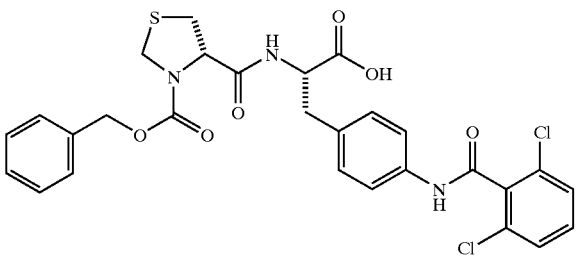

Example 21 was prepared from example 20 by the procedure described in preparation 6. Physical data as follows: IR (mull) 3290, 3034, 1666, 1606, 1562, 1537, 1516, 1431, 1413, 1351, 1326, 1270, 1215, 1195, 799 cm$^{-1}$; $^1$H NMR (DMSO-d$_6$) δ 12.85 (1H), 10.65 (1H), 7.39 (10H), 7.18 (2H), 4.98 (2H), 4.65 (2H), 4.55 (1H), 4.33 (1H), 3.06 (1H), 2.83 (2H); $^{13}$C NMR (CD$_3$OD) δ 172.6, 163.7, 154.4, 136.8, 136.2, 136.1, 131.9, 130.9, 129.6, 128.1, 127.9, 127.8, 127.7, 127.6, 120.0, 67.5, 66.7, 53.4, 36.5; MS (ESI−) for C$_{28}$H$_{25}$Cl$_2$N$_3$O$_6$S m/z 599.7 (M−H)$^-$; MS (FAB) m/z (rel. intensity) 602 (MH+, 99), 678 (37), 604 (74), 603 (33), 602 (99), 560 (32), 558 (48), 468 (35), 466 (51), 371 (50), 91 (73); HRMS (FAB) calcd for C$_{28}$H$_{25}$Cl$_2$N$_3$O$_6$S+H$_1$ 602.0919, found 602.0913; Anal. Calcd for C$_{28}$H$_{25}$Cl$_2$N$_3$O$_6$S.0.23H$_2$O: C, 55.45; H, 4.23; N, 6.93. Found: C, 55.53; H, 4.46; N, 6.88. % Water (KF): 0.67.

EXAMPLE 22

[S-(R*,R*)]-4-[[[1-[[4-[(2,6-Dichlorobenzoyl) amino]phenyl]methyl]-2-methoxy-2-oxoethyl] amino]carbonyl]-3-thiazolidinecarboxylic Acid 3-(Tricyclo[3.3.1.1$^{3,7}$]dec-1-yl)ester (Scheme A, A-7: where R$_{A-1}$ and R$_{A-2}$ are the same and equal to H, R$_3$ is 1-adamantyl, Y is CO$_2$, R$_5$ is 4-[(2,6-dichlorobenzoyl)amino]phenyl and stereochemistry is (S,S)).

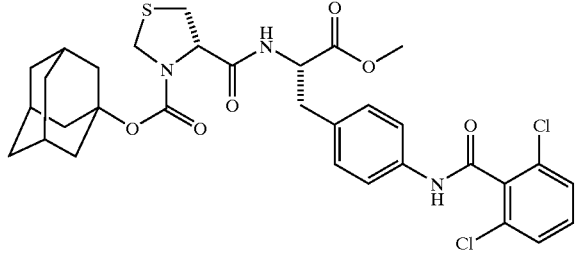

Example 22 was prepared as described in Scheme A from D-cysteine using 1-adamantyl fluoroformate to form the requisite carbamate. Physical data as follows: IR (mull) 3284, 3271, 1747, 1690, 1684, 1666, 1557, 1532, 1436, 1412, 1355, 1298, 1194, 1053, 799 cm$^{-1}$; $^1$H NMR (DMSO-d$_6$) δ 10.67 (1H), 8.41 (1H), 7.53 (5H), 7.17 (2H), 4.51 (3H), 4.23 (1H), 3.63 (3H), 3.22 (1H), 3.04 (1H), 2.90 (1H), 2.75 (1H), 2.01 (9H), 1.56 (1H); $^{13}$C NMR (DMSO-d$_6$) δ 172.1, 162.3, 152.7, 137.6, 136.9, 133.2, 131.8, 131.6, 130.0, 128.7, 119.8, 53.8, 52.4, 36.7, 36.1, 30.6; MS (ESI+) for C$_{32}$H$_{35}$Cl$_2$N$_3$O$_6$S m/z 659.7 (M+H)$^+$; MS (ESI−) for C$_{32}$H$_{35}$Cl$_2$N$_3$O$_6$S m/z 657.7 (M−H)$^-$; MS (FAB) m/z (rel. intensity) 660 (MH+, 8), 662 (5), 660 (8), 618 (6), 616 (8), 480 (5), 173 (7), 136 (11), 135 (99), 123 (14), 93 (8); Anal. Calcd for C$_{32}$H$_{35}$Cl$_2$N$_3$O$_6$S.0.04H$_2$O: C, 58.12; H, 5.35; N, 6.35. Found: C, 58.19; H, 5.62; N, 6.25. % Water (KF): 0.10.

EXAMPLE 23

[S-(R*,R*)]-4-[[[1-Carboxy-2-[4-[(2,6-dichlorobenzoyl)amino]phenyl]ethyl]amino] carbonyl]-3-thiazolidinecarboxylic Acid 3-(Tricyclo [3.3.1.1$^{3,7}$]dec-1-yl)ester (Scheme A, A-8: where R$_{A-1}$ and R$_{A-2}$ are the same and equal to H, R$_3$ is 1-adamantyl, Y is CO$_2$, R$_5$ is 4-[(2,6-dichlorobenzoyl)amino]phenyl and stereochemistry is (S,S)).

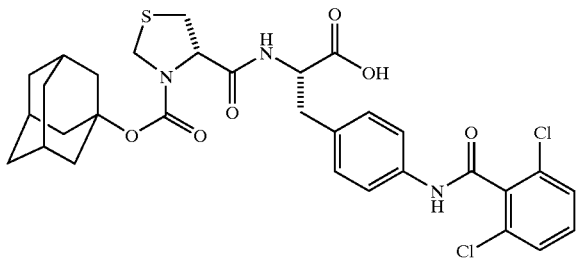

Example 23 was prepared from example 22 by the procedure described in preparation 6. Physical data as follows: IR (mull) 3287, 1667, 1606, 1562, 1537, 1516, 1431, 1412, 1353, 1326, 1299, 1274, 1220, 1194, 1049 cm$^{-1}$; $^1$H NMR (DMSO-d$_6$) δ 12.70 (1H), 10.67 (1H), 8.21 (1H), 7.58 (5H), 7.17 (2H), 4.51 (3H), 4.22 (1H), 3.20 (1H), 3.04 (1H), 2.88 (1H), 2.76 (1H), 2.07 (9H), 1.12 (6H); $^{13}$C NMR (DMSO-$d_6$) δ 173.1, 162.3, 152.7, 137.5, 136.9, 133.8, 131.8, 131.6, 130.1, 128.7, 119.7, 80.0, 53.8, 36.8, 36.1, 30.6; MS (ESI+) for $C_{31}H_{33}Cl_2N_3O_6S$ m/z 645.8 (M+H)$^+$; HRMS (FAB) calcd for $C_{31}H_{33}Cl_2N_3O_6S+H_1$ 646.1545, found 646.1564; Anal. Calcd for $C_{31}H_{33}Cl_2N_3O_6S \cdot 0.29H_2O$: C, 57.13; H, 5.19; N, 6.45. Found: C, 56.82; H, 5.21; N, 6.32. % Water (KF): 0.80.

EXAMPLE 24

[S-(R*,R*)]-4-[[[1-[[4-[(2,6-Dichlorobenzoyl) amino]phenyl]methyl]-2-methoxy-2-oxoethyl] amino]carbonyl]-3-thiazolidinecarboxylic Acid 3-[2-(4-Morpholinyl)ethyl]ester (Scheme A, A-7: where $R_{A-1}$ and $R_{A-2}$ are the same and equal to H, $R_3$ is 2-(4-morpholinyl)ethyl, Y is $CO_2$—, $R_5$ is 4-[(2,6-dichlorobenzoyl)amino]phenyl and stereochemistry is (S,S)).

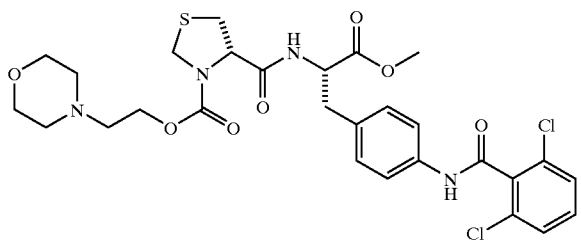

Example 24 was prepared as described in Scheme A from D-cysteine using 4-(2-hydroxyethyl)morpholine to form the requisite carbamate. Physical data as follows: IR (mull) 1745, 1705, 1679, 1605, 1536, 1515, 1431, 1414, 1344, 1323, 1269, 1216, 1194, 1183, 1117 cm$^{-1}$ $^1$H NMR (300 MHz, CDCl$_3$) δ 7.82 (1H), 7.56 (2H), 7.31 (3H), 7.12 (2H), 6.95 (1H), 4.65 (3H), 4.39 (3H), 3.74 (3H), 3.69 (3H), 3.34 (1H), 3.18 (3H), 2.763 (5H); $^{13}$C NMR (75 MHz, CDCl$_3$) δ 171.5, 169.8, 162.9, 154.4, 136.8, 136.1, 132.1, 130.6, 129.7, 127.9, 120.2, 66.3, 62.7, 57.0, 53.4, 53.2, 52.4, 36.7, 29.5; MS (ESI−) for $C_{28}H_{32}Cl_2N_4O_7S$ m/z 636.8 (M−H)$^-$; HRMS (FAB) calcd for $C_{28}H_{32}Cl_2N_4O_7S+H_1$ 639.1447, found 639.1419, Anal. Calcd for $C_{28}H_{32}Cl_2N_4O_7S$: C, 52.58; H, 5.04; N, 8.76. Found: C, 52.47; H, 5.17; N, 8.69.

EXAMPLE 25

[S-(R*,R*)]-4-[[[1-Carboxy-2-[-4-[(2,6-dichlorobenzoyl)amino]phenyl]ethyl]amino] carbonyl]-3-thiazolidinecarboxylic Acid 3-[2-(4-Morpholinyl)ethyl]ester (Scheme A, A-8: where $R_{A-1}$ and $R_{A-2}$ are the same and equal to H, $R_3$ is 2-(4-morpholinyl)ethyl, Y is $CO_2$—, $R_3$ is 4-[(2,6-dichlorobenzoyl)amino]phenyl and stereochemistry is (S,S)).

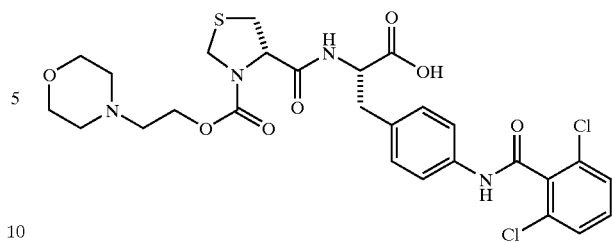

Example 25 was prepared from example 24 by the procedure described in preparation 6. Physical data as follows: IR (mull) 3278, 1667, 1606, 1562, 1541, 1515, 1431, 1413, 1351, 1326, 1270, 1195, 1134, 1118, 799 cm$^{-1}$; $^1$H NMR (300 MHz, DMSO-$d_6$) δ 10.64 (1H), 8.25 (1H), 7.50 (5H), 7.16 (2H), 4.60 (2H), 4.44 (1H), 4.27 (1H), 4.06 (2H), 3.51 (4H), 3.43 (2H), 3.29 (4H), 2.42 (4H); $^{13}$C NMR (75 MHz, DMSO-$d_6$) δ 173.0, 172.4, 169.8, 162.3, 137.5, 136.8, 133.5, 131.7, 130.1, 128.6, 119.7, 66.6, 63.3, 57.0, 53.7, 36.7, 21.5; MS (FAB) m/z (rel. intensity) 625 (MH+, 55), 629 (9), 628 (14), 627 (39), 626 (21), 625 (55), 308 (7), 141 (19), 114 (99), 113 (24), 100 (7); HRMS (FAB) calcd for $C_{27}H_{30}Cl_2N_4O_7S+H_1$ 625.1290, found 625.1309.

EXAMPLE 26

[S-(R*,S*)]-4-[[[1-[4-[(2,6-Dichlorobenzoyl)amino] phenyl]methyl]-2-methoxy-2-oxoethyl]amino] carbonyl]-3-thiazolidinecarboxylic Acid 3-1,1-Dimethylethyl)ester (Scheme A, A-7: where $R_{A-1}$ and $R_{A-2}$ are the same and equal to H, $R_3$ is t-butyl, Y is $CO_2$, $R_5$ is 4-[(2,6-dichlorobenzoyl)amino]phenyl and stereochemistry is (S,R)).

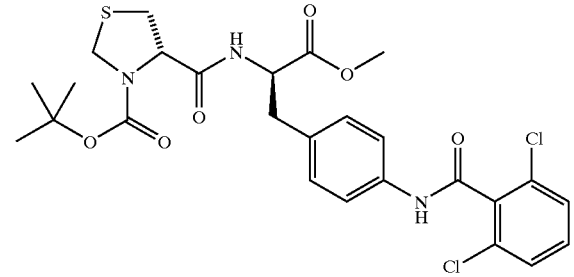

Example 26 was prepared as described in Scheme A from D-cysteine using di-t-butyl dicarbonate to form the requisite carbamate. Physical data as follows: IR (mull) 3293, 1746, 1666, 1606, 1562, 1538, 1516, 1432, 1413, 1324, 1260, 1216, 1195, 1162, 799 cm$^{-1}$; $^1$H NMR (CDCl$_3$) δ 7.55 (2H), 7.37 (4H), 7.14 (2H), 4.89 (1H), 4.66 (2H), 4.25 (1H), 3.75 (3H), 3.39 (1H), 3.24 (3H), 1.44 (9H); $^{13}$C NMR (CDCl$_3$) δ 171.2, 169.8, 162.3, 136.3, 135.8, 132.4, 132.3, 131.0, 130.2, 130.1, 129.9, 128.2, 128.1, 127.9, 120.5, 120.2, 120.1, 82.2, 53.2, 52.5, 37.3, 31.0, 28.4, 28.2; MS (ESI+) for $C_{26}H_{29}Cl_2N_3O_6S$ m/z 603.9 (M+Na)$^+$; MS (ESI−) for $C_{26}H_{29}Cl_2N_3O_6S$ m/z 580.0 (M−H)$^-$; HRMS (FAB) calcd for $C_{26}H_{29}Cl_2N_3O_6S+H_1$ 582.1232, found 582.1231, Anal. Calcd for $C_{26}H_{29}Cl_2N_3O_6S \cdot 0.26H_2O$: C, 53.18; H, 5.07; N, 7.16. Found: C, 52.78; H, 5.14; N, 6.91. % Water (KF): 0.66.

EXAMPLE 27

[S-(R*,S*)]-4-[[[1-Carboxy-2-[4-[(2,6-dichlorobenzoyl)amino]phenyl]ethyl]amino] carbonyl]-3-thiazolidinecarboxylic Acid 3-(1,1-Dimethylethyl)ester (Scheme A, A-8: where $R_{A-1}$ and $R_{A-2}$ are the same and equal to H, $R_3$ is t-butyl, Y is $CO_2$, $R_5$ is 4-[(2,6- dichlorobenzoyl)amino]phenyl and stereochemistry is (S,R)).

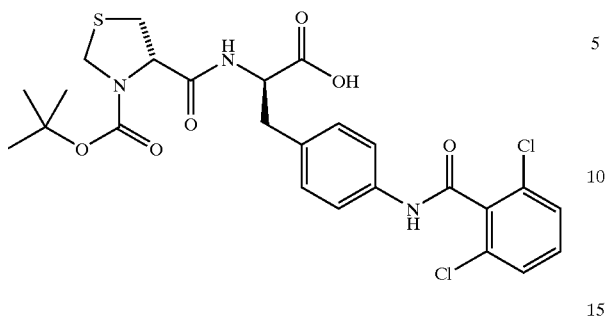

Example 27 was prepared from example 26 by the procedure described in preparation 6. Physical data as follows: IR (mull) 3286, 1665, 1606, 1562, 1538, 1516, 1432, 1413, 1394, 1326, 1259, 1216, 1195, 1161, 799 cm$^{-1}$; $^1$H NMR (DMSO-d$_6$) δ 12.70 (1H), 10.63 (1H), 8.13 (1H), 7.51 (5H), 7.20 (2H), 4.45 (4H), 2.96 (3H), 1.23 (9H); $^{13}$C NMR (DMSO-d$_6$) δ 173.1, 170.5, 162.3, 153.2, 137.5, 136.9, 131.8, 131.6, 130.0, 128.7, 119.7, 80.4, 62.2, 54.0, 49.8, 36.5, 28.3, 21.5; MS (ESI+) for $C_{25}H_{27}Cl_2N_3O_6S$ m/z 567.9 (M+H)$^+$; MS (ESI−) for $C_{25}H_{27}Cl_2N_3O_6S$ m/z 565.9 (M−H)$^-$; HRMS (EI) calcd for $C_{25}H_{27}Cl_2N_3O_6S$ 567.0997, found 568.1096, Anal. Calcd for $C_{25}H_{27}Cl_2N_3O_6S$·0.34H$_2$O: C, 52.82; H, 4.79; N, 7.39. Found: C, 52.17; H, 4.90; N, 7.25. % Water (KF): 1.07.

EXAMPLE 28

[S-(R*,R*)]-4-[[[1-[[4-[(2,6-Dichlorobenzoyl) amino]phenyl]methyl]-2-methoxy-2-oxoethyl] amino]carbonyl]-5,5-dimethyl-3-thiazolidinecarboxylic Acid 3-(1,1-Dimethylethyl) ester (Scheme A, A-7: where $R_{A-1}$ and $R_{A-2}$ are the same and equal to CH$_3$, R$_3$ is t-butyl, Y is CO$_2$, R$_5$ is 4-[(2,6-dichlorobenzoyl)amino]phenyl and stereochemistry is (S,S)).

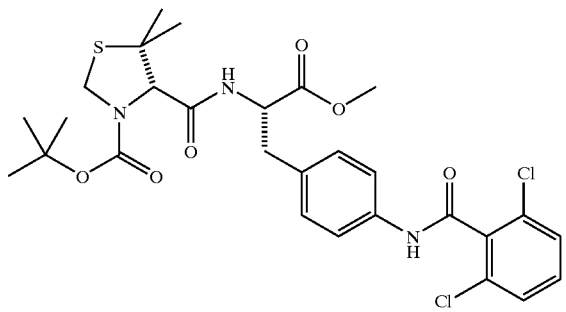

Example 28 was prepared as described in Scheme A from D-penicillamine using di-t-butyl dicarbonate to form the requisite carbamate. Physical data as follows: IR (mull) 1744, 1707, 1688, 1678, 1657, 1606, 1562, 1541, 1516, 1431, 1414, 1326, 1253, 1161, 1140 cm$^{-1}$; $^1$H NMR (CDCl$_3$) δ 7.58 (2H), 7.36 (3H), 7.14 (2H), 6.55 (1H), 4.87 (1H), 4.56 (2H), 4.10 (1H), 3.72 (3H), 3.08 (2H), 1.53 (3H), 1.44 (9H), 1.40 (3H); $^{13}$C NMR (DMSO-d$_6$) δ 171.6, 162.3, 153.6, 136.4, 135.8, 132.6, 132.4, 131.0, 130.1, 129.9, 129.8, 128.2, 120.7, 120.5, 120.3, 81.7, 73.0, 52.8, 52.6, 52.4, 48.4, 39.8, 39.5, 37.6, 30.3, 28.3, 28.0, 23.5; MS (ESI−) for $C_{28}H_{33}Cl_2N_3O_6S$ m/z 607.9 (M−H)$^-$; MS (FAB) m/z (rel. intensity) 610 (MH+, 6), 512 (26), 510 (44), 117 (30), 115 (16), 99 (16), 87 (16), 59 (99), 57 (27), 57 (20), 41 (23); HRMS (FAB) calcd for $C_{28}H_{33}Cl_2N_3O_6S$+H$_1$ 610.1545, found 610.1501; Anal. Calcd for $C_{28}H_{33}Cl_2N_3O_6S$·0.07H$_2$O: C, 54.97; H, 5.46; N, 6.87. Found: C, 54.92; H, 5.54; N, 7.11. % Water (KF): 0.21.

EXAMPLE 29

[S-(R*,R*)]-4-[[[1-Carboxy-2-[4-[(2,6-dichlorobenzoyl)amino]phenyl]ethyl]amino] carbonyl]-5,5-dimethyl-3-thiazolidinecarboxylic Acid 3-(1,1-Dimethylethyl)ester (Scheme A, A-8: where $R_{A-1}$ and $R_{A-2}$ are the same and equal to CH$_3$, R$_3$ is t-butyl, Y is CO$_2$, R$_5$ is 4-[(2,6-dichlorobenzoyl)amino]phenyl and stereochemistry is (S,S)).

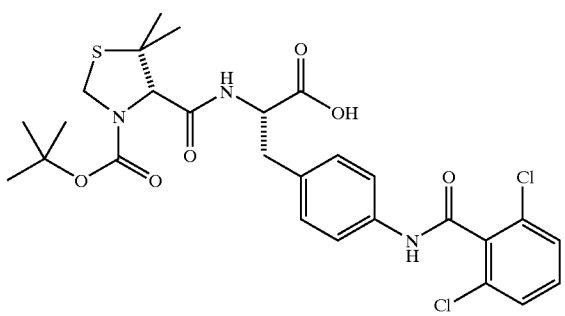

Example 29 was prepared from example 28 by the procedure described in preparation 6. Physical data as follows: IR (mull) 1739, 1666, 1606, 1562, 1535, 1516, 1432, 1413, 1394, 1325, 1270, 1260, 1194, 1160, 799 cm$^{-1}$; $^1$H NMR (DMSO-d$_6$) δ 12.62 (1H), 10.62 (1H), 8.18 (1H), 7.51 (5H), 7.19 (2H), 4.50 (3H), 4.24 (1H), 2.91 (2H), 1.33 (12H), 1.04 (3H); $^{13}$C NMR (DMSO-d$_6$) δ 172.8. 168.7, 161.9, 153.2, 137.2, 136.5, 133.1, 131.4, 131.3, 129.6, 128.3, 119.5, 80.0, 70.9, 53.7, 48.5, 37.0, 30.7, 28.1, 27.9, 24.6; MS (ESI+) for $C_{27}H_{31}Cl_2N_3O_6S$ m/z 595.9 (M+H)$^+$; MS (ESI−) for $C_{27}H_{31}Cl_2N_3O_5S$ m/z 593.8 (M−H)$^-$; MS (FAB) m/z (rel. intensity) 596 (MH+, 19), 672 (17), 596 (19), 499 (15), 498 (60), 497 (26), 496 (99), 494 (35), 173 (20), 116 (27), 57 (48); Anal. Calcd for $C_{27}H_{31}Cl_2N_3O_6S$·0.27H$_2$O: C, 53.93; H, 5.29; N, 6.99. Found: C, 53.73; H, 5.39; N, 7.10. % Water (KF): 0.80.

EXAMPLE 30

[S-(R*,R*)]-4-[[[1-[[4-[(2,6-Dichlorobenzoyl) amino]phenyl]methyl]-2-methoxy-2-oxoethyl) amino]carbonyl]-5,5-dimethyl-3-thiazolidinecarboxylic Acid 3-Ethyl Ester (Scheme A, A-7: where $R_{A-1}$ and $R_{A-2}$ are the same and equal to CH$_3$, R$_3$ is ethyl, Y is CO$_2$, R$_5$ is 4-[(2,6-dichlorobenzoyl)amino]phenyl and stereochemistry is (S,S)).

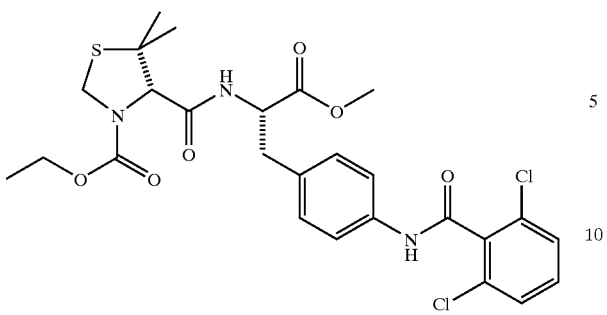

Example 30 was prepared as described in Scheme A from D-penicillamine using ethyl chloroformate to form the requisite carbamate. Physical data as follows: IR (mull) 3292, 1748, 1666, 1606, 1562, 1538, 1516, 1445, 1431, 1414, 1341, 1325, 1271, 1212, 1194 cm$^{-1}$; $^1$H NMR (CDCl$_3$) δ 7.57 (2H), 7.37 (4H), 7.11 (2H), 6.49 (1H), 4.86 (1H), 4.59 (2H), 4.14 (3H), 3.75 (3H), 3.09 (2H), 1.60 (3H), 1.54 (3H), 1.23 (3H); $^{13}$C NMR (DMSO-d$_6$) δ 171.6, 162.3, 154.5, 136.3, 135.8, 132.6, 132.4, 131.1, 130.2, 130.1, 129.8, 128.2, 120.5, 120.4, 72.7, 62.5, 52.7, 52.5, 37.3, 30.2, 23.7, 14.6, 14.1; MS (ESI+) for $C_{26}H_{29}Cl_2N_3O_6S$ m/z 581.9 (M+H)$^+$; MS (ESI−) for $C_{26}H_{29}Cl_2N_3O_6S$ m/z 579.8 (M−H)$^−$; HRMS (EI) calcd for $C_{26}H_{29}Cl_2N_3O_6S$ 581.1154, found 581.1132; Anal. Calcd for $C_{26}H_{29}Cl_2N_3O_6S \cdot 0.16H_2O$: C, 53.35; H, 5.05; N, 7.18. Found: C, 53.74; H, 5.12; N, 7.12. % Water (KF): 0.49.

EXAMPLE 31

[S-(R*,R*)]-4-[[[1-Carboxy-2-[4-[(2,6-dichlorobenzoyl)amino]phenyl]ethyl]amino]carbonyl]-5,5-dimethyl-3-thiazolidinecarboxylic Acid 3-Ethyl Ester (Scheme A, A-8: where $R_{A-1}$ and $R_{A-2}$ are the same and equal to CH$_3$, R$_3$ is ethyl, Y is CO$_2$, R$_5$ is 4-[(2,6-dichlorobenzoyl)amino]phenyl and stereochemistry is (S,S)).

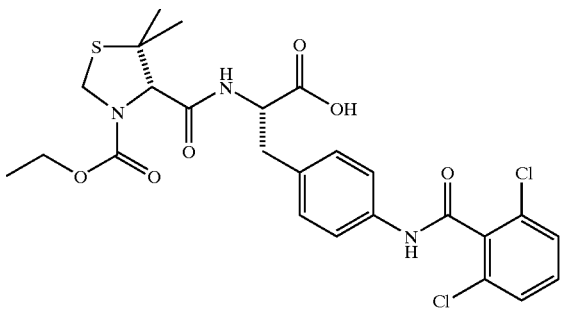

Example 31 was prepared from example 30 by the procedure described in preparation 6. Physical data as follows: IR (mull) 3287, 3070, 1666, 1606, 1562, 1538, 1516, 1431, 1414, 1342, 1328, 1271, 1213, 1194, 799 cm$^{-1}$; $^1$H NMR (DMSO-d$_6$) δ 12.58 (1H), 10.63 (1H), 8.22 (1H), 7.51 (5H), 7.20 (2H), 4.51 (3H), 3.95 (3H), 3.04 (1H), 2.86 (1H), 1.35 (3H), 1.16 (6H); $^{13}$C NMR (DMSO-d$_6$) δ 223.3, 184.1, 183.9, 172.8, 168.4, 161.7, 136.9, 136.3, 133.1, 131.2, 131.0, 129.4, 128.1, 119.2, 70.6, 61.1, 53.6, 53.4, 48.6, 36.2, 30.1, 25.4, 24.3, 21.0, 14.1; MS (ESI+) for $C_{25}H_{27}Cl_2N_3O_6S$ m/z 568.0 (M+H)$^+$; MS (ESI−) for $C_{25}H_{27}Cl_2N_3O_6S$ m/z 565.9 (M−H)$^−$; MS (FAB) m/z (rel. intensity) 568 (MH+, 86), 644 (18), 571 (19), 570 (61), 569 (30), 568 (86), 335 (16), 188 (99), 173 (19), 141 (53), 116 (23); HRMS (FAB) calcd for $C_{25}H_{27}Cl_2N_3O_6S+H_1$ 568.1075, found 568.1096; Anal. Calcd for $C_{25}H_{27}Cl_2N_3O_6S \cdot 0.4H_2O$: C, 52.16; H, 4.87; N, 7.30. Found: C, 52.46; H, 4.90; N, 7.15. % Water (KF): 1.25.

EXAMPLE 32

[S-(R*,R*)]-4-[[[1-[4-[(2,6-Dichlorophenyl)methoxy]phenyl]methyl]-2-methoxy-2-oxoethyl]amino]carbonyl]-3-thiazolidinecarboxylic Acid 3-(1,1-Dimethylethyl)ester (Scheme A, A-7: where $R_{A-1}$ and $R_{A-2}$ are the same and equal to H, R$_3$ is t-butyl, Y is CO$_2$—, R$_5$ is 4-[(2,6-dichlorophenyl)methoxy]phenyl and stereochemistry is (S,S)).

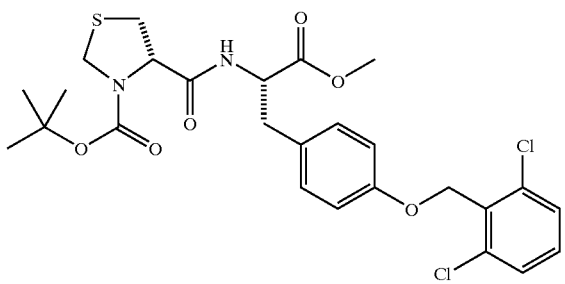

Example 32 was prepared as described in Scheme A from D-cysteine using di-t-butyl dicarbonate to form the requisite carbamate. Physical data as follows: IR (liq.) 1745, 1702, 1565, 1511, 1467, 1439, 1368, 1299, 1241, 1197, 1177, 1162, 1017, 778, 768 cm$^{-1}$; $^1$H NMR (CDCl$_3$) δ 7.36 (2H), 7.25 (1H), 7.06 (2H), 6.94 (2H), 5.23 (2H), 4.75 (3H), 4.12 (1H), 3.72 (3H), 3.37 (1H), 3.14 (3H), 1.45 (9H); $^{13}$C NMR (CDCl$_3$) δ 171.5, 157.9, 136.9, 132.0, 130.3, 128.4, 128.2, 115.0, 81.9, 65.1, 62.8, 53.2, 52.3, 49.2, 36.9, 28.1, 27.9; MS (ESI+) for $C_{26}H_{30}Cl_2N_2O_6S$ m/z 568.9 (M+H)$^+$; MS (ESI−) for $C_{26}H_{30}Cl_2N_2O_6S$ m/z 566.7 (M−H)$^−$; Anal. Calcd for $C_{26}H_{30}Cl_2N_2O_6S \cdot 0.09H_2O$: C, 54.68; H, 5.33; N, 4.91. Found: C, 54.62; H, 5.41; N, 4.73. % Water (KF): 0.28.

EXAMPLE 33

[S-(R*,R*)]-4-[[[1-Carboxy-2-[4-[(2,6-dichlorophenyl)methoxy]phenyl]ethyl]amino]carbonyl]-3-thiazolidinecarboxylic Acid 3-(1,1-Dimethylethyl)ester (Scheme A, A-8: where $R_{A-1}$ and $R_{A-2}$ are the same and equal to H, R$_3$ is t-butyl, Y is CO$_2$—, R$_5$ is 4-[(2,6-dichlorophenyl)methoxy]phenyl and stereochemistry is (S,S)).

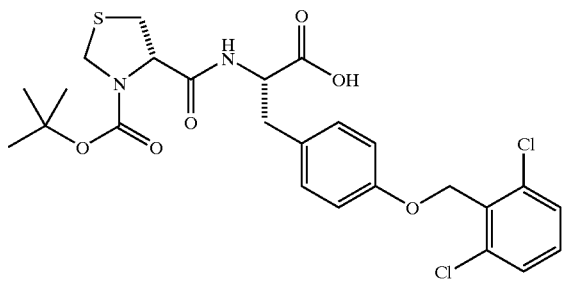

Example 33 was prepared from example 32 by the procedure described in preparation 6. Physical data as follows: IR (mull) 1734, 1704, 1676, 1612, 1565, 1511, 1439, 1393, 1300, 1241, 1196, 1178, 1162, 777, 769 cm$^{-1}$; $^1$H NMR (DMSO-d$_6$) δ 8.24 (1H), 7.50 (3H), 7.13 (2H), 6.93 (2H), 5.16 (2H), 4.52 (3H), 4.21 (1H), 2.91 (4H), 1.31 (9H); $^{13}$C NMR (DMSO-d$_6$) δ 172.7, 169.7, 157.1, 152.6, 135.9, 131.7, 131.5, 130.2, 129.8, 128.7, 114.2, 79.8, 64.8, 61.6, 53.2, 49.2, 36.0, 34.8, 27.8, 21.0; MS (ESI+) for C$_{25}$H$_{28}$Cl$_2$N$_2$O$_6$S m/z 554.9 (M+H)$^+$; MS (ESI−) for C$_{25}$H$_{28}$Cl$_2$N$_2$O$_6$S m/z 552.8 (M−H)$^-$; Anal. Calcd for C$_{25}$H$_{28}$Cl$_2$N$_2$O$_6$S.0.15H$_2$O: C, 53.79; H, 5.11; N, 5.02. Found: C, 54.17; H, 5.17; N, 5.00. % Water (KF): 0.50.

EXAMPLE 34

[S-(R*,R*)]-4-[[[1-[4-[(2,6-Dichlorophenyl)methoxy]phenylmethyl]-2-methoxy-2-oxoethyl]amino]carbonyl]-3-thiazolidinecarboxylic Acid 3-Ethyl Ester (Scheme A, A-7: where R$_{A-1}$ and R$_{A-2}$ are the same and equal to H, R$_3$ is ethyl, Y is CO$_2$—, R$_5$ is 4-[(2,6-dichlorophenyl)methoxy]phenyl and stereochemistry is (S,S)).

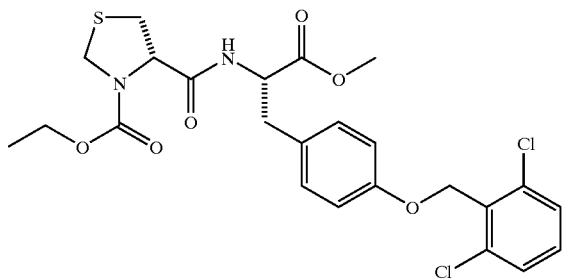

Example was prepared as described in Scheme A from D-cysteine using ethyl chloroformate to form the requisite carbamate. Physical data as follows: IR (mull) 3282, 1742, 1705, 1692, 1664, 1562, 1509, 1436, 1352, 1343, 1236, 1196, 1175, 1015, 786 cm$^{-1}$; $^1$H NMR (CDCl$_3$) δ 7.37 (2H), 7.25 (1H), 7.05 (2H), 6.94 (2H), 6.74 (1H), 5.23 (2H), 4.77 (3H), 4.34 (1H), 4.18 (2H), 3.74 (3H), 3.37 (1H), 3.13 (3H), 1.31 (3H); $^{13}$C NMR (CDCl$_3$) δ 171.6, 171.4, 158.0, 137.0, 132.1, 130.5, 130.4, 128.5, 128.2, 115.0, 65.2, 63.6, 63.2, 62.7, 53.6, 53.2, 52.4, 36.9, 14.5; MS (ESI+) for C$_{24}$H$_{26}$Cl$_2$N$_2$O$_6$S m/z 540.9 (M+H)$^+$; HRMS (EI) calcd for C$_{24}$H$_{26}$Cl$_2$N$_2$O$_6$S 540.0889, found 540.0878; Anal. Calcd for C$_{24}$H$_{26}$Cl$_2$N$_2$O$_6$S.0.26H$_2$O: C, 52.79; H, 4.89; N, 5.13. Found: C, 52.41; H, 4.82; N, 4.96. % Water (KF): 0.85.

EXAMPLE 35

[S-(R*,R*)]-4-[[[1-Carboxy-2-[4-[(2,6-dichlorophenyl)methoxy]phenyl]ethyl]amino]carbonyl]-3-thiazolidinecarboxylic Acid 3-Ethyl Ester (Scheme A, A-8: where R$_{A-1}$ and R$_{A-2}$ are the same and equal to H, R$_3$ is ethyl, Y is CO$_2$—, R$_5$ is 4-[(2,6-dichlorophenyl)methoxy]phenyl and stereochemistry is (S,S)).

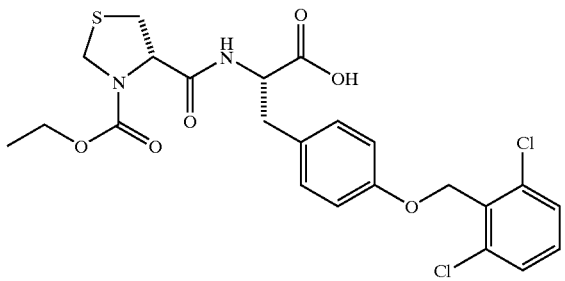

Example 35 was prepared from example 34 by the procedure described in preparation 6. Physical data as follows: IR (mull) 1709, 1675, 1612, 1565, 1511, 1439, 1416, 1346, 1300, 1241, 1196, 1179, 1115, 1018, 768 cm$^{-1}$; $^1$H NMR (CDCl$_3$) δ 7.34 (2H), 7.23 (1H), 7.12 (2H), 6.94 (2H), 6.85 (1H), 5.22 (2H), 4.77 (4H), 4.34 (1H), 4.16 (2H), 3.33 (4H), 1.26 (3H); $^{13}$C NMR (CDCl$_3$) δ 174.0, 170.2, 158.1, 155.1, 137.0, 132.0, 130.5, 128.5, 128.1, 115.0, 65.2, 63.9, 63.0, 62.9, 53.3, 36.4, 21.9, 14.5; MS (ESI+) for C$_{23}$H$_{24}$Cl$_2$N$_2$O$_6$S m/z 527.0 (M+H)$^+$; MS (ESI−) for C$_{23}$H$_{24}$Cl$_2$N$_2$O$_6$S m/z 524.9 (M−H)$^-$; HRMS (EI) calcd for C$_{23}$H$_{24}$Cl$_2$N$_2$O$_6$S 526.0732, found 526.0726; Anal. Calcd for C$_{23}$H$_{24}$Cl$_2$N$_2$O$_6$S.0.20H$_2$O: C, 52.02; H, 4.63; N, 5.27. Found: C, 52.12; H, 4.73; N, 5.34. % Water (KF): 0.69.

EXAMPLE 36

[S-(R*,R*)]-4-[[[1-[4-[(2,6-Dichlorophenyl)methoxy]phenyl]methyl]-2-methoxy-2-oxoethyl]amino]carbonyl]-3-thiazolidinecarboxylic Acid 3-[2-(4-Morpholinyl)ethyl]ester (Scheme A, A-7: where R$_{A-1}$ and R$_{A-2}$ are the same and equal to H, R$_3$ is 2-(4-morpholinyl)ethyl, Y is CO$_2$—, R$_5$ is 4-[(2,6-dichlorophenyl)methoxy]phenyl and stereochemistry is (S,S)).

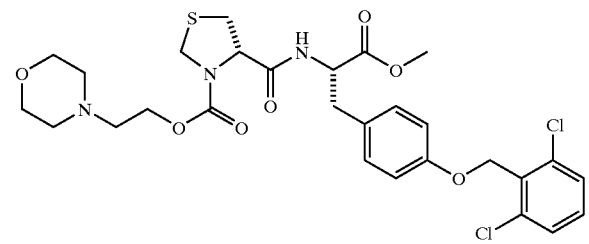

Example 36 was prepared as described in Scheme A from D-cysteine using 4-(2-hydroxyethyl)morpholine to form the requisite carbamate. Physical data as follows: mp 138–140° C.; IR (mull) 3286, 1743, 1705, 1660, 1559, 1513, 1435, 1428, 1302, 1245, 1226, 1215, 1176, 1015, 764 cm$^{-1}$; $^1$H NMR (300 MHz, DMSO-d$_6$) δ 8.43 (1H), 7.48 (3H), 7.13 (2H), 6.94 (2H), 5.16 (2H), 4.59 (2H), 4.48 (1H), 4.26 (1H), 4.07 (2H), 3.63 (3H), 3.51 (4H), 3.23 (1H), 3.01 (1H), 2.84 (1H), 2.71 (1H), 2.41 (6H); $^{13}$C NMR (75 MHz, DMSO-d$_6$) δ 172.2, 157.7, 153.9, 136.5, 132.2, 132.0, 130.8, 130.1, 129.2, 114.8, 66.6, 65.4, 63.4, 57.0, 53.9, 53.8, 52.4, 36.4; MS (ESI+) for $C_{28}H_{33}Cl_2N_3O_7S$ m/z 625.8 (M+H)$^+$; Anal. Calcd for $C_{28}H_{33}Cl_2N_3O_7S$: C, 53.67; H, 5.31; N, 6.71. Found: C, 53.69; H, 5.27; N, 6.69.

EXAMPLE 37

[S-(R*,R*)]-4-[[[1-Carboxy-2-[4-[(2,6-dichlorophenyl)methoxy]phenyl]ethyl]amino]carbonyl]-3-thiazolidinecarboxylic Acid 3-[2-Morpholinyl)ethyl]ester (Scheme A, A-8: where $R_{A-1}$ and $R_{A-2}$ are the same and equal to H, $R_3$ is 2-(4-morpholinyl)ethyl, Y is $CO_2$—, $R_5$ is 4-[(2,6-dichlorophenyl)methoxy]phenyl and stereochemistry is (S,S)).

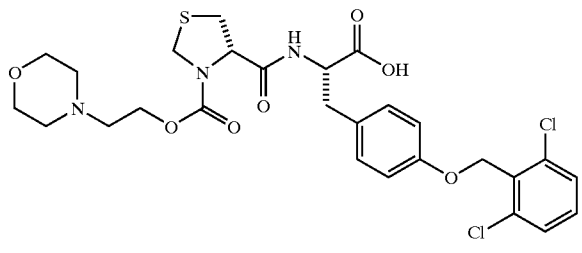

Example 37 was prepared from example 36 by the procedure described in preparation 6. Physical data as follows: IR (mull) 1710, 1610, 1585, 1565, 1511, 1439, 1408, 1351, 1301, 1240, 1196, 1179, 1116, 1017, 767 cm$^{-1}$; $^1$H NMR (300 MHz, DMSO-d$_6$) δ 8.27 (1H), 7.55 (2H), 7.45 (1H), 7.13 (2H), 6.94 (2H), 5.16 (2H), 4.59 (2H), 4.40 (1H), 4.27 (1H), 4.04 (2H), 3.52 (4H), 3.21 (1H), 2.86 (3H), 2.44 (6H), $^{13}$C NMR (75 MHz, DMSO-d$_6$) δ 173.2, 172.5, 157.6, 136.5, 132.2, 132.0, 130.8, 130.4, 129.2, 114.7, 66.5, 65.3, 63.2, 57.0, 53.9, 53.7, 36.5, 21.5; MS (ESI+) for $C_{27}H_{31}Cl_2N_3O_7S$ m/z 611.9 (M+H)$^+$; Anal. Calcd for $C_{27}H_{31}Cl_2N_3O_7S \cdot 1.0C_2H_4O_2 \cdot 0.63H_2O \cdot 0.28HCl$: C, 50.13; H, 5.31; N, 6.03; Cl, 11.59. Found: C, 49.80; H, 5.30; N, 6.05; Cl, 11.20. % Water (KF): 1.58.

EXAMPLE 38

[S-(R*,R*)]-4-[[[1-[4-[(2,6-Dichlorophenyl)methoxy]phenyl]methyl]-2-methoxy-2-oxoethyl]amino]carbonyl]-3-thiazolidinecarboxylic Acid 3-[(2-Pyridinyl)methyl]ester (Scheme A, A-7: where $R_{A-1}$ and $R_{A-2}$ are the same and equal to H, $R_3$ is 2-pyridinylmethyl, Y is $CO_2$—, $R_1$ is 4-[(2,6-dichlorophenyl)methoxy]phenyl and stereochemistry is (S,S)).

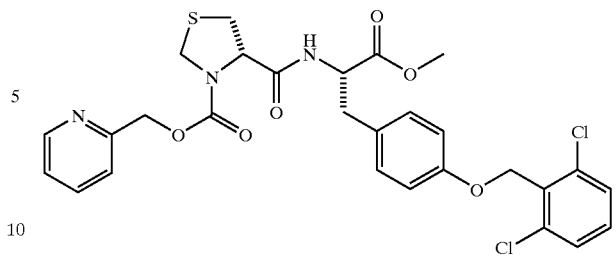

Example 38 was prepared as described in Scheme A from D-cysteine using 2-pyridinemethanol to form the requisite carbamate. Physical data as follows: mp 123–125° C.; IR (mull) 3334, 1728, 1709, 1668, 1531, 1511, 1441, 1405, 1345, 1294, 1286, 1236, 1228.1015, 762 cm$^{-1}$; $^1$H NMR (300 MHz, DMSO-d$_6$) δ 8.57 (2H), 7.79 (1H), 7.54 (2H), 7.42 (1H), 7.27 (2H), 7.12 (2H), 6.92 (2H), 5.13 (4H), 4.69 (2H), 4.49 (1H), 4.34 (1H), 3.59 (3H), 3.24 (1H), 2.89 (3H); $^{13}$C NMR (75 MHz, DMSO-d$_6$ δ 172.2, 169.9, 157.7, 156.5, 153.6, 137.3, 136.5, 132.2, 132.0, 130.8, 130.1, 129.2, 123.2, 121.0, 114.8, 67.7, 65.3, 62.0, 54.0, 52.4, 50.3, 36.3, 35.3; HRMS (EI) calcd for $C_{28}H_{27}Cl_2N_3O_6S$ 603.0997, found 603.0992; Anal. Calcd for $C_{28}H_{27}Cl_2N_3O_6S$: C, 55.63; H, 4.50; N, 6.95. Found: C, 55.56; H, 4.59; N, 6.93.

EXAMPLE 39

[S-(R*,R*)]-4-[[[1-[4-[(2,6-Dichlorophenyl)methoxy]phenyl]methyl]-2-methoxy-2-oxoethyl]amino]carbonyl]-3-thiazolidinecarboxylic Acid 3-[2-(1-Pyrrolidinyl)ethyl]ester (Scheme A, A-7: where $R_{A-1}$ and $R_{A-2}$ are the same and equal to H, $R_3$ is 2-(1-pyrrolidinyl)ethyl, Y is $CO_2$—, $R_5$ is 4-[(2,6-dichlorophenyl)methoxy]phenyl and stereochemistry is (S,S)).

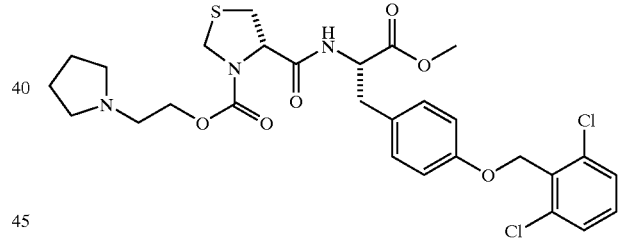

Example 39 was prepared as described in Scheme A from D-cysteine using 1-(2-hydroxyethyl)pyrrolidine to form the requisite carbamate. Physical data as follows: mp 130–132° C.; IR (mull) 1745, 1702, 1661, 1556, 1513, 1435, 1426, 1303, 1245, 1226, 1214, 1176, 1017,825, 765 cm$^{-1}$; $^1$H NMR (300 MHz, DMSO-d$_6$) δ 8.42 (1H), 7.48 (3H), 7.13 (2H), 6.94 (2H), 5.16 (2H), 4.59 (2H), 4.48 (1H), 4.27 (1H), 3.99 (2H), 3.63 (3H), 3.24 (1H), 2.68 (9H), 1.62 (4H); $^{13}$C NMR (75 MHz, DMSO-d$_6$) δ 172.2, 170.0, 157.7, 136.5, 132.2, 132.0, 130.8, 130.1, 129.2, 114.8, 65.3, 65.1, 54.4, 53.9, 52.42, 36.35, 23.6; MS (ESI+) for $C_{28}H_{33}Cl_2N_3O_6S$ m/z 609.8 (M+H)$^+$; Anal. Calcd for $C_{28}H_{33}Cl_2N_3O_6S$: C, 55.08; H, 5.45; N, 6.88. Found: C, 54.72; H, 5.58; N, 6.60.

EXAMPLE 40

[R-(R*,S*)]-4-[[[1-[4-[(2,6-Dichlorophenyl)methoxy]phenyl]methyl]-2-methoxy-2-oxoethyl]amino]carbonyl]-3-thiazolidinecarboxylic Acid 3-(1,1-Dimethylethyl)ester (Scheme A, A-7: where $R_{A-1}$ and $R_{A-2}$ are the same and equal to H, $R_3$ is t-butyl, Y is $CO_2$—, $R_5$ is 4-[(2,6- dichlorophenyl)methoxy]phenyl and stereochemistry is (R,S)).

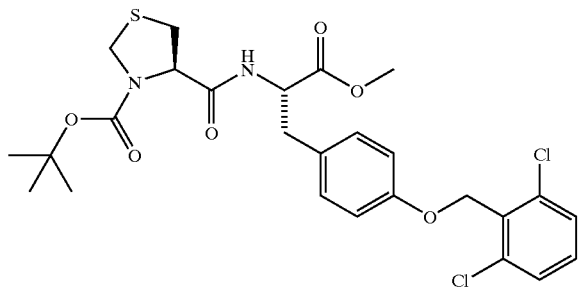

Example 40 was prepared as described in Scheme A from L-cysteine using di-t-butyl dicarbonate to form the requisite carbamate. Physical data as follows: IR (mull) 1746, 1702, 1611, 1565, 1511, 1439, 1299, 1241, 1197, 1177, 1162, 1118, 1016, 777, 768 cm$^{-1}$; $^1$H NMR (CDCl$_3$) δ 7.39 (2H), 7.25 (1H), 6.93 (2H), 6.93 (2H), 5.24 (2H), 4.72 (3H), 4.20 (1H), 3.74 (3H), 3.35 (1H), 3.12 (3H), 1.44 (9H); $^{13}$C NMR (CDCl$_3$) δ 171.7, 170.0, 169.5, 158.3, 137.3, 132.4, 130.7, 130.6, 128.8, 128.5, 115.2, 115.1, 82.4, 65.5, 53.5, 52.6, 50.3, 37.3, 28.4; MS (ESI+) for $C_{26}H_{30}Cl_2N_2O_6S$ m/z 554.9 (M+H)$^+$; MS (ESI−) for $C_{26}H_{30}Cl_2N_2O_6S$ m/z 552.8 (M−H)$^−$; Anal. Calcd for $C_{26}H_{30}Cl_2N_2O_6S \cdot 0.1H_2O$: C, 54.65; H, 5.33; N, 4.90. Found: C, 54.59; H, 5.30; N, 4.88. % Water (KF): 0.33.

EXAMPLE 41

[R-(R*,S*)]-4-[[[1-Carboxy-2-[4-[(2,6-dichlorophenyl)methoxy]phenyl]ethyl]amino]carbonyl]-3-thiazolidinecarboxylic Acid 3-(1,1-Dimethylethyl)ester (Scheme A, A-8: where $R_{A-1}$ and $R_{A-2}$ are the same and equal to H, $R_3$ is t-butyl, Y is CO$_2$—, $R_5$ is 4-[(2,6-dichlorophenyl)methoxy]phenyl and stereochemistry is (R,S)).

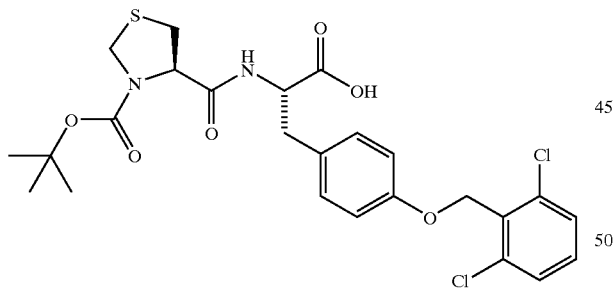

Example 41 was prepared from example 40 by the procedure described in preparation 6. Physical data as follows: IR (mull) 1737, 1705, 1679, 1612, 1565, 1512, 1439, 1300, 1241, 1196, 1178, 1163, 1117, 777, 769 cm$^{-1}$; $^1$H NMR (DMSO-d$_6$) δ 8.07 (1H), 7.54 (2H), 7.44 (1H), 7.16 (2H), 6.93 (2H), 5.16 (2H), 4.56 (1H), 4.39 (3H), 3.56 (1H) 2.84 (3H), 1.23 (9H); $^{13}$C NMR (DMSO-d$_6$) δ 172.7, 169.9, 157.0, 152.6, 135.9, 131.4, 130.1, 129.9, 129.8, 128.7, 114.1, 79.8, 66.9, 64.7, 61.7, 53.5, 49.3, 35.6, 34.8, 27.9, 27.6; MS (ESI+) for $C_{25}H_{28}Cl_2N_2O_6S$ m/z 554.9 (M+H)$^+$; MS (ESI−) for $C_{25}H_{28}Cl_2N_2O_6S$ m/z 552.8 (M−H)$^−$; Anal. Calcd for $C_{25}H_{28}Cl_2N_2O_6S \cdot 0.27H_2O$: C, 53.59; H, 5.13; N, 5.00. Found: C, 53.97; H, 5.14; N, 4.96. % Water (KF): 0.86.

EXAMPLE 42

4-[(2,6-Dichlorobenzoyl)amino]-N-[[(4S)-3-ethylsulfonyl)thiazolidinyl]carbonyl]-L-phenylalanine Methyl Ester (Scheme A, A-7: where $R_{A-1}$ and $R_{A-2}$ are the same and equal to H, $R_1$ is ethyl, Y is SO$_2$, $R_5$ is 4-[(2,6-dichlorobenzoyl)amino]phenyl and stereochemistry is (S,S)).

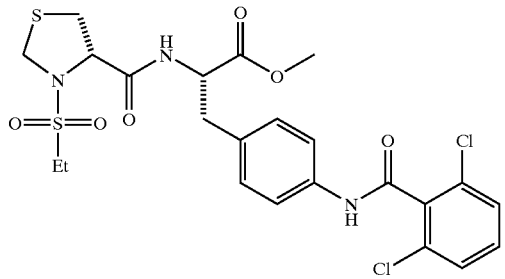

Example 42 was prepared as described in Scheme A from D-cysteine using ethanesulfonyl chloride to form the requisite sulfonamide. Physical data as follows: IR (mull) 1743, 1666, 1605, 1561, 1535, 1515, 1432, 1413, 1328, 1269, 1219, 1195, 1146, 799, 782 cm$^{-1}$; $^1$H NMR (CDCl$_3$) δ 7.58 (2H), 7.46 (1H), 7.32 (3H), 7.17 (2H), 7.07 (1H), 4.85 (1H), 4.73 (2H), 4.28 (1H), 3.76 (3H), 3.54 (1H), 3.26 (1H), 3.05 (4H), 1.40 (3H); $^{13}$C NMR (CDCl$_3$) δ 171.3, 168.2, 162.4, 136.4, 135.8, 132.4, 132.3, 131.0, 130.1, 128.2, 120.6, 64.9, 53.2, 52.6, 51.5, 45.8, 37.13, 4.2, 31.0, 29.3, 7.7; MS (ESI+) for $C_{23}H_{25}Cl_2N_3O_6S_2$ m/z 573.9 (M+H)$^+$; MS (ESI−) for $C_{23}H_{25}Cl_2N_3O_6S_2$ m/z 571.7 (M−H)$^−$; HRMS (FAB) calcd for $C_{23}H_{25}Cl_2N_3O_6S_2+H_1$ 574.0640, found 574.0634; Anal. Calcd for $C_{23}H_{25}Cl_2N_3O_6S_2 \cdot 0.1H_2O$: C, 47.97; H, 4.40; N, 7.30. Found: C, 48.36; H, 4.59; N, 6.80.

EXAMPLE 43

4-[(2,6-Dichlorobenzoyl)amino]-N-[[(4S)-3-ethylsulfonyl)-4-thiazolidinyl]carbonyl]-L-phenylalanine (Scheme A, A-8: where $R_{A-1}$ and $R_{A-2}$ are the same and equal to H, $R_1$ is ethyl, Y is SO$_2$, $R_5$ is 4-[(2,6-dichlorobenzoyl)amino]phenyl and stereochemistry is (S,S)).

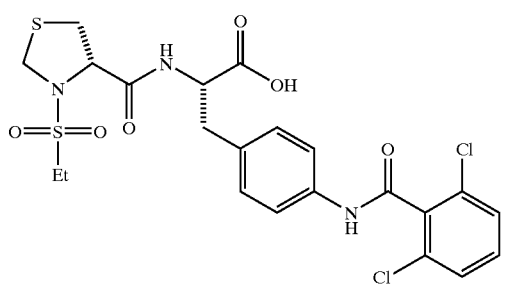

Example 43 was prepared from example 42 by the procedure described in preparation 6. Physical data as follows: IR (mull) 1734, 1664, 1605, 1562, 1536, 1516, 1432, 1414, 1330, 1272, 1234, 1195, 1146, 799, 781 cm$^{-1}$; $^1$H NMR (DMSO-d$_6$) δ 12.91 (1H), 10.65 (1H), 8.15 (1H), 7.51 (5H), 7.17 (2H), 4.77 (2H), 4.43 (1H), 4.29 (1H), 3.94 (6H), 1.20

(3H); $^{13}$C NMR (DMSO-d$_6$) δ 172.5, 168.9, 161.9, 137.1, 136.5, 133.2, 131.4, 131.3, 129.8, 128.3, 119.3, 63.7, 53.6, 51.4, 45.3, 36.1, 34.7; MS (ESI+) for C$_{22}$H$_{23}$Cl$_2$N$_3$O$_6$S$_2$ m/z 559.9 (M+H)$^+$; MS (ESI−) for C$_{22}$H$_{23}$Cl$_2$N$_3$O$_6$S$_2$ m/z 557.8 (M−H)$^−$; HRMS (FAB) calcd for C$_{22}$H$_{23}$Cl$_2$N$_3$O$_6$S$_2$+H$_1$ 560.0483, found 560.0488; Anal. Calcd for C$_{22}$H$_{23}$Cl$_2$N$_3$O$_6$S$_2$.0.72H$_2$O: C, 46.08; H, 4.30; N, 7.33. Found: C, 46.42; H, 4.37; N, 7.01. % Water (KF): 2.26.

EXAMPLE 44

4-[(2,6-Dichlorobenzoyl)amino]-N-[[(4S)-3-[[5-(trifluoromethyl)-2-pyridinyl]sulfonyl]-4-thiazolidinyl]carbonyl]-L-phenylalanine Methyl Ester (Scheme A, A-7: where R$_{A-1}$ and R$_{A-2}$ are the same and equal to H, R$_3$ is 2-(5-triflouromethylpyridyl), Y is SO$_2$, R$_5$ is 4-[(2,6-dichlorobenzoyl)amino]phenyl and stereochemistry is (S,S)).

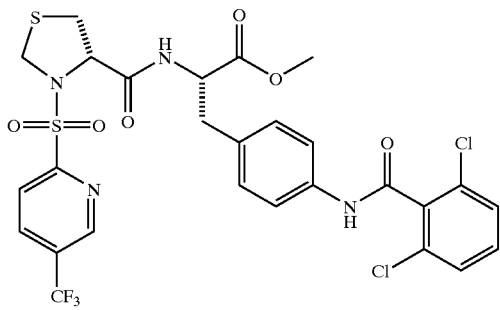

Example 44 was prepared as described in Scheme A from D-cysteine using 2-(5-triflouromethylpyridyl)sulfonyl chloride to form the requisite sulfonamide. Physical data as follows: IR (mull) 1745, 1668, 1603, 1535, 1515, 1432, 1413, 1327, 1219, 1179, 1142, 1108, 1073, 1016, 616 cm$^{-1}$; $^1$H NMR (CDCl$_3$) δ 8.76 (1H), 8.17 (2H), 7.90 (1H), 7.51 (2H), 7.32 (4H), 7.17 (2H), 5.18 (1H), 4.96 (1H), 4.66 (1H), 4.31 (1H), 3.78 (3H), 3.52 (1H), 3.15 (3H); $^{13}$C NMR (CDCl$_3$) δ 171.3, 168.4, 162.2, 147.2, 136.2, 136.0, 132.4, 131.0, 130.3, 128.2, 123.0, 120.4, 120.3, 65.7, 53.6, 52.5, 51.4, 37.3, 34.0; MS (ESI+) for C$_{27}$H$_{23}$Cl$_2$F$_3$N$_4$O$_6$S$_2$ m/z 690.8 (M+H)$^+$; MS (ESI+) for C$_{27}$H$_{23}$Cl$_2$F$_3$N$_4$O$_6$S$_2$ m/z 712.9 (M+Na)$^+$; Anal. Calcd for C$_{27}$H$_{23}$Cl$_2$F$_3$N$_4$O$_6$S$_2$.0.2H$_2$O: C, 46.68; H, 3.39; N, 8.06. Found: C, 46.60; H, 3.52; N, 7.92. % Water (KF): 0.47.

EXAMPLE 45

4-[(2,6-Dichlorobenzoyl)amino]-N-[[(4S)-3-[[5-(trifluoromethyl)-2-pyridinyl]sulfonyl-4-thiazolidinyl]carbonyl]-L-phenylalanine (Scheme A, A-8: where R$_{A-1}$ and R$_{A-2}$ are the same and equal to H, R$_3$ is 2-(5-triflouromethylpyridyl), Y is SO$_2$, R$_5$ is 4-[(2,6-dichlorobenzoyl)amino]phenyl and stereochemistry is (S,S)).

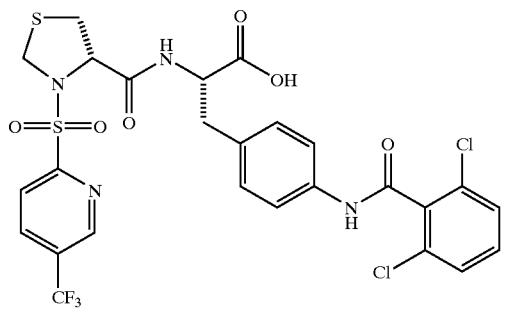

Example 45 was prepared from example 44 by the procedure described in preparation 6. Physical data as follows: IR (mull) 1740, 1666, 1602, 1562, 1533, 1517, 1432, 1354, 1327, 1179, 1143, 1108, 1074, 1016, 613 cm$^{-1}$; $^1$H NMR (DMSO-d$_6$) δ 10.63 (1H), 9.24 (1H), 8.54 (1H), 8.46 (1H), 8.18 (1H), 7.50 (5H), 7.17 (2H), 5.00 (1H), 4.74 (1H), 4.42 (2H), 3.04 (2H), 2.90 (1H), 2.78 (1H); $^{13}$C NMR (DMSO-d$_6$) δ 172.8, 168.9, 162.3, 159.0, 147.8, 137.5, 137.4, 136.9, 133.5, 131.8, 131.7, 130.2, 128.7, 123.8, 119.7, 64.7, 53.9, 52.3, 36.7, 35.1; MS (ESI+) for C$_{26}$H$_{21}$Cl$_2$F$_3$N$_4$O$_6$S$_2$ m/z 676.5 (M+H)$^+$; MS (ESI−) for C$_{26}$H$_{21}$Cl$_2$F$_3$N$_4$O$_6$S$_2$ m/z 674.5 (M−H)$^−$; Anal. Calcd for C$_{26}$H$_{21}$Cl$_2$F$_3$N$_4$O$_6$S$_2$.0.33: C, 45.69; H, 3.20; N, 8.20. Found: C, 45.81; H, 3.38; N, 8.13. % Water (KF): 0.88.

EXAMPLE 46

4-[(2,6-Dichlorobenzoyl)amino]-N-[[(4S)-3-(phenylsulfonyl)-4-thiazolidinyl]carbonyl]-L-phenylalanine Methyl Ester (Scheme A, A-7: where R$_{A-1}$ and R$_{A-2}$ are the same and equal to H, R$_3$ is phenyl, Y is SO$_2$, R$_5$ is 4-[(2,6-dichlorobenzoyl)amino]phenyl and stereochemistry is (S,S)).

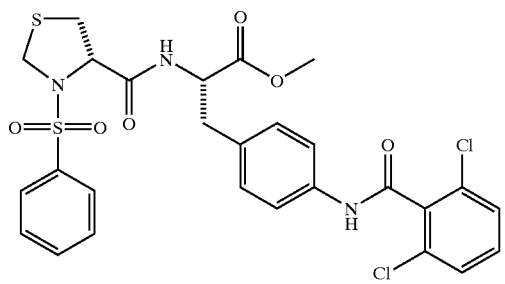

Example 46 was prepared as described in Scheme A from D-cysteine using benzenesulfonyl chloride to form the requisite sulfonamide. Physical data as follows: IR (mull) 1744, 1668, 1604, 1531, 1515, 1432, 1413, 1355, 1324, 1268, 1220, 1195, 1167, 1090, 730 cm$^{-1}$; $^1$H NMR (CDCl$_3$) δ 7.84 (2H), 7.65 (5H), 7.45 (1H), 7.30 (6H), 4.90 (1H), 4.63 (2H), 4.37 (1H), 3.75 (3H), 3.32 (1H), 3.15 (2H), 2.53 (1H); $^{13}$C NMR (CDCl$_3$) δ 171.2, 168.2, 162.4, 136.4, 136.3, 134.1, 132.4, 131.0, 130.2, 129.6, 128.2, 128.1, 127.9, 120.6, 65.3, 53.3, 52.6, 51.8, 37.4, 33.3; MS (ESI+) for C$_{27}$H$_{25}$Cl$_2$N$_6$O$_6$S$_2$ m/z 621.8 (M+H)$^+$; MS (ESI−) for C$_{27}$H$_{25}$Cl$_2$N$_6$O$_6$S$_2$ m/z 619.8 (M−H)$^−$; Anal. Calcd for C$_{27}$H$_{25}$Cl$_2$N$_6$O$_6$S$_2$.0.2H$_2$O: C, 51.84; H, 4.18; N, 6.72. Found: C, 51.72; H, 4.18; N, 6.52. % Water (KF): 0.48.

EXAMPLE 47

4[(2,6-Dichlorobenzoyl)amino]-N-[[(4S)-3-phenylsulfonyl)-4-thiazolidinyl]carbonyl]-L-phenylalanine (Scheme A, A-8: where $R_{A-1}$ and $R_{A-2}$ are the same and equal to H, $R_3$ is phenyl, Y is $SO_2$, $R_5$ is 4-[(2,6-dichlorobenzoyl)amino]phenyl and stereochemistry is (S,S)).

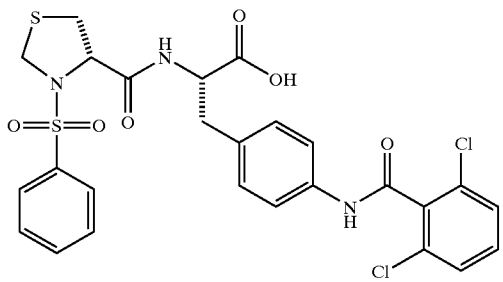

Example 47 was prepared from example 46 by the procedure described in preparation 6. Physical data as follows: IR (mull) 1735, 1666, 1605, 1562, 1533, 1516, 1432, 1414, 1352, 1328, 1195, 1180, 1167, 1090,731 cm$^{-1}$; $^1$H NMR (CDCl$_3$) δ 8.11 (1H), 7.82 (2H), 7.66 (3H), 7.56 (2H), 7.23 (6H), 4.91 (1H), 4.66 (1H), 4.60 (1H), 4.35 (1H), 3.30 (1H), 3.19 (2H), 2.59 (1H); $^{13}$C NMR (DMSO-d$_6$) δ 172.2, 168.2, 161.7, 137.0, 136.9, 136.3, 133.6, 133.0, 131.2, 131.1, 129.6, 129.3, 128.1, 127.6, 119.2, 63.9, 53.4, 51.5, 48.4, 36.0, 33.8; MS (ESI+) for $C_{26}H_{23}Cl_2N_3O_6S_2$ m/z 607.9 (M+H)$^+$; MS (FAB) m/z (rel. intensity) 608 (MH+, 85), 610 (67), 608 (85), 466 (30), 371 (41), 228 (38), 193 (38), 149 (30), 129 (31), 118 (99), 63 (35); HRMS (FAB) calcd for $C_{26}H_{23}Cl_2N_3O_6S_2+H_1$ 608.0483, found 608.0491; Anal. Calcd for $C_{26}H_{23}Cl_2N_3O_6S_2$.0.27H$_2$O: C, 50.91; H, 3.87; N, 6.85. Found: C, 50.68; H, 4.05; N, 6.65. % Water (KF): 0.79.

EXAMPLE 48

4-[(2,6-Dichlorobenzoyl)amino]-N-[[(4S)-3-[[5-(dimethylamino)-1-naphthalenyl]sulfonyl]-4-thiazolidinyl]carbonyl]-L-phenylalanine Methyl Ester (Scheme A, A-7: where $R_{A-1}$ and $R_{A-2}$ are the same and equal to H, $R_1$ is 5-dimethylamino-1-naphthyl, Y is $SO_2$, $R_5$ is 4-[(2,6-dichlorobenzoyl)amino]phenyl and stereochemistry is (S,S)).

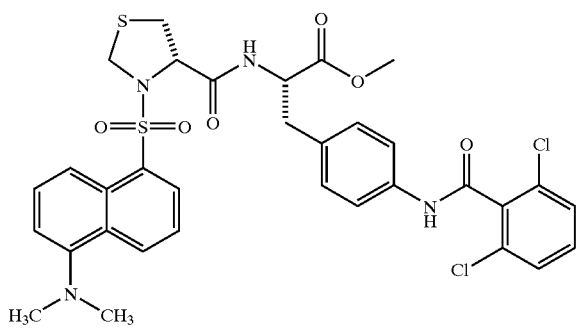

Example 48 was prepared as described in Scheme A from D-cysteine using 5-dimethylamino-1-napthalenesulfonyl chloride to form the requisite sulfonamide. Physical data as follows: IR (mull) 1744, 1684, 1605, 1562, 1533, 1515, 1431, 1412, 1350, 1324, 1231, 1202, 1163, 1145, 798 cm$^{-1}$; $^1$H NMR (CDCl$_3$) δ 8.64 (1H), 8.34 (2H), 7.53 (5H), 7.29 (4H), 6.87 (3H), 4.93 (1H), 4.75 (1H), 4.64 (1H), 4.31 (1H), 3.69 (3H), 3.47 (1H), 2.84 (8H), 2.46 (1H); $^{13}$C NMR (CDCl$_3$) δ 171.2, 167.7, 162.5, 136.3, 135.9, 132.4, 132.3, 131.9, 131.5, 131.0, 130.1, 129.7, 129.2, 128.2, 124.4, 120.4, 65.1, 53.3, 52.5, 50.1, 45.9, 37.1, 33.3; MS (ESI+) for $C_{33}H_{32}Cl_2N_4O_6S_2$ m/z 736.8 (M+Na)$^+$; Anal. Calcd for $C_{33}H_{32}Cl_2N_4O_6S_2$.0.17H$_2$O: C, 55.15; H, 4.54; N, 7.79. Found: C, 55.20; H, 4.73; N, 7.49. % Water (KF): 0.43.

EXAMPLE 49

4-[(2,6-Dichlorobenzoyl)amino]-N-[[(4S)-3-[[5-(dimethylamino)-1-naphthalenyl]sulfonyl]-4-thiazolidinyl]carbonyl]-L-phenylalanine (Scheme A, A-8: where $R_{A-1}$ and $R_{A-2}$ are the same and equal to H, $R_3$ is 5-dimethylamino-1-naphthyl, Y is $SO_2$, $R_5$ is 4-[(2,6-dichlorobenzoyl)amino]phenyl and stereochemistry is (S,S)).

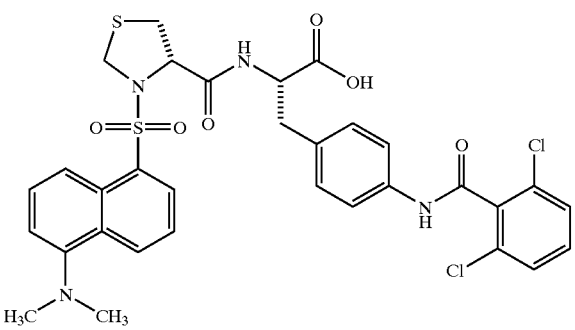

Example 49 was prepared from example 48 by the procedure described in preparation 6. Physical data as follows: IR (mull) 1666, 1605, 1587, 1577, 1562, 1532, 1516, 1431, 1412, 1395, 1325, 1163, 1145, 798, 631 cm$^{-1}$; $^1$H NMR (DMSO-d$_6$) δ 10.60 (1H), 8.54 (1H), 8.28 (2H), 7.54 (8H), 7.25 (1H), 6.93 (2H), 4.95 (1H), 4.84 (1H), 4.39 (1H), 4.17 (1H), 2.95 (2H), 2.80 (7H), 2.54 (1H); $^{13}$C NMR (DMSO-d$_6$) δ 167.2, 161.7, 151.4, 136.6, 136.3, 133.6, 133.1, 131.1, 130.8, 130.3, 129.5, 129.3, 129.0, 128.8, 128.1, 123.6, 118.9, 118.3, 115.3, 63.6, 54.2, 50.3, 44.9, 36.7, 33.9, 21.0; MS (ESI+) for $C_{32}H_{30}Cl_2N_4O_6S_2$ m/z 700.8 (M+H)$^+$; HRMS (FAB) calcd for $C_{32}H_{30}Cl_2N_4O_6S_2+H_1$ 701.1062, found 701.1039.

EXAMPLE 50

O-[(2,6-Dichlorophenyl)methyl]-N-[[(4S)-3-(methylsulfonyl)-4-thiazolidinyl]carbonyl]-L-tyrosine Methyl Ester (Scheme A, A-7: where $R_{A-1}$ and $R_{A-2}$ are the same and equal to H, $R_3$ is methyl, Y is $SO_2$, $R_5$ is 4-[(2,6-dichlorophenyl)methoxy]phenyl and stereochemistry is (S,S)).

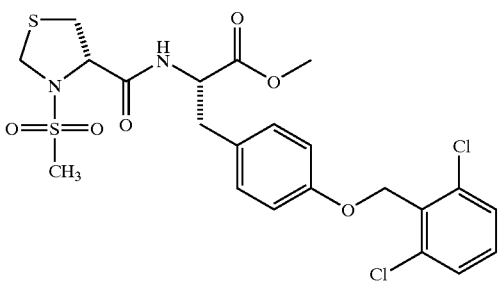

Example 50 was prepared as described in Scheme A from D-cysteine using methanesulfonyl chloride to form the requisite sulfonamide. Physical data as follows: IR (mull) 1742, 1680, 1611, 1564, 1510, 1439, 1345, 1299, 1240, 1179, 1158, 1016, 976, 779, 768 cm$^{-1}$; $^1$H NMR (CDCl$_3$) δ 7.36 (2H), 7.24 (1H), 7.08 (3H), 6.97 (2H), 5.25 (2H), 4.77 (3H), 4.29 (1H), 3.74 (3H), 3.43 (1H), 3.53 (1H), 3.10 (2H), 2.93 (3H); $^{13}$C NMR (CDCl$_3$) δ 171.4, 168.0, 158.2, 137.0, 132.1, 130.3, 128.5, 127.9, 115.3, 65.2, 65.0, 59.4, 53.5, 53.3, 52.5, 51.9, 42.2, 37.3, 36.9, 34.2; MS (ESI+) for C$_{22}$H$_{24}$Cl$_2$N$_2$O$_6$S$_2$ m/z 546.8 (M+H)$^+$; MS (ESI+) for C$_{22}$H$_{24}$Cl$_2$N$_2$O$_6$S$_2$ m/z 568.8 (M+H)$^+$; HRMS (EI) calcd for C$_{22}$H$_{24}$Cl$_2$N$_2$O$_6$S$_2$ 546.0453, found 546.0448; Anal. Calcd for C$_{22}$H$_{24}$Cl$_2$N$_2$O$_6$S$_2$·0.07H$_2$O: C, 48.15; H, 4.43; N, 5, 10. Found: C, 48.17; H, 4.51; N, 5.02. % Water (KF): 0.24.

EXAMPLE 51

O-[(2,6-Dichlorophenyl)methyl]-N-[[(4S)-3-(methylsulfonyl)-4-thiazolidinyl]carbonyl]-L-tyrosine (Scheme A, A-8: where R$_{A-1}$ and R$_{A-2}$ are the same and equal to H, R$_1$ is methyl, Y is SO$_2$, R$_5$ is 4-[(2,6-dichlorophenyl)methoxy)phenyl and stereochemistry is (S,S)).

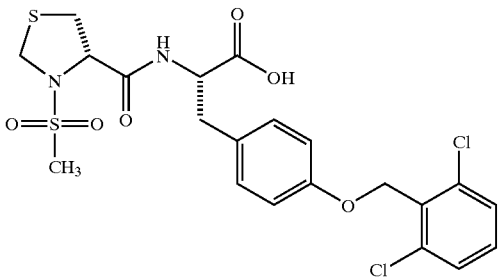

Example 51 was prepared from example 50 by the procedure described in preparation 6. Physical data as follows: IR (mull) 1737, 1675, 1611, 1565, 1511, 1439, 1345, 1300, 1241, 1197, 1179, 1157, 1016, 778, 769 cm$^{-1}$; $^1$H NMR (CDCl$_3$) δ 7.34 (2H), 7.16 (5H), 6.99 (2H), 5.23 (2H), 4.85 (1H), 4.68 (2H), 4.27 (1H), 3.51 (1H), 3.32 (1H), 3.15 (2H), 2.93 (3H); $^{13}$C NMR (CDCl$_3$) δ 174.8, 168.7, 158.3, 137.0, 132.1, 130.5, 130.4, 128.5, 127.6, 115.4, 115.2, 65.2, 64.9, 53.1, 52.0, 37.1, 36.4, 34.3; MS (ESI+) for C$_{21}$H$_{22}$Cl$_2$N$_2$O$_6$S$_2$ m/z 532.8 (M+H)$^+$; MS (ESI−) for C$_{21}$H$_{22}$Cl$_2$N$_2$O$_6$S$_2$ m/z 530.7 (M−H)$^-$; HRMS (FAB) calcd for C$_{21}$H$_{22}$Cl$_2$N$_2$O$_6$S$_2$+H$_1$ 533.0374, found 533.0386; Anal. Calcd for C$_{21}$H$_{22}$Cl$_2$N$_2$O$_6$S$_2$·0.06H$_2$O: C, 47.19; H, 4.17; N, 5.24. Found: C, 47.58; H, 4.35; N, 5.10. % Water (KF): 0.20.

EXAMPLE 52

4-[(2,6-Dichlorobenzoyl)amino]-N-[[(4S)-3-[[(1,1-dimethylethyl)amino]carbonyl]-4-thiazolidinyl]carbonyl]-L-phenylalanine (Scheme A, A-8: where R$_{A-1}$ and R$_{A-2}$ are the same and equal to H, R$_3$ is t-butyl, Y is CONH—, R$_5$ is 4-[(2,6-dichlorobenzoyl)amino]phenyl and stereochemistry is (S,S)).

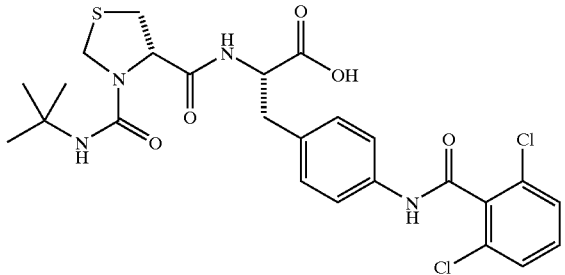

Example 52 was prepared from example 6 by the procedure described in preparation 6. Physical properties as follows: IR (mull) 3289, 1728, 1664, 1607, 1580, 1561, 1536, 1432, 1414, 1394, 1326, 1270, 1242, 1213, 1195 cm$^{-1}$; $^1$H NMR (300 MHz, CD$_3$OD) δ 7.47 (2H), 7.24 (3H), 7.04 (2H), 4.63 (2H), 4.37 (1H), 4.17 (1H), 3.09 (4H), 1.22 (9H); $^{13}$C NMR (75 MHz, CDCl$_3$) δ 176.9, 174.8, 167.2, 159.9, 140.5, 140.0, 136.4, 136.1, 134.6, 133.8, 131.8, 124.5, 66.6, 57.1, 55.3, 53.0, 40.1, 37.1 32.9; MS (ESI+) for C$_{25}$H$_{28}$Cl$_2$N$_4$O$_5$S m/z 566.9 (M+H)$^+$, 588.9 M+Na)$^+$; MS (ESI+) for C$_{25}$H$_{28}$Cl$_2$N$_4$O$_5$S m/z 566.9 (M+H)$^+$; HRMS (FAB) calcd for C$_{25}$H$_{28}$Cl$_2$N$_4$O$_5$S+H1 567.1235, found 567.1253.

EXAMPLE 53

4-[(2,6-Dichlorobenzoyl)amino]-N-[[(4S)-3-[(diethylamino)carbonyl]-4-thiazolidinyl]carbonyl]-L-phenylalanine (Scheme A, A-8: where R$_{A-1}$ and R$_{A-2}$ are the same and equal to H, R$_3$ is ethyl, Y is CON(CH$_2$CH$_3$)—, R$_5$ is 4-[(2,6-dichlorobenzoyl)amino]phenyl and stereochemistry is (S,S)).

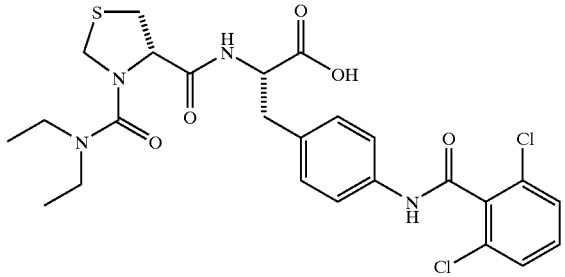

Example 53 was prepared from example 7 by the procedure described in preparation 6. Physical properties as follows: IR (mull) 3269, 1734, 1663, 1607, 1562, 1535, 1515, 1431, 1415, 1348, 1325, 1269, 1213, 1195, 799 cm$^{-1}$; $^1$H NMR (300 MHz, CD$_3$OD) δ 7.57 (2H), 7.35 (3H), 7.09 (2H), 5.09 (1H), 4.76 (1H), 4.38 (2H), 3.31 (3H), 3.13 (5H), 1.05 (6H); $^{13}$C NMR (75 MHz, CD$_3$OD) δ 176.6, 173.9, 167.1, 166.3, 140.7, 140.1, 136.1, 134.6, 133.8, 131.8, 124.1, 68.5, 57.4, 56.6, 45.9, 40.4, 36.6, 16.8; MS (ESI+) for $C_{25}H_{28}Cl_2N_4O_5S$ m/z 567.1 $(M+H)^+$; Anal. Calcd for $C_{25}H_{28}Cl_2N_4O_5S$: C, 52.91; H, 4.97; N, 9.87. Found: C, 52.60; H, 5.13; N, 9.47.

EXAMPLE 54

4-[(2,6-Dichlorobenzoyl)amino]-N-[[(4S)-3-[[methyl[2-(2-pyridinyl)ethyl]amino]carbonyl]-4-thiazoidinyl]carbonyl]-L-phenylalanine Methyl Ester (Scheme A, A-7: where $R_{A-1}$ and $R_{A-2}$ are the same and equal to H, $R_3$ is 2-(2-pyridyl)ethyl, Y is $CON(CH_3)$—, $R_5$ is 4-[(2,6-dichlorobenzoyl)amino]phenyl and stereochemistry is (S,S)).

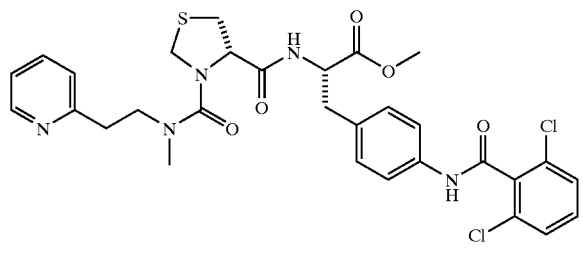

Example 54 was prepared as described in Scheme A from D-cysteine using 2-(2-methylaminoethyl)pyridine to form the requisite urea. Physical data as follows: mp 80–90° C. (dec); IR (mull) 1743, 1665, 1606, 1561, 1538, 1514, 1489, 1432, 1413, 1395, 1323, 1268, 1216, 1195, 799 cm$^{-1}$; $^1$H NMR (300 MHz, DMSO-d$_6$) δ 8.44 (1H), 8.34 (1H), 7.66 (1H), 7.51 (5H), 7.19 (4H), 4.72 (1H), 4.48 (1H), 4.40 (1H), 4.20 (1H), 3.85 (4H), 3.42 (1H), 3.89 (10H); $^{13}$C NMR (75 MHz, DMSO-d$_6$) δ 172.1, 170.3, 162.3, 161.8, 159.4, 149.4, 137.6, 137.0, 136.8, 133.3, 131.8, 131.7, 130.0, 128.7, 123.8, 122.0. 119.8, 64.58, 53.8, 52.7, 52.5, 49.7, 36.5, 36.2, 35.7, 33.4; MS (ESI+) for $C_{30}H_{31}Cl_2N_5O_5S$ m/z 643.9 $(M+H)^+$; Anal. Calcd for $C_{30}H_{31}Cl_2N_5O_5S$: C, 55.90; H, 4.85; N, 10.86. Found: C, 55.52; H, 5.09; N, 10.64.

EXAMPLE 55

4-[(2,6-Dichlorobenzoyl)amino]-N-[[(4S)-3-[[methyl[2-(2-pyridinyl)ethyl]amino]carbonyl]-4-thiazolidinyl]carbonyl]-L-phenylalanine (Scheme A, A-8: where $R_{A-1}$ and $R_{A-2}$ are the same and equal to H, $R_3$ is 2-(2-pyridyl)ethyl, Y is $CON(CH_3)$—, $R_5$ is 4-[(2,6-dichlorobenzoyl)amino]phenyl and stereochemistry is (S,S)).

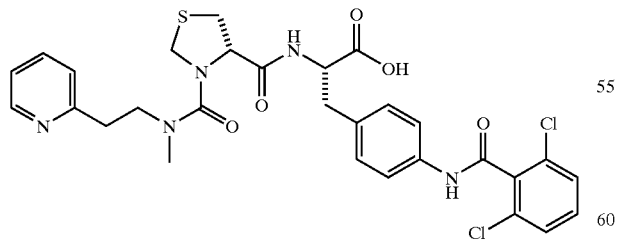

Example 55 was prepared from example 54 by the procedure described in preparation 6. Physical data as follows: IR (mull) 1682, 1656, 1606, 1561, 1540, 1513, 1432, 1413, 1398, 1323, 1268, 1242, 1195 799, 780 cm$^{-1}$; $^1$H NMR (300 MHz, DMSO-d$_6$) δ 10.66 (1H), 8.45 (1H), 8.09 (1H), 7.66 (1H), 7.51 (5H), 7.20 (4H), 4.72 (1H), 4.40 (2H), 4.23 (1H), 3.61 (1H), 3.40 (1H), 3.04 (7H), 2.79 (3H); MS (ESI+) for $C_{29}H_{29}Cl_2N_5O_5S$ m/z 629.9 $(M+H)^+$; Anal. Calcd for $C_{29}H_{29}Cl_2N_5O_5S \cdot 0.61H_2O$: C, 54.29; H, 4.75; N, 10.92. Found: C, 54.29; H, 5.00; N, 10.32. % Water (KF): 1.72.

EXAMPLE 56

4-[(2,6-Dichlorobenzoyl)amino]-N-[[(4S)-3-(4-morpholinylcarbonyl)-4-thiazolidinyl]carbonyl]-L-phenylalanine Methyl Ester (Scheme A, A-7: where $R_{A-1}$ and $R_{A-2}$ are the same and equal to H, $R_3$ and Y together form CO-morpholino, $R_5$ is 4-[(2,6-dichlorobenzoyl)amino]phenyl and stereochemistry is (S,S)).

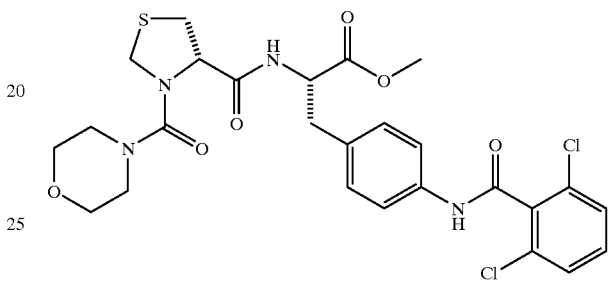

Example 56 was prepared as described in Scheme A from D-cysteine using morpholine to form the requisite urea. Physical data as follows: mp 223–225° C.; $^1$H NMR (300 MHz, DMSO-d$_6$) δ 10.66 (1H), 8.25 (1H), 7.51 (5H), 7.16 (2H), 4.81 (1H), 4.60 (1H), 4.50 (1H), 4.28 (1H), 3.64 (3H), 3.53 (4H), 3.09 (8H); $^{13}$C NMR (75 MHz, DMSO-d$_6$) 172.1, 170.3, 162.3, 161.4, 137.6, 136.8, 133.3, 131.8, 131.7, 130.0, 128.7, 119.8, 66.2, 64.3, 53.8, 52.8, 52.5, 46.8, 36.1, 33.7; HRMS (FAB) calcd for $C_{26}H_{28}Cl_2N_4O_6S+H_1$ 595.1185, found 595.1189; Anal. Calcd for $C_{26}H_{28}Cl_2N_4O_6S$: C, 52.44; H, 4.74; N. 9.41. Found; C, 52.42; H, 4.96; N, 9.23.

EXAMPLE 57

N-[[(4S)-3-[[bis(2-Hydroxyethyl)amino]carbonyl]-4-thiazolidinyl]carbonyl]-4-[(2,6-dichlorobenzoyl)amino]-L-phenylalanine Methyl Ester (Scheme A, A-7: where $R_{A-1}$ and $R_{A-2}$ are the same and equal to H, $R_3$ is 2-hydroxyethyl and Y is CON $(CH_2CH_2OH)$, $R_5$ is 4-[(2,6-dichlorobenzoyl)amino]phenyl and stereochemistry is (S,S)).

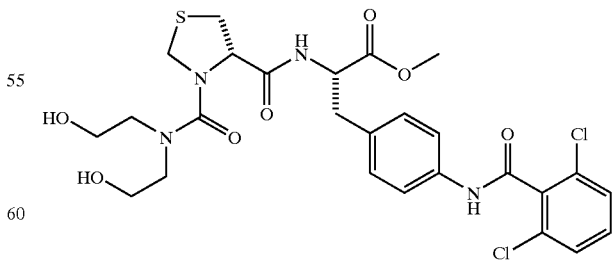

Example 57 was prepared as described in Scheme A from D-cysteine using diethanolamine to form the requisite urea. Physical data as follows: mp 105–107° C.; IR (mull) 3284, 1743, 1662, 1608, 1561, 1539, 1516, 1432, 1414, 1355, 1326, 1270, 1217, 1196, 799 cm$^{-1}$; $^1$H NMR (300 MHz, DMSO-d$_6$) δ 10.69 (1H), 8.28 (1H), 7.56 (4H), 7.47 (1H), 7.16 (2H), 4.87 (3H), 4.66 (1H), 4.47 (1H), 4.25 (1H), 3.63 (3H), 3.47 (6H), 3.02 (6H); MS (ESI+) for C$_{26}$H$_{30}$Cl$_2$N$_4$O$_7$S m/z 612.9 (M+H)$^+$; Anal. Calcd for C$_{26}$H$_{30}$Cl$_2$N$_4$O$_7$S.0.47H$_2$O: C, 50.21; H, 5.01; N, 9.01. Found: C, 50.02; H, 5.00; N, 8.93. % Water (KF): 1.36.

EXAMPLE 58

N-[[(4S)-3-[[bis(2-Hydroxyethyl)amino]carbonyl]thiazoldinyl]carbonyl]-4-[(2,6-dichlorobenzoyl)amino]-L-phenylalanine (Scheme A, A-8: where R$_{A-1}$ and R$_{A-2}$ are the same and equal to H, R$_3$ is 2-hydroxyethyl and Y is CON(CH$_2$CH$_2$OH), R$_5$ is 4-[(2,6-dichlorobenzoyl)amino]phenyl and stereochemistry is (S,S)).

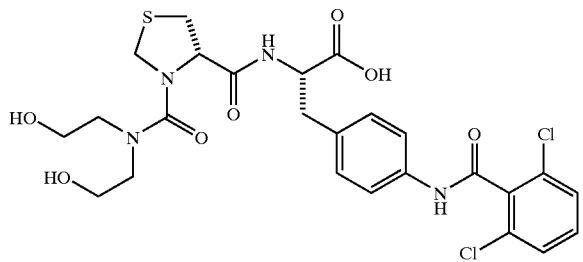

Example 58 was prepared from example 57 by the procedure described in preparation 6. Physical data as follows: IR (mull) 3281, 3196, 1724, 1660, 1608, 1580, 1561, 1542, 1515, 1431, 1415, 1354, 1328, 1271, 1196 cm$^{-1}$; $^1$H NMR (300 MHz, DMSO-d$_6$) δ 10.65 (1H), 8.13 (1H), 7.55 (4H), 7.47 (1H), 7.16 (2H), 4.85 (2H), 4.66 (1H), 4.40 (1H), 4.27 (1H), 3.48 (6H), 3.01 (6H); MS (ESI+) for C$_{25}$H$_{28}$Cl$_2$N$_4$O$_7$S m/z 598.9 (M+H)$^+$; Anal. Calcd for C$_{25}$H$_{28}$Cl$_2$N$_4$O$_7$S.1.04H$_2$O: C, 58.58; H, 4.90; N, 9.06. Found: C, 48.88; H, 5.05; N, 8.79. % Water (KF): 3.02.

EXAMPLE 59

[S-(R*,R*)]-4-[[[1-[4-[(2,6-dichlorobenzoyl)amino]phenyl]methyl]-2-methoxy-2-oxoethyl]amino]carbonyl]-δ-oxo-3-thiazolidinepentanoic Acid 3-Methyl Ester (Scheme A, A-7: where R$_{A-1}$ and R$_{A-2}$ are the same and equal to H, R$_3$ is CH$_2$CH$_2$CH$_2$CO$_2$CH$_3$, Y is CO, R$_5$ is 4-[(2,6-dichlorobenzoyl)amino]phenyl, and stereochemistry is (S,S)).

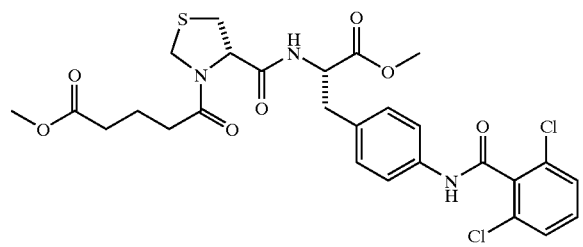

Example 59 was prepared as described in Scheme A from D-cysteine using methyl glutaryl chloride to form the requisite amide. Physical data as follows: IR (mull) 3266, 1741, 1734, 1685, 1678, 1630, 1610, 1560, 1545, 1441, 1435, 1414, 1327, 1268, 1227 cm$^{-1}$; $^1$H NMR (DMSO-d$_6$) δ 10.65 (1H), 8.43 (1H), 7.50 (5H), 7.15 (2H), 4.72 (2H), 4.44 (2H), 3.63 (3H), 3.56 (3H), 3.10 (4H), 2.15 (4H), 1.70 (2H); $^{13}$C NMR (CDCl$_3$) δ 171.6, 170.6, 170.1, 169.9, 169.6, 161.9, 137.2, 136.5, 132.9, 131.3, 129.7, 128.3, 119.4, 61.4, 53.7, 53.5, 52.0, 51.3, 48.7, 36.4, 35.8, 35.1, 33.1, 32.8, 32.5, 25.4, 19.8; MS (ESI+) for C$_{27}$H$_{29}$N$_3$O$_7$SCl$_2$ m/z 610.0 (M+H)$^+$; MS (ESI–) for C$_{27}$H$_{29}$N$_3$O$_7$SCl$_2$ m/z 608.0 (M–H)$^-$; Anal. Calcd for C$_{27}$H$_{29}$N$_3$O$_7$S: C, 53.12; H, 4.79; N, 6.88. Found: C, 52.81; H, 4.90; N, 6.88.

EXAMPLE 60

[S-(R*,R*)]-4-[[[1-Carboxy-2-[4-[(2,6-dichlorobenzoyl)amino]phenyl]ethyl]amino]carbonyl]-δ-oxo-3-thiazolidinepentanoic Acid (Scheme A, A-8: where R$_{A-1}$ and R$_{A-2}$ are the same and equal to H, R$_3$ is CH$_2$CH$_2$CH$_2$CO$_2$H, Y is CO, R$_5$ is 4-[(2,6-dichlorobenzoyl)amino]phenyl, and stereochemistry is (S,S)).

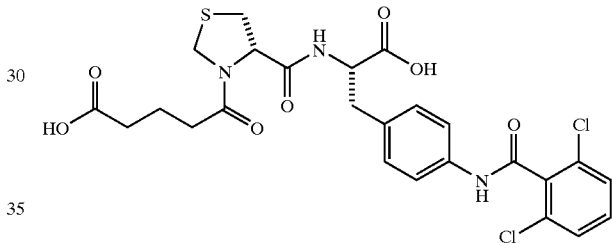

Example 60 was prepared from example 59 by the procedure described in preparation 12. Physical data as follows: IR (mull) 3271, 3193, 3124, 1725, 1661, 1607, 1561, 1539, 1516, 1432, 1414, 1327, 1271, 1195, 799 cm$^{-1}$; $^1$H NMR (DMSO-d$_6$) δ 12.40 (1H), 10.63 (1H), 8.31 (1H), 7.50 (5H), 7.16 (2H), 4.75 (2H), 4.34 (2H), 2.95 (4H), 2.15 (4H), 1.66 (2H); $^{13}$C NMR (CD$_3$CN) δ 175.0, 172.7, 172.6, 171.0, 163.5, 137.8, 137.0, 134.4, 132.7, 132.3, 131.1, 130.9, 129.1, 120.7, 63.2, 54.5, 49.9, 37.2, 34.1, 33.3, 20.7; MS (ESI+) for C$_{25}$H$_{25}$Cl$_2$N$_3$O$_7$S m/z 582.0 (M+H)$^+$; MS (ESI–) for C$_{25}$H$_{25}$Cl$_2$N$_3$O$_7$S m/z 579.9 (M–H)$^-$; Anal. Calcd for C$_{25}$H$_{25}$Cl$_2$N$_3$O$_7$S.H$_2$O: C, 50.01; H, 4.53; N, 7.00. Found: C, 49.61; H, 4.38; N, 6.61.

EXAMPLE 61

N-[[(4S)-3-Acetyl-4-thiazolidinyl]carbonyl]-4-[(2,6-dichlorobenzoyl)amino]-L-phenylalanine Methyl Ester (Scheme A, A-7: where R$_{A-1}$ and R$_{A-2}$ are the same and equal to H, R$_3$ is CH$_3$, Y is CO, R$_5$ is 4-[(2,6-dichlorobenzoyl)amino]phenyl, and stereochemistry is (S,S)).

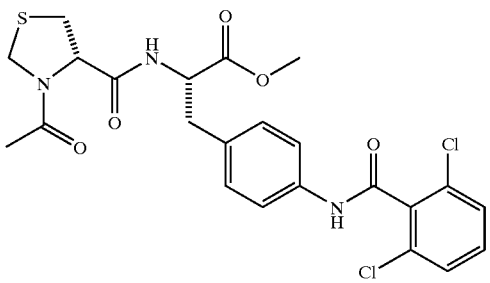

Example 61 was prepared as described in Scheme A from D-cysteine using acetyl chloride to form the requisite amide. Physical data as follows: IR (mull) 3260, 3067, 1748, 1686, 1623, 1608, 1561, 1542, 1515, 1445, 1429, 1419, 1324, 1267, 1221 cm$^{-1}$; $^1$H NMR (DMSO-d$_6$) δ 8.44 (1H), 7.52 (5H), 7.17 (2H), 4.78 (2H), 4.37 (2H), 3.63 (3H), 3.06 (4H), 1.94 (3H); $^{13}$C NMR (DMF-d$_7$) δ 172.4, 170.6, 138.4, 137.5, 133.8, 132.3, 131.9, 130.6, 128.9, 120.0, 70.9, 63.6, 62.4, 54.7, 52.3, 50.2, 49.8, 49.2, 37.2, 36.6, 22.7; MS (ESI+) for C$_{23}$H$_{23}$Cl$_2$N$_3$O$_5$S m/z 523.9 (M+H)$^+$; MS (ESI+) for C$_{23}$H$_{23}$Cl$_2$N$_3$O$_5$S m/z 545.8 (M+Na)$^+$; HRMS (FAB) calcd for C$_{23}$H$_{23}$Cl$_2$N$_3$O$_5$S+H$_1$ 524.0814, found 524.0812; Anal. Calcd for C$_{23}$H$_{23}$Cl$_2$N$_3$O$_5$S.0.1H$_2$O: C, 52.46; H, 4.45; N, 7.98. Found: C, 52.85; H, 4.42; N, 8.00. % Water (KF): 0.24.

EXAMPLE 62

N-[[(4S)-3-Acetyl-4-thiazolidinyl]carbonyl]-4-[(2,6-dichlorobenzoyl)amino]-L-phenylalanine (Scheme A, A-8: where R$_{A-1}$ and R$_{A-2}$ are the same and equal to H, R$_3$ is CH$_3$, Y is CO, R$_5$ is 4-[(2,6-dichlorobenzoyl)amino]phenyl, and stereochemistry is (S,S)).

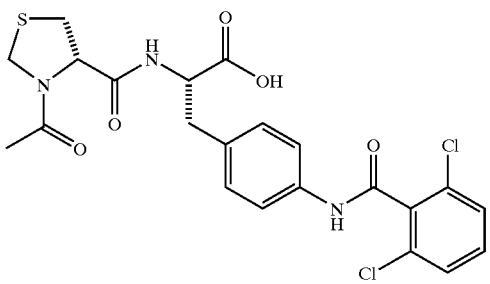

Example 62 was prepared from example 61 by the procedure described in preparation 6. Physical data as follows: IR (mull) 3070, 1747, 1682, 1663, 1625, 1608, 1580, 1561, 1548, 1514, 1443, 1431, 1416, 1278, 1220 cm$^{-1}$; $^1$H NMR (DMSO-d$_6$) δ 12.48 (1H), 10.63 (1H), 8.29 (1H), 7.50 (5H), 4.73 (2H), 4.34 (2H), 2.97 (4H), 1.93 (3H); $^{13}$C NMR (DMSO-d$_6$) δ 172.4, 169.6, 169.2, 168.5, 168.0, 161.7, 136.9, 136.3, 133.2, 133.0, 131.2, 129.6, 128.1, 119.2, 62.2, 61.0, 53.5, 53.3, 49.3, 48.4, 36.3, 35.7, 35.0, 33.1, 22.4, 20.9; MS (ESI–) for C$_{22}$H$_{21}$Cl$_2$N$_3$O$_5$S m/z 507.9 (M–H)$^-$; Anal. Calcd for C$_{22}$H$_{21}$Cl$_2$N$_3$O$_5$S.0.1H$_2$O: C, 51.57; H, 4.18; N, 8.20. Found: C, 51.49; H, 4.36; N, 8.07. % Water (KF): 0.40.

EXAMPLE 63

[S-(R*,R*)]-4-[[[1-Carboxy-2-[4-[(2,6-dichlorobenzoyl)amino]phenyl]ethyl]amino]carbonyl]-5,5-dimethyl-δ-oxo-3-thiazolidinebutanoic Acid (Scheme A, A-8: where R$_{A-1}$ and R$_{A-2}$ are the same and equal to CH$_3$, R$_3$ is CH$_2$CH$_2$CO$_2$H, Y is CO, R$_5$ is 4-[(2,6-dichlorobenzoyl)amino]phenyl, and stereochemistry is (S,S)).

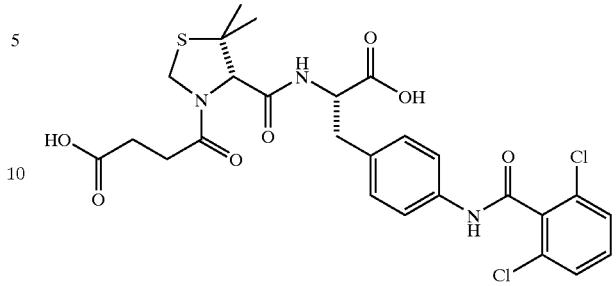

Example 63 was prepared as described in Scheme A from D-penicillamine using methyl succinyl chloride to form the requisite amide. Physical data as follows: IR (mull) 3264, 3198, 3071, 1721, 1660, 1608, 1562, 1541, 1516, 1432, 1415, 1327, 1270, 1195, 799 cm$^{-1}$; $^1$H NMR (DMSO-d$_6$) δ 10.62 (1H), 8.15 (1H), 7.52 (5H), 7.18 (2H), 4.72 (2H), 4.43 (3H), 2.91 (4H), 2.17 (2H), 1.36 (3H), 1.07 (3H); $^{13}$C NMR (DMSO-d$_6$) δ 173.5, 172.6, 170.2, 169.7, 168.4, 168.1, 161.7, 136.9, 136.3, .133.3, 131.1, 129.6, 129.4, 128.1, 119.2, 70.6, 53.8, 53.5, 51.6, 48.4, 47.7, 35.9, 30.7, 30.5, 28.9, 28.6, 24.1; MS (ESI+) for C$_{26}$H$_{27}$Cl$_2$N$_3$O$_7$S m/z 596.0 (M+H)$^+$; MS (ESI+) for C$_{26}$H$_{27}$Cl$_2$N$_3$O$_7$S m/z 617.9 (M+Na)$^+$; MS (ESI–) for C$_{26}$H$_{27}$Cl$_2$N$_3$O$_7$S m/z 593.8 (M–H)$^-$; MS (FAB) m/z (rel. intensity) 596 (MH+, 20), 598 (15), 596 (20), 331 (11), 193 (13), 141 (15), 139 (99), 116 (16), 107 (13), 105 (50), 89 (25); HRMS (FAB) calcd for C$_{26}$H$_{27}$Cl$_2$N$_3$O$_7$S+H$_1$ 596.1025, found 596.1036.

EXAMPLE 64

[S-(R*,R*)]-4-[[[1-Carboxy-2-[4-[(2,6-dichlorophenyl)methoxy]phenyl]ethyl]amino]carbonyl]-γ-oxo-3-thiazolidinebutanoic Acid (Scheme A, A-8: where R$_{A-1}$ and R$_{A-2}$ are the same and equal to H, R$_3$ is CH$_2$CH$_2$CO$_2$H, Y is CO, R$_5$ is 4-[(2,6-dichlorophenyl)methoxy]phenyl, and stereochemistry is (S,S)).

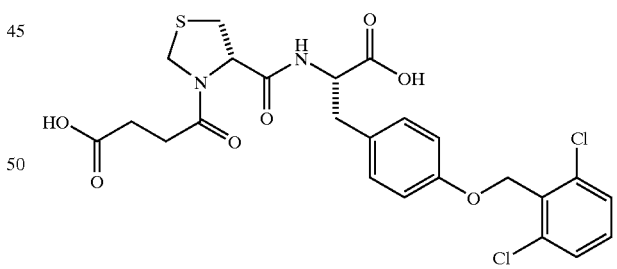

Example 64 was prepared as described in Scheme A from D-cysteine using methyl succinyl chloride to form the requisite amide. Physical data as follows: IR (mull) 3073, 3031, 1725, 1640, 1612, 1585, 1565, 1535, 1511, 1439, 1300, 1241, 1196, 1179, 768 cm$^{-1}$; $^1$H NMR (DMSO-d$_6$) δ 8.26 (1H), 7.53 (2H), 7.44 (1H), 7.12 (2H), 6.93 (2H), 5.16 (2H), 4.75 (2H), 4.40 (2H), 4.20 (1H), 2.81 (4H), 2.32 (2H), 2.07 (1H); $^{13}$C NMR (DMSO-d$_6$) δ 173.8, 172.6, 170.0, 169.3, 157.1, 136.0, 131.5, 130.4, 130.0, 129.8, 128.7, 114.2, 64.8, 61.5, 53.6, 48.5, 36.1, 35.5, 35.0, 33.1, 28.9, 28.6, 21.0; MS (ESI+) for C$_{24}$H$_{24}$Cl$_2$N$_2$O$_5$S m/z 554.8 (M+H)$^+$; MS (ESI–) for C$_{24}$H$_{24}$Cl$_2$N$_2$O$_5$S m/z 552.7

(M–H)⁻; HRMS (FAB) calcd for C₂H₂₄Cl₂N₂O₇S+H₁ 555.0759, found 555.0750.

EXAMPLE 65

N-[[(4S)-3-Acetyl-4-thiazolidinyl]carbonyl]-O-[(2,6-dichlorophenyl)methyl]-L-tyrosine Methyl Ester (Scheme A, A-7: where $R_{A-1}$ and $R_{A-2}$ are the same and equal to H, $R_3$ is $CH_3$, Y is CO, $R_5$ is 4-[(2,6-dichlorophenyl)methoxy]phenyl, and stereochemistry is (S,S)).

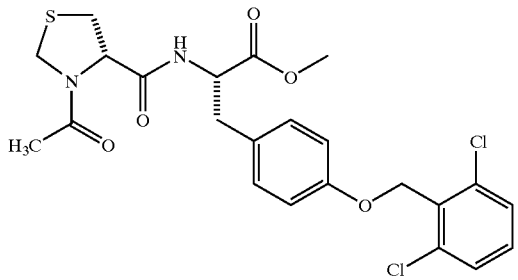

Example 65 was prepared as described in Scheme A from D-cysteine using acetyl chloride to form the requisite amide. Physical data as follows: IR (mull) 1744, 1657, 1612, 1585, 1564, 1511, 1438, 1405, 1352, 1299, 1240, 1197, 1179, 1016, 768 cm⁻¹; ¹H NMR (CDCl₃) δ 7.36 (2H), 7.24 (1H), 6.97 (5H), 5.24 (2H), 5.04 (1H), 4.78 (1H), 4.50 (2H), 3.74 (3H), 3.45 (1H), 3.17 (3H), 2.02 (3H); ¹³C NMR (CDCl₃) δ 172.7, 171.6, 171.4, 169.8, 168.9, 168.7, 157.8, 131.9, 130.3, 129.9, 128.6, 128.4, 114.9, 65.1, 61.6, 56.0, 53.6, 53.3, 49.6, 36.7, 31.7, 22.5; MS (ESI+) for C₂₃H₂₄Cl₂N₂O₅S m/z 532.9 (M+Na)⁺; MS (EI) m/z (rel. intensity) 510 (M+, 1), 338 (42), 337 (12), 336 (63), 267 (12), 265 (18), 163 (10), 161 (63), 159 (99), 130 (9), 88 (43); Anal. Calcd for C₂₃H₂₄Cl₂N₂O₅S.0.19H₂O: C, 53.66; H, 4.77; N, 5.44. Found: C, 53.81; H, 4.75; N, 5.33. % Water (KF): 0.66.

EXAMPLE 66

N-[[(4S)-3-Acetyl-4-thiazolidinyl]carbonyl]-O-[(2,6-dichlorophenyl)methyl]-L-tyrosine (Scheme A, A-8: where $R_{A-1}$ and $R_{A-2}$ are the same and equal to H, $R_3$ is $CH_3$, Y is CO, $R_5$ is 4-[(2,6-dichlorophenyl)methoxy]phenyl, and stereochemistry is (S,S)).

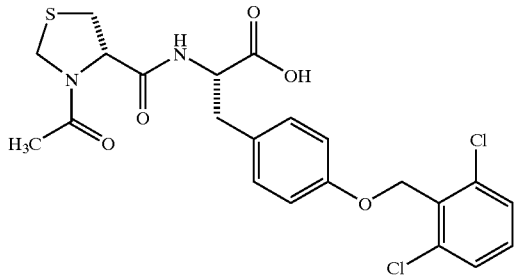

Example 66 was prepared from example 65 by the procedure described in preparation 6. Physical data as follows: IR (mull) 1730, 1646, 1612, 1585, 1565, 1511, 1439, 1414, 1299, 1240, 1196, 1179, 1016, 779, 768 cm⁻¹; ¹H NMR (DMSO-d₆) δ 8.26 (1H), 7.54 (2H), 7.44 (1H), 7.13 (2H), 6.92 (2H), 5.16 (2H), 4.72 (2H), 4.31 (2H), 2.91 (5H), 1.92 (3H); ¹³C NMR (DMSO-d₆) δ 172.6, 169.2, 168.0, 157.1, 136.0, 131.7, 131.5, 130.3, 128.7, 114.2, 64.8, 62.2, 61.0, 53.7, 49.4, 48.5, 36.1, 35.5, 35.1, 33.2, 22.4, 21.0; MS (ESI+) for C₂₂H₂₂Cl₂N₂O₅S m/z 496.9 (M+H)⁺; MS (ESI–) for C₂₂H₂₂Cl₂N₂O₅S m/z 494.8 (M–H)⁻; MS (FAB) m/z (rel. intensity) 497 (MH+, 99), 617 (29), 573 (12), 539 (25), 500 (11), 499 (78), 498 (38), 497 (99), 496 (11), 225 (62), 130 (14); HRMS (FAB) calcd for C₂₂H₂₂Cl₂N₂O₅S+H₁ 497.0705, found 497.0713; Anal. Calcd for C₂₂H₂₂Cl₂N₂O₅S.0.41H₂O: C, 52.35; H, 4.56; N, 5.55. Found: C, 52.65; H, 4.51; N, 5.50. % Water (KF): 1.46.

EXAMPLE 67

[R-(R*,S*)]-4-[[[1-Carboxy-2-[4-[(2,6-dichlorobenzoyl)amino]phenyl]ethyl]amino]carbonyl]-γ-oxo-3-thiazolidinebutanoic Acid (Scheme A, A-8: where $R_{A-1}$ and $R_{A-2}$ are the same and equal to H, $R_3$ is $CH_2CH_2CO_2H$, Y is CO, $R_5$ is 4-[(2,6-dichlorobenzoyl)amino]phenyl, and stereochemistry is (R,S)).

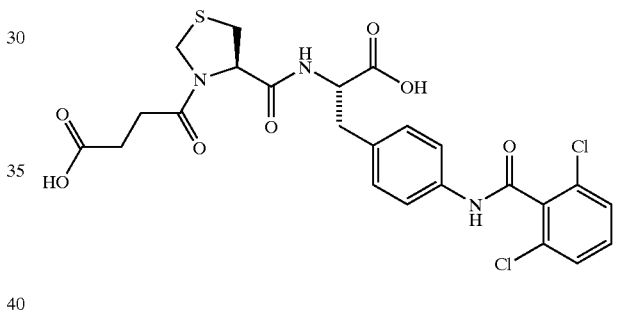

Example 67 was prepared as described in Scheme A from L-cysteine using methyl succinyl chloride to form the requisite amide. Physical data as follows: ¹H NMR (CD₃CN) δ 8.86 (1H), 7.55 (2H), 7.42 (3H), 7.24 (2H), 7.11 (1H), 4.90 (1H), 4.65 (2H), 4.33 (1H), 3.14 (3H), 2.47 (6H), 1.80 (1H); ¹³C NMR (CD₃CN) δ 174.7, 172.6, 172.3, 170.7, 163.4, 137.7, 137.0, 134.4, 132.7, 132.2, 130.9, 129.1, 63.2, 60.9, 54.4, 49.7. 37.1, 36.7, 32.7, 30.6, 30.0, 29.5, 21.1, 14.4; MS (FAB) m/z (rel. intensity) 568 (MH+, 99), 646 (11), 644 (16), 572 (13), 571 (12), 570 (73), 569 (38), 568 (99), 567 (15), 216 (22), 88 (27); Anal. Calcd for C₂₄H₂₃Cl₂N₃O₇S.0.5H₂O: C, 49.92; H, 4.19; N, 7.23. Found: C, 50.01; H, 4.54; N, 7.05.

EXAMPLE 68

[R-(R*,S*)]-4-[[[1-Carboxy-2-[4-[(2,6-dichlorobenzoyl)amino]phenyl]ethyl]amino]carbonyl]-δ-oxo-3-thiazolidinepentanoic Acid (Scheme A, A-8: where $R_{A-1}$ and $R_{A-2}$ are the same and equal to H, $R_3$ is $CH_2CH_2CH_2CO_2H$, Y is CO, $R_5$ is 4-[(2,6-dichlorobenzoyl)amino]phenyl, and stereochemistry is (R,S)).

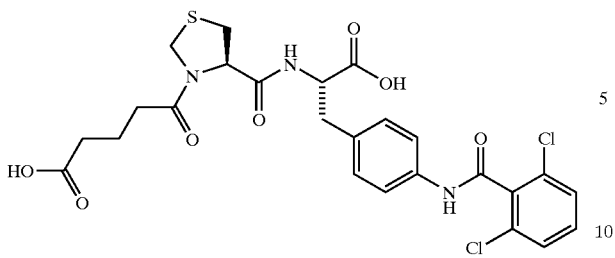

Example 67 was prepared as described in Scheme A from L-cysteine using methyl glutaryl chloride to form the requisite amide. Physical data as follows: $^1$H NMR (CD$_3$CN) δ 8.85 (1H), 7.55 (2H), 7.44 (3H), 7.17 (3H), 4.86 (1H), 4.64 (2H), 4.34 (1H), 3.64 (1H), 3.13 (3H), 2.27 (4H), 1.79 (4H); $^{13}$C NMR (CD$_3$CN) δ 175.0, 172.9, 172.7, 170.6, 163.4, 137.7, 137.0, 134.2, 132.7, 132.2, 131.0, 129.1, 120.7, 68.2, 63.1, 54.2, 49.8, 37.1, 36.9, 34.0, 33.2, 32.6, 26.2, 20.6; MS (FAB) m/z (rel. intensity) 582 (MH+, 99), 585 (12), 584 (68), 583 (35), 582 (99), 581 (11), 88 (23), 69 (8), 57 (9), 55 (11), 43 (11); Anal. Calcd for C$_{25}$H$_{25}$Cl$_2$N$_3$O$_7$S.0.2H$_2$O: C, 51.24; H, 4.37; N, 7.17. Found: C, 51.25; H, 4.68; N, 6.92.

EXAMPLE 69

N-[[(4R)-3-Acetyl-4-thiazolidinyl]carbonyl]-4-[(2,6-dichlorobenzoyl)amino]-L-phenylalanine Methyl Ester (Scheme A, A-7: where R$_{A-1}$ and R$_{A-2}$ are the same and equal to H, R$_3$ is CH$_2$, Y is CO, R$_5$ is 4-[(2,6-dichlorobenzoyl)amino]phenyl, and stereochemistry is (R,S)).

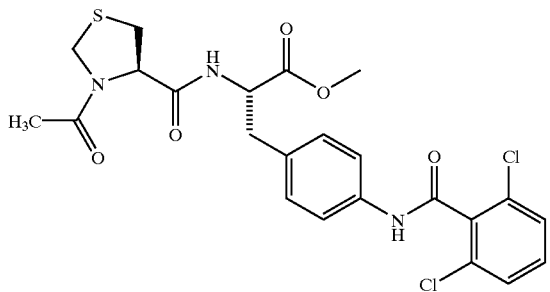

Example 69 was prepared as described in Scheme A from L-cysteine using acetyl chloride to form the requisite amide. Physical data as follows: IR (mull) 3268, 1743, 1662, 1607, 1561, 1538, 1515, 1431, 1413, 1354, 1324, 1270, 1217, 1195, 799 cm$^{-1}$; $^1$H NMR (CDCl$_3$) δ 7.56 (3H), 7.31 (4H), 7.14 (2H), 4.92 (2H), 4.49 (1H), 4.29 (1H), 3.77 (3H), 3.54 (1H), 3.26 (1H), 3.00 (2H), 2.11 (3H); $^{13}$C NMR (CDCl$_3$) δ 171.5, 170.3, 168.9, 152.5, 135.9, 135.7, 132.9, 132.3, 131.0, 130.1, 129.9, 128.2, 128.0, 127.9, 120.4, 63.9, 61.4, 53.1, 52.5, 49.7, 37.0, 31.2, 22.6; MS (ESI+) for C$_{23}$H$_{23}$Cl$_2$N$_3$O$_5$S m/z 523.8 (M+H)$^+$.

EXAMPLE 70

N-[[(4R)-3-Acetyl-4-thiazolidinyl]carbonyl]-4[(2,6-dichlorobenzoyl)amino]-L-phenylalanine (Scheme A, A-8: where R$_{A-1}$ and R$_{A-2}$ are the same and equal to H, R$_3$ is CH$_2$, Y is CO, R$_5$ is 4-[(2,6-dichlorobenzoyl)amino]phenyl, and stereochemistry is (R,S)).

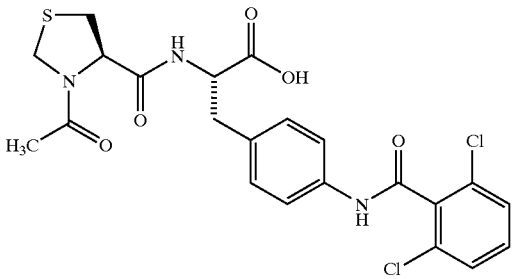

Example 70 was prepared from example 69 by the procedure described in preparation 6. Physical data as follows: IR (mull) 3276, 3068, 1727, 1661, 1607, 1561, 1540, 1516, 1444, 1431, 1414, 1327, 1271, 1218, 1195 cm$^{-1}$; $^1$H NMR (DMSO-d$_6$) 12.78 (1H), 10.67 (1H), 8.27 (1H), 7.49 (4H), 7.19 (2H), 4.75 (2H), 4.45 (3H), 3.01 (3H), 1.96 (3H); $^{13}$C NMR (DMSO-d$_6$) δ 172.6, 172.3, 169.4, 168.6, 168.2, 161.7, 136.9, 136.3, 133.3, 132.8, 131.1, 129.6, 128.1, 119.1, 62.2, 60.9, 53.4, 49.3, 48.7, 35.9, 35.1, 32.7, 22.4; MS (ESI+) for C$_{22}$H$_{21}$Cl$_2$N$_3$O$_5$S m/z 509.8 (M+H)$^+$; MS (ESI−) for C$_{22}$H$_{21}$Cl$_2$N$_3$O$_5$S m/z 507.8 (M−H)$^-$; HRMS (FAB) calcd for C$_{22}$H$_{21}$Cl$_2$N$_3$O$_5$S m/z 509.8 +H$_1$ 510.0657, found 510.0667.

EXAMPLE 71

4-[(2,6-Dichlorobenzoyl)amino]-N-[[(4R)-4-thiazolidinyl]carbonyl]-L-phenylalanine Monohydrochloride Salt (Scheme A, A-10: where R$_{A-1}$ and R$_{A-2}$ are the same and equal to H, R$_5$ is 4-[(2,6-dichlorobenzoyl)amino]phenyl, and stereochemistry is (R,S)).

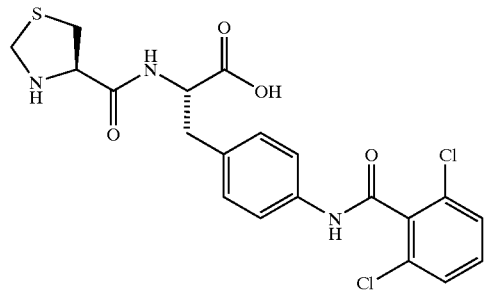

Example 71 was prepared as described in Scheme A from L-cysteine. Physical data as follows: IR (mull) 3249, 3190, 3036, 1729, 1662, 1605, 1578, 1562, 1541, 1516, 1432, 1414, 1328, 1271, 1195 cm$^{-1}$; $^1$H NMR (DMSO-d$_6$) δ 10.71 (1H), 8.83 (1H), 7.56 (5H), 7.24 (2H), 4.50 (1H), 4.25 (1H), 4.21 (2H), 3.62 (1H), 3.01 (4H); $^{13}$C NMR (DMSO-d$_6$) δ 172.0, 166.8, 161.8, 137.7, 132.7, 131.3, 131.0, 129.5, 128.1, 119.4, 72.0, 70.4, 62.3, 53.8, 49.0, 35.7, 33.4; MS (ESI+) for C$_{20}$H$_{19}$Cl$_2$N$_3$O$_4$S m/z 468.1 (M+H)$^+$;

Scheme B

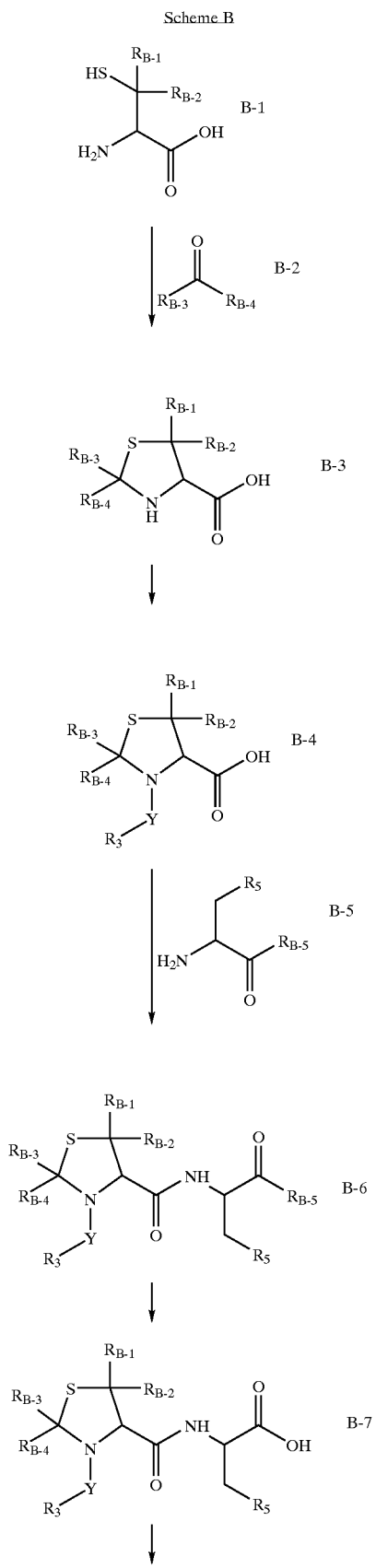

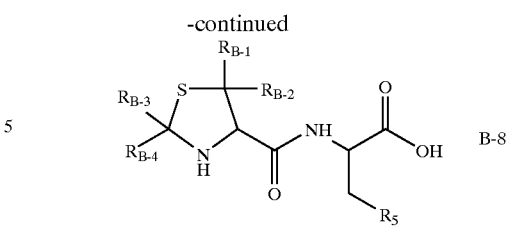

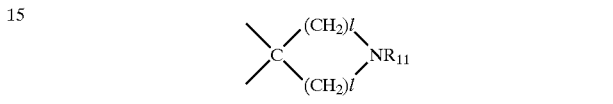

where $R_{B-1}$, $R_{B-2}$, $R_{B-3}$ and $R_{B-4}$ are defined as $R_1$ and in addition $R_{B-3}$ and $R_{B-4}$ may be attached to the same carbon atom and form a cyclic ring of 5–8 atoms of the formula:

$$\diagdown_{C}\diagup^{(CH_2)l}_{(CH_2)l}\diagdown_{NR_{11}}$$

together with the carbon atom to which they are attached: $R_{B-5}$ is defined as OH or O—($C_{1-6}$ alkyl).

Scheme B describes a general method for the preparation of thiazolidine-4-carboxylic acid derivatives of general structure B-6, B-7 and B-8 which are disubstituted at the 2 position (i.e., $R_{B-3}$ and $R_{B-4}$ are not equal to H). Within this class of structures, the nitrogen is derivatized immediately after forming the heterocyclic ring. Accordingly, a commercially available or readily prepared sulfur-containing amino acid of structure B-1 (which is the same structure as A-1) is condensed with a commercially available or readily prepared ketone to afford the thiazolidine-4-carboxylic acid of general formula B-3 (preparation 15) (for a general discussion of the condensation of aldehydes and ketones with cysteine or similar sulfur containing amino acids see: Coppola, G. M.; Schuster, H. F. *Asymmetric Synthesis: Construction of Chiral Molecules Using Amino Acids*; John Wiley: New York, 1987; Chapter 6, 171.). The amine group may be reacted with a variety of electrophilic reagents such as sulfonyl chlorides, carbonates, chloroformates, isocyanates, phosgene (or a suitable equivalent) and an amine, acid chlorides, and carboxylic acid anhydrides as described in Scheme A for the reaction of A-6. Preparation 16 is provided as a specific example of the synthesis of a compound of general structure B-4. Condensation of B-4 with amino acid derivative B-5 under standard peptide synthesis conditions provides the compound of general structure B-6 (preparation 17). Mild base hydrolysis of the methyl ester of general structure B-6 (where $R_{B-5}$ is $OCH_3$) may be effected as described and exemplified in Scheme A (preparation 6 or 13) to afford compounds of the general structure B-7. Alternatively, in those cases where $R_{B-5}$ is O-i-Bu, mild acidolysis can also provide compounds of the general structure B-7 (by the procedure described in preparation 4 of Scheme A). In the case of t-butoxycarbonyl derivatised analogs of general structure B-7 (i.e. where $R_3$ is t-butyl and Y is $CO_2$), mild acidolysis affords compounds of general structure B-8 (by the procedure described in preparation 4 of Scheme A).

PREPARATION 15

(Scheme B, B-3: where $R_{B-1}$ and $R_{B-2}$ are the same and equal to H, $R_{B-1}$ and $R_{B-4}$ are the same and equal to $CH_3$, and stereochemistry is (R)).

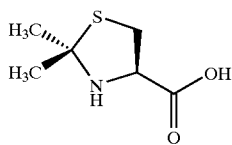

A suspension of L-cysteine hydrochloride monohydrate (Scheme B, B-1: where $R_{B-1}$ and $R_{B-2}$ are the same and equal to H and stereochemistry is (R)) (20 g, 0.11 mol) in acetone (Scheme B, B-2: where $R_{B-3}$ and $R_{B-4}$ are equal to $CH_3$) (800 mL) was heated to reflux for 8 h. Cooling to room temperature resulted in precipitation of a solid which was collected by filtration, washed with acetone and dried in vacuo to afford the title compound (17.46 g) as a white solid: mp 165–167° C.; (Lit. 165–168° C.: Sheehan, J. C.; Yang, D-D. H. *J. Am. Chem. Soc.* 1957, 80, 1158) $^1$H NMR ($D_2O$) δ 4.75 (1H), 3.59 (1H), 3.44 (1H), 1.73 (3H), 1.71 (3H); MS (ESI–) for $C_6H_{11}NO_2S$ m/z 159.9 (M–H)$^-$.

PREPARATION 16

(Scheme B, B-4: where $R_{B-1}$ and $R_{B-2}$ are the same and equal to H, $R_{B-3}$ and $R_{B-4}$ are the same and equal to $CH_3$, Y is $CO_2$, $R_3$ is t-butyl and stereochemistry is (R)).

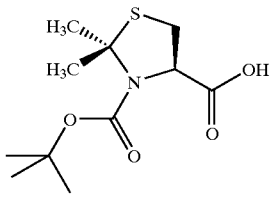

To a solution of B-3 (Scheme B where $R_{B-1}$ and $R_{B-2}$ are the same and equal to H, $R_{B-3}$ and $R_{B-4}$ are the same and equal to $CH_3$, and stereochemistry is (R)) (17.46 g, 0.11 mol) in acetonitrile (250 mL) at ambient temperature was added di-i-butyl dicarbonate (25.64 g, 0.117 mol) followed by N,N-diisopropylethylamine (16.9 mL, 0.097 mol). The reaction mixture was stirred for 2 days and volatiles remove in vacuo. The residue was slurried in diethyl ether and filtered through a pad of celite. The filtrate was washed with 0.1 N HCl, water, brine, dried ($Na_2SO_4$), filtered and concentrated in vacuo. Crystallization of the clear oil from hexane provided the title compound (3.85 g) as a white solid: mp 125–126° C.; (Lit. 114° C.: Woodward, R. B.; Heusler, K.; Gosteli, J.; Naegeli, P.; Oppolzer, W.; Ramage, R.; Ranganathan, S.; Vorbruggen, H. *J. Am. Chem. Soc.* 1966. 88, 852) $^1$H NMR ($CDCl_3$) δ 8.70 (1H), 4.89 (1H), 3.27 (2H), 1.81 (6H); MS (ESI–) for $C_{11}H_{19}NO_4S$ m/z 260.1 (M–H)$^-$.

PREPARATION 17 AND EXAMPLE 72

[R-(R*,S*)]-4-[[[1-[[4-[(2,6-Dichlorobenzoyl) amino]phenyl]methyl]-2-methoxy-2-oxo-ethyl] amino]carbonyl]-2,2-dimethyl-3-thiazolidinecarboxylic Acid 3-(1,1-Dimethylethyl) ester (Scheme B, B-6: where $R_{B-1}$ and $R_{B-2}$ are the same and equal to H, $R_{B-3}$ and $R_{B-4}$ are the same and equal to $CH_3$, Y is $CO_2$, $R_3$ is t-butyl, $R_{B-5}$ is $OCH_3$, $R_5$ is 4-[(2,6-dichlorobenzoyl)amino]phenyl and stereochemistry is (R,S)).

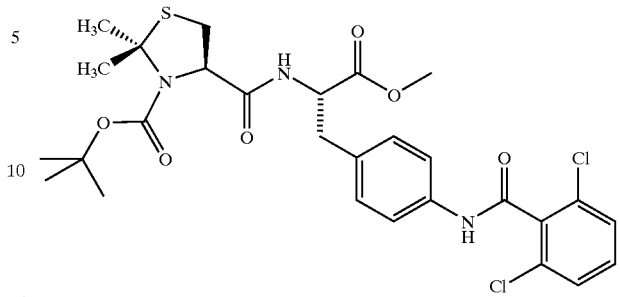

To a cooled (0–5° C.) suspension of B-4 (Scheme B where $R_{B-1}$ and $R_{B-2}$ are the same and equal to H, $R_{B-3}$ and $R_{B-4}$ are the same and equal to $CH_3$, Y is $CO_2$, $R_3$ is -butyl and stereochemistry is (R)) (1.0 g, 3.83 mmol) and HOBt (638 mg, 4.17 mmol) in $CH_2Cl_2$ (20 mL) was added a solution of EDC (799 mg, 4.17 mmol) in $CH_2Cl_2$ (20 mL). After 30 min at 0–5° C., B-5 (Scheme B where $R_{B-5}$ is $OCH_3$, $R_5$ is 4-[(2,6-dichlorobenzoyl)amino]phenyl and stereochemistry is (S)) (1.93 g, 4.77 mmol) was added followed by 4-methylmorpholine (520 μL, 4.77 mmol). The reaction mixture was gradually warmed to room temperature, stirred an additional 18 h and diluted with $CH_2Cl_2$. The organic layer was separated and washed with 0.1 N HCl, sat. aqueous $NaHCO_2$, brine, dried ($Na_2SO_4$), filtered and concentrated in vacuo. Flash chromatography of the residue using $CH_2Cl_2$/acetone (3%) as eluant afforded the title compound (2.05 g) as a white solid: IR (mull) 1746, 1666, 1606, 1562, 1537, 1515, 1432, 1413, 1347, 1325, 1259, 1214, 1195, 1169, 799 cm$^{-1}$; $^1$H NMR ($CDCl_3$) δ 7.54 (2H), 7.32 (4H), 7.20 (2H), 6.90 (1H), 4.78 (2H), 3.74 (3H), 3.17 (4H), 1.74 (3H), 1.43 (9H); $^{13}$C NMR ($CDCl_3$) δ 171.6 136.7, 136.2, 135.9, 132.7, 132.4, 132.3, 131.0, 130.6, 130.4, 130.0, 129.9, 128.2, 127.9, 120.5, 120.2, 120.1, 67.3, 53.4, 52.4, 42.8, 37.3, 36.9, 34.9, 30.9, 28.3; MS (ESI+) for $C_{28}H_{33}Cl_2N_3O_6S$ m/z 610 (M+H)$^+$; MS (ESI–) for $C_{28}H_{33}Cl_2N_3O_6S$ m/z 610 (M–H)$^-$; Anal. Calcd for $C_{28}H_{33}Cl_2N_3O_6S\cdot 0.13H_2O$: C, 54.88; H, 5.47; N, 6.86. Found: C, 54.66; H, 5.57; N, 6.73. % Water (KF): 0.37.

EXAMPLE 73

[R-(R*,S*)]-4-[[[Carboxy-2-[4-[(2,6-dichlorobenzoyl)amino]phenyl]ethyl]amino] carbonyl]-2,2-dimethyl-3-thiazolidinecarboxylic Acid 3-(1,1-Dimethylethyl)ester (Scheme B, B-7: where $R_{B-1}$ and $R_{B-2}$ are the same and equal to H, $R_{B-3}$ and $R_{B-4}$ are the same and equal to $CH_3$, Y is $CO_2$, $R_3$ is 1-butyl, $R_5$ is 4-[(2,6-dichlorobenzoyl)amino] phenyl and stereochemistry is (R,S)).

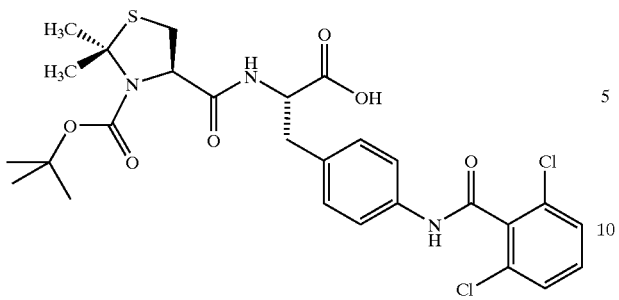

Example 73 was prepared from example 72 by the procedure described in preparation 6. Physical data as follows: IR (mull) 1738, 1665, 1606, 1562, 1535, 1516, 1432, 1413, 1347, 1259, 1213, 1194, 1167, 799, 777 cm$^{-1}$; $^1$H NMR (CD,CN) δ 8.89 (1H), 7.54 (2H), 7.41 (3H), 7.25 (2H), 4.66 (2H), 3.15 (4H), 1.72 (3H), 1.70 (3H), 1.35 (9H); $^{13}$C NMR (CD$_3$CN) δ 177.3, 171.8, 163.4, 137.9, 137.1, 133.9, 132.7, 132.3, 131.3, 129.1, 120.7, 81.2, 79.3, 68.0, 54.5, 37.4, 28.4; MS (ESI−) for C$_{27}$H$_{31}$Cl$_2$N$_3$O$_6$S m/z 593.9 (M−H)$^-$; Anal. Calcd for C$_{27}$H$_{31}$Cl$_2$N$_3$O$_6$S.0.5H$_2$O: C, 53.56; H, 5.33; N, 6.94. Found: C, 53.77; H, 5.39; N, 6.70.

EXAMPLE 74

4-[(2,6-Dichlorobenzoyl)amino]-N-[[(4R)-2,2-dimethyl-4-thiazolidinyl]carbonyl]-L-phenylalanine (Scheme B, B-8: where R$_{B-1}$ and R$_{B-2}$ are the same and equal to H, R$_{B-3}$ and R$_{B-4}$ are the same and equal to CH$_3$, R$_5$ is 4-[(2,6-dichlorobenzoyl)amino]phenyl and stereochemistry is (R,S)).

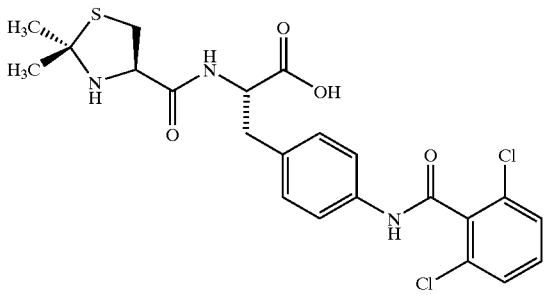

Example 74 was prepared from example 73 by the procedure described in preparation 4. Physical data as follows: IR (mull) 3244, 3192, 3049, 1726, 1664, 1605, 1578, 1562, 1541, 1516, 1432, 1414, 1327, 1195, 799 cm$^{-1}$; $^1$H NMR (DMSO-d$_6$) δ 13.00 (1H), 10.69 (1H), 7.52 (6H), 7.24 (2H), 4.52 (2H), 3.12 (2H), 2.93 (1H), 1.62 (9H); $^{13}$C NMR (CD$_3$OD) δ 166.9, 136.8, 136.0, 133.5, 131.8, 130.9, 129.5, 129.4, 127.9, 120.4, 120.2, 120.1, 60.8, 54.3, 54.0, 36.2, 36.0, 25.1; MS (ESI+) for C$_{22}$H$_{23}$Cl$_2$N$_3$O$_4$S m/z 496.2 (M+H)$^+$; MS (ESI−) for C$_{22}$H$_{23}$Cl$_2$N$_3$O$_4$S m/Z 494.2 (M−H)$^-$; Anal. Calcd for C$_{22}$H$_{23}$Cl$_2$N$_3$O$_4$S.HCl.0.50H$_2$O: C, 48.76; H, 4.65; N, 7.75. Found: C, 48.56; H, 4.72; N, 7.49.

EXAMPLE 75

[S-(R*,R*)]-4-[[[1-[[4-[(2,6-Dichlorobenzoyl)amino]phenyl]methyl]-2-methoxy-2-oxo-ethyl]amino]carbonyl]-2,2-dimethyl-3-thiazolidinecarboxylic Acid 3-(1,1-Dimethylethyl) ester (Scheme B, B-6: where R$_{B-1}$ and R$_{B-2}$ are the same and equal to H, R$_{B-3}$ and R$_{B-4}$ are the same and equal to CH$_3$, Y is CO$_2$, R$_3$ is t-butyl, R$_5$ is 4-[(2,6-dichlorobenzoyl)amino]phenyl and stereochemistry is (S,S)).

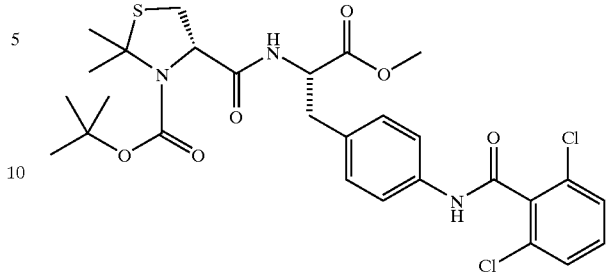

Example 75 was prepared as described in Scheme B from D-cysteine and acetone using di-t-butyl dicarbonate to form the requisite carbamate. Physical data as follows: IR (mull) 1745, 1686, 1666, 1605, 1537, 1515, 1432, 1413, 1349, 1325, 1259, 1213, 1206, 1195, 1169 cm$^{-1}$; $^1$H NMR (CDCl$_3$) δ 7.56 (2H), 7.32 (3H), 7.16 (2H), 6.92 (1H), 4.83 (2H), 3.73 (3H), 3.20 (4H), 1.78 (6H), 1.45 (9H); $^{13}$C NMR (CDCl$_3$) δ 171.6, 170.0, 132.6, 132.4, 131.0, 130.9, 130.1, 129.9, 128.2, 120.5, 120.4, 67.3, 53.3, 52.5, 52.4, 37.4, 28.4; MS (ESI+) for C$_{28}$H$_{33}$Cl$_2$N$_3$O$_6$S m/z 610.0 (M+H)$^+$; MS (ESI−) for C$_{28}$H$_{33}$Cl$_2$N$_3$O$_6$S m/z 607.9 (M−H)$^-$; Anal. Calcd for C$_{28}$H$_{33}$Cl$_2$N$_3$O$_6$S: C, 55.08; H, 5.45; N, 6.88; Cl, 11.61; S, 5.25. Found: C, 54.87; H, 5.47; N, 6.78.

EXAMPLE 76

[S-(R*,R*)]-4-[[[1-Carboxy-2-[4-[(2,6-dichlorobenzoyl)amino]phenyl]ethyl]amino]carbonyl]-2,2-dimethyl-3-thiazolidinecarboxylic Acid 3-(1,1-Dimethylethyl)ester (Scheme B, B-7: where R$_{B-1}$ and R$_{B-2}$ are the same and equal to H, R$_{B-3}$ and R$_{B-4}$ are the same and equal to CH$_3$, Y is CO$_2$, R$_3$ is t-butyl, R$_5$ is 4-[(2,6-dichlorobenzoyl)amino]phenyl and stereochemistry is (S,S)).

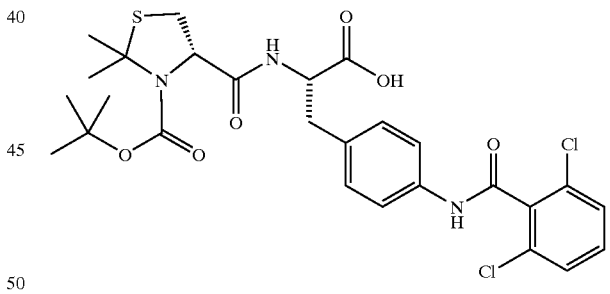

Example 76 was prepared from example 75 by the procedure described in preparation 6. Physical data as follows: IR (mull) 3280, 1739, 1665, 1606, 1562, 1535, 1516, 1432, 1413, 1348, 1272, 1259, 1195, 1167, 799 cm$^{-1}$; $^1$H NMR (CD,CN) δ 8.83 (1H), 7.55 (2H), 7.43 (3H), 7.22 (2H), 6.83 (1H), 4.68 (2H), 3.07 (5H), 1.73 (6H), 1.40 (9H); $^{13}$C NMR (CD$_3$CN) δ 172.6, 163.3, 137.9, 133.4, 133.3, 132.7, 132.1, 131.1, 130.2, 130.1, 129.1, 128.1, 128.0, 120.6, 119.5, 54.1, 37.4, 29.4, 28.5, 27.6; MS (ESI+) for C$_{27}$H$_{31}$Cl$_2$N$_3$O$_6$S m/z 595.9 (M+H)$^+$; MS (ESI−) for C$_{27}$H$_{31}$Cl$_2$N$_3$O$_6$S m/z 593.7 (M−H)$^-$; MS (FAB) m/z (rel. intensity) 596 (MH+, 16), 598 (12), 596 (16), 500 (16), 499 (19), 498 (71), 497 (32), 496 (99), 173 (16), 116 (19), 57 (51); HRMS (FAB) calcd for C$_{27}$H$_{31}$Cl$_2$N$_3$O$_6$S+H$_1$ 596.1389, found 596.1364; Anal. Calcd for C$_{27}$H$_{31}$Cl$_2$N$_3$O$_6$S.0.5H$_2$O: C, 53.56; H, 5.33; N, 6.94. Found: C, 53.86; H, 5.35; N, 6.90.

EXAMPLE 77

[S-(R*,R*)]-3-[[[1-[[4-[(2,6-Dichlorobenzoyl)amino]phenyl]methyl]-2-methoxy-2-oxoethyl]amino]carbonyl]-1-thia-4-azaspiro[4.4]nonane-4-carboxylic Acid 4-Ethyl Ester (Scheme B, B-6: where $R_{B-1}$ and $R_{B-2}$ are the same and equal to H, $R_{B-3}$ and $R_{B-4}$ together form a carbocyclic ring of 5 atoms, Y is $CO_2$, $R_3$ is ethyl, $R_5$ is 4-[(2,6-dichlorobenzoyl)amino]phenyl and stereochemistry is (S,S)).

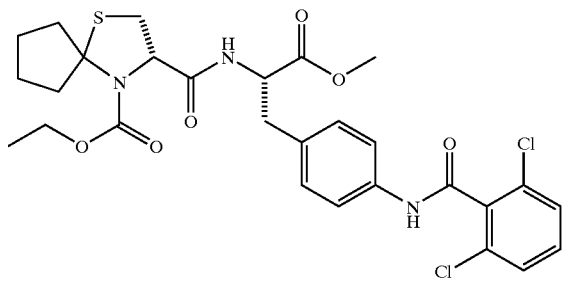

Example 77 was prepared as described in Scheme B from D-cysteine and cyclopentanone using ethyl chloroformate to form the requisite carbamate. Physical data as follows: IR (mull) 1760, 1739, 1694, 1656, 1607, 1560, 1543, 1517, 1445, 1429, 1411, 1334, 1273, 1253, 1116 cm$^{-1}$; $^1$H NMR (CDCl$_3$) δ 7.56 (2H), 7.44 (1H), 7.34 (3H), 7.11 (2H), 6.70 (1H), 4.84 (2H), 4.14 (2H), 3.74 (3H), 3.12 (4H), 2.67 (1H), 2.51 (1H), 1.73 (6H), 1.25 (3H); $^{13}$C NMR (CDCl$_3$) δ 171.4, 170.7, 162.3, 136.3, 135.8, 132.5, 132.4, 131.0, 130.1, 128.2, 120.2, 66.4, 62.1, 5S3.1, 52.5, 37.3, 32.3, 31.9, 25.1, 24.6, 14.5, 14.1; MS (ESI+) for $C_{28}H_{31}Cl_2N_3O_6S$ m/z 630.0 (M+Na)$^+$; HRMS (EI) calcd for $C_{28}H_{31}Cl_2N_3O_6S$ 607.1310, found 607.1315; Anal. Calcd for $C_{28}H_{31}Cl_2N_3O_6S \cdot 0.75H_2O$: C, 54.06; H, 5.27; N, 6.90. Found: C, 53.98; H, 5.16; N, 6.72.

EXAMPLE 78

[S-(R*,R*)]-3-[[[1-Carboxy-2-[4-[(2,6-dichlorobenzoyl)amino]phenyl]ethyl]amino]carbonyl]-1-thia-4-azaspiro[4.4]nonane-4-carboxylic Acid 4-Ethyl Ester (Scheme B, B-7: where $R_{B-1}$ and $R_{B-2}$ are the same and equal to H, $R_{B-3}$ and $R_{B-4}$ together form a carbocyclic ring of 5 atoms, Y is $CO_2$, $R_3$ is ethyl, $R_5$ is 4-[(2,6-dichlorobenzoyl)amino]phenyl and stereochemistry is (S,S)).

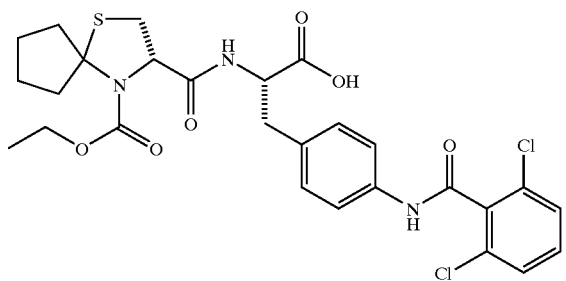

Example 78 was prepared from example 77 by the procedure described in preparation 6. Physical data as follows: IR (mull) 3276, 1664, 1606, 1562, 1537, 1515, 1445, 1432, 1413, 1335, 1273, 1239, 1195, 1116, 799 cm$^{-1}$; $^1$H NMR (CDCl$_3$) δ 8.08 (1H), 7.62 (2H), 7.24 (3H), 7.14 (2H), 6.72 (1H), 4.85 (2H), 4.13 (2H), 3.21 (4H), 2.53 (2H), 1.75 (6H), 1.22 (3H); $^{13}$C NMR (CDCl$_3$) δ 175.2, 171.2, 162.6, 136.7, 135.7, 132.3, 132.0, 130.7, 130.2, 127.9, 120.2, 66.3, 62.2, 53.2, 37.3, 36.6, 32.3, 25.2, 24.6, 20.5, 14.5; MS (ESI+) for $C_{27}H_{29}Cl_2N_3O_6S$ m/z 593.8 (M+H)$^+$; MS (ESI−) for $C_{27}H_{29}Cl_2N_3O_6S$ m/z 591.8 (M−H)$^-$; HRMS (FAB) calcd for $C_{27}H_{29}Cl_2N_3O_6S+H_1$ 594.1232, found 594.1226; Anal. Calcd for $C_{27}H_{29}Cl_2N_3O_6S \cdot 0.37H_2O$: C, 53.95; H, 4.99; N, 6.99. Found: C, 54.28; H, 5.10; N, 7.03. % Water (KF): 1.10.

EXAMPLE 79

[S-(R*,R*)]-3-[[[1-[[4-[(2,6-Dichlorobenzoyl)amino]phenyl]methyl]-2-methoxy-2-oxoethyl]amino]carbonyl]-1-thia-4-azaspiro[4.5]decanecarboxylic Acid 4-Ethyl Ester (Scheme B, B-6: where $R_{B-1}$ and $R_{B-2}$ are the same and equal to H, $R_{B-3}$ and $R_{B-4}$ together form a carbocyclic ring of 6 atoms, Y is $CO_2$, $R_3$ is ethyl, $R_5$ is 4-[(2,6-dichlorobenzoyl)amino]phenyl and stereochemistry is (S,S)).

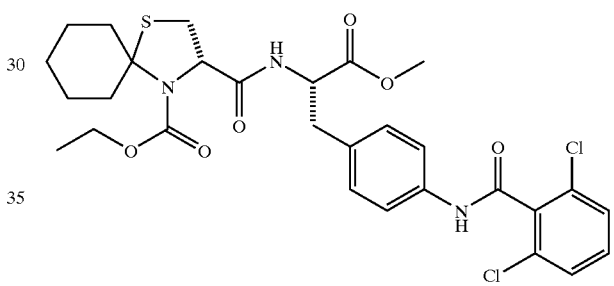

Example 79 was prepared as described in Scheme B from D-cysteine and cyclohexanone using ethyl chloroformate to form the requisite carbamate. Physical data as follows: IR (mull) 1745, 1704, 1683, 1668, 1607, 1561, 1538, 1514, 1431, 1413, 1327, 1269, 1213, 1196, 1117 cm$^{-1}$; $^1$H NMR (CDCl$_3$) δ 7.57 (2H), 7.46 (1H), 7.33 (3H), 7.11 (2H), 6.72 (1H), 4.88 (2H), 4.14 (2H), 3.74 (3H), 3.13 (4H), 2.51 (1H), 1.69 (8H), 1.22 (5H); $^{13}$C NMR (CDCl$_3$) δ 171.4, 170.7, 168.1, 162.3, 136.3, 135.7, 132.4, 131.0, 128.2, 120.3, 66.9, 62.8, 62.0, 55.1, 53.1, 52.5, 42.0, 39.9, 37.3, 36.9, 31.1, 29.6, 27.6, 27.1, 26.0, 25.3, 24.7, 23.1, 14.5; MS (ESI−) for $C_{29}H_{33}Cl_2N_3O_6S$ m/z 621.9 (M)$^-$; HRMS (FAB) calcd for $C_{29}H_{33}Cl_2N_3O_6S+H_1$ 622.1545, found 622.1536.

EXAMPLE 80

[S-(R*,R*)]-3-[[[1-Carboxy-2-[4-[(2,6-dichlorobenzoyl)amino]phenyl]ethyl]amino]carbonyl]-1-thia-4-azaspiro[4.5]decane-4-carboxylic Acid 4-Ethyl Ester (Scheme B, B-7: where $R_{B-1}$ and $R_{B-2}$ are the same and equal to H, $R_{B-3}$ and $R_{B-4}$ together form a carbocyclic ring of 6 atoms, Y is $CO_2$, $R_3$ is ethyl, $R_5$ is 4-[(2,6-dichlorobenzoyl)amino]phenyl and stereochemistry is (S,S)).

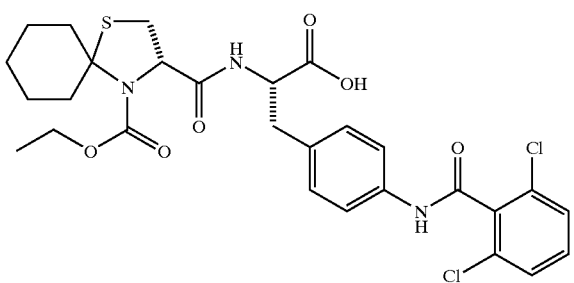

Example 80 was prepared from example 79 by the procedure described in preparation 6. Physical data as follows: IR (mull) 3276, 1710, 1664, 1606, 1562, 1537, 1515, 1432, 1413, 1329, 1272, 1256, 1195, 1117, 800 cm$^{-1}$; $^1$H NMR (CDCl$_3$) δ 8.07 (1H), 7.62 (2H), 7.24 (3H), 7.14 (2H), 6.75 (1H), 4.88 (2H), 4.12 (3H), 3.14 (4H), 2.74 (1H), 2.50 (1H), 1.69 (6H), 1.19 (5H); $^{13}$C NMR (CDCl$_3$) δ 175.4, 175.1, 171.3 162.6, 136.7, 135.7, 132.3, 132.0, 130.7, 130.3, 130.1, 128.0, 120.2, 66.8, 62.1, 53.2, 42.0, 36.9, 30.5, 27.0, 26.0, 25.3, 25.0, 24.6, 20.5, 14.4, 3.7; MS (ESI+) for $C_{28}H_{31}Cl_2N_3O_6S$ m/z 608.1 (M+H)$^+$; MS (ESI−) for $C_{28}H_{31}Cl_2N_3O_6S$ m/z 605.9 (M−H)$^-$; HRMS (EI) calcd for $C_{28}H_{31}Cl_2N_3O_6S$ 607.1310, found 607.1309; Anal. Calcd for $C_{28}H_{31}Cl_2N_3O_6S \cdot 0.3H_2O$: C, 54.78; H, 5.19; N, 685. Found: C, 54.56; H, 5.24; N, 6.90. % Water (KF): 0.87.

EXAMPLE 81

[S-(R*,R*)]-4-[[[1-[[4-[(2,6-Dichlorobenzoyl)amino]phenyl]methyl]-2-methoxy-2-oxoethyl]amino]carbonyl]-2,2,5,5-tetramethyl-3-thiazolidinecarboxylic Acid 3-Ethyl Ester (Scheme B, B-6: where $R_{B-1}$, $R_{B-2}$, $R_{B-3}$ and $R_{B-4}$ are the same and equal to CH$_3$, Y is CO$_2$, $R_3$ is t-butyl, $R_5$ is 4-[(2,6-dichlorobenzoyl)amino]phenyl and stereochemistry is (S,S)).

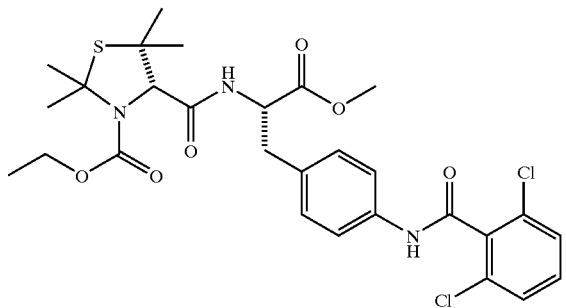

Example 81 was prepared as described in Scheme B from D-penicillamine and acetone using ethyl chloroformate to form the requisite carbamate. Physical data as follows: IR (mull) 1748, 1666, 1606, 1562, 1538, 1516, 1432, 1413, 1327, 1275, 1233, 1215, 1195, 1080, 799 cm$^{-1}$; $^1$H NMR (CDCl$_3$) δ 7.55 (2H), 7.33 (4H), 7.09 (3H), 6.59 (1H), 4.91 (1H), 4.47 (1H), 4.16 (2H), 3.75 (3H), 3.13 (2H), 1.92 (3H), 1.75 (3H), 1.67 (3H), 1.60 (3H), 1.21 (3H); $^{13}$C NMR (CDCl$_3$) δ 171.5, 170.0, 162.2, 136.1, 135.7, 132.5, 132.3, 131.9, 130.9, 130.7, 129.7, 128.1, 120.3, 120.1, 120.0, 61.6, 61.4, 52.9, 52.4, 52.2, 49.3, 37.4, 37.3, 34.1, 31.4, 30.8, 29.5, 24.9; MS (ESI−) for $C_{28}H_{33}Cl_2N_3O_6S$ m/z 607.9 (M−H)$^-$; HRMS (EI) calcd for $C_{28}H_{33}Cl_2N_3O_6S$ 609.1467, found 609.1461; Anal. Calcd for $C_{28}H_{33}Cl_2N_3O_6S \cdot 0.19H_2O$: C, 54.77; H, 5.48; N, 6.84. Found: C, 55.00; H, 5.48; N, 6.78. % Water (KF): 0.56.

EXAMPLE 82

[S-(R*,R*)]-4-[[[1-Carboxy-2-[4-[(2,6-dichlorobenzoyl)amino]phenyl]ethyl]amino]carbonyl]-2,2,5,5-tetramethyl-3-thiazolidinecarboxylic Acid 3-Ethyl Ester (Scheme B, B-7: where $R_{B-1}$, $R_{B-2}$, $R_{B-3}$ and $R_{B-4}$ are the same and equal to CH$_3$, Y is CO$_2$, $R_3$ is i-butyl, $R_5$ is 4-[(2,6-dichlorobenzoyl)amino]phenyl and stereochemistry is (S,S)).

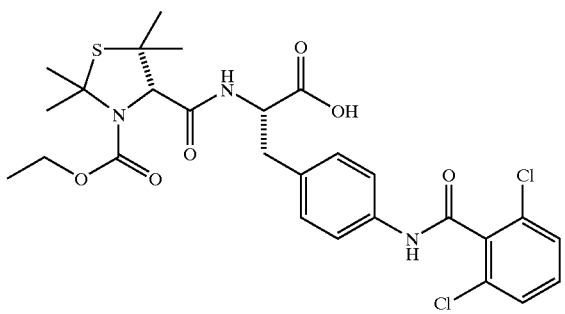

Example 82 was prepared from example 81 by the procedure described in preparation 6. Physical data as follows: IR (mull) 3275, 1750, 1735, 1678, 1666, 1609, 1562, 1543, 1516, 1432, 1413, 1333, 1276, 1195, 1077 cm$^{-1}$; $^1$H NMR (DMSO-d$_6$) 12.48 (1H), 10.63 (1H), 8.36 (1H), 7.53 (5H), 7.19 (2H), 4.49 (2H), 3.96 (2H), 3.03 (1H), 2.79 (1H), 1.78 (6H), 1.48 (3H), 1.15 (3H), 0.90 (3H); $^{13}$C NMR (DMSO-d$_6$) δ 172.9, 168.7, 161.7, 152.3, 137.0, 136.3, 132.9, 131.2, 131.1, 129.5, 128.1, 119.2, 74.7, 71.3, 60.5, 53.5, 49.0, 48.4, 38.3, 36.7, 33.5, 31.8, 28.1, 24.7, 21.0, 14.0; MS (ESI+) for $C_{27}H_{31}Cl_2N_3O_6S$ m/z 595.8 (M+H)$^+$; MS (ESI−) for $C_{27}H_{31}Cl_2N_3O_6S$ m/z 593.8 (M−H)$^-$; HRMS (FAB) calcd for $C_{27}H_{31}Cl_2N_3O_6S+H_1$ 596.1389, found 596.1362; Anal. Calcd for $C_{27}H_{31}Cl_2N_3O_6S \cdot 0.56H_2O$: C, 53.46; H, 5.34; N, 6.93. Found: C, 53.73; H, 5.35; N, 6.73. % Water (KF): 1.67.

EXAMPLE 83

N-[[(4S)-3-Acetyl-2,2-dimethyl-4-thiazolidinyl]carbonyl]-4-[(2,6-dichlorobenzoyl)amino]-L-phenylalanine Methyl Ester (Scheme B, B-6: where $R_{B-1}$ and $R_{B-2}$ are the same and equal to H, $R_{B-3}$ and $R_{B-4}$ are the same and equal to CH$_3$, Y is CO, $R_3$ is methyl, $R_5$ is 4-[(2,6-dichlorobenzoyl)amino]phenyl and stereochemistry is (S,S)).

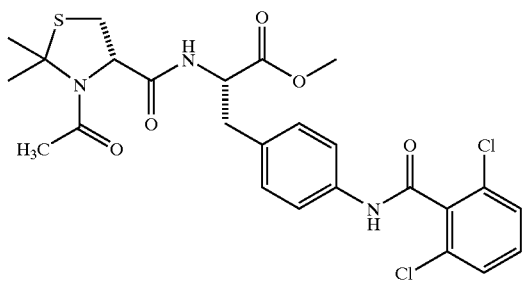

Example 83 was prepared as described in Scheme B from D-cysteine and acetone using acetyl chloride to form the requisite amide. Physical data as follows: IR (mull) 1745, 1682, 1662, 1628, 1610, 1579, 1561, 1541, 1515, 1431, 1412, 1326, 1270, 1240, 1211 cm$^{-1}$; $^1$H NMR (CDCl$_3$) δ 7.55 (3H), 7.32 (3H), 7.19 (1H), 7.11 (1H), 6.66 (1H), 4.89 (1H), 4.60 (1H), 3.78 (3H), 3.24 (4H), 2.04 (3H), 1.87 (3H), 1.79 (3H); $^{13}$C NMR (DMSO-d$_6$) δ 171.6, 171.5, 169.9, 169.4, 167.9, 161.8, 137.1, 136.3, 132.8, 132.6, 131.1, 129.5, 128.1, 119.2, 72.6, 66.5, 53.7, 53.3, 52.0, 51.9, 35.8, 31.7, 29.0, 26.9, 24.7, 24.5; MS (ESI+) for C$_{25}$H$_{27}$Cl$_2$N$_3$O$_5$S m/z 551.9 (M+H)$^+$; HRMS (EI) calcd for C$_{25}$H$_{27}$Cl$_2$N$_3$O$_5$S 551.1049, found 551.1053; MS (EI) m/z (rel. intensity) 551 (M+, 7), 351 (46), 349 (68), 278 (16), 186 (14), 175 (63), 173 (98), 158 (23), 116 (99), 100 (20), 99 (69).

EXAMPLE 84

N-[[(4S)-3-Acetyl-2,2-dimethyl-4-thiazolidinyl]carbonyl]-4-[(2,6-dichlorobenzoyl)amino]-L-phenylalanine (Scheme B, B-7: where R$_{B-1}$ and R$_{B-2}$ are the same and equal to H, R$_{B-3}$ and R$_{B-4}$ are the same and equal to CH$_3$, Y is CO, R$_3$ is methyl, R$_5$ is 4-[(2,6-dichlorobenzoyl)amino]phenyl and stereochemistry is (S,S)).

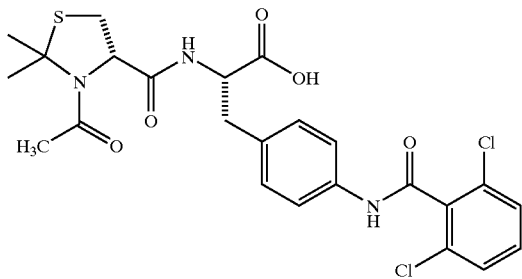

Example 84 was prepared from example 83 by the procedure described in preparation 6. Physical data as follows: IR (mull) 3279, 1723, 1661, 1608, 1562, 1542, 1516, 1432, 1413, 1349, 1329, 1270, 1238, 1207, 1195 cm$^{-1}$; $^1$H NMR (DMSO-d$_6$) δ 12.47 (1H), 10.62 (1H), 7.51 (5H), 7.18 (2H), 4.80 (1H), 4.67 (1H), 4.47 (1H), 2.98 (3H), 1.68 (9H); $^{13}$C NMR (DMSO-d$_6$) δ 184.2, 172.6, 171.9, 169.8, 169.2, 167.8, 136.9, 136.3, 133.1, 131.2, 131.0, 129.5, 128.1, 119.2, 72.6, 66.6, 53.7, 53.3, 36.2, 31.7, 29.0, 27.0, 24.8, 24.6, 21.0; MS (ESI+) for C$_{24}$H$_{25}$Cl$_2$N$_3$O$_5$S m/z 538.0 (M+H)$^+$; MS (ESI−) for C$_{24}$H$_{25}$Cl$_2$N$_3$O$_5$S m/z 535.9 (M−H)$^-$; HRMS (FAB) calcd for C$_{24}$H$_{25}$Cl$_2$N$_3$O$_5$S+H$_1$ 538.0970, found 538.0961.

EXAMPLE 85

[S-(R*,R*)]-4-[[[1-Carboxy-2-[4-[(2,6-dichlorobenzoyl)amino]phenyl]ethyl]amino]carbonyl]-2,2-dimethyl-γ-oxo-3-thiazolidinebutanoic Acid (Scheme B, B-7: where R$_{B-1}$ and R$_{B-2}$ are the same and equal to H, R$_{B-3}$ and R$_{B-4}$ are the same and equal to CH$_3$, Y is CO, R$_3$ is CH$_2$CH$_2$CO$_2$H, R$_5$ is 4-[(2,6-dichlorobenzoyl)amino]phenyl and stereochemistry is (S,S)).

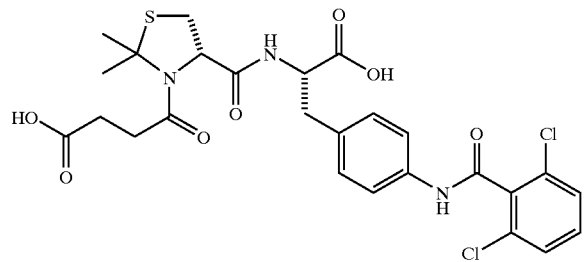

Example 85 was prepared as described in Scheme B from D-cysteine and acetone using methyl succinyl chloride to form the requisite amide. Physical data as follows: IR (mull) 3264, 3125, 3071, 1724, 1658, 1607, 1562, 1537, 1517, 1432, 1414, 1326, 1241, 1195, 1181 cm$^{-1}$; $^1$H NMR (DMSO-d$_6$) δ 12.31 (1H), 10.65 (1H), 8.20 (1H), 7.50 (5H), 7.19 (2H), 5.81 (1H), 4.50 (1H), 3.02 (3H), 2.30 (3H), 1.71 (6H); $^{13}$C NMR (DMSO-d$_6$) δ 174.1, 172.8, 169.4, 161.9, 137.1, 136.5, 13.2, 131.4, 131.3, 129.7, 128.3, 119.3, 73.1, 65.7, 53.5, 36.3, 32.0, 30.5, 29.1, 29.0, 27.1; MS (ESI+) for C$_{26}$H$_{27}$Cl$_2$N$_3$O$_7$S m/z 595.9 (M+H)$^+$; MS (ESI−) for C$_{26}$H$_{27}$Cl$_2$N$_3$O$_5$S m/z 593.8 (M−H)$^-$; Anal. Calcd for C$_{26}$H$_{27}$Cl$_2$N$_3$O$_5$S.0.51H$_2$O: C, 51.55; H, 4.66; N, 6.94. Found: C, 51.71; H, 4.85S N, 6.93. % Water (KF): 1.53.

EXAMPLE 86

[S-(R*,R*)]-4-[[[1-[[4-[(2,6-Dichlorobenzoyl)amino]phenyl]methyl]-2-methoxy-2-oxoethyl]amino]carbonyl]-2,2,5,5-tetramethyl-γ-oxo-3-thiazolidinebutanoic Acid Methyl Ester (Scheme B, B-6: where R$_{B-1}$, R$_{B-2}$, R$_{B-3}$ and R$_{B-4}$ are the same and equal to CH$_3$, Y is CO, R$_3$ is CH$_2$CH$_2$CO$_2$CH$_3$, R$_5$ is 4-[(2,6-dichlorobenzoyl)amino]phenyl and stereochemistry is (S,S)).

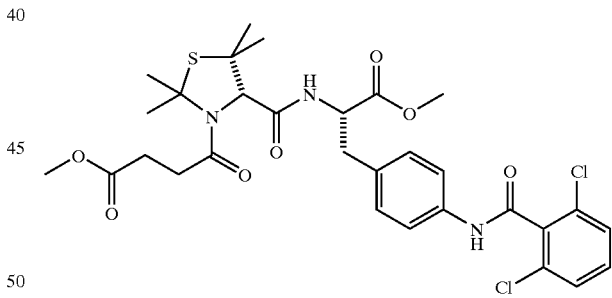

Example 86 was prepared as described in Scheme B from D-penicillamine and acetone using methyl succinyl chloride to form the requisite amide. Physical data as follows: IR (mull) 3287, 1741, 1660, 1608, 1562, 1540, 1516, 1432, 1413, 1323, 1267, 1241, 1225, 1196, 1168 cm$^{-1}$; $^1$H NMR (CDCl$_3$) δ 7.55 (2H), 7.29 (3H), 7.13 (2H), 6.94 (1H), 4.95 (1H), 4.39 (1H), 3.74 (3H), 3.67 (3H), 3.27 (1H), 3.10 (1H), 2.80 (1H), 2.57 (3H), 2.18 (1H), 1.95 (3H), 1.77 (3H), 1.72 (3H), 1.68 (3H) 1.63 (3H); $^{13}$C NMR (CDCl$_3$) δ 173.3, 171.6, 170.3, 169.9, 162.4, 136.3, 132.5, 132.4, 131.0, 130.2, 129.8, 128.2, 120.8, 120.7, 120.5, 73.8, 53.1, 52.6, 51.8, 49.9, 40.0, 37.4, 333.9, 31.6, 31.4,29.4, 29.1, 24.3; MS (ESI+) for C$_{30}$H$_{35}$Cl$_2$N$_3$O$_7$S m/z 652.1 (M+H)$^+$; Anal. Calcd for C$_{30}$H$_{35}$Cl$_2$N$_3$O$_7$S.0.31H$_2$O: C, 54.75; H, 5.45; N, 6.38. Found: C, 55.04; H, 5.50; N, 6.69. % Water (KF): 0.84.

EXAMPLE 87

N-[[(4S)-3-Acetyl-2,2,5,5-tetramethyl-4-thiazolidinyl]carbonyl]-4-[(2,6-dichlorobenzoyl)amino]-L-phenylalanine Methyl Ester (Scheme B, B-6: where $R_{B-1}$, $R_{B-2}$, $R_{B-3}$ and $R_{B-4}$ are the same and equal to $CH_2$, Y is CO, $R_3$ is methyl, $R_5$ is 4-[(2,6-dichlorobenzoyl)amino]phenyl and stereochemistry is (S,S)).

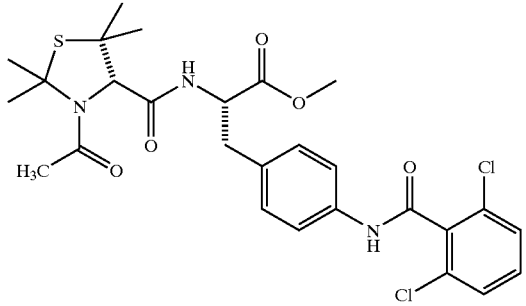

Example 87 was prepared as described in Scheme B from D-penicillamine and acetone using acetyl chloride to form the requisite amide. Physical data as follows: IR (mull) 1741, 1692, 1676, 1629, 1606, 1563, 1538, 1516, 1431, 1410, 1352, 1320, 1276, 1251, 1223 cm$^{-1}$; $^1$H NMR (DMSO-d$_6$) δ 10.70 (1H), 8.57 (1H), 7.56 (4H), 7.22 (2H), 4.63 (1H), 4.49 (1H), 3.65 (3H), 3.30 (1H), 3.12 (1H), 2.84 (1H), 1.92 (3H), 1.82 (3H), 1.78 (3H), 1.51 (3H), 0.80 (3H); $^{13}$C NMR (DMSO-d$_6$) δ 184.2, 171.9, 168.9, 168.1, 161.8, 137.1, 136.3, 132.4, 131.3, 131.2, 131.0, 129.4, 128.1, 119.3, 75.9, 72.8, 53.5, 52.0, 49.2, 48.4, 36.0, 33.5, 31.9, 27.6, 24.9, 24.5; MS (ESI+) for $C_{27}H_{31}Cl_2N_3O_5S$ m/z 580.1 (M+H)$^+$; MS (ESI−) for $C_{27}H_{31}Cl_2N_3O_5S$ m/z 577.9 (M−H)$^-$; Anal. Calcd for $C_{27}H_{31}Cl_2N_3O_5S$·0.12H$_2$O: C, 55.66; H, 5.40; N, 7.21. Found: C, 55.68; H, 5.39; N, 7.16. % Water (KF): 0.36.

EXAMPLE 88

[R-(R*,S*)]-4-[[[1-Carboxy-2-[4-[(2,6-dichlorobenzoyl)amino]phenyl]ethyl]amino]carbonyl]-2,2,5,5-tetramethyl-δ-oxo-3-thiazolidinepentanoic Acid (Scheme B, B-6: where $R_{B-1}$, $R_{B-2}$, $R_{B-3}$ and $R_{B-4}$ are the same and equal to $CH_2$, Y is CO, $R_3$ is $CH_2CH_2CH_2CO_2H$, $R_5$ is 4-[(2,6-dichlorobenzoyl)amino]phenyl and stereochemistry is (R,S)).

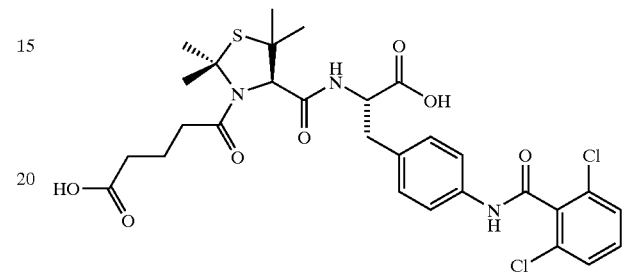

Example 88 was prepared as described in Scheme B from D-penicillamine and acetone using methyl glutaryl chloride to form the requisite amide. Physical data as follows: $^1$H NMR (DMSO-d$_6$) δ 10.65 (1H), 8.45 (1H), 7.53 (5H), 7.22 (2H), 4.51 (1H), 3.11 (3H), 2.77 (1H), 2.21 (4H), 1.89 (3H), 1.82 (3H), 1.11 (2H), 1.48 (3H), 0.77 (3H); $^{13}$C NMR (DMSO-d$_6$) δ 184.2, 174.2, 173.1, 170.1, 168.7, 161.7, 137.0, 136.3, 133.1, 131.3, 131.1, 129.4, 128.1, 119.2, 74.9, 73.0, 53.8, 49.3, 36.1, 34.8, 33.5, 32.7, 31.9, 27.7, 24.5, 20.0; MS (ESI+) for $C_{29}H_{33}Cl_2N_3O_7S$ m/z 638.0 (M+H)$^+$; MS (ESI−) for $C_{29}H_{33}Cl_2N_3O_7S$ m/z 635.9 (M−H)$^-$; HRMS (FAB) calcd for $C_{29}H_{33}Cl_2N_3O_7S+H_1$ 638.1494, found 638.1481; Anal. Calcd for $C_{29}H_{33}Cl_2N_3O_7S$·0.75H$_2$O: C, 53.42; H, 5.33; N, 6.44; Found: C, 53.20; H, 5.26; N, 6.45.

Scheme C

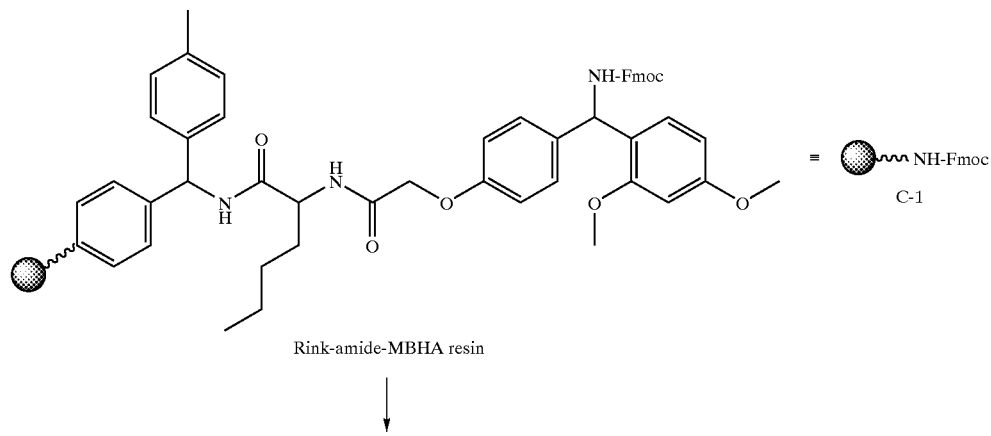

Rink-amide-MBHA resin

-continued
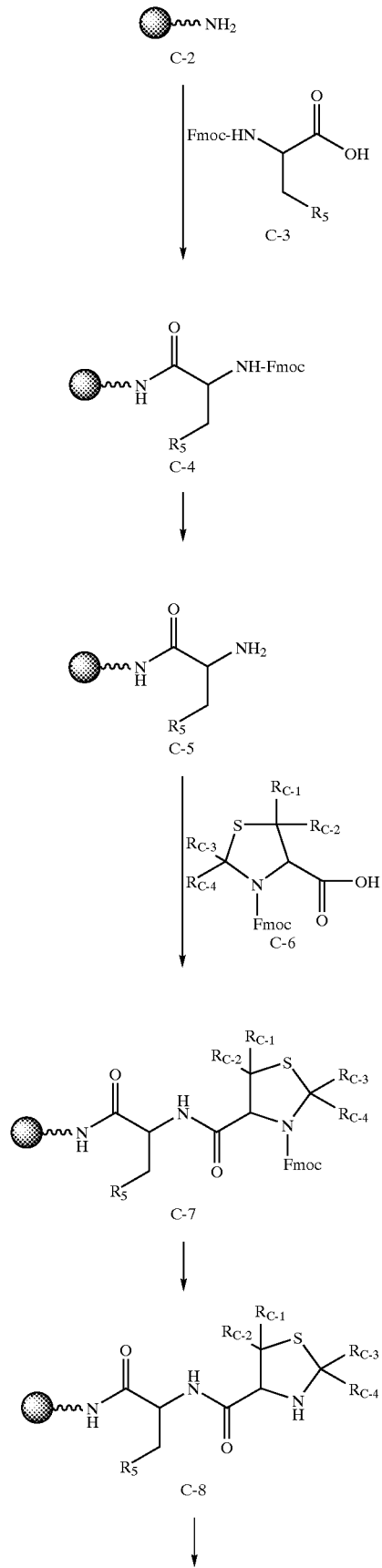

-continued

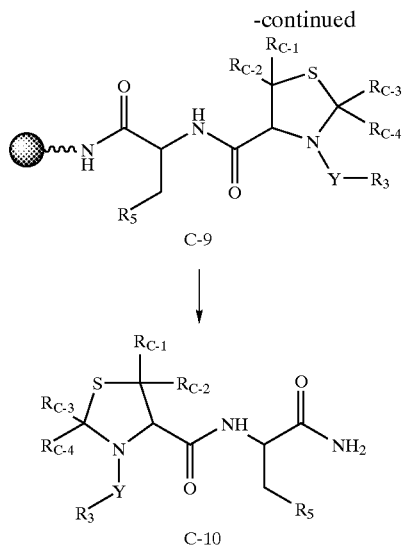

C-9

↓

C-10

Where: $R_{C-1}$, $R_{C-2}$, and $R_{C-3}$ are defined independently as $R_1$. $R_{C-4}$ is defined as $R_2$.

Scheme C describes a method for the preparation of examples of the formula C-10. Commercially available Rink Amide MBHA resin is deprotected under standard solid-phase peptide synthesis conditions (Atherton, E.; Sheppard R. C. *Solid Phase Peptide Synthesis: A Practical Approach*; IRL Press at Oxford University Press: Oxford, 1989) to afford the amine of formula C-2. Acylation with a commercially available or readily prepared amino acid residue of general C-3 affords the resin bound derivative of formula C-4. Removal of the Fmoc group under standard conditions provides amine of general structure C-5 which is acylated with a commercially available or readily prepared thiazolidine-4-carboxylic acid of general formula C-6 to afford the resin bound intermediate C-7. Standard Fmoc deprotection affords the resin bound amine of general formula C-8 which may be reacted with a variety of electrophilic reagents as described in Scheme A to afford resin bound amides, ureas, sulfonamides and carbamates of general structure C-9. Preparation 18 details an example of the reaction of a mixed carbonate to afford a carbamate of general structure C-9 (where Y is equal to $CO_2$). Standard acidolysis affords the amide of general structure C-10.

PREPARATION 18 AND EXAMPLE 89

[S-(R*,R*)]-4-[[[1-[[4-[(2,6-Dichlorophenyl) methoxy]phenyl]methyl]-2-amino-2-oxoethyl] amino]carbonyl]-3-thiazolidinecarboxylic Acid 3-[2-(4-morpholinyl)ethyl]ester (Scheme C, C-10: where $R_{C-1}$, $R_{C-2}$, $R_{C-3}$ and $R_{C-4}$ are the same and equal to proton, $R_3$ is 2-(4-morpholinyl)ethyl, $R_5$ is 4-[(2,6-dichlorophenyl)methoxy]phenyl, Y is $CO_2$ and stereochemistry is (S,S)).

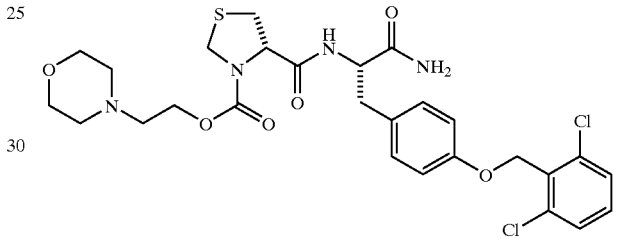

To a mixture of Rink Amide MBHA resin (Scheme C, C-1) (Nova Biochem., 1.2 g, ca. 0.59 mmol) in methylene chloride (20 mL) was added a solution of piperidine in DMF (30%, 20 mL). A slow stream of nitrogen was bubbled through the mixture to effect mixing for 20 min. The resin was filtered and washed with DMF. The resin was suspended in a solution of piperidine in DMF (30%, 40 ml) and mixed for 40 min. The resin was filtered and washed with DMF, methylene chloride, methanol and methylene chloride to afford resin C-2, which was diluted with DMF (40 mL). To this mixture was added Fmoc-Tyr(2,6-$Cl_2$-Bn) (Scheme C, C-3: where $R_5$ is 4-[(2,6-dichlorophenyl)methoxy]phenyl and stereochemistry is (S)) (Advanced Chemtech, 1.32 g, 2.35 mmol), HOBt (0.36 g, 2.35 mmol), PyBOP (1.20 g, 2.35) and DIEA (1.03 mL, 5.90 mmol). The reaction was mixed for 4 h and the resin filtered and washed with DMF, methylene chloride. MeOH and methylene chloride to afford the intermediate resin-bound amino acid derivative C-4 (Scheme C, where $R_5$ is 4-[(2,6-dichlorophenyl)methoxy] phenyl and stereochemistry is (S)) which was used without characterization.

To a mixture of resin C-4 described above in methylene chloride (20 mL) was added a solution of piperidine in DMF (30%, 20 mL). A slow stream of nitrogen was bubbled through the mixture to effect mixing for 20 min. The resin was filtered and washed with DMF. The resin was suspended in a solution of piperidine in DMF (30%, 40 ml) and mixed for 40 min. The resin was filtered and washed with DMF, methylene chloride, methanol and methylene chloride to afford the resin of structure C-5 (Scheme C, where $R_5$ is 4-[(2,6-dichlorophenyl)methoxy]phenyl and stereochemistry is (S)), which was diluted with DMF (40 mL). To this mixture was added Fmoc-D-thiazolidine-4-carboxylic acid (Scheme C, C-6: where $R_{C-1}$, $R_{C-2}$, $R_{C-3}$ and $R_{C-4}$ are the same and equal to proton and stereochemistry is (S)) (Advanced Chemtech, 832 mg, 2.35 mmol), HOBt (0.36 g, 2.35 mmol), PyBOP (1.20 g, 2.35) and DIEA (1.03 mL, 5.90 mmol). The reaction was mixed for 4 h and the resin filtered and washed with DMF, methylene chloride, MeOH and methylene chloride to afford the intermediate resin-bound derivative C-7 (Scheme C, where $R_{C-1}$, $R_{C-2}$, $R_{C-3}$ and $R_{C-4}$ are the same and equal to proton, $R_5$ is 4-[(2,6-dichlorophenyl)methoxy]phenyl and stereochemistry is (S,S)) which was used without characterization.

To a mixture of resin C-7 described above in methylene chloride (20 mL) was added a solution of piperidine in DMF (30%, 20 mL). A slow stream of nitrogen was bubbled through the mixture to effect mixing for 20 min. The resin was filtered and washed with DMF. The resin was suspended in a solution of piperidine in DMF (30%, 40 ml) and mixed for 40 min. The resin was filtered and washed with DMF, methylene chloride, methanol and methylene chloride to provide the intermediate of structure C-8 (Scheme C, where $R_{C-1}$, $R_{C-2}$, $R_{C-3}$ and $R_{C-4}$ are the same and equal to proton, $R_5$ is 4-[(2,6-dichlorophenyl)methoxy]phenyl and stereochemistry is (S,S)), which was diluted with methylene chloride (10 mL). To this mixture was added a solution of the mixed carbonate prepared from 4-(2-hydroxyethyl) morpholine (2.14 mL, 17.7 mmol) and N,N-disuccinimidyl carbonate (4.53 g, 17.7 mmol) as described in preparation 8 in methylene chloride (20 mL) followed by triethylamine (0.33 mL, 2.36 mmol). The reaction was mixed for 24 h and the resin filtered and washed extensively with DMF, methylene chloride. MeOH, and anhydrous ethyl ether. The resin was dried in vacuo to afford the resin-bound carbamate C-9 (Scheme C, where $R_{C-1}$, $R_{C-2}$, $R_{C-3}$ and $R_{C-4}$ are the same and equal to proton, $R_3$ is 2-(4-morpholinyl)ethyl, $R_5$ is 4-[(2,6-dichlorophenyl)methoxy]phenyl, Y is $CO_2$ and stereochemistry is (S,S)).

Resin C-9 was swelled with a minimum of methylene chloride (ca. 2 mL) and suspended with 95% aqueous TFA (20 mL). The mixture was mixed by magnetic stirring for 1 h and filtered. The resin was washed with additional TFA (2×5 mL), followed by methylene chloride and methanol. The combined filtrates were evaporated in vacuo, and partioned between ethyl acetate and saturated aqueous sodium bicarbonate. The organic layer was separated and washed with brine, dried ($MgSO_4$), filtered and evaporated in vacuo. The residue was purified by flash chromatography using methylene chloride/methanol (1 to 3%) as eluant to afford the title compound (215 mg) as an amorphous powder: IR (mull) 3288, 1676, 1657, 1611, 1564, 1511, 1439, 1424, 1346, 1302, 1237, 1179, 1116, 1021, 767 $cm^{-1}$; $^1$H NMR ($CDCl_3$, 300 MHz) δ 7.24 (5H), 6.93 (2H), 5.20 (2H), 4.63 (3H), 4.34 (1H), 4.22 (2H), 3.63 (4H), 3.11 (4H), 2.50 (6H), $^{13}$C NMR ($CDCl_3$, 75 MHz) δ 173.4, 170.1, 157.9, 154.5, 136.9, 132.0, 130.4, 129.1, 128.4, 115.1, 66.8, 65.2, 63.4, 57.1, 54.0, 53.7, 53.5, 49.4, 35.2; MS (EI) m/z (rel. intensity) 610 ($M^+$, 1), 323 (13), 321 (20), 161 (34), 159 (53), 114 (31), 113 (98), 100 (99), 88 (13), 70 (8), 56 (11); MS (FAB) m/z (rel. intensity) 611 ($MH^+$, 71), 614 (18), 613 (49), 612 (27), 611 (71), 123 (60), 114 (99), 113 (76), 112 (19), 107 (22), 100 (28); HRMS (FAB) calcd for $C_{27}H_{32}Cl_2N_4O_6S+H_1$ 611.1498, found 611.1494, Anal. Calcd for $C_{27}H_{32}Cl_2N_4O_6S$: C, 53.03; H, 5.27; N, 9.16. Found: C, 52.74; H, 5.17; N, 9.01.

EXAMPLE 90

[S-(R*,R*)]-4-[[[1-[[4-[(2,6-Dichlorophenyl) methoxy]phenyl]methyl]-2-amino-2-oxoethyl] amino]carbonyl]-3-thiazolidinecarboxylic Acid 3-Ethyl Ester (Scheme C, C-10: where $R_{C-1}$, $R_{C-2}$, $R_{C-3}$ and $R_{C-4}$ are the same and equal to proton, $R_3$ is ethyl, $R_5$ is 4-[(2,6-dichlorophenyl)methoxy]phenyl, Y is $CO_2$ and stereochemistry is (S,S)).

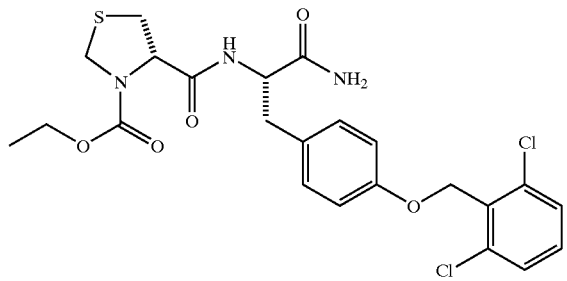

Example 90 was prepared as described in Scheme C. Physical data as follows: IR (mull) 3369, 3308, 3192, 1713, 1667, 1650, 1629, 1539, 1513, 1441, 1344, 1290, 1240, 1016, 768 $cm^{-1}$; $^1$H NMR ($CDCl_3$, 300 MHz) δ 7.33 (3H), 7.16 (2H), 6.95 (2H), 5.25 (2H), 4.48 (4H), 4.20 (2H), 3.03 (4H), 1.26 (3H); $^{13}$C NMR ($CDCl_3$, 75 MHz) δ 173.6, 170.5, 157.8, 154.7, 136.8, 313.9, 130.4, 130.2, 129.0, 128.4, 114.9, 67.9, 65.1, 63.1, 62.5, 53.8, 36.5, 14.3; MS (EI) m/z (rel. intensity) 525 ($M^+$, 1), 323 (44), 322 (13), 321 (68), 267 (9), 265 (14), 163 (12), 161 (65), 160 (35), 159 (99), 88 (30); MS (FAB) m/z m/z (rel. intensity) 526 ($MH^+$, 58), 528 (40), 527 (19), 526 (58), 321 (27), 188 (29), 161 (37), 160 (9), 159 (48), 107 (26), 88 (39); HRMS (FAB) calcd for $C_{23}H_{25}Cl_2N_3O_5+H_1$ 526.0970, found 526.0942, Anal. Calcd for $C_{23}H_{25}Cl_2N_3O_5S$: C, 52.47; H, 4.79; N, 7.98. Found: C, 52.34; H, 4.81; N, 7.90.

Scheme D

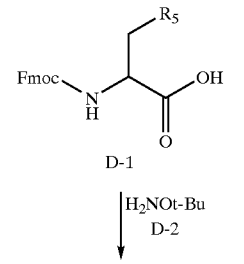

D-1

↓ $H_2NOt$-Bu
D-2

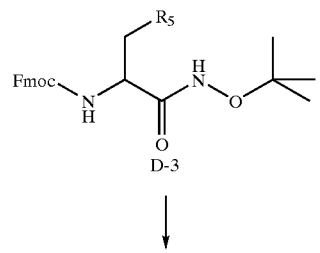

D-3

↓

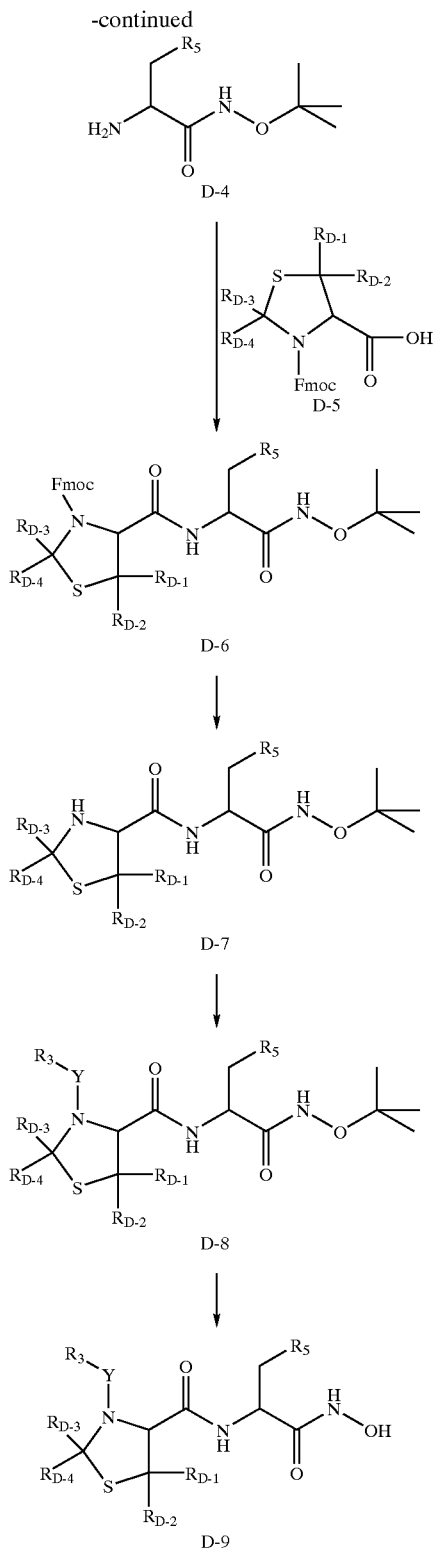

D-4

D-5

D-6

D-7

D-8

D-9

$R_{D-1}$, $R_{D-2}$ and $R_{D-3}$ are defined independently as $R_1$. $R_{D-4}$ is defined as $R_2$.

Scheme D describes a method for the preparation of examples of general formula D-9. Commercially available or readily prepared N-α-Fmoc protected amino acids of general structure D-1 are coupled with O-(tert-butyl) hydroxylamine (D-2) under standard coupling conditions as previously referenced to afford the 1-butyl hydroxamate of general structure D-3. Standard Fmoc deprotection affords the intermediate amine of formula D-4. Coupling of this amine with a commercially available or readily prepared N-α-Fmoc-thiazolidine-4-carboxylic acid of general structure D-5 affords the pseudodipeptide intermediate of general structure D-6. Standard Fmoc deprotection affords the intermediate amine of general structure D-7 which may be reacted under the variety of conditions described in Scheme A to afford amides, carbamates, sulfonamides and ureas of general structure D-8. Preparation 22 provides a specific example of the reaction of an amine of general structure D-7 with a carbonate to afford a carbamate of general structure D-8. Mild acidolysis affords the hydroxamate of general structure D-9.

PREPARATION 19

(Scheme D, D-3: where $R_5$ is 4-[(2,6-dichlorophenyl)methoxy]phenyl and stereochemistry is (S)).

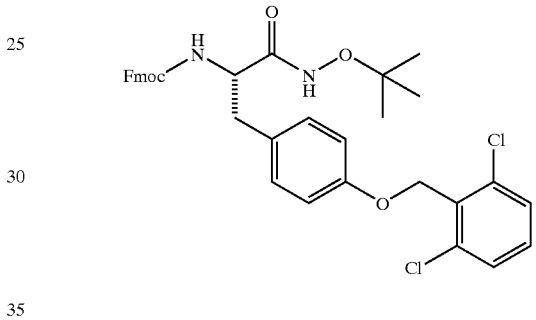

To a cooled (0–5° C.) solution of Fmoc-Tyr(2,6-Cl$_2$-Bn) (Scheme D, D-1: where $R_5$ is 4-[(2,6-dichlorophenyl)methoxy]phenyl and stereochemistry is (S)) (Advanced Chemtech, 6.0 g, 10.7 mmol), HOBt (1.63 g, 10.7 mmol), O-(tert-butyl)hydroxylamine hydrochloride (Scheme D, D-2) (1.61 g, 12.80 mmol) in methylene chloride (30 mL) was added PyBOP (6.66 g, 12.80 mmol) followed by DIEA (6.51 mL, 37.35 mmol). The mixture was stirred at 0–5° C. for 1 hour, gradually allowed to warm to room temperature and stirred an additional 2 h. The mixture was diluted with methylene chloride and 0.25 N HCl, the organic layer separated and washed with saturated aqueous NaHCO$_3$, and brine, dried (MgSO$_4$), filtered and evaporated in vacuo. The residue was purified by flash chromatography using methylene chloride/methanol (0–2.5%) as eluant to afford the title compound (5.87 g) as an amorphous powder: $^1$H NMR (CDCl$_3$, 300 MHz) δ 8.08 (1H), 7.76 (2H), 7.54 (2H), 7.29 (9H), 6.95 (2H), 5.43 (1H), 5.30 (2H), 4.28 (4H), 3.06 (2H), 1.19 (9H); $^{13}$C NMR (CDCl$_3$, 75 MHz) δ 169.7, 157.8, 156.3, 143.6, 141.2, 136.8, 132.0, 130.4, 128.9, 128.4, 127.7, 127.0, 125.0, 119.9, 115.0, 82.3, 67.1, 65.1, 54.0, 46.9, 37.6, 26.0; MS (ESI+) for C$_{35}$H$_{34}$Cl$_2$N$_2$O$_5$ m/z 632.9 (M+H)$^+$, MS (ESI+) for C$_{35}$H$_{34}$Cl$_2$N$_2$O$_5$ m/z 654.9 (M+Na)$^+$.

PREPARATION 20

(Scheme D, D-6: where $R_{D-1}$, $R_{D-2}$, $R_{D-3}$ and $R_{D-4}$ are the same and equal to proton. $R_5$ is 4-(2,6-dichlorophenyl)methoxy]phenyl and stereochemistry is (S,S)).

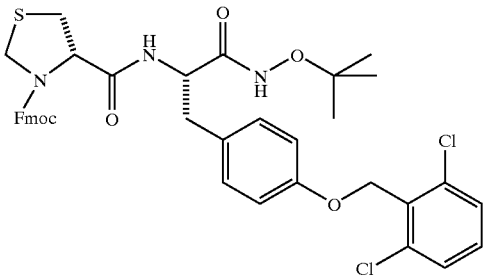

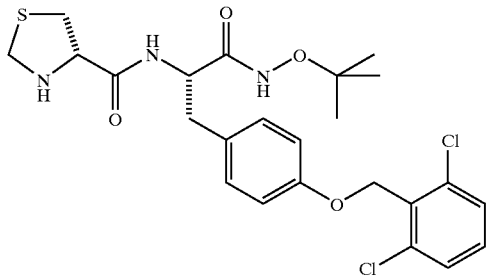

To a solution of D-3 (Scheme D, where $R_5$ is 4-[(2,6-dichlorophenyl)methoxy]phenyl and stereochemistry is (S)) (5.87 g, 9.28 mmol) in anhydrous DMF (94 mL) was added diethylamine (9.40 mL, 90.84 mmol) at ambient temperature. The solution was stirred for 90 min and volatiles were removed in vacuo to afford the intermediate amine D-4 (Scheme D, where $R_5$ is 4-[(2,6-dichlorophenyl)methoxy]phenyl and stereochemistry is (S)) as an oil which was used without further purification.

To a cooled (0–5° C.) solution of Fmoc-D-thiazolidine-4-carboxylic acid (Scheme D, D-5: where $R_{D-1}$, $R_{D-2}$, $R_{D-3}$ and $R_{D-4}$ are the same and equal to proton and stereochemistry is (S)) (Advanced Chemtech. 3.93 g, 11.10 mmol) and HOAt (1.51 g, 11.10 mmol) in methylene chloride/DMF (4:1, 30 mL) was added EDC (2.12 g, 11.10 mmol). The reaction mixture was allowed to stir for 15 min and a solution of the amine (D-4 described above) in methylene chloride/DMF (4:1, 30 mL) was added followed by DIEA (1.61 mL, 9.28 mmol). After 1 h at 0–5° C., an additional equivalent of DIEA (1.61 mL, 9.28 mmol) was added and the mixture allowed to warm to room temperature. After stirring overnight, volatiles were removed in vacuo and the residue partitioned between ethyl acetate and 0.25 N aqueous HCl. The organic layer was separated and washed with water, saturated aqueous $NaHCO_3$, brine, dried ($Na_2SO_4$), filtered and concentrated in vacuo. The residue was purified by flash chromatography using $CH_2Cl_2$/acetone (3%) containing isopropanol (0.1%) as eluant to afford the title compound (2.4 g) as an amorphous solid: $^1H$ NMR (300 MHz, $CDCl_3$) δ 7.77 (2H), 7.55 (2H), 7.32 (7H), 7.12 (2H), 6.92 (2H), 6.70 (1H), 5.19 (3H), 4.55 (5H), 4.26 (2H), 3.30 (1H), 3.11 (2H), 1.14 (9H); $^{13}C$ NMR (75 MHz, $CDCl_3$) δ 170.0, 168.8, 158.0, 143.4, 141.3, 137.0, 132.1, 130.4, 128.5, 127.9, 127.2, 124.9, 120.1, 115.3, 82.5, 68.4, 65.3, 52.8, 47.1, 36.5, 26.2. MS (ESI+) for $C_{39}H_{39}Cl_2N_3O_6S$ m/z 747.9 $(M+H)^+$; MS (ESI+) for $C_{39}H_{39}Cl_2N_3O_6S$ m/z 769.8 $(M+Na)^+$; MS (ESI–) for $C_{39}H_{39}Cl_2N_3O_6S$ m/z 745.7 $(M-H)^-$.

PREPARATION 21

(Scheme D, D-7: where $R_{D-1}$, $R_{D-2}$, $R_{D-3}$ and $R_{D-4}$ are the same and equal to proton, $R_5$ is 4-[(2,6-dichlorophenyl)methoxy]phenyl and stereochemistry is (S,S)).

To a solution of D-6 (Scheme D, where $R_{D-1}$, $R_{D-2}$, $R_{D-3}$ and $R_{D-4}$ are the same and equal to proton, $R_5$ is 4-[(2,6-dichlorophenyl)methoxy]phenyl and stereochemistry is (S,S)) (500 mg, 0.67 mmol) in anhydrous DMF (7 mL) was added diethylamine (0.70 mL, 6.55 mmol) at ambient temperature. The solution was stirred for 90 min and volatiles were removed in vacuo. The residue was washed with ethyl ether/hexane (3:2) to afford the title compound (352 mg) as an amorphous solid which was used without further purification: $^1H$ NMR (300 MHz, DMSO-$d_6$) δ 10.61 (1H), 8.27 (1H), 7.54 (2H), 7.44 (1H), 7.15 (2H), 6.94 (2H), 5.15 (2H), 4.50 (1H), 4.03 (2H), 3.75 (1H), 3.19 (1H), 2.82 (3H), 2.57 (1H), 1.06 (9H); MS (ESI+) for $C_{24}H_{29}Cl_2N_3O_4S$ m/z 526.1 $(M+H)^+$; MS (ESI–) for $C_{24}H_{29}Cl_2N_3O_4S$ m/z 524.1 $(M-H)^-$.

PREPARATION 22

(Scheme D, D-8: where $R_{D-1}$, $R_{D-2}$, $R_{D-3}$ and $R_{D-4}$ are the same and equal to proton, $R_3$ is 2-(4-morpholinyl)ethyl, $R_5$ is 4-[(2,6-dichlorophenyl)methoxy]phenyl, Y is $CO_2$ and stereochemistry is (S,S)).

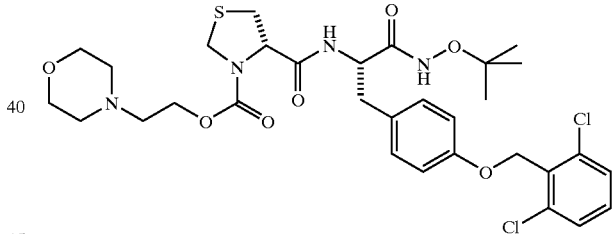

To a solution of 4-(2-hydroxyethyl)morpholine (1.22 mL, 10.05 mmol) in $CH_3CN$ (55 mL) at ambient temperature was added N,N-disuccinimidyl carbonate (2.49 g, 10.05 mmol) and triethylamine (4.20 mL, 30.15 mmol). The solution was stirred at room temperature for 4 h and concentrated in vacuo to give a viscous oil. The oil was dissolved in a minimal amount of methylene chloride (15 mL) and added to a solution of D-7 (Scheme D, where $R_{D-1}$, $R_{D-2}$, $R_{D-3}$ and $R_{D-4}$ are the same and equal to proton, $R_5$ is 4-[(2,6-dichlorophenyl)methoxy]phenyl and stereochemistry is (S,S) (350 mg, 0.67 mmol), triethylamine (0.10 m, 0.74 mmol) and DMAP (1 mg) in $CH_2Cl_2$ (4 mL). The reaction mixture was stirred overnight and diluted with $CH_2Cl_2$ (15 mL). Propylamine (8.6 mL, 100.5 mmol) was slowly added (exothermic) and the solution stirred vigorously for 15 min, then diluted with water. The organic layer was separated and washed with 0.1 M HCl, saturated aqueous $NaHCO_3$, and brine, dried ($MgSO_4$), filtered and concentrated in vacuo. Purification of the residue by flash chromatography using ethyl acetate/acetone (3:1) as eluant afforded the title compound (251 mg) as an white powder: IR (mull) 3264, 1709, 1661, 1564, 1531, 1512, 1439, 1419, 1345, 1301, 1241, 1181, 1118, 1016, 767 cm$^{-1}$; $^1$H NMR (300 MHz, CDCl$_3$) δ 8.48 (1H), 7.36 (2H), 7.24 (1H), 7.17 (2H), 6.96 (2H), 5.23 (2H), 4.60 (3H), 4.31 (3H), 3.71 (4H), 3.33 (4H), 2.59 (6H), 1.15 (9H); $^{13}$C NMR (75 MHz, CDCl$_3$) δ 168.9, 158.0, 137.0, 132.1, 130.5, 128.7, 128.5, 115.3, 82.5, 66.8, 65.3, 63.4, 57.2, 53.7, 52.9, 36.4, 30.6, 29.3, 26.2, 19.1, 13.7; MS (ESI+) for C$_{31}$H$_{40}$Cl$_2$N$_4$O$_7$S m/z 682.9 (M+H)$^+$, MS (ESI+) for C$_{31}$H$_{40}$Cl$_2$N$_4$O$_7$S m/z 705.0 (M+Na)$^+$; Anal. Calcd for C$_{31}$H$_{40}$Cl$_2$N$_4$O$_7$S·0.35H$_2$O: C, 53.97; H, 5.95; N, 7.95. Found: C, 54.22; H, 6.11; N, 7.95. % Water (KF): 0.91.

PREPARATION 23 AND EXAMPLE 91

(Scheme D, D-9: where R$_{D-1}$, R$_{D-2}$, R$_{D-3}$ and R$_{D-4}$ are the same and equal to proton, R$_3$ is 2-(4-morpholinyl)ethyl, R$_5$ is 4-[(2,6-dichlorophenyl)methoxy]phenyl, Y is CO$_2$ and stereochemistry is (S,S)).

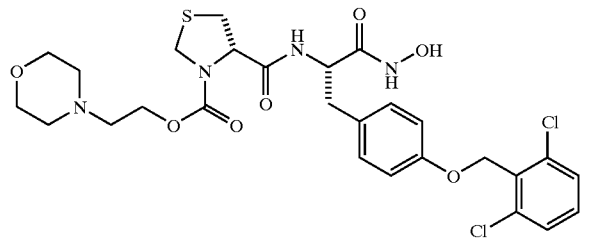

Hydroxamate D-8 (Scheme D, where R$_{D-1}$, R$_{D-2}$, R$_{D-3}$ and R$_{D-4}$ are the same and equal to proton, R$_3$ is 2-(4-morpholinyl)ethyl, R$_5$ is 4-[(2,6-dichlorophenyl)methoxy]phenyl, Y is CO$_2$ and stereochemistry is (S,S)) (150 mg, 0.22 mmol) was dissolved in anhydrous TFA (12 mL) at ambient temperature and gradually warmed to 40° C. After 5 h at 40° C., volatiles were removed in vacuo and the residue partitioned between ethyl acetate and saturated aqueous NaHCO$_3$. The organic layer was separated and washed with brine, dried (MgSO$_4$), filtered and concentrated in vacuo. Purification of the residue by flash chromatography using methylene chloride/methanol (5%) as eluant afforded the title compound (51 mg) as an amorphous solid: IR (mull) 3273, 3229, 1708, 1652, 1564, 1546, 1511, 1439, 1422, 1346, 1236, 1180, 1114, 1022, 768 cm$^{-1}$; $^1$H NMR (300 MHz, DMSO-d$_6$) δ 10.70 (1H), 8.93 (1H), 8.32 (1H), 7.54 (2H), 7.45 (1H), 7.12 (2H), 6.93 (2H), 5.16 (2H), 4.56 (2H), 4.36 (1H), 4.25 (1H), 4.06 (2H), 3.51 (4H), 2.76 (3H), 2.36 (4H); $^{13}$C NMR (75 MHz, DMSO-d$_6$) δ 169.8, 167.9, 157.6, 136.5, 132.2, 132.0, 130.8, 130.5, 129.2, 114.7, 66.7, 65.3, 63.3, 59.1, 57.1, 53.8, 52.1, 37.8, 31.3, 30.1; MS (ESI+) for C$_{27}$H$_{32}$Cl$_2$N$_4$O$_7$S m/z 627.0 (M+H)$^+$; MS (ESI-) for C$_{27}$H$_{32}$Cl$_2$N$_4$O$_7$S m/z 624.9 (M-H)$^-$; Anal. Calcd for C$_{27}$H$_{32}$Cl$_2$N$_4$O$_7$S·0.46H$_2$O: C, 51.00; H, 5.22; N, 8.81. Found: C, 51.34; H, 5.23; N, 8.67. % Water (KF): 1.31.

EXAMPLE 92

(Scheme D, D-9: where R$_{D-1}$, R$_{D-2}$, R$_{D-3}$ and R$_{D-4}$ are the same and equal to proton, R$_3$ is ethyl, R$_5$ is 4-[(2,6-dichlorophenyl)methoxy]phenyl, Y is CO$_2$ and stereochemistry is (S,S).

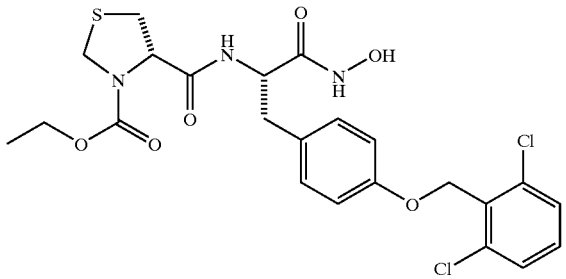

Example 92 was prepared as described in Scheme D from Fmoc-Tyr(2,6-Cl$_2$-Bn) using ethyl chloroformate to provide the requisite carbamate. Physical properties as follows: IR (mull) 3278, 1654, 1612, 1585, 1564, 1547, 1511, 1439, 1347, 1237, 1195, 1179, 1022, 782, 769 cm$^{-1}$; $^1$H NMR (300 MHz, CDCl$_3$) δ 7.39 (3H), 7.17 (2H), 6.94 (2H), 5.24 (2H), 4.53 (4H), 4.18 (2H), 3.15 (2H), 2.87 (2H), 1.28 (3H); $^{13}$C NMR (75 MHz, CD$_3$OD) δ 172.7, 170.1, 159.4, 156.2, 138.1, 133.7, 132.1, 131.6, 130.8, 129.8, 115.9, 66.3, 64.4, 63.6, 38.6, 36.8, 35.1, 15.0; HRMS (FAB) calcd for C$_{23}$H$_{25}$Cl$_2$N$_3$O$_6$S+H$_1$ 542.0919, found 542.0921; Anal. Calcd for C$_{23}$H$_{25}$Cl$_2$N$_3$O$_6$S: C, 50.93; H, 4.64; N, 7.75. Found: C, 50.79; H, 4.79; N, 7.52.

EXAMPLE 93

(Scheme D, D9: where R$_{D-1}$, R$_{D-2}$, R$_{D-3}$ and R$_{D-4}$ and RDA are the same and equal to proton, R$_3$ is 2-(1-piperidinyl)ethyl, R$_5$ is 4-[(2,6-dichlorophenyl)methoxy]phenyl, Y is CO, and stereochemistry is (S,S)).

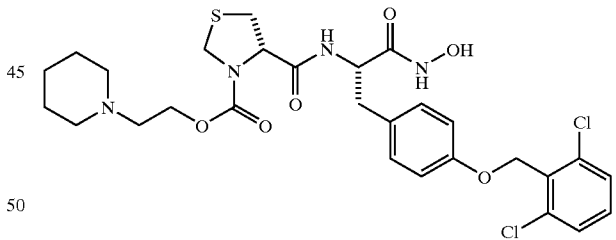

Example 93 was prepared as described in Scheme D from Fmoc-Tyr(2,6-Cl$_2$-Bn) using 1-(2-hydroxyethyl)piperidine to provide the requisite carbamate. Physical properties as follows: IR (mull) 3276, 1707, 1653, 1611, 1584 1564, 1511, 1439, 1237, 1195, 1179, 1144, 1113, 1093, 1021 cm$^{-1}$; $^1$H NMR (300 MHz, DMSO-d$_6$) δ 7.54 (2H), 7.44 (1H), 7.12 (2H), 6.93 (2H), 5.16 (2H), 4.58 (2H), 4.36 (1H), 4.25 (1H), 4.00 (3H), 4.36 (3H), 2.31 (3H), 1.62 (1H), 1.42 (3H), 1.26 (8H); $^{13}$C NMR (75 MHz, DMSO-d$_6$) δ 172.2, 168.9, 167.3, 157.0, 135.9, 131.7, 131.4, 130.2, 129.9, 128.7, 114.1, 64.7, 63.0, 54.0, 51.6, 36.2, 30.9, 25.5, 24.7, 23.8, 22.0, 21.5, 13.9; MS (ESI+) for C$_{28}$H$_{34}$Cl$_2$N$_4$O$_6$S m/z 624.9 (M+H)$^+$.

Scheme E
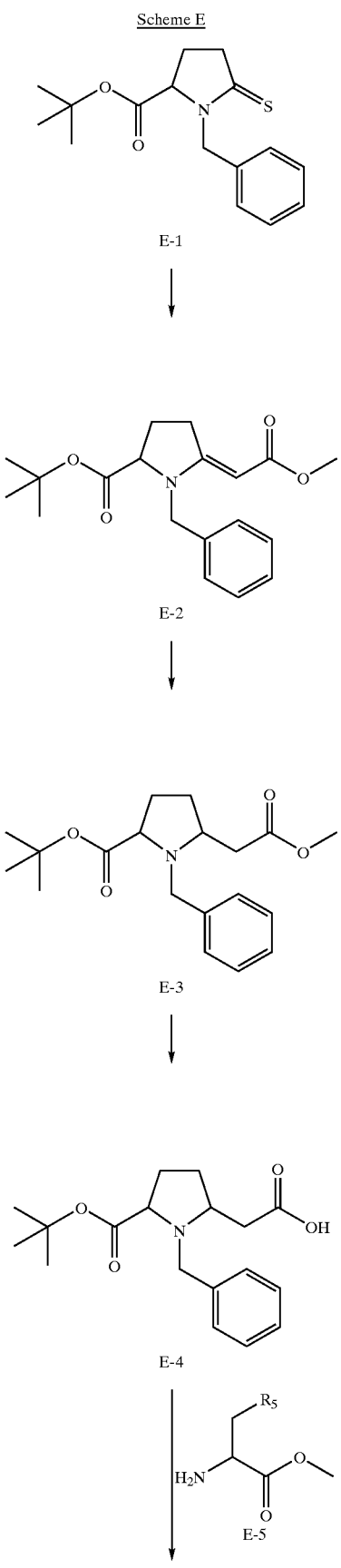
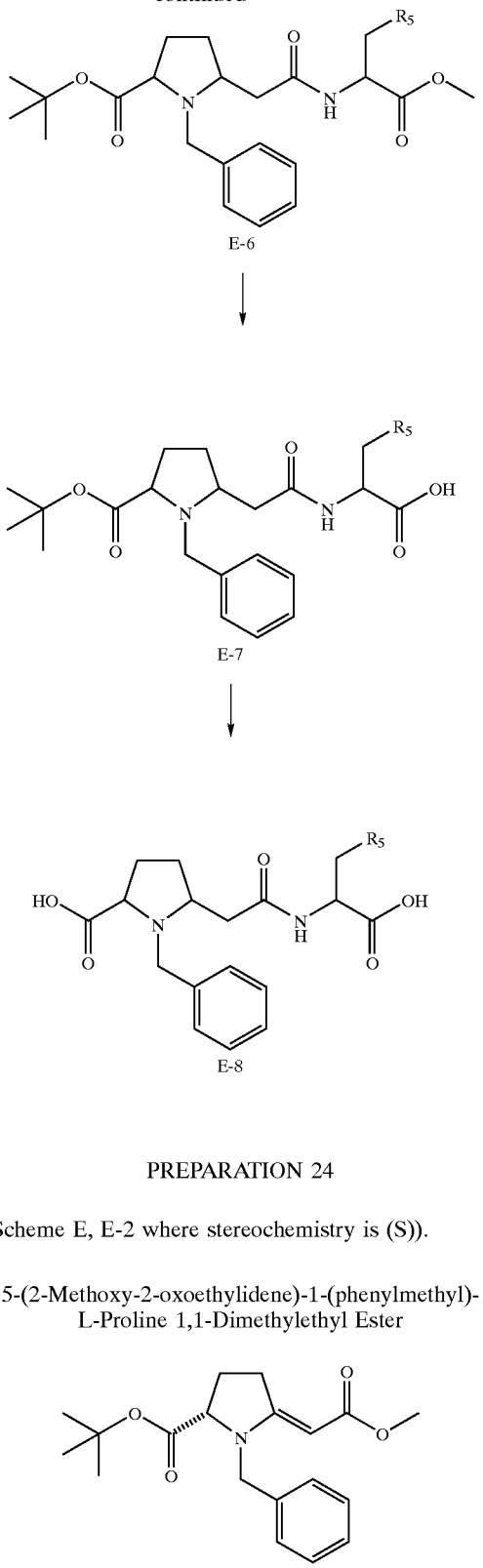
PREPARATION 24
(Scheme E, E-2 where stereochemistry is (S)).
5-(2-Methoxy-2-oxoethylidene)-1-(phenylmethyl)-L-Proline 1,1-Dimethylethyl Ester
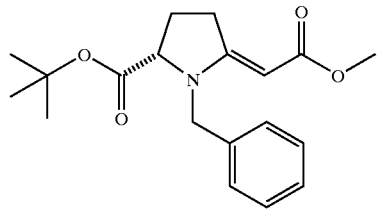
To a stirring solution of E-1 (Scheme E where stereochemistry is (S)) (3.62 g, 12.4 mmol), prepared by the method of Rapoport (*J. Am. Chem. Soc.* 1984, 106, 4539), in CH₃CN (10 mL) was added methyl bromoacetate (1.4 mL, 14.9 mmol). After stirring for 70 h, CH₂Cl₂ (70 mL) was added. The solution stirred for 10 minutes before Ph₃P (4.89 g, 18.6 mmol) was added, and after 2 minutes Et₃N (5.2 mL, 37.3 mmol) was added. After stirring for 20 h, the solution was washed with 1M NaH₂PO₄ (100 mL), and the aqueous phase was extracted with CH₂Cl₂ (50 mL). The combined organic phases were washed with brine, dried (Na₂SO₄), filtered, and evaporated in vacuo. The resulting yellow oil/white solid was dissolved in CHCl₃ and chromatographed on silica gel (300 g, 230–400 mesh, 70 mm OD column, packed CHCl₃, eluted with CHCl₃, 3 L, then 10:90 EtOAc-CHCl₃, 250 mL fractions) using the flash technique. Fractions 19–23 provided the title compound (3.23 g) as a pale yellow oil. ¹H-NMR: (300 MHz, CDCl₃): δ=7.17–7.36 (5H), 4.75 (1H), 4.54 (1H), 4.20 (1H), 3.96 (1H), 3.61 (3H), 3.36–3.47 (1H), 3.08 (1H), 2.04–2.28 (2H), 1.41 (9H); EI/MS (70 eV) m/z (rel. intensity): 331 (M⁺, 17.3), 275 (11.9), 230 (95.0), 170 (26.0), 91 (base); IR (neat): 2979, 2948, 1735, 1692, 1600, 1454, 1435, 1414, 1369, 1299, 1277, 1184, 1137, 1059, 964, 843, and 789 cm⁻¹; HRMS: Calcd. for C₁₉H₂₅N₁O₄: 331.1783. Found: 331.1771; [α]_D²⁵: +107° (c=0.939, CH₂Cl₂).

PREPARATION 25

(Scheme E, E-3 where stereochemistry is (2R,5S)).

(2R-cis)-5-[(1,1-Dimethylethoxy)carbonyl]-1-(phenylmethyl)-2-pyrrolidineacetic Acid Methyl Ester ((2R,5S))

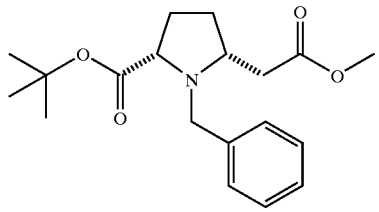

Raney-Nickel (20 g of a 50% slurry in H₂O) was washed with abs. EtOH (3×25 mL) and suspended in abs. EtOH (50 mL), and a solution of E-2 (Scheme E, where stereochemistry is (S)) (9.34 g, 28.2 mmol) in abs. EtOH (50 mL) was added. After stirring for 3 h, the Ra-Ni was removed by filtration, and the filtrate was evaporated in vacuo. The residue was dissolved in EtOAc (100 mL), 5% Pt/C (3.0 g) was added, and the mixture was hydrogenated under 50 psi H₂ for 12 h. The catalyst was removed by filtration and the filtrate was evaporated in vacuo. The residue was chromatographed on silica gel (300 g, 230–400 mesh, 70 mm OD column, packed and eluted with 15:85 EtOAc-hexanes, 270 mL fractions) using the flash technique. Fractions 5–8 provided the title compound (6.55 g) as a clear, colorless oil. ¹H-NMR: (300 MHz, CDCl₃): δ=7.22–7.34 (5H), 3.86 (1H), 3.79 (1H), 3.62 (3H), 3.21–3.29 (2H), 2.57 (1H), 2.33 (1H), 1.64–2.05 (4H), 1.37 (9H); EI/MS (70 eV) m/z (rel. intensity): 232 (base), 91 (39.8); IR (nujol): 2977, 1739, 1454, 1437, 1367, 1295, 1251, 1197, 1153, 1074, 844, 753, and 699 cm⁻¹; Anal: Calcd. for C₁₉H₂₇N₁O₄: C, 68.44; H, 8.16; N, 4.20. Found: C, 68.39; H, 8.1 5; N, 4.11; [α]_D²⁵: −22° (c 1.051, CH₂Cl₂).

PREPARATION 26

(Scheme E, E-4 where stereochemistry is (2R,5S)).

(2R-cis)-5-[(1,1-Dimethylethoxy)carbonyl]-1-(phenylmethyl)-2-pyrrolidineacetic Acid ((2R,5S))

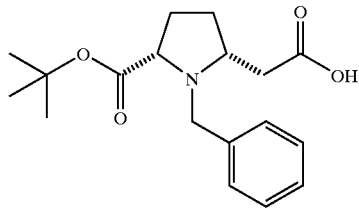

To a stirring solution of E-3 (Scheme E, where stereochemistry is (2R,5S)) (2.00 g, 6.00 mmol) in MeOH (60 mL) was added 1M K₂CO₃ (20 mL). After stirring for 12 h, the reaction mixture was evaporated in vacuo, the residue was dissolved in H₂O (0.1 L), the pH was adjusted to ca. 6 with 1M HCl, and the mixture was extracted with CHCl₃ (2×0.1 L). The combined extracts were washed with H₂O, brine, dried (Na₂SO₄), and evaporated in vacuo to afford the title compound (1.89 g) as a white solid. MP: 95–96° C. (lit. 98–101° C.); ¹H-NMR: (300 MHz, CDCl₃): δ=7.30–7.37 (5H), 4.00 (1H), 3.68 (1H), 3.45 (1H), 3.20 (1H), 2.59 (1H), 2.46 (1H), 1.76–2.21 (4H), 1.31 (9H); EI/MS (70 eV) m/z (rel. intensity): 218 (base), 91 (86.7); IR (nujol): 1719, 1497, 1451, 1367, 1296, 1285, 1260, 1160, 1153, 1079, 965, and 757 cm⁻¹; Anal: Calcd. for C₁₈H₂₅N₁O₄: C, 67.69; H, 7.89; N, 4.39. Found: C, 67.55; H, 7.97; N, 4.15; [α]_D²⁵: +27° (c=0.795, CH₂Cl₂).

PREPARATION 27

(Scheme E, E-6 where R₅ is 4-[(2,6-dichlorophenyl)methoxy]phenyl, and stereochemistry of the pyrrolidine ring is (2R,5S) and the amino acid is (S)).

(5R)-5-[2-[[(1S)-1-Methoxycarbonyl-2-[4-[(2,6-dichlorophenyl)methoxy]phenyl]ethyl]amino]-2-oxoethyl]-1-(phenylmethyl)-L-proline 1,1-Dimethylethyl Ester ((1S,5R,L))

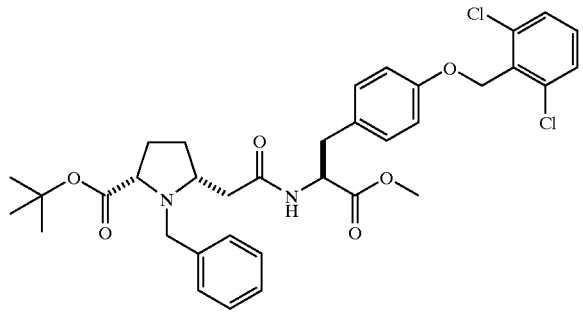

To a stirring solution of E-4 (Scheme E, where stereochemistry is (2R,5S)) (0.48 g, 1.50 mmol) in CH₂Cl₂ (10 mL) was added 1-(3-dimethylaminopropyl)-3-ethylcarbodiimide hydrochloride (0.29 g, 1.50 mmol), 1-hydroxybenzotriazole hydrate (0.20 g, 1.50 mmol), 4-dimethylaminopyridine (0.05 g, 0.45 mmol), and 2,6-dichlorobenzyl-L-tyrosine methyl ester hydrochloride (Scheme E, E-5: where R₅ is 4-[(2,6-dichlorophenyl)methoxy]phenyl and stereochemistry is (S)) (0.59 g, 1.50 mmol) to give a heterogeneous mixture. Upon addition of triethylamine (0.3 mL) the reaction mixture became homogeneous and stirred for 12 h. The reaction mixture was partitioned between $CH_2Cl_2$ (50 mL) and 1N HCl (50 mL). The organic phase was washed with sat'd aq. $NaHCO_3$, $H_2O$, brine, dried ($Na_2SO_4$), filtered and evaporated in vacuo. The resulting yellow oil was chromatographed on silica gel (150 g, 230–400 mesh, 70 mm OD column, packed and eluted acetone/$CH_2Cl_2$ 5:95, 40 mL fractions). Fractions 36–48 furnished the title compound (0.90 g) as a glass. $^1$H-NMR: (300 MHz, $CDCl_3$): δ=9.09 (1H), 7.38 (2H), 7.10–7.30 (8H), 6.97 (2H), 5.22 (2H), 4.75 (1H), 3.81 (1H), 3.60 (1H), 3.15–3.35 (3H), 3.04 (1H), 2.42 (1H), 2.21 (1H), 1.86–2.07 (4H), 1.37 (9H); FAB/MS m/z (rel. intensity): 655 (M+H, 46.4), 599 (11.3), 553 (23.6), 260 (18.8), 204 (91.4), 91 (base); IR (nujol): 3262, 3001, 1733, 1665, 1612, 1585, 1565, 1512, 1439, 1392, 1240, 1226, 1197, 1177, 1153, 1018, and 768 $cm^{-1}$; Anal: Calcd. for $C_{35}H_{40}N_2O_6Cl_2$: C, 64.12; H, 6.15; N, 4.27; Cl, 10.82. Found: C, 63.75; H, 6.29; N, 4.11; Cl, 10.88; $[α]_D^{25}$: +6° (c=0.863, $CHCl_3$).

PREPARATION 28

(Scheme E, E-7 where $R_5$ is 4-[(2,6-dichlorophenyl)methoxy]phenyl, and stereochemistry of the pyrrolidine ring is (2R,5S) and the amino acid is (S)).

(5R)-5-[2-[[(1S)-1-Carboxy-2-[4-[(2,6-dichlorophenyl)methoxy]phenyl]ethyl]amino]-2-oxoethyl]-1-(phenylmethyl)-L-proline 1,1-Dimethylethyl Ester ((1S,5R,L))

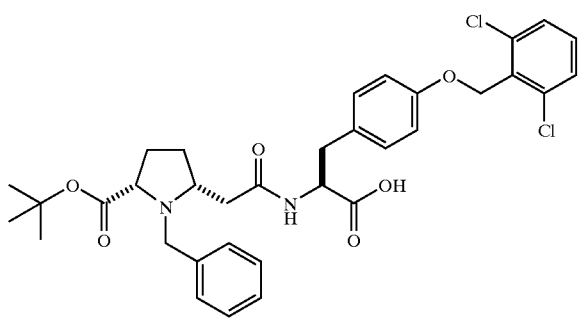

To a stirring solution of E-6 (Scheme E, where $R_5$ is 4-[(2,6-dichlorophenyl)methoxy]phenyl, and stereochemistry of the pyrrolidine ring is (2R,5S) and the amino acid is (S)) (1.00 g, 1.53 mmol) in MeOH (50 mL) was added 1M $K_2CO_3$ (10 mL). After stirring for 12 h, the reaction mixture was evaporated in vacuo, the residue was dissolved in $H_2O$ (0.1 L), the pH was adjusted to ca. 6 with 1M HCl, and the mixture was extracted with $CHCl_3$ (2×0.1 L). The combined extracts were washed with $H_2O$, brine, dried ($Na_2SO_4$), and evaporated in vacuo to afford the title compound (0.85 g) as a white solid. MP: 80–83° C.; $^1$H-NMR: (300 MHz, $CDCl_3$): δ=9.87 (1H), 7.35 (2H), 7.21–7.26 (7H), 7.13 (2H), 6.94 (2H), 5.22 (2H), 4.64 (1H), 3.80 (1H), 3.55 (1H), 3.29–3.37 (3H), 3.04 (1H), 2.48 (1H), 2.26 (1H), 1.94 (1H), 1.76 (1H), 1.59 (1H), 1.41 (1H), 1.34 (9H); FAB/MS m/z (rel. intensity): 641 (M+H, 45.8), 585 (13.0), 260 (6.1), 204 (base), 91 (96.8); IR (nujol): 1732, 1642, 1612, 1585, 1565, 1534, 1511, 1439, 1240, 1230, 1196, 1178, 1153, 1018, 779, and 767 $cm^{-1}$; HRMS: Calcd. for $C_{34}H_{38}Cl_2N_2O_6$: 641.2185. Found. 641.2164; $[α]_D^{25}$: +5° (c 0.795, $CHCl_3$).

PREPARATION 29 AND EXAMPLE 94

(Scheme E, E-8 where $R_5$ is 4-[(2,6-dichlorophenyl)methoxy]phenyl, and stereochemistry of the pyrrolidine ring is (2R,5S) and the amino acid is (S)).

(5R)-5-[2-[[(1S)-1-Carboxy-2-[4-[(2,6-dichlorophenyl)methoxy]phenyl]ethyl]amino]-2-oxoethyl]-1-(phenylmethyl)-L-proline ((1S,5R,L))

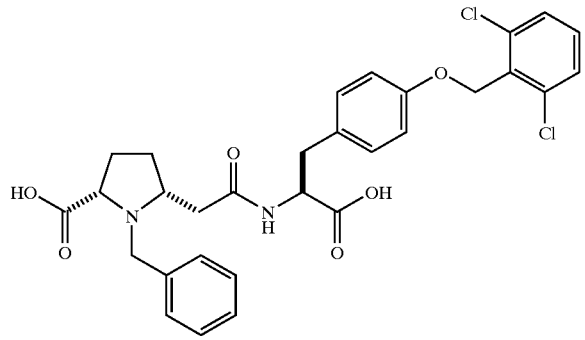

To a solution of E-7 (Scheme E, where $R_5$ is 4-[(2,6-dichlorophenyl)methoxy]phenyl, and stereochemistry of the pyrrolidine ring is (2R,5S) and the amino acid is (S)) (0.85 g, 1.32 mmol) in $H_2O$/n-PrOH (1:1, 0.1 L) was added HOAc (6 mL), and the solution refluxed for 5 h, then stirred at RT for 12 h. Evaporation in vacuo afforded the title compound (0.78 g) as a white solid. MP: 198–202° C.; $^1$H-NMR: (300 MHz, DMSO): δ=8.56 (1H), 7.56–7.59 (2H), 7.45–7.50 (1H), 7.25–7.29 (5H), 7.21 (2H), 6.96 (2H), 5.18 (2H), 4.41 (1H), 3.89 (1H), 3.74 (1H), 3.31 (1H), 3.03–3.09 (2H), 2.85 (1H), 2.18–2.34 (2H), 1.88–2.00 (1H), 1.63–1.84 (2H), 1.44–1.58 (1H); FAB/MS m/z (rel. intensity): 585 (M+H, 21.6), 539 (2.1), 246 (14.5), 204 (60.9), 159 (12.6), 91 (base); IR (nujol): 3309, 3083, 3037, 3014, 1662, 1644, 1562, 1514, 1440, 1377, 1348, 1241, 1197, 1178, 1018, 998, 815, and 771 $cm^{-1}$; Anal: Calcd. for $C_{30}H_{30}N_2O_6Cl_2.0.38H_2O$: C, 60.83; H, 5.24; N, 4.73. Found: C, 60.83; H, 5.33; N, 4.69; Karl Fischer water: 0.42%.

EXAMPLE 95

(Scheme E, E-8 where $R_5$ is 4-[(2,6-dichlorophenyl)methoxy]phenyl, and stereochemistry of the pyrrolidine ring is (2S,5R) and the amino acid is (S)).

(5S)-5-[2-[[(1S)-1-Carboxy-2-[4-[(2,6-dichlorophenyl)methoxy]phenyl]ethyl]amino]-2-oxoethyl]-1-(phenylmethyl)-D-proline ((1S,5S,D))

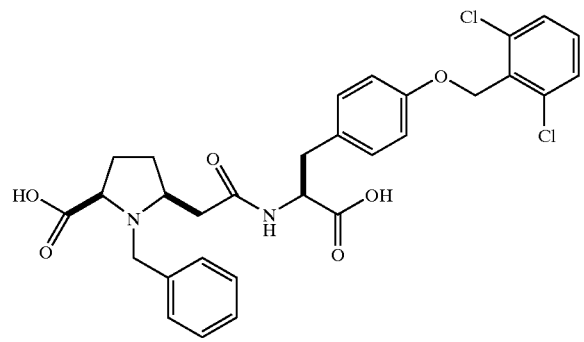

Example 95 was prepared as described in Scheme E from E-1 (Scheme E where stereochemistry is (R) prepared by the method of Rapoport (*J. Am. Chem. Soc.* 1984, 106, 4539). Physical data as follows: 198–204° C.; $^1$H-NMR: (300 MHz, DMSO): δ=8.60 (1H), 7.54–7.68 (3H), 7.26–7.41 (8H), 7.05

(2H), 5.27 (2H), 4.57 (1H), 3.96 (1H), 3.82 (1H), 3.40 (1H), 3.14 (2H), 2.86–2.94 (1H), 2.27–2.47 (2H), 1.96–2.10 (1H), 1.72–1.88 (1H), 1.55–1.72 (1H), 1.30–1.42 (1H); FAB/MS m/z (rel. intensity): 585 (M+H, 50.5), 539 (4.5), 332 (32.1), 331 (18.1), 246 (6.2), 244 (6.0), 204 (77.2), 91 (base); IR (nujol): 3211, 3033, 3006, 1724, 1647, 1610, 1565, 1512, 1438, 1354, 1301, 1273, 1240, 1196, 1018, 871, and 767 cm$^{-1}$; Anal: Calcd. for $C_{30}H_{30}N_2O_6Cl_2 \cdot 0.43H_2O$: C, 60.77; H, 5.24; N, 4.72. Found: C, 60.76; H, 5.37; N, 4.59; Karl Fischer water analysis: 1.71%.

Where $R_{F-3}$ is defined as proton or $C_{1-6}$ alkyl.

Scheme F describes a general method for the preparation of examples of the formula F-4, F-5, F-6, F-7, and F-8. A commercially available or readily prepared sulfur containing amino acid of structure F-1 is condensed with amino acid derivative F-2 under standard peptide synthesis conditions as described in Scheme A. Deprotection of the carbamate from F-3 provides the useful intermediate F-4. The amine group may be reacted with a variety of electrophilic reagents as described in Scheme A to provide esters of general structure F-5. Mild base hydrolysis provides acids of structure F-6. Mild hydrolysis of esters of general structure F-3

Scheme F

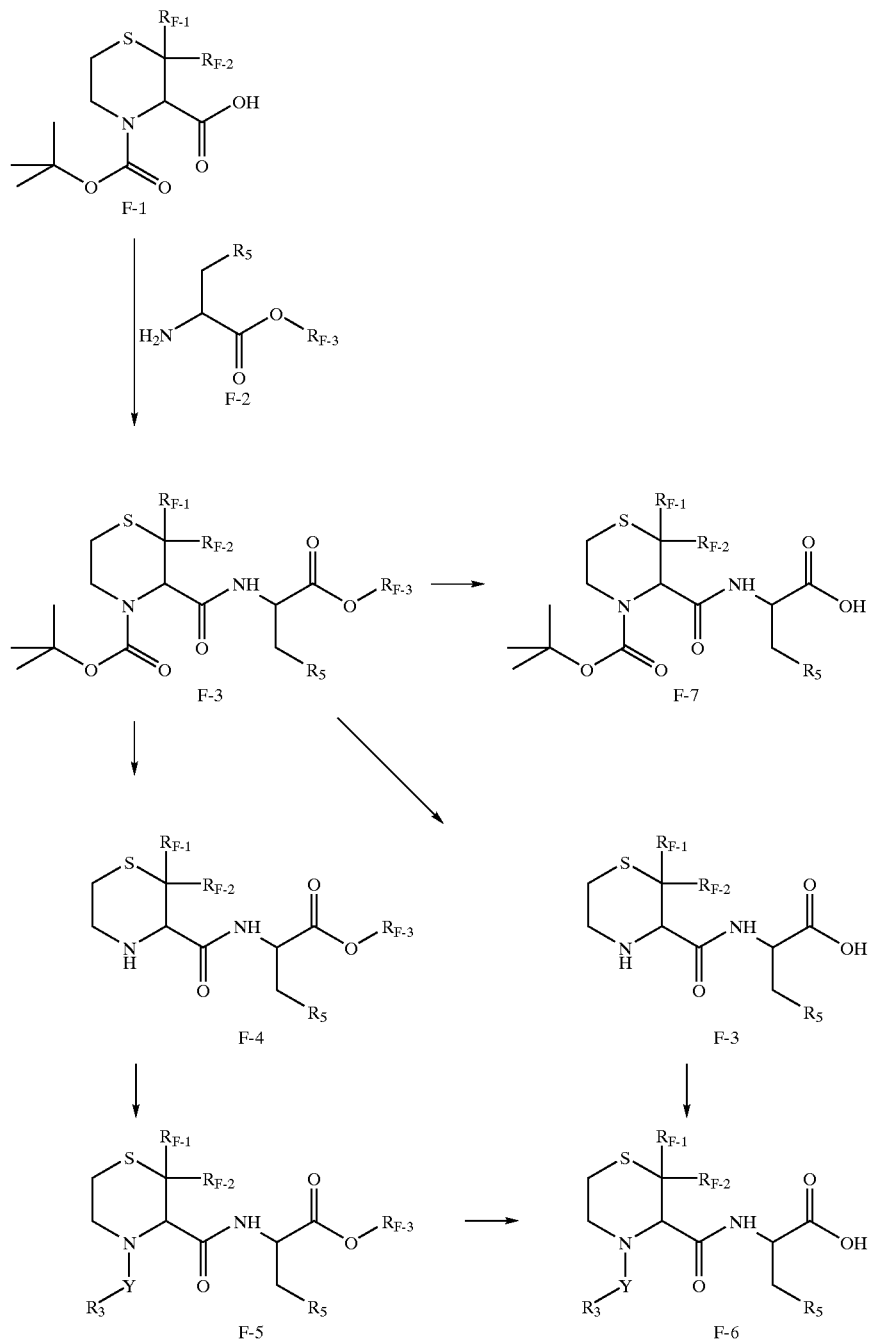

provides acid of formula F-7. In those cases in which $R_{F-3}$ is equal to t-butyl, mild acidolysis of compounds of general structure F-3 afford the amino acid of general structure F-8.

PREPARATION 30 AND EXAMPLE 96

(Scheme F, F-3: where $R_{F-1}$ and $R_{F-2}$ are the same and equal to proton, $R_{F-3}$ is $CH_3$, $R_5$ is 4-[(2,6-dichlorobenzoyl)amino]phenyl and stereochemistry is (R,S)).

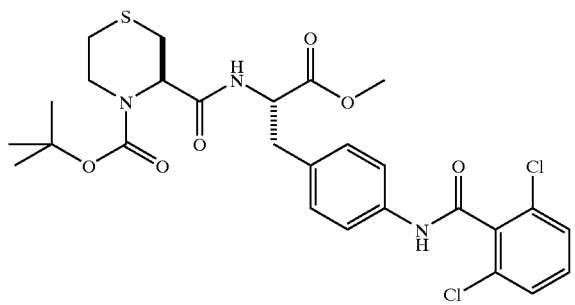

To a cooled (0° C.) solution of Boc-L-thiomorpholine-3-carboxylic acid ((a) Van Der Auwera, C.; Anteunis, M. J. O. Iit. J. Peptide Protein Res. 1987, 29, 574: (b) Kogami, Y.; Okawa, K. Bull. Chem. Soc. Jpn. 1987, 60, 2963: (c) Larsson U.; Carlson R. ACTA Chemica. Scand. 1994, 48, 517: (d) Carson J. F.; Wong F. F. J. Org. Chem. 1964, 29, 2203.) (Scheme F, F-1: where $R_{F-1}$ and $R_{F-2}$ are the same and equal to proton and stereochemistry is (R)) (6.7 g, 27 mmol) in $CH_2Cl_2$ (100 mL) was added HOBt (4.0 g, 29.7 mmol), DMAP (700 mg), EDC (5.7 g, 29.7 mmol) and triethylamine (13.5 mL, 97 mmol). The reaction mixture was stirred for 10 min, then the amino acid derivative F-2 (Scheme F, where $R_5$ is 4-[(2,6-dichlorobenzoyl)amino]phenyl, $R_{F-3}$ is $CH_3$, and stereochemistry is (S)) (10.0 g, 24.7 mmol) was added. After 20 h, volatiles were removed in vacuo and the residue partitioned between 2.5% aqueous HCl (100 mL) and $H_2O$ (100 mL). The organic layer was separated and washed saturated aqueous $NaHCO_3$ (100 mL), dried and concentrated in vacuo. Purification of the residue by chromatography on $SiO_2$ (500 g) using $CH_2Cl_2$/ethyl acetate (10%) as eluent afforded the title compound (12.31 g) as a solid: $^1$H NMR ($CDCl_3$) δ 1.44 (9H), 2.35 (1H), 2.70 (3H), 3.13 (2H), 3.33 (1H), 3.77 (3H), 4.22 (1H), 5.00 (1H), 6.48 (1H), 7.18 (2H), 7.31 (3H), 7.44 (1H), 7.56 (2H); $^{13}$C NMR ($CDCl_3$) δ 171.6, 168.9, 162.5, 136.5, 135.9, 132.4, 131.0, 130.2, 128.2, 120.5, 81.7, 77.3, 53.3, 52.6, 37.0, 28.2, 26.5; IR (mull) 3296, 2924, 1744, 1685, 1668, 1605, 1536, 1515, 1432, 1412, 1321, 1294, 1260, 1244, 1213, 1195, 1161, 798 cm$^{-1}$; MS (FAB) m/z (rel. intensity) 598 (M+H, 3), 596 (M+H, 5), Anal. Calcd for $C_{27}H_{31}Cl_2N_3O_6S$: C, 54.36; H, 5.24; N, 7.04. Found: C, 54.23; H, 5.24; N, 6.86. Corrected for 0.60% $H_2O$, found by Karl Fischer analysis.

PREPARATION 31 AND EXAMPLE 97

(Scheme F, F-4: where $R_{F-1}$ and $R_{F-2}$ are the same and equal to proton, $R_{F-3}$ is $CH_3$, $R_5$ is 4-[(2,6-dichlorobenzoyl)amino]phenyl and stereochemistry is (R,S))

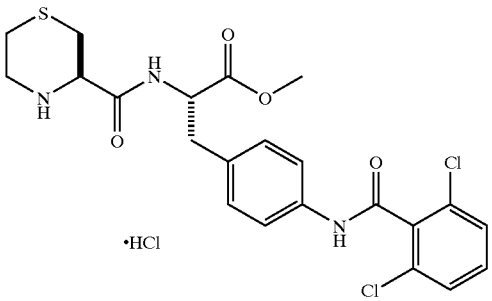

Acetyl chloride (1.75 mL, 24 mmol) was slowly added to MeOH (26 mL) at 0–5° C. After 15 min, a solution of the carbamate F-3 (Scheme F, where $R_{F-1}$ and $R_{F-2}$ are the same and equal to proton, $R_{F-3}$ is $CH_3$, $R_5$ is 4-[(2,6-dichlorobenzoyl)amino]phenyl and stereochemistry is (R,S)) (2.4 g, 4.0 mmol) in methanol (8 mL) was added. After 50.5 h at 0° C., the solvent was removed in vacuo to yield the title compound (2.11 g): $^1$H NMR (300 MHz, DMSO-$d_6$) δ 2.68 (1H), 3.00 (6H), 3.47 (1H), 3.64 (3H), 4.02 (1H), 4.52 (1H), 7.28 (2H), 7.54 (5H), 9.15 (1H), 9.3 (1H), 9.70 (1H), 10.7 (1H); IR (mull) 3191, 3031, 1742, 1664, 1604, 1577, 1561, 1540, 1516, 1432, 1414, 1326, 1271, 1210, 799 cm$^{-1}$; MS (EI) m/z (rel. intensity) 495 (M+, 1).

PREPARATION 32 AND EXAMPLE 98

(Scheme F, F-5: where $R_{F-1}$ and $R_{F-2}$ are the same and equal to proton, $R_{F-3}$ is $CH_3$, $R_3$ is $CH_2CH_2CO_2CH_3$, $R_5$ is 4-[(2,6-dichlorobenzoyl)amino]phenyl, Y is CO—, and stereochemistry is (R,S)).

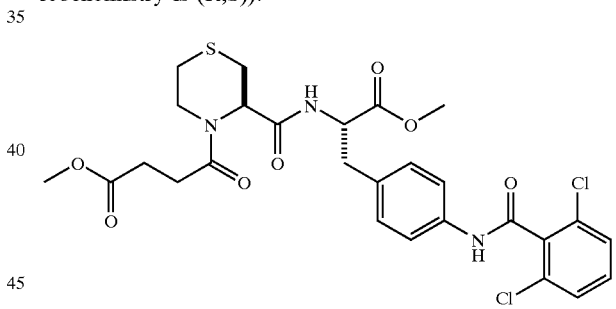

To a solution of amine F-4 (Scheme F, where $R_{F-1}$ and $R_{F-2}$ are the same and equal to proton, $R_{F-3}$ is $CH_3$, $R_5$ is 4-[(2,6-dichlorobenzoyl)amino]phenyl and stereochemistry is (R,S)) (650 mg, 1.2 mmol) was added mono-methyl succinate (320 mg, 2.4 mmol), EDC (460 mg, 2.4 mmol), pyridine (10 mL) and DMAP at ambient temperature. After 27 h, the mixture was diluted with 25 mL of saturated $NaHCO_3$ was extracted with methylene chloride. The combined organic extracts were dried and concentrated in vacuo. Purification of the residue by flash chromatography using methylene chloride/ethyl acetate (3:2) as eluant followed by Lyophilization afforded the title compound (600 mg) as an amorphous solid: IR (mull) 1742, 1659, 1657, 1608, 1537, 1516, 1432.,1414, 1324, 1269, 1259, 1228, 1214, 1195, 1176 cm$^{-1}$; $^1$H NMR (300 MHz, $CDCl_3$) δ2.63 (7H), 3.21 (3H), 3.68 (3H), 3.78 (3H), 3.90 (1H), 4.80 (2H), 5.50 (1H), 6.56 (1H), 7.29 (5H), 7.57 (2H); $^{13}$C NMR (75 MHz, $CDCl_3$) δ 173.9, 172.0, 171.7, 168.5, 162.7, 136.1, 135.9, 133.3, 132.3, 131.0, 130.1, 128.2, 121.0, 120.7, 53.1, 52.5, 52.3, 52.0, 44.4, 36.7, 29.4, 27.7, 26.9, 26.4; MS (EI) m/z

PREPARATION 33 AND EXAMPLE 99

[R-(R*,S*)]-3-[[[1-Carboxy-2-[4-[(2,6-dichlorobenzoyl)amino]phenyl]ethyl]amino]carbonyl]-γ-oxo-4-thiomorpholinebutanoic Acid (Scheme F, F-6: where $R_{F-1}$ and $R_{F-2}$ are the same and equal to proton, $R_{F-3}$ is proton, $R_3$ is $CH_2CH_2CO_2H$, $R_5$ is 4-[(2,6-dichlorobenzoyl)amino]phenyl, Y is CO—, and stereochemistry is (R,S)).

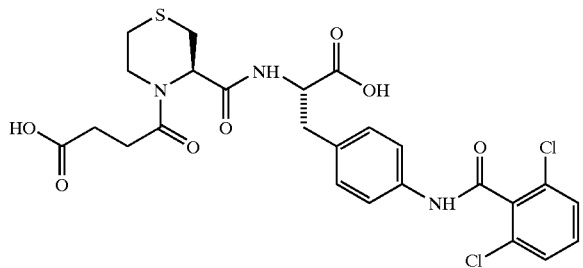

To a solution of the diester F-5 (Scheme F, where $R_{F-1}$ and $R_{F-2}$ are the same and equal to proton, $R_{F-3}$ is $CH_3$, $R_3$ is $CH_2CH_2CO_2CH_3$, $R_5$ is 4-[(2,6-dichlorobenzoyl)amino]phenyl, Y is CO—, and stereochemistry is (R,S)) (490 mg, 0.80 mmol) in THF (20 mL) and MeOH (6 mL) was added a solution of LiOH.H$_2$O (178 mg, 4.25 mmol) in H$_2$O (6 mL). After 22 h, the mixture was concentrated in vacuo. The residue was partially dissolved in 10% HCl (20 mL) and the resulting solid collected by filtration. The solid was washed with water and lyophilized from aqueous acetonitrile to afford the title compound (400 mg) as an amorphous solid: IR (mull) 3267, 3193, 3058, 3034, 2924, 1725, 1658, 1607, 1562, 1537, 1516, 1432, 1414, 1326, 1195, 1178, 800 cm$^{-1}$; $^1$H NMR (300 MHz, DMSO-d$_6$) δ 2.62 (7H), 3.17 (3H), 3.95 (1H), 4.57 (2H), 5.26 (1H), 7.18 (2H), 7.55 (5H), 8.02 (1H), 10.64 (1H), 12.34 (1H); MS (FAB) m/z (rel. intensity) 582 (M+H, 18).

PREPARATION 34 AND EXAMPLE 100

[R-(R*,S*)]-3-[[[1-Carboxy-2-[4-[(2,6-dichlorobenzoyl)amino]phenyl]ethyl]amino]carbonyl]-4-thiomorpholinecarboxylic Acid 4-(1,1-Dimethylethyl)ester (Scheme F, F-7: where $R_{F-1}$ and $R_{F-2}$ are the same and equal to proton, $R_{F-3}$ is proton, $R_5$ is 4-[(2,6-dichlorobenzoyl)amino]phenyl and stereochemistry is (R,S)).

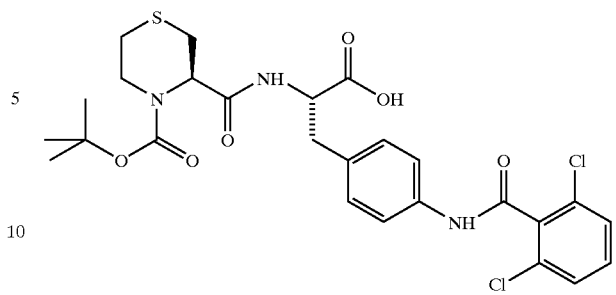

To a solution of ester F-3 (Scheme F, where $R_{F-1}$ and $R_{F-2}$ are the same and equal to proton, $R_{F-3}$ is $CH_3$, $R_5$ is 4-[(2,6-dichlorobenzoyl)amino]phenyl and stereochemistry is (R,S)) (656 mg, 1.02 mmol) in MeOH (25 mL) was added K$_2$CO$_3$ (550 mg, 4 mmol) and H$_2$O (13 mL). After 3 h, volatiles were partially removed and the solution diluted with 10% HCl (20 mL) causing precipitation of a solid. The product was collected by filtration, washed with H$_2$O and dried in a vacuum oven to afford the product (610 mg): IR (mull) 1736, 1665, 1606, 1562, 1537, 1516, 1432, 1413, 1323, 1294, 1260, 1244, 1211, 1195, 1160 cm$^{-1}$; $^1$H NMR (300 MHz, DMSO-d$_6$) δ 1.35 (9H), 2.45 (2H), 2.74 (5H), 4.00 (1H), 4.47 (1H), 4.70 (1H), 7.19 (2H), 7.52 (5H), 7.92 (1H), 10.60 (1H), 12.75 (1H); MS (FAB) m/z (rel. intensity) 582 (M+H, 12), Anal. Calcd for C$_{26}$H$_{29}$Cl$_2$N$_3$O$_6$S: C, 53.61; H, 5.02; N, 7.21. Found: C, 53.20; H, 5.12; N, 7.10. Corrected for 2.30% H$_2$O found by Karl Fischer analysis.

PREPARATION 35

(Scheme F, F-3: where $R_{F-1}$ and $R_{F-2}$ are the same and equal to proton, $R_{F-3}$ is t-butyl, $R_5$ is 4-[(2,6-dichlorobenzoyl)amino]phenyl and stereochemistry is (R,S)).

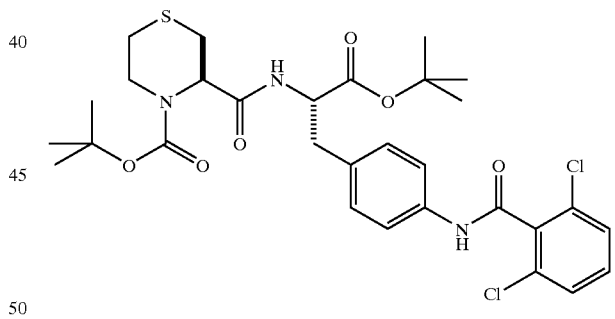

To a cooled (0–5° C.) solution of Boc-L-thiomorpholine-3-carboxylic acid (Scheme F, F-1: where $R_{F-1}$ and $R_{F-2}$ are the same and equal to proton and stereochemistry is (R)) (1.34 g, 5.4 mmol) in methylene chloride (20 mL) was added HOBt (800 mg, 5.94 mmol), DMAP (140 mg, EDC (1.14 g, 5.94 mmol) and triethylamine (2.7 mL, 19.4 mmol). After 10 min, F-2 (Scheme F where $R_{F-1}$ and $R_{F-2}$ are the same and equal to proton, $R_{F-3}$ is t-butyl, $R_5$ is 4-[(2,6-dichlorobenzoyl)amino]phenyl and stereochemistry is (S)) (2.02 g, 4.94 mmol) was added, the reaction allowed to warm to ambient temperature and stirred for 24 h. Volatiles were removed in vacuo and the residue partitioned between methylene chloride and 2.5% aqueous HCl. The organic layer was separated and washed with sat. aqueous NaHCO$_3$, dried and concentrated in vacuo. Purification of the residue by flash chromatography using methylene chloride/ethyl acetate (5%) as eluant afforded the title compound (1.64 g): IR (mull) 1730, 1687, 1667, 1606, 1538, 1515, 1431, 1412, 1395, 1320, 1294, 1258, 1250, 1194, 1158 cm$^{-1}$; $^1$H NMR (300 MHz, CDCl$_3$) δ 1.44 (9H), 1.46 (9H), 2.35 (1H), 2.67 (3H), 3.22 (3H), 4.25 (1H), 4.73 (1H), 4.97 (1H), 6.52 (1H), 7.29 (5H), 7.53 (3H); MS (FAB) m/z (rel. intensity) 638 (M+H, 2), Anal. Calcd for C$_{30}$H$_{37}$Cl$_2$N$_3$O$_6$S: C, 56.42; H, 5.84; N, 6.58. Found: C, 56.13; H, 5.98; N, 6.58.

PREPARATION 36 AND EXAMPLE 101

4-[(2,6-Dichlorobenzoyl)amino]-N-[[(3R)-3-thiomorpholinyl]carbonyl]-L-phenylalanine Monohydrochloride (Scheme F, F-8: where R$_{F-1}$ and R$_{F-2}$ are the same and equal to proton, R$_{F-3}$ is proton, R$_5$ is 4-[(2,6-dichlorobenzoyl)amino]phenyl and stereochemistry is (R,S)).

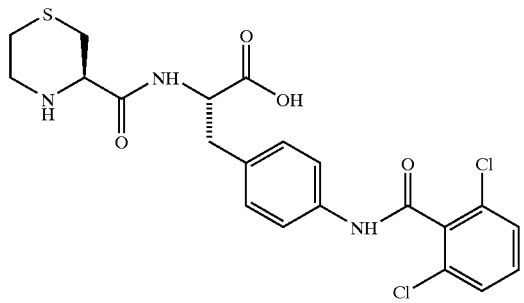

To a solution of HCl saturated in ethyl ether (5 mL) at ambient temperature was added carbamate F-3 (Scheme F, where R$_{F-1}$ and R$_{F-2}$ are the same and equal to proton, R$_{F-3}$ is t-butyl, R$_5$ is 4-[(2,6-dichlorobenzoyl)amino]phenyl and stereochemistry is (R,S)) (100 mg, 0.15 mmol) with vigorous stirring. After 43.5 h, the precipitate was collected by filtration and washed with ethyl ether to afford the title compound (90 mg): IR (mull) 3241, 3189, 3033, 2731, 1725, 1661, 1605, 1578, 1562, 1542, 1515, 1432, 1414, 1328, 1195 cm$^{-1}$; $^1$H NMR (300 MHz, DMSO-d$_6$) δ 2.66 (1H), 2.99 (6H), 3.50 (1H), 3.98 (1H), 4.45 (1H), 7.26 (1H), 7.52 (5H), 9.00 (2H), 9.30 (1H), 10.69 (1H); MS (FAB) m/z (rel. intensity) 482 (M+H, 83), 540 (32), 539 (9), 538 (42), 486 (13), 485 (16), 482 (83), 173 (11), 102 (99), Anal. Calcd for C$_{21}$H$_{21}$Cl$_2$N$_3$O$_4$S.HCl: C, 48.61; H, 4.27; N, 8.10; Cl, 20.50; S, 6.18. Found: C, 48.92; H, 4.27; N, 7.79; Cl, 19.68. Corrected for 6.53% H$_2$O found by Karl Fischer analysis.

EXAMPLE 102

4-[(2,6-Dichlorobenzoyl)amino]-N-[[(3R)-4-[1-oxo-3-(1H-tetrazol-5-yl)propyl]-3-thiomorpholinyl] carbonyl]-L-phenylalanine Methyl Ester (Scheme F, F-5: where R$_{F-1}$ and R$_{F-2}$ are the same and equal to proton, R$_{F-3}$ is CH$_3$, R$_3$ is 2-(5-1H-tetrazolyl)ethyl, R$_5$ is 4-[(2,6-dichlorobenzoyl)amino]phenyl, Y is CO—, and stereochemistry is (R,S)).

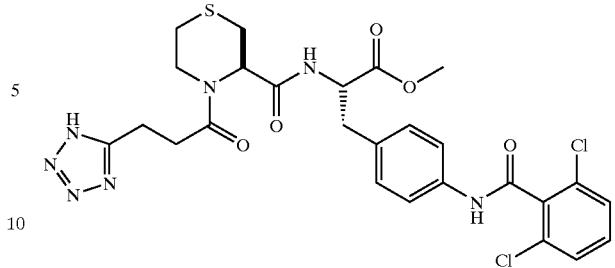

Example 102 was prepared as described in Scheme F using 1H-tetrazole-5-propanoic acid (Hutchinson, D. W.; Naylor, M. Nucleic Acids Res. 1985, 13, 8519) to form the requisite amide. Physical data as follows: IR (mull) 3264, 3047, 1742, 1659, 1607, 1561, 1537, 1516, 1432, 1415, 1324, 1268, 1219, 1195, 799 cm$^{-1}$; $^1$H NMR (300 MHz, DMSO-d$_6$) δ 2.26 (1H), 2.66 (2H), 3.02 (8H), 3.61 (3H), 3.87 (1H), 4.56 (1H), 5.25 (1H), 7.21 (2H), 7.50 (5H), 8.18 (1H), 8.45 (1H), 8.64 (1H); MS (FAB) m/z (rel. intensity) 620 (M+H, 61).

EXAMPLE 103

4-[(2,6-Dichlorobenzoyl)amino]-N-[[(3R)-4-[1-oxo-3-(1H-tetrazol-5-yl)propyl]-3-thiomorpholinyl]-carbonyl]-L-phenylalanine (Scheme F, F-6: where R$_{F-1}$ and R$_{F-2}$ are the same and equal to proton, R$_{F-3}$ is proton, R$_3$ is 2-(5-1H-tetrazolyl)ethyl R$_5$ is 4-[(2,6-dichlorobenzoyl)amino]phenyl, Y is CO—, and stereochemistry is (R,S)).

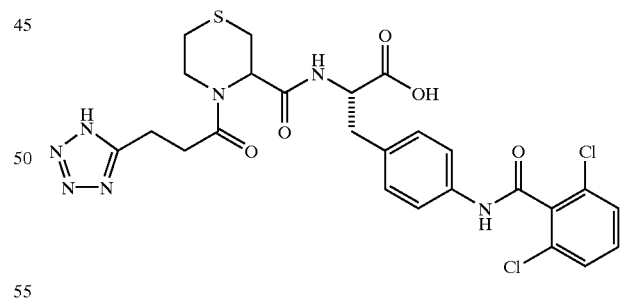

Example 103 was prepared from example 102 by the procedure described in preparation 34. Physical data as follows: IR (mull) 3376, 3296, 3267, 3127, 1746, 1683, 1669, 1641, 1623, 1610, 1542, 1522, 1444, 1436, 1411 cm$^{-1}$; MS (ESI+)for C$_{25}$H$_{25}$Cl$_2$N$_7$O$_5$S m/z 605.8 (M+H)$^+$; MS (FAB) m/z (rel. intensity) 606 (MH$^+$, 51), 682 (17), 608 (40), 607 (28), 606 (51), 605 (16), 254 (99), 226 (23), 175 (17), 137 (20), 102 (33); HRMS (FAB) calcd for C$_{25}$H$_{25}$Cl$_2$N$_7$O$_5$S+H$_1$ 606.1093, found 606.1105.

EXAMPLE 104

N-[[(3R)-4-(3-Cyano-1-oxopropyl)-3-thiomorpholinyl]carbonyl]-4-[[2,6-dichlorobenzoyl)amino]-L-phenylalanine (Scheme F, F-6: where $R_{F-1}$ and $R_{F-2}$ are the same and equal to proton, $R_{F-3}$ is proton, $R_3$ is $CH_2CH_2CN$, $R_5$ is 4-[(2,6-dichlorobenzoyl)amino]phenyl, Y is CO—, and stereochemistry is (R,S)).

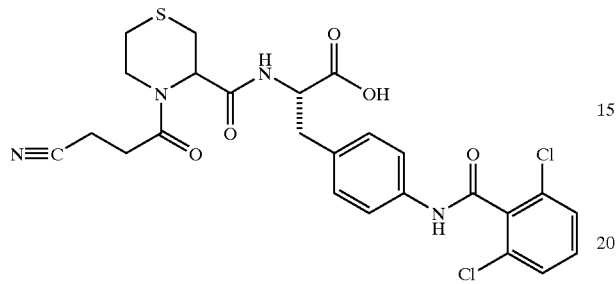

Example 104 was prepared as described in Scheme F using 3-cyanopropanoic acid (readily prepared from commercially available 3-cyanopropanoic acid) to form the requisite amide. Physical data as follows: IR (mull) 2251, 1735, 1655, 1612, 1585, 1565, 1512, 1439, 1298, 1240, 1196, 1179, 1016, 1000, 779, 768 cm$^{-1}$; $^1$H NMR (300 MHz, CDCl$_3$) δ 2.40 (12H), 4.88 (1H), 5.22 (2H), 6.72 (1H), 6.96 (2H), 7.23 (5H).

EXAMPLE 105

[R-(R*,S*)]-3-[[[1-Carboxy-2-[4-[(2,6-dichlorophenyl)methoxy]phenyl]ethyl]amino]carbonyl]-γ-oxo-4-thiomorpholinebutanoic Acid (Scheme F, F-6: where $R_{F-1}$ and $R_{F-2}$ are the same and equal to proton, $R_{F-3}$ is proton, $R_3$ is $CH_2CH_2CO_2H$, $R_5$ is 4-[(2,6-dichlorophenyl)methoxy]phenyl, Y is CO—, and stereochemistry is (R,S)).

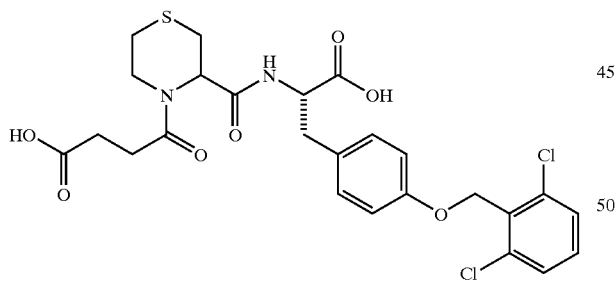

Example 105 was prepared as described in Scheme F using mono-methyl succinate to form the requisite amide. Physical data as follows: IR (mull) 3031, 1726, 1646, 1612, 1585, 1565, 1511, 1439, 1421, 1297, 1240, 1196, 1179, 1016, 768 cm$^{-1}$; $^1$H NMR (300 MHz, DMSO-d$_6$) δ 2.62 (8H), 3.64 (3H), 4.39 (2H), 5.20 (2H), 6.92 (2H), 7.15 (2H), 7.50 (3H), 7.98 (2H); $^{13}$C NMR (75 MHz, DMSO-d$_6$) δ 174.5, 173.2, 171.9, 168.9, 136.5, 132.3, 132.0, 130.8, 130.7, 129.2, 114.8, 65.3, 54.3, 52.5, 36.0, 29.7, 28.0, 27.0; MS (FAB) m/z (rel. intensity) 569 (M+H, 24), Anal. Calcd for $C_{25}H_{26}Cl_2N_2O_7S$: C, 52.73; H, 4.60; N, 4.92; Cl, 12.45. Found: C, 52.51; H, 4.60; N, 4.94; Cl, 12.78. Corrected for 3.37% H$_2$O found by Karl Fischer analysis.

Scheme G

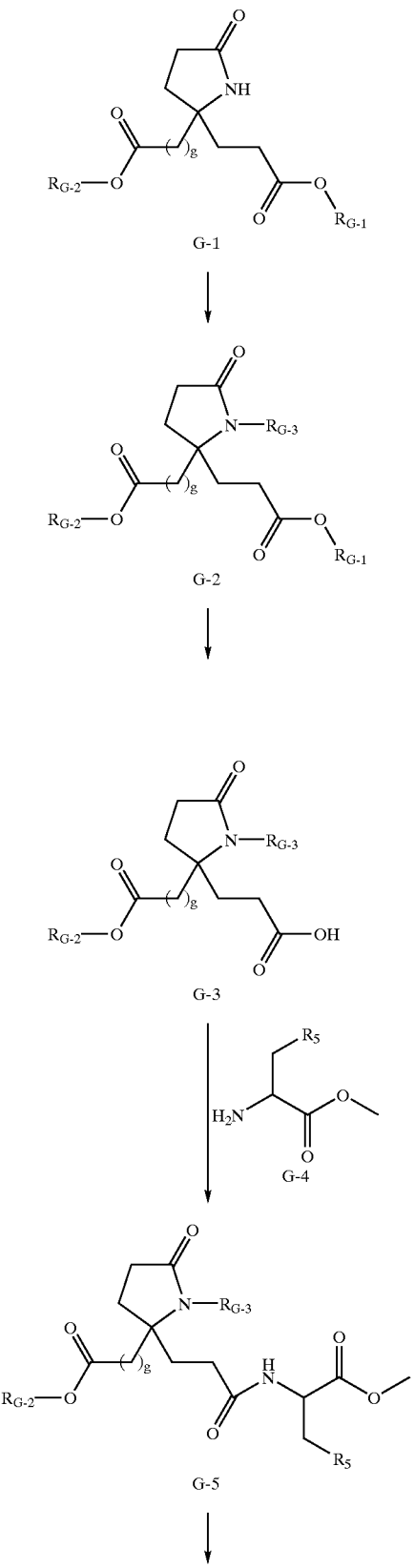

113

-continued

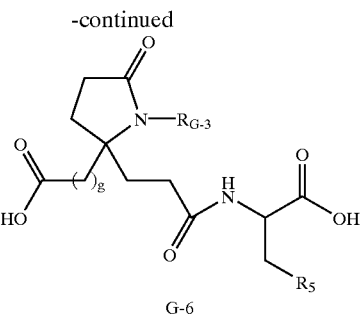

G-6

Where $R_{G-1}$ and $R_{G-2}$ are defined independently as H or $CH_3$; $R_3$ is defined as H, $C_{1-6}$ alkyl or $C_{3-6}$ alkenyl; and g is defined as 0 or 2.

Scheme G describes a general method to prepare lactam examples of general structures G-5 and G-6. Readily prepared lactams of general structure G-1 may be alkylated by the reaction of an appropriate alkylating in the presence of a suitable base as described in preparation 37 to provide intermediates of general structure G-2. Mild hydrolysis provides the monoacid of general structure G-3 which may be condensed with an amino acyl intermediate of structure G-4 as described in Scheme A. Full hydrolysis of the diester of general structure G-5 affords the diacid of structure G-6.

PREPARATION 37

(Scheme G, G-2: where $R_{G-1}$ and $R_{G-2}$ are $CH_3$, $R_{G-3}$ is $CH_3$ and g is equal to 2).

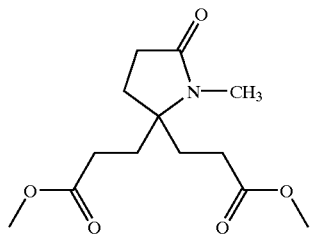

To a cooled (0–5° C.) solution of dimethyl ester G-1 (Scheme G, where $R_{G-1}$ and $R_{G-2}$ are $CH_3$, $R_{G-3}$ is H and g is equal to 2) (Thomas, E. T.; Rynbrandt, R. H; Zimmermann, D. C.; Bell, L. T.; Muchmore, C. R.; Yankee, E. W. *J. Org. Chem.* 1989, 54, 4535) (25.7 g, 0.1 mole) and iodomethane (30 mL, 0.48 mol) in THF (200 mL) was added NaH (4.8 g, 0.12 mmol, 60% in oil dispersion). After 22 h, the reaction was quenched by the addition of $H_2O$ (100 mL) and diluted with $CH_2Cl_2$, (50 mL). The organic layer was separated, dried and dried in vacuo. The crude brown oil was triturated with hexanes (200 mL) and the residue concentrated in vacuo to afford the crude product (18.44 g) which was used without further purification: $^1H$ NMR (300 MHz, $CDCl_3$) δ 2.03 (12H), 2.64 (3H), 3.64 (6H).

114

PREPARATION 38

(Scheme G, G-3: where $R_{G-2}$ is $CH_3$, $R_{G-3}$ is $CH_3$ and g is equal to 2).

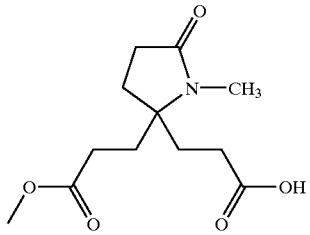

To a cooled (0–5° C.) solution of diester G-2 (Scheme G, where $R_{G-1}$ and $R_{G-2}$ are $CH_3$, $R_{G-3}$ is $CH_3$ and g is equal to 2) (10.0 g, 36.9 mmol) in aqueous methanol (66%, 75 mL) was added $LiOH.H_2O$ (1.55 g, 36.9 mmol). After 22 h, the mixture was partially concentrated in vacuo and diluted with water. The aqueous layer was washed with methylene chloride and acidified (pH ca. 2) with 10% HCl. The aqueous layer was extracted with methylene chloride and the combined organic extracts dried and concentrated in vacuo to afford the title compound (3.63 g) as a yellow solid: IR (mull) 1735, 1630, 1442, 1429, 1418, 1405, 1330, 1308, 1287, 1255, 1217, 1185, 1122, 1016, 642 cm$^{-1}$; $^1H$ NMR (300 MHz, $CDCl_3$) δ 1.90 (6H), 2.24 (4H), 2.43 (2H), 2.68 (3H), 3.67 (3H); $^{13}C$ NMR (75 MHz, $CDCl_3$) δ 176.3, 175.5, 173.2), 64.6, 52.0, 33.1, 32.9, 29.9, 28.41, 28.38, 26.0, 24.9; MS (EI) m/z (rel. intensity) 257 (M+, 1).

PREPARATION 39 AND EXAMPLE 106

2-[3-[[(1S)-1-[4-[[(2,6-Dichlorophenyl)methoxy] phenyl]methyl]-2-methoxy-2-oxoethyl]amino]-3-oxopropyl]-1-methyl-5-oxo-2-pyrrolidinepropanoic Acid Methyl Ester (Scheme G, G-5: where $R_{G-2}$ and $R_{G-3}$ are both equal to $CH_3$, $R_5$ is 4-[(2,6-dichlorophenyl)methoxy]phenyl, g is equal to 2 and stereochemistry is (S)).

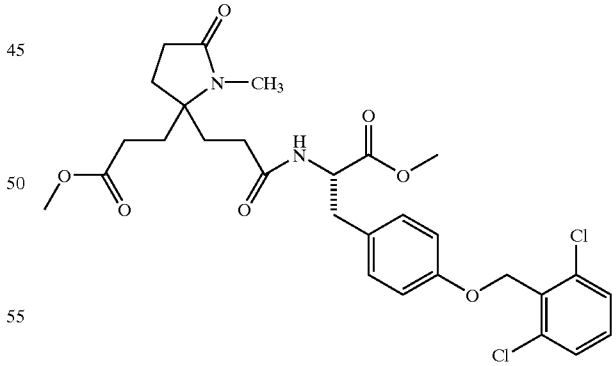

To a solution of acid G-3 (Scheme G, where $R_{G-2}$ and $R_{G-3}$ are equal to $CH_3$ and g is equal to 2) (1.0 g, 3.9 mmol), amine G4 (Scheme G, where $R_5$ is 4-[(2,6-dichlorophenyl) methoxy]phenyl and stereochemistry is (S)) (1.82 g, 4.67 mmol), and DMAP (100 mg, 0.8 mmol) in pyridine (15 mL) was added EDC (895 mg, 4.67 mmol). After 21 h, the reaction was diluted with saturated aqueous $NaHCO_3$ and methylene chloride. The organic layer was separated and washed with 10% aqueous HCl, dried and concentrated in vacuo. Purification of the residue by flash chromatography using methylene chloride/ethyl acetate (20%) as eluant followed by lyophilization from aqueous acetonitrile afforded the title compound (1.71 g) as an amorphous solid: IR (mull) 3284, 2924, 1738, 1666, 1665, 1564, 1539, 1511, 1439, 1398, 1299, 1240, 1198, 1178, 1117, 1016, 768 cm$^{-1}$; $^1$H NMR (300 MHz, CDCl$_3$) δ 2.10 (12H), 2.66 (3H), 3.07 (2H), 3.66 (3H), 3.73 (3H), 4.83 (1H), 5.24 (2H), 5.98 (1H), 6.95 (2H), 7.02 (2H), 7.25 (1H), 7.36 (2H); $^{13}$C NMR (75 MHz, CDCl$_3$) δ 174.7, 174.66, 173.2, 172.0, 171.2), 158.1, 137.0), 132.1, 130.5, 130.3, 128.5, 128.3, 115.2, 65.2, 64.3, 53.3, 52.4, 51.9, 37.0, 33.2, 30.2, 30.17, 28.4, 26.0, 24.7; MS (EI) m/z (rel. intensity) 592 (M+, 4), Anal. Calcd for C$_{29}$H$_{34}$Cl$_2$N$_2$O$_7$: C, 58.69; H, 5.77; N, 4.72; Cl, 11.95. Found: C, 58.33; H, 5.65; N, 4.76; Cl, 11.89.

PREPARATION 40 AND EXAMPLE 107

2-[3-[[(1S)-1-Carboxy-2-[4-[(2,6-dichlorophenyl)methoxy]phenyl]ethyl]amino]-3-oxo-propyl]-1-methyl-5-oxo-2-pyrrolidinepropanoic Acid (Scheme G, G-6: where R$_{G-3}$ is equal to CH$_3$, R$_5$ is 4-[(2,6-dichlorophenyl)methoxy]phenyl, g is equal to 2 and stereochemistry is (S)).

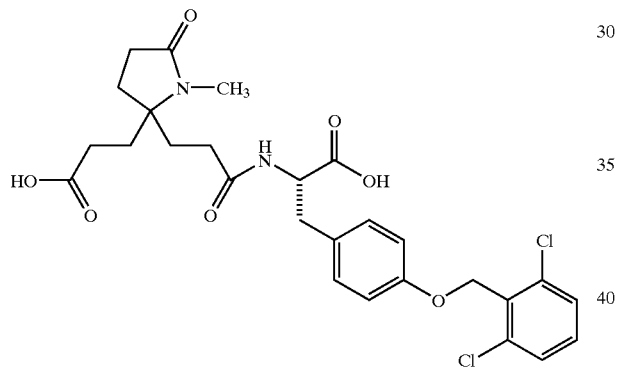

To a solution of diester G-5 (Scheme G, where R$_{G-2}$ and R$_{G-3}$ are both equal to CH$_3$, R$_5$ is 4-[(2,6-dichlorophenyl)methoxy]phenyl, g is equal to 2 and stereochemistry is (S) (1.0 g, 1.68 mmol), in THF (30 mL) and MeOH (9 mL) was added LiOH.H$_2$O (370 mg, 8.8 mmol). After 22.5 h, the reaction mixture was acidified with 10% aqueous HCl (30 mL) causing precipitation of a solid. The solid was collected by filtration and lyophilized from aqueous acetonitrile to afford the title compound (0.91 g) as an amorphous solid: IR (mull) 3031, 2925, 1727, 1637, 1585, 1564, 1543, 1511, 1439, 1424, 1404, 1299, 1240, 1196, 1179, 768 cm$^{-1}$; $^1$H NMR (300 MHz, DMSO-d$_6$) δ 1.77 (12H), 2.76 (1H), 3.97 (1H), 4.36 (1H), 5.16 (2H), 6.94 (2H), 7.15 (2H), 7.49 (3H), 8.16 (1H); $^{13}$C NMR (75 MHz, CDCl$_3$) δ 174.6, 174.1, 173.6, 172.2, 157.6, 136.5, 132.2, 132.0, 130.7, 130.6, 129.2, 114.7, 65.3, 64.1, 54.0, 36.5, 33.7, 33.1, 30.1, 30.05, 29.8, 28.7, 25.7, 24.6; MS (FAB) m/z (rel. intensity) 565 (M+H, 99), Anal. Calcd for C$_{27}$H$_{30}$Cl$_2$N$_2$O$_7$: C, 57.35; H, 5.35; N, 4.95; Cl, 12.54. Found: C, 56.93; H, 5.15; N, 5.02; Cl, 12.42. Corrected for 1.03% H$_2$O found by Karl Fischer analysis.

EXAMPLE 108

2-[3-[[(1S)-1-[[4-[(2,6-Dichlorophenyl)methoxy]phenyl]methyl]-2-methoxy-2-oxoethyl]amino]-3-oxopropyl]-1-(3-methyl-2-butenyl)-5-oxo-2-pyrrolidinepropanoic Acid Methyl Ester (Scheme G, G-5: where R$_{G-2}$ is CH$_3$, R$_{G-3}$ is 1-(3-methyl-2-butenyl), R$_5$ is 4-[(2,6-dichlorophenyl)methoxy]phenyl, g is equal to 2 and stereochemistry is (S)).

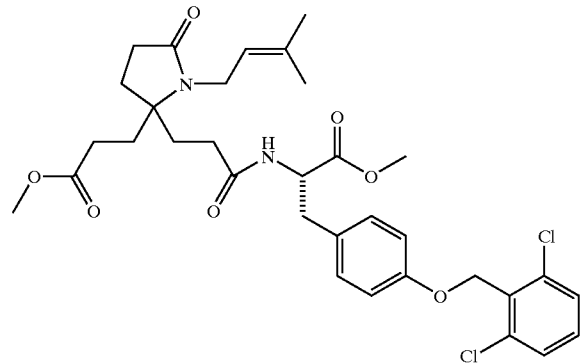

Example 108 was prepared as described in Scheme G using 1-bromo-3-methyl-2-butene to form the requisite N-alkyl lactam. Physical data as follows: IR (mull) 32.95, 29.52, 1740, 1678, 1662, 1564, 1538, 1512, 1439, 1414, 1300, 1279, 1240, 1199, 1178, 1017, 768 cm$^{-1}$; $^1$H NMR (300 MHz, CDCl$_3$) δ 1.64 (3H), 1.70 (3H), 2.06 (12H), 3.09 (2H), 3.66 (3H), 3.74 (2H), 3.74 (3H), 4.85 (1H), 5.20 (1H), 5.24 (2H), 6.95 (2H), 7.02 (2H), 7.25 (1H), 7.36 (2H); $^{13}$C NMR (75 MHz, CDCl$_3$) δ 174.7, 173.3, 172.1, 172.0, 171.3, 158.1, 137.0, 135.1, 132.1, 130.5, 130.3, 128.5, 128.3, 119.7, 115.2, 65.2, 65.1, 53.2, 52.4, 51.9, 37.5, 37.0, 34.4, 34.2, 30.6, 29.9, 28.6, 26.6, 25.6, 25.5, 17.9; MS (FAB) m/z (rel. intensity) 647 (M+H, 24).

EXAMPLE 109

2-[3-[[(1S)-1-Carboxy-2-[4-[(2,6-dichlorophenyl)methoxy]phenyl]ethyl]amino]-3-oxo-propyl]-1-(3-methyl-2-butenyl)-5-oxo-2-pyrrolidinepropanoic Acid (Scheme G, G-6: where R$_{G-3}$ is 1-(3-methyl-2-butenyl), R$_5$ is 4-[(2,6-dichlorophenyl)methoxy]phenyl, g is equal to 2 and stereochemistry is (S)).

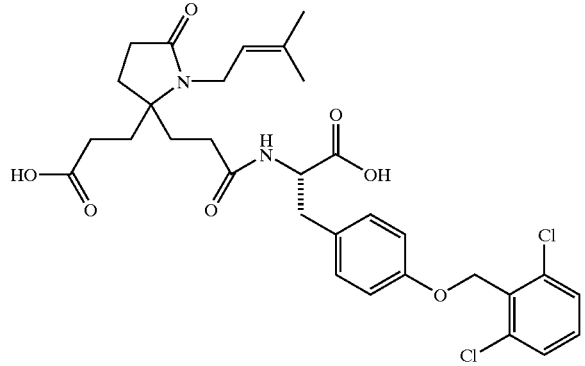

Example 109 was prepared from example 108 by the procedure described in preparation 40. Physical data as follows: IR (mull) 3290, 2921, 1726, 1635, 1585, 1565, 1545, 1511, 1439, 1419, 1341, 1299, 1240, 1197, 1179, 780, 768 cm$^{-1}$; $^1$H NMR (300 MHz, DMSO-d$_6$) δ 1.57 (3H), 1.62 (3H), 1.72 (6H), 2.02 (6H), 2.77 (1H), 2.98 (1H), 3.55 (2H), 5.05 (1H), 5.16 (2H), 6.94 (2H), 7.15 (2H), 7.49 (2H), 7.54 (2H), 8.15 (1H); $^{13}$C NMR (75 MHz, DMSO-d$_6$) δ 174.6, 174.3, 173.6, 173.56, 172.2, 157.6, 136.5, 134.0, 132.2, 132.0, 130.6, 129.2, 121.1, 121.0, 114.7, 65.2, 65.0, 54.1, 54.0, 37.1, 36.5, 34.5, 34.1, 30.0, 29.9, 28.8, 26.3, 25.84), 25.81, 18.1; MS (FAB) m/z (rel. intensity) 619 (M+H, 99).

EXAMPLE 110

2-[3-[[(1S)-1-[[4-[(2,6-Dichlorobenzoyl)amino]phenyl]methyl]-2-methoxy-2-oxoethyl]amino]-3-oxopropyl]-1-methyl-5-oxo-2-pyrrolidinepropanoic Acid Methyl Ester (Scheme G, G-5: where R$_{G-2}$ and R$_{G-3}$ are equal to CH$_3$, R$_5$ is 4-[(2,6-dichlorobenzoyl)amino]phenyl, g is equal to 2 and stereochemistry is (S)).

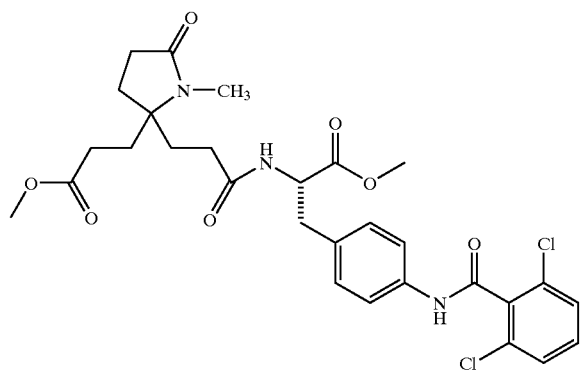

Example 110 was prepared as described in Scheme G using iodomethane to form the requisite N-alkyl lactam. Physical data as follows: IR (mull) 3258, 2922, 1738, 1662, 1606, 1561, 1539, 1515, 1432, 1414, 1401, 1323, 1268, 1196, 1177, 799 cm$^{-1}$; $^1$H NMR (300 MHz, CDCl$_3$) δ 2.01 (12H), 2.61 (3H), 3.09 (2H), 3.64 (3H), 3.75 (3H), 4.85 (1H), 6.15 (1H), 7.09 (2H), 2.31 (3H), 7.58 (2H), 7.99 (1H); MS (EI) m/z (rel. intensity) 607 (M+, 4), 605 (M+, 6); Anal. Calcd for C$_{29}$H$_{33}$Cl$_2$N$_3$O$_7$: C, 57.43; H, 5.48; N, 6.93; Cl, 11.69. Found: C, 57.18; H, 5.56; N, 6.85; Cl, 11.68. Corrected for 0.93% H$_2$O, found by Karl Fischer analysis.

EXAMPLE 111

2-[3-[[(1S)-1-Carboxy-2-[4-[(2,6-dichlorobenzoyl)amino]phenyl]ethyl]amino]-3-oxo-propyl]-1-methyl-5-oxo-2-pyrrolidinepropanoic Acid (Scheme G, G-6: where R$_{G-3}$ is CH$_3$, R$_5$ is 4-[(2,6-dichlorobenzoyl)amino]phenyl, g is equal to 2 and stereochemistry is (S)).

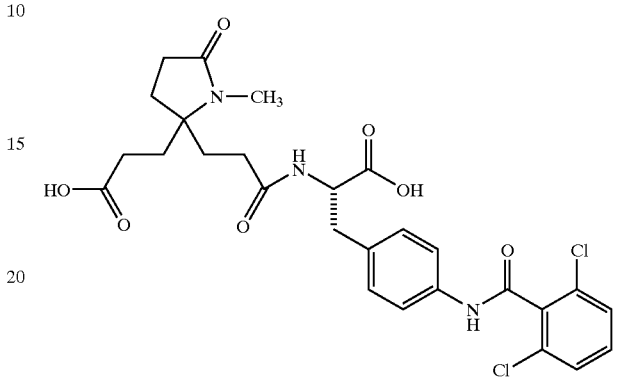

Example 111 was prepared from example 110 by the procedure described in preparation 40. Physical data as follows: IR (mull) 3265, 3056, 2925, 1724, 1658, 1609, 1579, 1561, 1542, 1516, 1432, 1414, 1327, 1271, 1217, 1195, 800 cm$^{-1}$; $^1$H NMR (300 MHz, DMSO-d$_6$) δ 1.89 (12H), 2.49 (3H), 2.78 (1H), 2.99 (1H), 4.38 (1H), 7.18 (2H), 7.51 (5H), 8.17 (1H), 10.64 (1H); MS (FAB) m/z (rel. intensity) 580.5 (M+H, 68).

EXAMPLE 112

2-[3-[[(1S)-1-[[4-[(2,6-Dichlorophenyl)methoxy]phenyl]methyl]-2-methoxy-2-oxoethyl]amino]-3-oxopropyl]-5-oxo-2-pyrrolidinepropanoic Acid Methyl Ester (Scheme G, G-5: where R$_{G-2}$ is CH$_3$, R$_{G-3}$ is proton, R$_5$ is 4-[(2,6-dichlorophenyl)methoxy]phenyl, g is equal to 2 and stereochemistry is (S)).

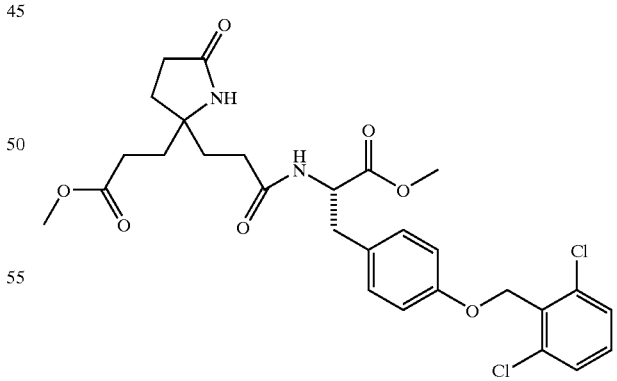

Example 112 was prepared as described in Scheme G. Physical data as follows: IR (mull) 3276, 3029, 1738, 1686, 1564, 1538, 1511, 1439, 1299, 1279, 1239, 1197, 1178, 1016, 767, cm$^{-1}$; $^1$H NMR (300 MHz, CDCl$_3$) δ 1.85 (6H), 2.24 (2H), 2.35 (4H), 3.03 (2H), 3.66 (3H), 3.74 (3H), 4.82 (1H), 5.24 (2H), 6.50 (2H), 6.95 (2H), 7.05 (2H), 7.27 (1H), 7.37 (2H); MS (EI) m/z (rel. intensity) 578 (M+, 0.2); Anal.

Calcd for $C_{28}H_{32}Cl_2N_2O_7$: C, 58.04; H, 5.57; N, 4.83. Found: C, 57.93; H, 5.43; N, 4.97. Corrected for 1.14% $H_2O$ found by Karl Fischer analysis.

EXAMPLE 113

2-[3-[[(1S)-1-Carboxy-2-[4-[(2,6-dichlorophenyl)methoxy]phenyl]ethyl]amino]-3-oxo-propyl]-5-oxo-2-pyrrolidinepropanoic Acid (Scheme G, G-6: where R-3 is proton, $R_5$ is 4-[(2,6-dichlorophenyl)methoxy]phenyl, g is equal to 2 and stereochemistry is (S)).

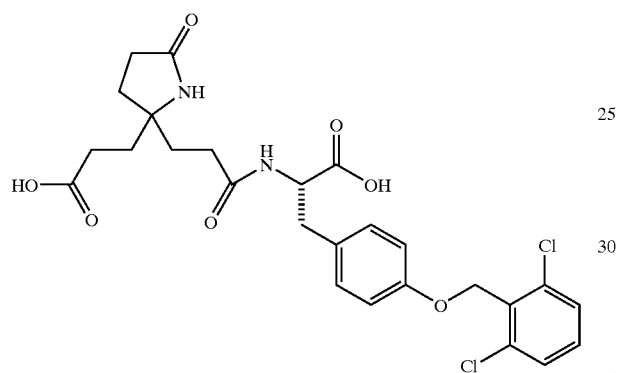

Example 113 was prepared from example 112 by the procedure described in preparation 40. Physical data as follows: IR (mull) 3294, 3033, 1716, 1647, 1585, 1565, 1544, 1511, 1439, 1420, 1299, 1240, 1197, 1179, 768 cm$^{-1}$; $^1$H NMR (300 MHz, DMSO-d$_6$) δ 1.60 (6H), 2.12 (6H), 2.78 (1H), 2.99 (1H), 4.36 (1H), 5.19 (2H), 6.97 (2H), 7.17 (2H), 7.45 (1H), 7.58 (2H), 7.70 (1H), 8.22 (1H); MS (FAB) n?/z (rel. intensity) 551 (M+H, 99); Anal. Calcd for $C_{26}H_{28}Cl_2N_2O_7$: C, 56.63; H, 5.12; Cl, 12.86; N, 5.08. Found: C, 56.28; H, 5.01; Cl, 13.08; N, 5.24. Corrected for 1.47% $H_2O$ found by Karl Fischer analysis.

EXAMPLE 114

2-[3-[[(1S)-1-[[4-[(2,6-Dichlorobenzoyl)amino]phenyl]methyl]-2-methoxy-2-oxoethyl]amino]-3-oxopropyl]-5-oxo-2-pyrrolidinepropanoic Acid Methyl Ester (Scheme G, G-5: where $R_{G-2}$ is $CH_3$, $R_{G-3}$ is proton, $R_5$ is 4-[(2,6-dichlorobenzoyl)amino]phenyl, g is equal to 2 and stereochemistry is (S)).

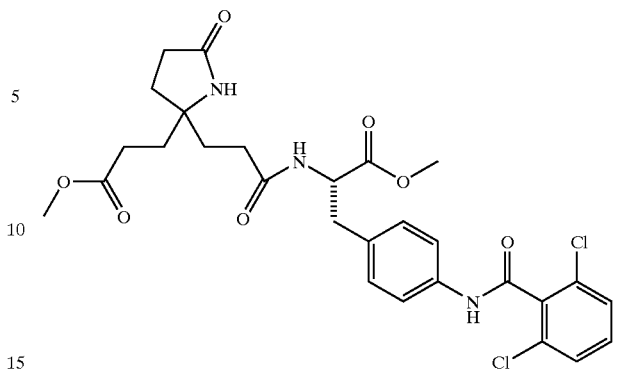

Example 114 was prepared as described in Scheme G. Physical data as follows: $^1$H NMR (300 MHz, CDCl$_3$) δ 1.81 (6H), 2.27 (6H), 3.10 (2H), 3.63 (3H), 3.75 (3H), 4.89 (1H), 6.46 (1H), 6.58 (1H), 7.10 (2H), 7.26 (3H), 7.58 (2H), 8.14 (1H); MS (FAB) m/z 592 (M+H)$^+$, 568, 367, 349, 307, 278, 226, 194, 173.

EXAMPLE 115

2-[3-[[(1S)-1-Carboxy-1-[4-[(2,6-dichlorobenzolyl)amino]phenyl]ethyl]amino]-3-oxopropyl)-5-oxo-2-pyrrolidinepropanoic Acid (Scheme G, G-6: where $R_{G-3}$ is proton, $R_5$ is 4-[(2,6-dichlorobenzoyl)amino]phenyl, g is equal to 2 and stereochemistry is (S)).

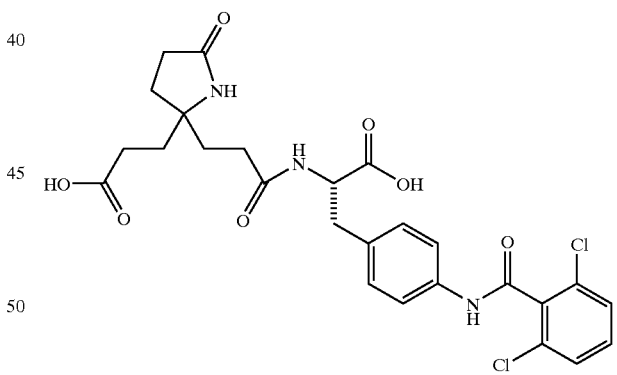

Example 115 was prepared from example 114 by the procedure described in preparation 40. Physical data as follows: IR (mull) 3272, 3195, 3121, 3063, 2953, 2923, 2868, 2855, 1715, 1659, 1608, 1579, 1561, 1541, 1516, 1456, 1432, 1414, 1377, 1367, 1326, 1271, 1221, 1195, 800 cm$^{-1}$; $^1$H NMR (300 MHz, DMSO-d$_6$ δ 1.63 (6H), 2.13 (6H), 2.79 (1H), 3.00 (1H), 4.38 (1H), 7.19 (2H), 7.51 (5H), 7.64 (1H), 8.16 (1H), 10.58 (1H), 12.37 (2H); MS (FAB) m/z 564 (M+H)$^+$, 546, 519, 335, 280, 194, 173, Anal. Calc'd for $C_{26}H_{27}Cl_2N_3O_7$: C, 55.33; H, 4.82; Cl, 12.56; N, 7.44. Found: C, 55.10; H, 4.76; Cl, 12.56; N, 7.36. Corrected for 2.49% $H_2O$, found by Karl Fischer analysis.

EXAMPLE 116

2-[3-[[(1S)-1-[[4-[(2,6-Dichlorophenyl)methoxy]phenyl]methyl]-2-methoxy-2-oxoethyl]amino]-3-oxopropyl]-5-oxoproline (Scheme G, G-5: where $R_{G-2}$ and $R_{G-3}$ are equal to proton, R5 is 4-[(2,6-dichlorophenyl)methoxy]phenyl, g is equal to 0 and stereochemistry is (S)).

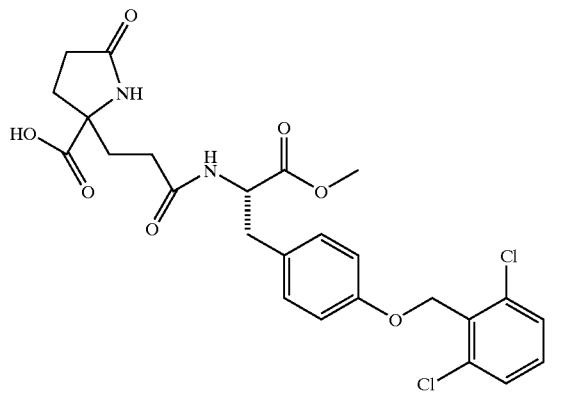

Example 115 was prepared as described in Scheme G from 2-carboxy-5-oxo-2-pyrrolidinepropanoic acid (Majer, Z.; Kajtar, M.; Tichy, M.; Blaha, K. *Coll. Czech. Chem. Commun.* 1982, 47, 950). Physical data as follows: IR (mull) 3302, 1736, 1671, 1612, 1585, 1564, 1535, 1511, 1439, 1298, 1240, 1197, 1179, 1016, 768 cm$^{-1}$; $^1$H NMR (300 MHz, CDCl$_3$) δ 2.12 (8H), 3.02 (2H), 3.65 (3H), 4.81 (1H), 5.21 (2H), 6.94 (2H), 7.07 (2H), 7.22 (1H), 7.35 (2H), 7.86 (1H), 8.34 (1H); MS (FAB) m/z (rel. intensity) 537 (M+H, 99).

EXAMPLE 117

2-[3-[[(1S)-1-Carboxy-2-[4-[(2,6-dichlorophenyl)methoxy]phenyl]ethyl]amino]-3-oxo-propyl]-5-oxoproline (Scheme G, G-6: where $R_{G-3}$ is proton, $R_5$ is 4-[(2,6-dichlorophenyl)methoxy]phenyl, g is equal to 0 and stereochemistry is (S)).

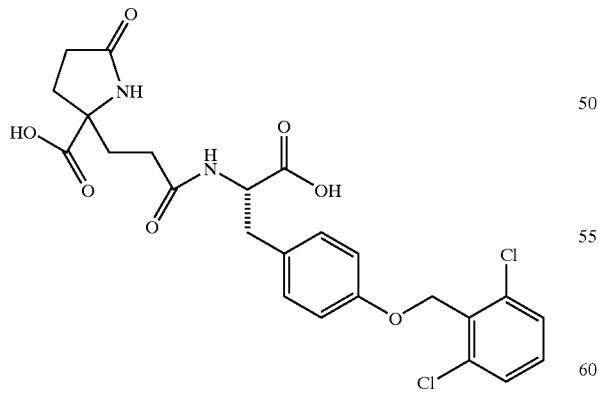

Example 116 was prepared from example 115 by the procedure described in preparation 40. Physical data as follows: IR (mull) 3292, 3059, 3029, 1718, 1650, 1612, 1585, 1565, 1537, 1511, 1439, 1240, 1196, 1179, 768 cm$^1$; $^1$H NMR (300 MHz, CDCl$_3$) δ 2.11 (8H), 2.83 (1H), 3.20 (1H), 4.74 (1H), 5.24 (2H), 6.95 (2H), 7.15 (2H), 7.25 (1H), 7.36 (2H); MS (FAB) m/z (rel. intensity) 523 (M+H, 99); Anal. Calcd for C$_{24}$H$_{24}$Cl$_2$N$_2$O$_7$: C, 55.08; H, 4.62; N, 5.35; Cl, 13.55. Found: C, 54.68; H, 4.66; N, 5.13; Cl, 13.70. Corrected for 1.59% H$_2$O found by Karl Fischer analysis.

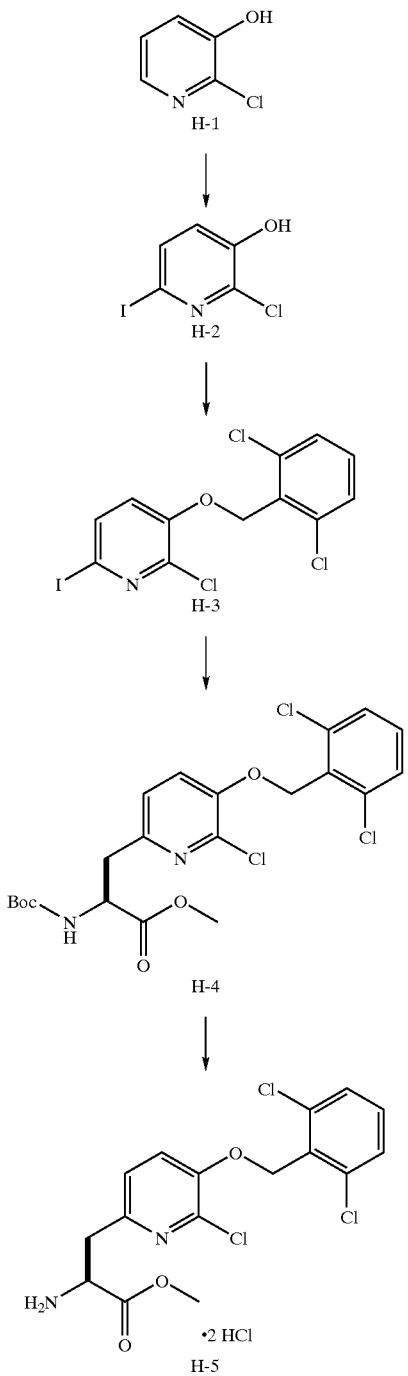

Scheme H teaches a general method for the preparation of 6-chloroazatyrosine examples of structures H-4 and H-5, by adaption of the methodology for the preparation of protected azatyrosine reagents as described by Kawata, S.; Ashizawa, S.; Hirama, M. *J. Am. Chem. Soc.* 1997, 119, 12012–12013 and references cited therein. Thus regioselective iodination of 2-chloro-3-pyridinol gives the chloro-iodopyridinol H-2, that is O-alkylated as exemplified by the synthesis of H-3. Palladium-catalyzed reaction of H-3 with the organozinc derived from a suitably protected β-iodoalanine, provides the protected 5-chloroazatyrosine H-4. N-deprotection of H-4 gives the aminoester H-5, that is used (as exemplified by reagent A-4 of Scheme A, and by reagent B-5 of Scheme B) for the synthesis of Examples of this invention.

PREPARATION 41

(Scheme H: H-2).

2-Chloroiodo-3-pyridinol ($C_5H_3ClINO$)

To a solution of 2-chloro-3-pyridinol H-1 (10.2 g, 78.7 mmol) and $K_2CO_3$ (38.9 g, 0.274 mol) in $H_2O$ (120 mL) is added I2 (24.3 g, 95.8 mmol), and the reaction mixture is stirred at rt for 4 h. The reaction mixture is quenched by the addition of aq satd $Na_2S_2O_3.5H_2O$, and its pH is lowered to pH 2 with the addition of 12 M aq HCl. The mixture is extracted with EtOAc. The combined EtOAc extracts are dried, filtered and concnetrated to a yellow solid, that is crystallized from 120:25 heptane/EtOAc (145 mL) to give, as a yellow solid, 11.2 g of the title compound: $^1H$ NMR ($CD_3SOCD_3$, 300 MHz) δ 9.87 (1H), 7.59 (1H), 7.06 (1H); $^{13}C$ NMR ($CD_3SOCD_3$, 75 MHz) δ 150.68, 138.07, 134.98, 127.02, 101.18.

PREPARATION 42

(Scheme H: H-3).

2-Chloro-3-[(2,6-dichlorophenyl)methoxy]-6-iodopyridine ($C_{12}H_7Cl_3INO$)

To a solution of H-2 (5.11 g, 20.0 mmol), $PPh_3$ (5.30 g, 20.0 mmol), and 2,6-dichlorobenzylalcohol (3.54 g, 20.0 mmol) in dry THF (100 mL) at 0° C. under Ar is added DEAD (3.15 mL, 20.0 mmol). The reaction mixture is kept at 0° C. for 1.5 h and at rt for 1.5 h. It is concentrated to a residue, that is purified by silica flash chromatography (17:3 hexanes/EtOAc) to give 7.61 g of the title compound: TLC (1 7:3 hexanes/EtOAc) $R_f$ 0.57; $^1H$ NMR ($CD_3SOCD_3$, 300 MHz) δ 7.85 (1H), 7.62 (1H), 7.58–7.45 (3H), 5.34 (2H).

PREPARATION 43

(Scheme H: H-4).

(S) 2-Chloro-3-[(2,6-dihlorophenyl)methoxy]-α-(1,1-dimethylethoxy)carbonyl]amino] pyridinepropanoic Acid Methyl Ester ($C_{21}H_{23}Cl_3N_2O_5$)

To an amberized flask containing activated Zn dust (0.777 g, 11.89 mmol) under Ar is added sequentially N-[(1,1-dimethylethoxy)carbonyl]-3-iodo-L-alanine methyl ester [93267-04-0] (3.91 g, 1.89 mmol), THF (11.9 mL), and dimethylacetamide (11.9 mL). The reaction mixture was purged of $O_2$ by the bubbling of Ar through the mixture for 5 min. It is stirred at 65±5° C. for 2 h, and is cooled to rt. To this mixture is added $PdCl_2(PPh_3)_2$ (0.412 g), followed immediately afterward by a degassed solution of H-3 (2.46 g, 5.94 mmol) in 1:1 THF/dimethylacetamide (11.8 mL). The reaction mixture is stirred at 65±5° C. for 5 h. It is cooled to 0° C. and quenched with sat'd aq $NH_4Cl$ (100 mL). The reaction mixture is extracted with EtOAc. The combined extracts are washed with brine, dried, filtered and concentrated to a green-yellow oil; that is purified by silica flash chromatography to give 1.90 g of the title compound: TLC (7:3 hexanes/EtOAc) $R_f$ 0.32; $^1H$ NMR ($CDCl_3$, 300 MHz) δ 7.76 (1H), 7.57 (2H), 7.48 (1H), 7.29 (1H), 7.27 (1H), 5.30 (2H), 4.32 (1H), 3.60 (3H), 3.01 (1H), 2.98 (1H), 1.31 (9H).

PREPARATION 44

(Scheme H: H-4).

(S)-2-Chloro-3-[(2,6-dichlorophenyl)methoxy]-α-amino-6-pyridinepropanoic Acid Methyl Ester Dihydrochloride Salt ($C_{16}H_{15}Cl_3N_2O_3.2HCl$)

A solution of H-4 (1.90 g, 3.88 mmol) in 4 M HCl in dioxane (35 mL) is stirred at rt under Ar for 20 h. The reaction mixture is concentrated in vacuo. The residue is taken up in $H_2O$ (40 mL), and extracted with $Et_2O$. The aqueous solution is frozen and lyophilized to give 1.39 g of the title compound: $^1H$ NMR ($CD_3SOCD_3$, 300 MHz) δ 8.62 (3H), 7.81 (1H), 7.58 (2H), 7.48 (1H), 7.38 (1H), 5.32 (2H), 4.37 (1H), 3.72 (3H), 3.27 (2H).

EXAMPLE 118

(Scheme A, A-5).

[S-(R*,R*)]-4-[[[1-[[2-Chloro-3-[(2,6-dichlorophenyl)methoxy]-6-pyridyl]methyl]-2-methoxy-2-oxoethyl]amino]carbonyl]-3-thiazolidinecarboxylic Acid (1,1-Dimethylethyl) ester ($C_{30}H_{37}Cl_3N_3O_6S$)

Example 118 was prepared as described in Scheme A from D-cysteine using the product of preparation 44 as amino acid intermediate A-4. Physical properties as follows: TLC (1:1 hexanes/EtOAc) $R_f$ 0.27; $^1H$ NMR ($CDCl_3$, 300 MHz) δ 8.43 (1H), 7.74 (1H), 7.58 (2H), 7.48 (1H), 7.29 (1H), 5.29 (2H), 4.67 (1H), 4.53 (1H), 4.44 (1H), 4.23 (1H), 3.62 (3H), 3.06 (3H), 2.82 (1H), 1.27 (9H).

EXAMPLE 119

(Scheme A, A-9).

[S-(R*,R*)]-4-[[1-Carboxy-2-[[2-Chloro-3-[(2,6-dichlorophenyl)methoxy]-6-pyridyl]ethyl]amino] carbonyl]-3-thiazolidinecarboxylic Acid (1,1-Dimethylethyl)ester ($C_{24}H_{26}Cl_3N_3O_6S$)

Example 119 was prepared from example 118 by the procedure described in preparation 12. Physical data as follows: mp 93–95° C.; TLC (600:400:2 EtOAc/hexanes/$HCO_2H$) $R_f$ 0.38; $^1H$ NMR ($CD_3SOCD_3$, 300 MHz) δ 8.30 (1H), 7.74 (1H), 7.57 (2H), 7.48 (1H), 7.27 (1H), 5.29 (2H), 4.67–4.36 (2H), 4.53 (1H), 4.23 (1H), 3.37–3.11 (3H), 2.97 (1H), 1.27 (9H).

Scheme I.

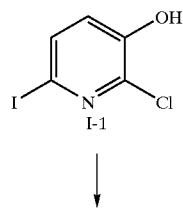

I-1

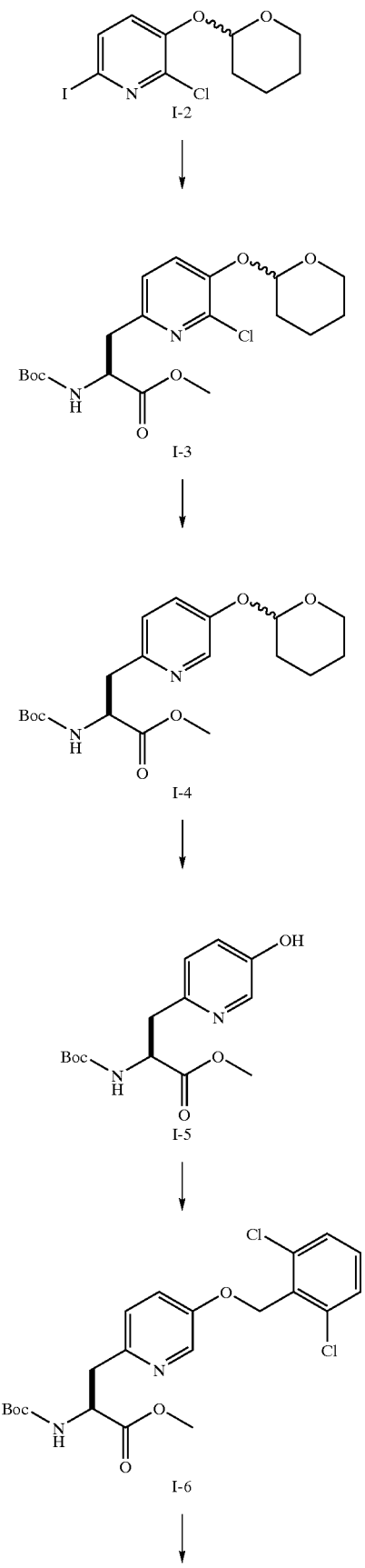

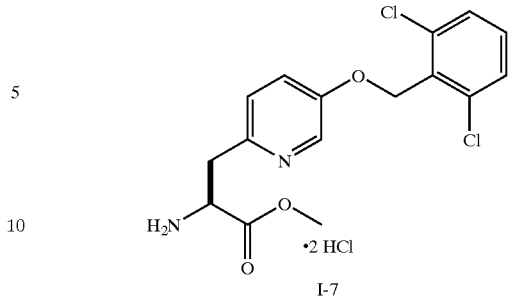

Scheme I teaches a general method for the preparation of azatyrosine reagents I-3, I-4, I-5, I-6 and I-7, by adaptation of the methodology for the preparation of protected azatyrosine reagents as described by Kawata, S.; Ashizawa, S.; Hirama, M. *J. Am. Chem. Soc.* 1997, 119, 12012–12013 and references cited therein. Thus O-protection of chloroiodopyridinol I-1 (identical to H-2) is followed by reaction with the organozinc, derived from a suitably protected β-iodoalanine, to provide the protected 6-chloroazatyrosine I-3. Reductive dehalogenation of I-3 gives I-4, that is O-deprotected to give I-5. Reagent I-5 is O-alkylated, as exemplified by the preparation of I-6. N-deprotection of I-6 gives the aminoester I-7, that is used (as exemplified by reagent A-4 of Scheme A, and by reagent B-5 of Scheme B) for the synthesis of Examples of this invention.

PREPARATION 45

(Scheme I, I-2).

(±)-2-Chloro-3-[(2-tetrahydropyranyl)oxy]-6-iodopyridine ($C_{10}H_{11}ClINO_2$)

To a solution of chloroiodopyridinol I-1 (same as H-2, the product of preparation 41) (1.00 g, 3.91 mmol) and dihydropyran (1.0 mL, 10.6 mmol) in $CH_2Cl_2$ (10 mL) under Ar at rt is added pyridinium chloride (0.050 g). The reaction mixture is stirred for 72 h. It is diluted with $CH_2Cl_2$, and is washed with satd aq $NaHCO_3$ and brine. The $CH_2Cl_2$ solution is dried, filtered and concentrated to an oil, that is purified by silica flash chromatography (19:1 hexanes/EtOAc) to give 1.06 g of the title product: TLC (19:1 hexanes/EtOAc) $R_f$ 0.24; $^1H$ NMR ($CDCl_3$, 300 MHz) δ 7.55 (1H), 7.17 (1H), 5.50 (1H), 3.77 (1H), 3.61 (1H), 2.07–1.57 (6H).

PREPARATION 46

(Scheme I, I-3).

(S)-2-Chloro-α-[[(1,1-dimethylethoxy)carbonyl]amino]-3-[(2-tetrahydropyranyl)oxy]pyridinepropanoic Acid Methyl Ester ($C_{19}H_{27}ClN_2O_6$)

To an amberized flask containing activated Zn dust (0.349 g, 5.51 mmol) under Ar is added THF (2 mL) and 1,2-dibromoethane (0.018 mL, 0.21 mmol). The suspension is brought to reflux for several minutes, cooled to approximately 30° C., and TMSCl (0.17 mL of a 1 M solution in THF) is added. The reaction mixture is stirred at 40±5° C. for 30 min and then is cooled to below rt. A solution of N-[(1,1-dimethylethoxy)carbonyl]-3-iodo-L-alanine methyl ester [93267-04-0] (1.81 g, 5.50 mmol) in 11:7 dimethylacetamide/THF (9.0 mL) is added, and the resulting reaction mixture is stirred at 45° C. for 5 h. The reaction mixture is cooled to below rt, and solid PdCl$_2$(PPh$_3$)$_2$ (0.192 g) is added, followed immediately by addition of a degassed solution of the iodopyridine (0.936 g, 2.76 mmol) in 1:1 THF/dimethylacetamide (5.6 mL). This reaction mixture is stirred for 4 h at 45° C. It is cooled to 0° C., quenched with sat'd aq NH$_4$Cl, and extracted with EtOAc. The combined EtOAc portions are washed with sat'd aq NH$_4$Cl and brine. The EtOAc solution is dried, filtered and concentrated to give a green-yellow colored foam, that upon purification by silica flash chromatography (7:3 hexanes/EtOAc) gives 0.879 g (1.85 mmol, 60%) of the title product: TLC (7:3 hexanes/EtOAc) R$_f$ 0.21; $^1$H NMR (CDCl$_3$, 300 MHz) d 7.39 (1H), 7.00 (1H), 5.46 (1H), 4.61 (1H), 4.13 (1H), 3.80 (3H), 3.62 (1H), 3.20 (1H), 2.13–1.53 (6H), 1.42 (9H).

PREPARATION 47

(Scheme I, I-4).

(S)-α-[[(1,1-Dimethylethoxy)carbonyl]amino]-3-[(2-tetrahydropyranyl)oxy]-6-pyridinepropanoic Acid Methyl Ester (C$_{19}$H$_{28}$N$_2$O$_6$)

A suspension of pre-reduced Pd/CaCO$_3$ (3.5 g) and I-3 (1.15 g, 2.77 mmol) in EtOH (40 mL) is hydrogenated (30 psi H$_2$) for 19 h at rt. The mixture is filtered, and the filtrate is evaporated to give a yellow-colored foam, that is purified by silica flash chromatography (600:400:1 hexanes/EtOAc/iPrOH) to give 0.367 g of the title compound: TLC (1:1 hexanes/EtOAc) R$_f$ 0.27; $^1$H NMR (CDCl$_3$, 300 MHz) δ 8.30 (1H), 7.29 (1H), 7.03 (1H), 5.81 (1H), 5.39 (1H), 4.65 (1H), 3.86 (1H), 3.73 (3H), 3.62 (1H), 3.21 (2H), 1.96–1.53 (6H), 1.42 (9H).

PREPARATION 48

(Scheme I, I-5).

(S)-α-[[(1,1-Dimethylethoxy)carbonyl]amino]-5-hydroxy-2-pyridinepropanoic Acid Methyl Ester (C$_{14}$H$_{20}$N$_2$O$_5$)

A solution of 14 (0.346 g, 0.91 mmol) and pyridinium ptoluenesulfonate (0.031 g, 0.12 mmol) in EtOH (8 mL) is stirred at 55±5° C. for 20 h. The reaction mixture is cooled to rt, and concentrated in vacuo. The residue is taken up in EtOAc. The solution is washed with brine, and dried, filtered and concentrated to a pale yellow-colored oil that is purified by silica flash chromatography (500:500:1 hexanes/EtOAc/iPrOH). Evaporation of the column fractions gives 0.132 g of the title compound: TLC (1:1 hexanes/EtOAc) R$_f$ 0.18; $^1$H NMR (CDCl$_3$, 300 MHz) δ 8.13 (1H), 7.13 (1H), 7.03 (1H), 5.71 (1H), 4.65 (1H), 3.70 (3H), 3.20 (2H), 1.39 (9H).

PREPARATION 49

(Scheme I, I-6).

(S)-5(2,6-Dichlorophenyl)methoxy]-α-[[(1,1-dimethylethoxy)carbonyl]amino]-2-pyridinepropanoic Acid Methyl Ester (C$_{21}$H$_{24}$Cl$_2$N$_2$O$_5$)

To a solution of I-5 (0.126 g, 0.43 mmol), 2,6-dichlorobenzylalcohol (0.075 g, 0.43 mmol) and PPh$_3$ (0.113 g, 0.43 mmol) in dry THF (4 mL) at 0° C. under Ar is added DEAD (0.068 mL). The reaction mixture is permitted to warm to rt, and is stirred for 18 h. It is concentrated, and the residue is purified by silica flash chromatography (700:300:1 hexanes/EtOAc/iPrOH) to give 0.149 g of the title compound: TLC (7:3 hexanes/EtOAc) R$_f$ 0.34; 1H NMR (CDCl$_3$, 300 MHz) δ 8.31 (1H), 7.37 (2H), 7.25 (2H), 7.08 (1H), 5.81 (1H), 5.29 (2H), 4.65 (1H), 3.70 (3H), 3.24 (2H), 1.63 (1H), 1.43 (9H).

PREPARATION 50

(Scheme I, I-7).

(S)-α-Amino-5-(2,6-dichlorophenyl)methoxy]-2-pyridinepropanoic Acid Methyl Ester Dihydrogen Chloride Salt (C$_{16}$H$_{16}$Cl$_2$N$_2$O$_3$.2HCl)

A solution of carbamate 16 (0.546 g, 1.20 mmol) in 4 M HCl in dioxane (12 mL) is stirred at rt under Ar for 16 h. The reaction mixture is concentrated in vacuo. The residue is dissolved in H$_2$O (40 mL), and this solution is extracted with Et$_2$O. The aqueous solution is frozen and lyophilized to give, as a light yellow-colored solid, 0.485 g of the title compound: $^1$H NMR (CD$_3$SOCD$_3$, 300 MHz) δ 8.75 (3H), 8.47 (1H), 7.81 (1H), 7.57 (3H), 7.48 (1H), 5.35 (2H), 4.49 (1H), 3.67 (3H), 3.42 (2H).

EXAMPLE 120

(Scheme A, A-5).

[S-(R*,R*)]-4-[[[1-[[3-[(2,6-Dichlorophenyl)methoxy]-6-pyridyl]methyl]-2-methoxy-2-oxoethyl]amino]carbonyl]-3-thiazolidinecarboxylic Acid (1,1-Dimethylethyl)ester (C$_{25}$H$_{30}$Cl$_2$N$_3$O$_6$S)

Example 120 was prepared as described in Scheme A from D-cysteine using the product of preparation 49 as amino acid intermediate A-4. Physical properties as follows: TLC (1:1 hexanes/EtOAc) R$_f$ 0.22; 1H NMR (CDCl$_3$, 300 MHz) δ 8.28 (2H), 7.38 (2H), 7.28 (2H), 7.09 (1H), 5.29 (2H), 4.90–4.74 (3H), 4.40 (1H), 3.67 (3H), 3.38–3.22 (3H), 1.61 (2H), 1.40 (9H).

EXAMPLE 121

(Scheme A, A-9).

[S-(R*,R*)]-4-[[[1-Carboxy-2-[3-[(2,6-dihlorophenyl)methoxy]-6-pyridyl]ethyl]amino]carbonyl]-3-thiazolidinecarboxylic Acid (1,1-Dimethylethyl)ester (C$_{24}$H$_{28}$Cl$_2$N$_3$O$_6$S)

Example 121 was prepared from example 120 by the procedure described in preparation 12. Physical data as follows: mp 92–94°; TLC (500:500:3 hexanes/EtOAc/HCO$_2$H) R$_f$ 0.10; $^1$H NMR (CDCl$_3$, 300 MHz) δ 8.31 (1H), 8.26 (1H), 7.55 (2H), 7.28 (2H), 7.46 (1H), 7.21 (1H), 5.25 (2H), 4.72–4.38 (2H), 4.60 (1H), 4.23 (1H), 3.21–3.12 (2H), 3.09–2.94 (1H), 2.74 (1H), 1.29 (9H).

Scheme J.

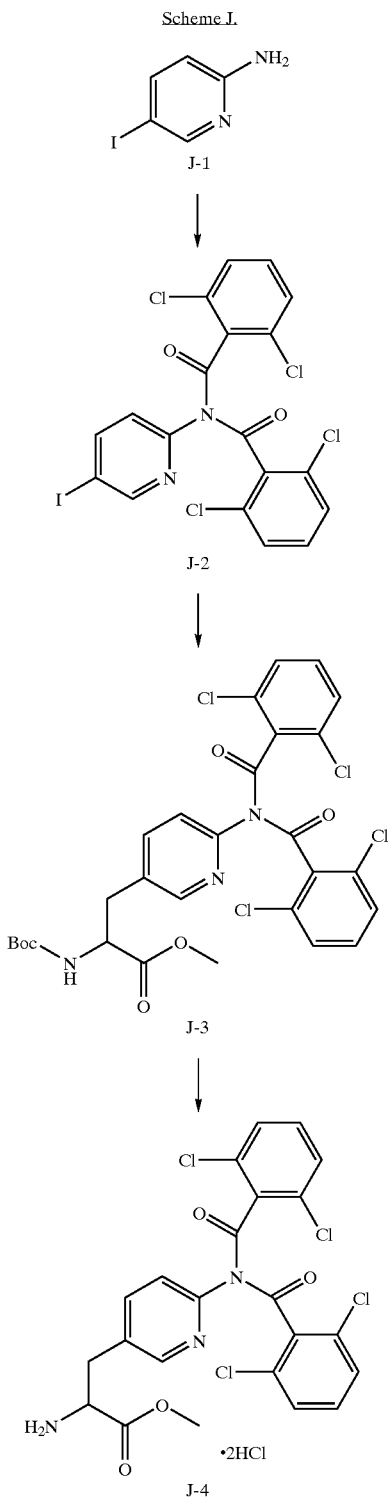

Scheme J teaches a general method for the preparation of para-acylamino derivatives of aza-phenylalanine. Thus bis-acylation of 2-amino-5-iodopyridine J-1 gives the imide J-2, that is reacted with the organozinc, derived from a suitably protected β-iodoalanine, to provide the protected acylamino azaphenylalanine J-3. N-deprotection of J-3 gives the aminoester J-4, that is used (as exemplified by reagent A-4 of Scheme A, and by reagent B-5 of Scheme B) for the synthesis of Examples of this invention.

PREPARATION 51

(Scheme J: J-2).

2-[[bis(2,6-Dichlorobenzoyl)]amino]-5-iodopyridine
($C_{19}H_9Cl_4IN_2O_2$)

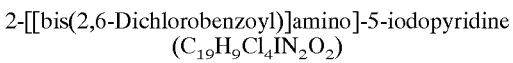

To a solution of 2-amino-5-iodopyridine J-1 (2.20 g, 10.0 mmol) and $Et_3N$ (2.12 mL, 15.0 mmol) in dry THF (100 mL) at rt under Ar, is added dropwise 2,6-dichlorobenzoylchloride (1.60 mL, 11.0 mmol) over 45 min. The reaction mixture is stirred for 15 h. It is diluted with EtOAc (300 mL), and is washed with cold aq 1 M NaOH and brine. The solution is dried, filtered and concentrated to give a yellow-colored waxy solid, that is purified by silica flash chromatography (3:1 hexanes/EtOAc) to give 2.60 g of the title compound: TLC (7:3 hexanes/EtOAc) $R_f$ 0.60; $^1H$ NMR ($CDCl_3$, 300 MHz) δ 8.59 (1H), 8.03 (1H), 7.99 (1H), 7.44–7.26 (6H).

PREPARATION 52

(Scheme J: J-3).

(S)-2-[[bis-(2,6-Dichlorobenzoyl)]amino]-α-[[(1,1-Dimethylethoxy)carbonyl]amino]-5-pyridinepropanoic Acid Methyl Ester
($C_{28}H_{25}Cl_4N_3O_6$)

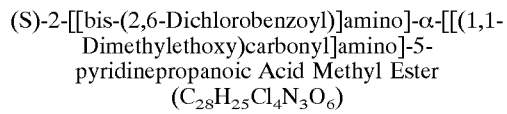

To an amberized flask containing activated Zn dust (0.865 g, 13.23 mmol) under Ar is added sequentially N-[(1,1-dimethylethoxy)carbonyl]-3-iodo-L-alanine methyl ester (4.36 g, 13.23 mmol), THF (13 mL) and N,N-dimethylacetamide (13 mL). The reaction mixture is purged of $O_2$ by the bubbling Ar through the mixture for 5 min, and then is warmed to 45±5° C. for 7 h. It is cooled to rt. To this mixture is added $PdCl_2(PPh_3)_2$ (0.461 g) followed immediately by a degassed solution of iodide J-2 (2.60 g, 4.59 mmol) in 1:1 THF/N,N-dimethylacetamide (18 mL). The reaction mixture is stirred at 45±5° C. under Ar for 13 h. It is cooled to 0° C. and quenched with satd aq $NH_4Cl$ (150 mL). The mixture is extracted with EtOAc. The combined EtOAc extracts are washed with brine, dried, filtered and concentrated to a green-yellow-colored paste, that is purified by silica flash chromatography (700:300:1 hexanes/EtOAc/iPrOH) to give 1.43 g of the title compound: TLC (7:3 hexanes/EtOAc) $R_f$ 0.29: $^1H$ NMR ($CDCl_3$, 300 MHz) δ 8.13 (1H), 7.57 (1H), 7.46 (1H), 7.26 (6H), 4.80 (1H), 4.50 (1H) 3.67 (31H), 3.05 (2H), 1.46 (9H).

PREPARATION 53

(Scheme J: J-4).

(S)-α-Amino-2-[[bis-(2,6-dichlorobenzoyl)]amino]-5-pyridinepropanoic Acid Methyl Ester Dihydrochloride Salt ($C_{23}H_{17}Cl_4N_3O_4$·HCl)

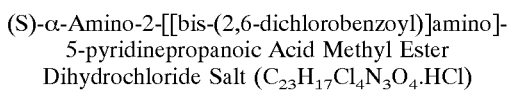

A solution of J-3 (0.69 g, 1.08 mmol) in 4 M HCl in dioxane (15 mL) is stirred under Ar for 20 h. The reaction mixture is concentrated in vacuo, diluted with $H_2O$, and extracted with $Et_2O$. The aqueous solution is frozen and lyophilized to give, as a pale yellow-colored solid. 0.627 g of the title compound: $^1H$ NMR ($CD_3SOCD_3$, 300 MHz) δ 8.80 (2H), 8.27 (1H), 7.82 (1H), 7.67–7.26 (7H), 4.25 (I1), 3.52 (3H), 3.16 (2H), 3.04 (1H); MS (ESI+) m/z 541.7.

EXAMPLE 122

(Scheme A, A-5).

[S-(R*,R*)]-4-[[[1-[[2-[[bis-(2,6-Dichlorobenzoyl)]amino]-5-pyridyl]methyl]-2-methoxy-2-oxoethyl]amino]carbonyl]-3-thiazolidinecarboxylic Acid (1,1-Dimethylethyl)ester ($C_{15}H_{30}Cl_2N_3O_6S$)

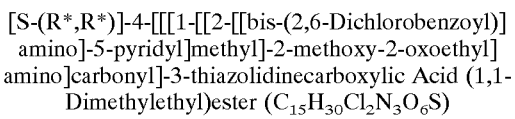

Example 122 was prepared as described in Scheme A from D-cysteine using the product of preparation 52 as amino acid intermediate A-4. Physical properties as follows: TLC (1:1 hexanes/EtOAc) $R_f$ 0.22; $^1$H NMR (CDCl$_3$, 300 MHz) δ 8.28 (2H), 7.38 (2H), 7.28 (2H), 7.09 (1H), 5.29 (2H), 4.90–4.74 (3H), 4.40 (1H), 3.67 (3H), 3.38–3.22 (3H), 1.61 (2H), 1.40 (9H).

EXAMPLE 123

(Scheme A, A-9).

[S-(R*,R*)]-4-[[[[1-Carboxy-2-[2-[[bis-(2,6-dichlorobenzoyl)]amino]-5-pyridyl]]ethyl]amino] carbonyl]-3-thiazolidinecarboxylic Acid (1,1-Dimethylethyl)ester ($C_{31}H_{28}Cl_4N_4O_7S$)

Example 123 was prepared from example 122 by the procedure described in preparation 12. Physical data as follows: mp 158–160°; TLC (50:50:2 hexanes/EtOAc/HCO$_2$H) $R_f$ 0.18; $^1$H NMR (CD$_3$SOCD$_3$, 300 MHz) δ 8.42 (1H), 8.22 (1H), 7.75 (1H), 7.69–7.17 (5H), 7.53 (1H), 4.59 (1H), 4.40 (2H), 4.19 (1H), 3.19–3.02 (2H), 2.84 (1H), 2.56 (1H), 1.34 (9H).

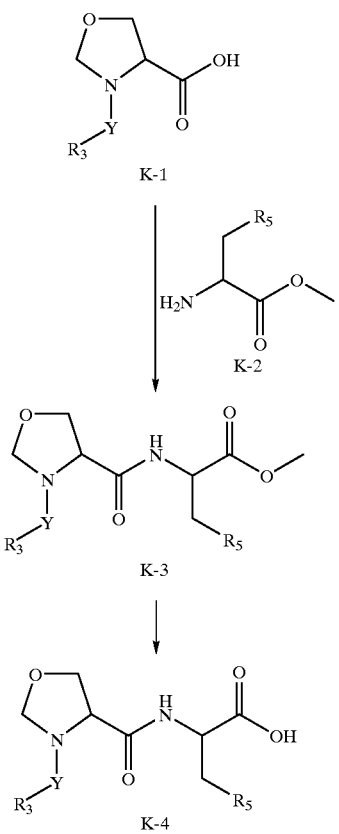

Scheme K

Scheme K teaches a general method for the preparation of oxazolidinecarboxylic acid Examples K-3 and K-4, where $R_3$, $R_5$ and Y are identical to the definitions of Scheme B. Thus coupling of oxazolidinecarboxylic acid K-1 and aminoester K-2 (as exemplified by the reaction of reagents A-3 and A-4 of Scheme A, and B-4 and B-5 of Scheme B) provides Examples K-3, that are hydrolyzed to Examples K-4 of this invention.

EXAMPLE 124

(Scheme K: K-3, where $R_3$ is (phenyl)methyl, $R_5$ is 4-[(2,6-dichlorobenzoyl)amino]phenyl, Y is CO$_2$ and the stereochemistry is [S-(R*,R*)]).

[S-(R*,R*)]-4-[[[1-[[4-[(2,6-Dichlorobenzoyl) amino]phenyl]methyl]-2-methoxy-2-oxoethyl] amino]carbonyl]-3-oxazolidinecarboxylic Acid 3-Phenylmethyl Ester ($C_{29}H_{27}Cl_2N_3O_7$)

Example 124 was prepared as by coupling commercially available (S)-3,4-oxazolidinedicarboxylic acid 3-(phenylmethyl)ester to amino acid K-2 (Scheme K, where $R_5$ is 4-[(2,6-dichlorobenzoyl)amino]phenyl stereochemistry is (S)) under the conditions described by preparation 3. Physical properties as follows: TLC (3:2 Heptane/EtOAc) $R_f$=0.17; UV (MeOH) $I_{max}$ 225 (e 12600, sh), 251 (17900); $^{13}$C NMR (d$_6$-dimethylsulfoxide) δ 188.75, 171.96, 169.86, 162.40, 162.30, 152.99, 137.59, 137.47, 136.87, 136.81, 133.23, 131.79, 131.65, 130.08, 128.80, 128.67, 128.28, 127.76, 119.84, 119.75, 79.82, 66.77, 57.85, 53.85, 52.47, 36.62 (23 lines expected; 26 lines observed); MS (FAB) m/z 602, 600, 558, 556, 531, 466, 371, 351, 349,280, 278, 175, 173; MS (FAB) m/z 600.1312 (calcd [M+H]$^+$ 600.1304; Anal. C, 57.75; H, 4.75; N, 6.80; Cl, 11.86; (calcd for 0.42% H$_2$O: C, 57.77; H, 4.56; N, 6.97; Cl, 11.76).

EXAMPLE 125

(Scheme K: K-4 where $R_3$ is (phenyl)methyl, $R_5$ is 4-[(2,6-dichlorobenzoyl)amino]phenyl, Y is CO$_2$ and the stereochemistry is [S-(R*,R*)]).

[S-(R*,R*)]-4-[[[1-Carboxy-2-[4-[(2,6-dichlorobenzoyl)amino]phenyl]ethyl]amino]- carbonyl]-3-oxazolidinecarboxylic Acid 3-Phenylmethyl Ester ($C_{28}H_{25}Cl_2N_3O_7$)

Example 125 was prepared from example 124 by the procedure described in preparation 12. Physical properties as follows: TLC (950:50:1 CH$_2$Cl$_2$/MeOH/HCO$_2$H) $R_f$=0.34; $^1$H NMR (d$_6$-dimethylsulfoxide) δ 10.65 (1H), 8.31 (1H), 7.61–7.42 (5H), 7.40–7.20 (5H), 7.15 (2H), 5.19–4.85 (2H), 4.90 (1H), 4.76 (1H), 4.43 (1H), 4.36 (1H), 4.11 (1H), 3.65 (1H), 3.04 (1H), 2.87 (1H); MS (FAB) m/z 588, 586 544, 542, 532, 391, 337, 335, 327, 269, 267, 161, 147, 133, 129, 117, 115, 103, 101.91; MS (FAB) 586.1132 (calcd 586.1147).

EXAMPLE 126

(Scheme K: K-3 where $R_3$ is benzyl, $R_5$ is 4-[(2,6-dichlorobenzoyl)amino]phenyl, Y is CO$_2$ and the stereochemistry is [R-(R*,S*)]).

[R-(R*S*)]-4-[[[1-[[4-[(2,6-Dichlorobenzoyl)amino] phenyl]methyl]-2-methoxy-2-oxoethyl]amino] carbonyl]-3-oxazolidinecarboxylic Acid 3-Phenylmethyl Ester ($C_{29}H_{27}Cl_2N_3O_7$)

Example 126 was prepared as described in Scheme K from commercially available (R)-3,4-oxazolidinedicarboxylic acid 3-(phenylmethyl)ester. Physical properties as follows: TLC (3:2 heptane/EtOAc) $R_f$=0.19; UV (MeOH) $\lambda_{max}$ 225 (e 12400, sh), 252 (17700), 284 (2960, sh); $^{13}$C NMR (CDCl$_3$) δ 171.23, 169.14, 162.43, 154.26, 136.47, 135.93, 135.65, 132.37, 132.28, 130.91, 130.00, 128.62, 128.39, 128.11.1120.30, 79.66, 67.94, 58.38, 53.14, 52.49, 37.19 (23 lines expected; 21 lines observed); MS (FAB) m/z 602, 600, 558, 556, 466, 351, 349, 280, 278, 175, 173; MS (FAB) m/z 600.1299 (calcd for [M+H]$^+$ 600.1304); Anal. C, 57.69; H, 4.90; N, 6.71; Cl, 11.49; (calcd for 0.35% $H_2O$: C, 57.81; H, 4.56; N, 6.97; Cl, 11.77).

EXAMPLE 127

(Scheme K: K-4 where $R_1$ is benzyl, $R_5$ is 4-[(2,6-dichlorobenzoyl)amino]phenyl, Y is $CO_2$ and the stereochemistry is [R-(R*,S*)]).

[R-(R*,S*)]-4-[[[1-Carboxy-2-[4-[(2,6-dichlorobenzoyl)amino]phenyl]ethyl]amino]-carbonyl]-3-oxazolidinecarboxylic Acid 3-(Phenylmethyl)ester ($C_{28}H_{25}Cl_2N_3O_7$)

Example 127 was prepared from example 126 by the procedure described in preparation 12. Physical properties as follows: TLC (950:50:1 $CH_2Cl_2$/MeOH/$HCO_2H$) $R_f$=0.31; $^1H$ NMR ($d_4$-methanol) δ 7.60 (2H), 7.49–7.23 (8H), 7.21 (2H), 5.23–4.97 (21H), 4.95 (1H), 4.88 (1H), 4.70 (1H), 4.36 (1H), 4.14 (1H), 3.85–3.73 (1H), 3.23 (1H), 3.00 (1H); MS (FAB) m/z 588, 586, 544, 542, 532, 391, 371, 337, 335, 245, 177, 173, 149, 123, 105, 103, 91; MS (FAB) m/z 586.1163 (calcd 586.1147).

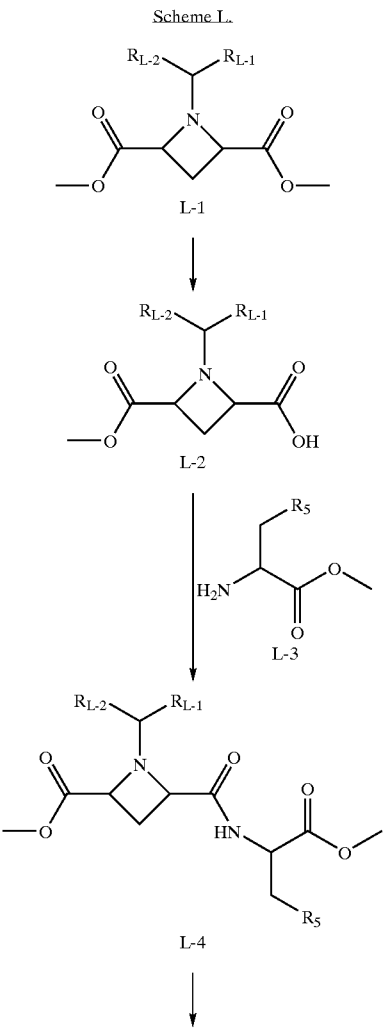

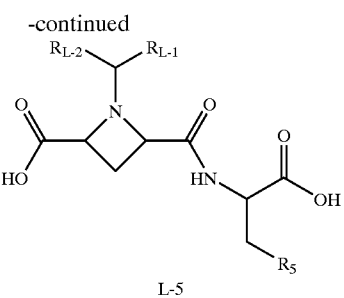

Scheme L teaches a general method for the preparation of N-alkylaryl azetidinedicarboxylic acid Examples L-4 and L-5, where $R_{L-1}$ is $C_{1-6}$ alkyl, $R_{L-2}$ is $C_{6-10}$ aryl and $R_5$ is defined as in Scheme B. The N-phenylethyl-2,4-azetidinedicarboxylic acid dimethyl ester stereoisomers of general structure L1 were prepared as described (Hoshino, J.; Hiraoka, J.; Hata, Y.; Sawada, S.; Yamamoto, Y. *J. Chem. Soc. Perkin Trans.* 1 1995, 693–697) and separated by silica flash chromatography. Thus partial saponification of diester L-1 gives the half-acid L-2, that is coupled with reagent L-3 (as exemplified by the use of reagents A-3 and A-4 of Scheme A, and B-4 and B-5 of Scheme B) to provide Examples L-4, that are then hydrolyzed to Examples L-5 of this invention.

PREPARATION 54

(Scheme L: L-1 where $R_{L-1}$ is methyl, $R_{L-2}$ is phenyl and stereochemistry is [2S-[1(R*),2α,4β]]).

[2S-[1(R*),2α,4β]]-1-(1-Phenylethyl)-2,4-azetidinedicarboxylic Acid Dimethyl Ester [168647-92-5] ($C_{15}H_{19}NO_4$)

Physical properties as follows: TLC (4:1 Hexanes/EtOAc) $R_f$=0.42; $^{13}C$ NMR ($CDCl_3$) δ 173.61, 142.41, 128.31, 127.39, 127.35, 60.95, 60.67, 51.64, 24.96, 21.72.

PREPARATION 55

(Scheme L: L-1 where $R_{L-1}$ is methyl, $R_{L-2}$ is phenyl and stereochemistry is [2R-[(S*),2α,4β]]).

[2R-[1(S*),2α,4β]]-1-(1-Phenylethyl)-2,4-azetidinedicarboxylic Acid Dimethyl Ester ($C_{15}H_{19}NO_4$)

Physical properties as follows: TLC (4:1 Hexanes/EtOAc) $R_f$=0.31; $^{13}C$ NMR ($CDCl_3$) δ 172.97, 141.21, 128.44, 128.07, 127.68, 61.54, 60.69, 51.61, 24.91, 19.55.

PREPARATION 56

(Scheme L: L-1 where $R_{L-1}$ is methyl, $R_{L-2}$ is phenyl and stereochemistry is [1(S)-cis]).

[1(S)-cis]-1-(1-Phenylethyl)-2,4-azetidinedicarboxylic Acid Dimethyl Ester [168753-32-0] ($C_{15}H_{19}NO_4$)

Physical properties as follows: TLC (4:1 Hexanes/EtOAc) $R_f$=0.21; $^{13}C$ NMR ($CDCl_3$) δ 172.58, 172.08, 140.84, 128.22, 128.15, 127.65, 66.32, 60.10, 59.65, 52.06, 51.59, 24.26, 19.91.

PREPARATION 57

(Scheme L: L-1 where $R_{L-1}$ is methyl, $R_{L-2}$ is phenyl and stereochemistry is [2R-[1(R*),2α,4β]]).

[2R-[1(R*),2α,4β]]-1-(1-Phenylethyl)-2,4-azetidinedicarboxylic Acid Dimethyl Ester ($C_{15}H_{19}NO_4$)

Physical properties as follows: TLC (8:2 hexanes/EtOAc) $R_f$=0.42; $^{13}$C NMR (CDCl$_3$) δ 173.61, 142.41, 128.31, 127.39, 127.35, 60.95, 60.67, 51.64, 24.96, 21.72; MS (+ESI) m/z 278.3.

PREPARATION 58

(Scheme L: L-1 where $R_{L-1}$ is methyl, $R_{L-2}$ is phenyl and stereochemistry is [2S-[1(S*),2α,4β]]).

[2S-[1(S*),2α,4β]]-1-(1-Phenylethyl)-2,4-azetidinedicarboxylic Acid Dimethyl Ester ($C_{15}H_{19}NO_4$)

Physical properties as follows: TLC (8:2 hexanes/EtOAc) $R_f$=0.31; $^{13}$C NMR (CDCl$_3$) δ 172.97, 141.21, 128.44, 128.07, 127.68, 61.54, 60.69, 51.61, 24.91, 19.55; MS (+ESI) m/z 278.3.

PREPARATION 59

(Scheme L: L-1 where $R_{L-1}$ is methyl, $R_{L-2}$ is phenyl and stereochemistry is [1(R)-cis]).

[1(R)-cis]-1-(1-Phenylethyl)-2,4-azetidinedicarboxylic Acid Dimethyl Ester ($C_{15}H_{19}NO_4$)

Physical properties as follows: TLC (8:2 hexanes/EtOAc) $R_f$=0.21; $^{13}$C NMR (CDCl$_3$) δ 172.58, 172.08, 140.84, 128.22, 128.15, 127.65, 66.32, 60.10, 59.65, 52.06, 51.59, 24.26, 19.91; MS (+ESI) m/z 278.3.

PREPARATION 60

(Scheme L: L-2 where $R_{L-1}$ is methyl, $R_{L-2}$ is phenyl and stereochemistry is [2S-[1(R*),2α,4β]]).

[2S-[1(R*),2α,4β]]-1-(1-Phenylethyl)-2,4-azetidinedicarboxylic Acid Monomethyl Ester ($C_{14}H_{17}NO_4$)

A mixture of L-1 (Scheme L, where $R_{L-1}$ is methyl, $R_{L-2}$ is phenyl and stereochemistry is [2S-[1(R*),2α,4β]], the product of preparation 54) (7.95 g; 28.7 mmol) and LiOH (30 mmol) in 1:1 MeOH/H$_2$O (240 mL) is stirred at rt for 42 h. The reaction mixture is adjusted to pH 5 with HOAc, and is concentrated. The resulting concentrate is diluted with brine and extracted repeatedly with CHCl$_3$. The combined CHCl$_3$ extracts are dried, filtered and concentrated to give a yellow foam (6.61 g), that is purified by preparative C18 reverse phase chromatography to give the title compound as a crystalline solid: mp 112–113° C.: TLC (650:350:1 hexanes/EtOAc/HCO$_2$H) $R_f$=0.17; MS (FAB) m/z 527, 264, 248, 218, 204, 192, 186, 177, 160, 114, 105; Anal. C, 64.04; H, 6.57; N, 5.37; (calcd C, 63.87; H, 6.51; N, 5.32).

PREPARATION 61 AND EXAMPLE 128

(Scheme L: L-4 where $R_{L-1}$ is methyl, $R_{L-2}$ is phenyl, $R_5$ is 4-[(2,6-dichlorobenzoyl)amino]phenyl and stereochemistry is [2S-[1(R*),2α,4β(R*)]]).

[2S-[1(R*),2α,4β(R*)-]]-4-[[[1-[[4-[(2,6-Dichlorobenzoyl)amino]phenyl]methyl]-2-methoxy-2-oxoethyl]amino]carbonyl]-1-(1-phenylethyl)-2-azetidinecarboxylic Acid Methyl Ester ($C_{31}H_{31}Cl_2N_3O_6$)

A mixture of L-2 (Scheme L, where $R_{L-1}$ is methyl, $R_{L-2}$ is phenyl and stereochemistry is [2S-[1(R*),2α,4β]], the product of preparation 60) (0.62 g, 2.4 mmol), L-3 (Scheme L where $R_5$ is 4-[(2,6-dichlorobenzoyl)amino]phenyl and stereochemistry is (S)) (0.95 g, 2.4 mmole), and BOP-Cl (0.68 g; 2.7 mmol) in CH$_2$Cl$_2$ (10 mL) is treated with (i-Pr)$_2$NEt (1.7 mL, 9.8 mmol). The reaction mixture is stirred at rt under N$_2$ for 19 h. It is diluted with half-saturated NaHCO$_3$ and extracted with CH$_2$Cl$_2$. The CH$_2$Cl$_2$ extracts are dried, filtered and concentrated to give a beige-colored foam (1.40 g), that is purified by silica flash chromatography to give the title compound: TLC (1:1Hexanes/EtOAc) $R_f$=0.23; $^{13}$C NMR (CDCl$_3$) δ 173.25, 172.73, 171.63, 162.57, 141.86, 136.76, 136.01, 132.44, 132.39, 130.90, 130.00, 128.57, 128.12, 127.55, 127.08, 120.37, 63.25, 60.06, 59.17, 52.41, 52.12, 51.47, 37.65, 26.06, 21.25; MS (FAB) m/z 612.1658; Anal. C, 59.66; H, 5.14; N, 6.64; (calcd C, 60.79; H, 5.10; N, 6.86).

PREPARATION 62 AND EXAMPLE 129

(Scheme L: L-5 where $R_{L-1}$ is methyl, $R_{L-2}$ is phenyl, $R_5$ is 4-[(2,6-dichlorobenzoyl)amino]phenyl and stereochemistry is [2S-[1(R*),2α,4β(R*)]]).

[2S-[1(R*),2α,4β(R*)]]-4-[[[1-Carboxy-2-[4-[(2,6-dichlorobenzoyl)amino]phenyl]ethyl]-amino]carbonyl]-1-(1-phenylethyl)-2-azetidinecarboxylic Acid Dilithium Salt ($C_{29}H_{25}Cl_2Li_2N_3O_6$)

A mixture of L-4 (Scheme L, where $R_{L-1}$ is methyl, $R_{L-2}$ is phenyl, $R_5$ is 4-[(2,6-dichlorobenzoyl)amino]phenyl and stereochemistry is [2S-[1(R*),2α,4β(R*)]], the product of preparation 61) (0.684 g, 1.12 mmol) and LiOH.H$_2$O (0.25 g, 6.0 mmol) is dissolved by warming in MeOH (10 mL). This solution is diluted with 1:1H$_2$O/THF (20 mL), and the reaction mixture is stirred at rt for 22 h. The mixture is adjusted with 1 N HCl to pH 6. The solution is concentrated to give a white solid, that is purified by preparative C18 reverse phase chromatography (MeCN/H$_2$O gradient). Evaporation of the column fractions gives a white solid, that is dissolved in warm H$_2$O. The solution is frozen and lyophilized to give, as a white solid, the title compound: mp 270° C.; TLC (850:150:1 CHCl$_2$/MeOH/HCO$_2$H) $R_f$=0.21–0.36; $^{13}$C NMR (CD$_3$OD) δ 178.05, 174.59, 174.01, 162.20, 142.33, 135.09, 134.91, 133.04, 130.54, 129.24, 128.61, 126.46, 126.41, 126.17, 124.94, 118.33, 82.70, 61.70, 60.50, 53.30, 36.23, 25.85, 18.65; MS (FAB) m/z 584.1350; Anal. C, 55.17; H, 5.01; N, 6.63; Cl, 1.16; (calcd for 7.52% H$_2$O: C, 54.02; H, 4.75; N, 6.52; Cl, 11.21).

EXAMPLE 130

(Scheme L: L-4 where $R_{L-1}$ is methyl, $R_{L-2}$ is phenyl, $R_5$ is 4-[(2,6- dichlorobenzoyl)amino]phenyl and stereochemistry is [2R-[1(S*),2α,4β(S*)]]).

[2R-[1(S*),2α,4β(S*)]]-4-[[[1-[[4-[(2,6-Dichlorobenzoyl)amino]phenyl]methyl]-2-methoxy-2-oxoethyl]amino]carbonyl]-1-(1-phenylethyl)-2-azetidinecarboxylic Acid Methyl Ester ($C_{31}H_{31}Cl_2N_3O_6$)

Example 130 was prepared as described in Scheme L using the product of preparation 55 as intermediate L-1. Physical properties as follows: TLC (3:2 EtOAc/Hexanes) $R_f$=0.43; $[α]^{25}_D$ +58 (c 0.91, MeOH): $^{13}$C NMR (CDCl$_3$) δ 173.24, 172.15, 172.05, 162.58, 140.75, 136.45, 136.01, 132.89, 132.38, 130.91, 129.60, 128.67, 128.39, 128.11, 127.97, 120.39, 63.54, 60.19, 59.54, 53.15, 52.16, 51.91, 37.86, 26.12, 18.3. MS (EI) m/z 613, 611, 598, 596, 554, 552, 527, 525, 508, 506, 450, 448, 351, 349, 218, 191, 175, 173, 160, 131, 114, 105; Anal. C, 60.68; H, 5.18; N, 6.67; Cl, 1.24; (calcd for C, 60.79; H, 5.10; N, 6.86; Cl, 11.58).

EXAMPLE 131

(Scheme L: L-5 where $R_{L-1}$ is methyl, $R_{L-2}$ is phenyl, $R_5$ is 4-[(2,6-dichlorobenzoyl)amino]phenyl and stereochemistry is [2R-[1(S*),2α,4β(S*)]]).

[2R-[1(S*),2α,4β(S*)]]-4-[[[1-Carboxy-2-[4-[(2,6-dichlorobenzoyl)amino]phenyl]ethyl]-amino]carbonyl]-1-(1-phenylethyl)-2-azetidincearboxylic Acid, Dilithium Salt ($C_{29}H_{25}Cl_2Li_2N_3O_6$)

Example 131 was prepared from Example 130 by the procedure described in preparation 62. Physical properties as follows: $[\alpha]^{25}_D$ +84 (c 0.95, MeOH); $^{13}C$ NMR ($CD_3OD$) δ 179.18, 176.55, 174.13, 163.58, 141.88, 136.32, 136.29, 134.96, 131.90, 130.86, 129.47, 128.49, 128.07.127.87, 127.16, 119.74, 63.70 63.49, 59.77, 56.27, 38.24, 26.25, 18.70; MS (FAB) m/z 598, 596, 592, 590, 552, 550, 546, 544, 161; Anal. C, 55.20; H, 5.52; N, 6.59; (calcd for 10.98% $H_2O$: C, 52.00; H, 4.99; N, 6.27).

EXAMPLE 132

(Scheme L: L-4 where $R_{L-1}$ is methyl, $R_{L-2}$ is phenyl, $R_5$ is 4-[(2,6-dichlorobenzoyl)amino]phenyl and stereochemistry is [1(S),2α,4α(S)], a single diastereomer having a cis relative configuration but unknown absolute configuration at C-2 and C-4 of the azetidine.)

[1(S)2α,4α(S)]-4-[[[1-[[4-[(2,6-Dichlorobenzoyl)amino]phenyl]methyl]-2-methoxy-2-oxoethyl]amino]carbonyl]-1-(1-phenylethyl)-2-azetidinecarboxylic Acid 2-Methyl Ester ($C_{31}H_{31}Cl_2N_3O_6$)

Example 132 was prepared as described in Scheme L using the product of preparation 56 as intermediate L-1. Physical properties as follows: TLC (9:1 $CHCl_3$/acetone) $R_f$=0.29; $^{13}C$ NMR ($CDCl_3$) δ 172.70, 172.29, 171.65, 162.49, 140.97, 136.71, 136.12, 132.47, 132.39, 130.81, 130.22, 128.35, 128.07, 127.82, 120.17, 66.61, 61.52, 59.99, 52.38, 52.24, 51.79, 37.73, 25.16, 20.09.

EXAMPLE 133

(Scheme L: L-5 where $R_{L-1}$ is methyl, $R_{L-2}$ is phenyl, $R_5$ is 4-[(2,6-dichlorobenzoyl)amino]phenyl and stereochemistry is [1(S),2α,4α], a single diastereomer having a cis relative configuration but unknown absolute configuration at C-2 and C-4 of the azetidine.)

[1(S),2α,4α(S)]-4-[[[1-Carboxy-2-[4-[(2,6-dichlorobenzoyl)amino]phenyl]ethyl]amino]-carbonyl]-1-(1-phenylethyl)-2-azetidinecarboxylic Acid ($C_{29}H_{27}Cl_2N_3O_6$)

Example 133 was prepared from Example 132 by the procedure described in preparation 62. Physical properties as follows: $[\alpha]^{25}_D$ +20 (c 0.88, MeOH); $^{13}C$ NMR ($CD_3OD$) δ 173.70, 173.05, 172.61, 163.69, 140.09, 1,6.93, 136.20, 133.18, 131.89, 130.89, 129.95, 128.09, 127.89.127.88, 127.65, 120.03, 66.07, 61.29, 59.86, 52.70, 36.98, 25.03, 18.81; MS (FAB) m/z 662, 660, 586, 584, 539, 482, 480, 436, 434, 204, 175, 173, 160, 133, 109, 105; Anal. C, 57.90; H, 5.01; N, 6.93; (calcd for 4.98% $H_2O$: C, 56.63; H, 4.98; N, 6.83).

EXAMPLE 134

(Scheme L: L-4 where $R_{L-1}$ is methyl, $R_{L-2}$ is phenyl, $R_5$ is 4-[(2,6-dichlorobenzoyl)amino]phenyl and stereochemistry is [2R-[1(R*),2α,4β(S*)]]).

[2R-[1(R*),2α,4β(S*)]]-4-[[[1-[[4-[(2,6-Dichlorobenzoyl)amino]phenyl]methyl]-2-methoxy-2-oxoethyl]amino]carbonyl]-1-(1-phenylethyl)-2-azetidinecarboxylic Acid Methyl Ester ($C_{31}H_{31}Cl_2N_3O_6$)

Example 134 was prepared as described in Scheme L using the product of preparation 57 as intermediate L-1. Physical properties as follows: TLC (1:1 EtOAc/Hexanes) $R_f$=0.30; $^{13}C$ NMR ($CDCl_3$) δ 173.78, 172.76, 172.10, 162.47, 141.81, 136.70, 135.96, 132.43, 132.38, 130.88, 129.79, 128.551, 128.10, 127.58, 127.00, 120.58, 63.32, 60.06, 59.27, 52.70, 52.50, 51.44, 37.08, 25.76, 21.52; MS (+ESI, 200:1 MeOH/$HCO_2H$ solution) m/z 613.8, 611.8.

EXAMPLE 135

(Scheme L: L-5 where $R_{L-1}$ is methyl, $R_{L-2}$ is phenyl, $R_5$ is 4-[(2,6-dichlorobenzoyl)amino]phenyl and stereochemistry is [2R-[1(R*),2α,4β(S*)]]).

[2R-[1(R*),2α,4β(S*)]]-4-[[[1-Carboxy-2-[4-[(2,6-dichlorobenzoyl)amino]phenyl]-ethyl]-amino]carbonyl]-1-(1-phenylethyl)-2-azetidinecarboxylic Acid Dilithium Salt ($C_{29}H_{25}Cl_2Li_2N_3O_6$)

Example 135 was prepared from Example 134 by the procedure described in preparation 62. Physical properties as follows: $[\alpha]^{25}_D$ +76 (c 0.89, MeOH); $^{13}C$ NMR ($CD_3OD$) δ 179.44, 176.71, 175.90, 163.55, 143.81, 136.54, 136.26, 134.47, 131.90, 120.81, 129.70, 127.83, 127.34, 126.33, 119.88, 63.06, 62.11, 58.71, 55.46, 37.17, 26.76, 20.56; MS (FAB) m/z 598, 596, 592, 590, 552, 550, 546, 544, 237, 105; Anal. C, 55.12; H, 5.24; N, 6.59; Cl, 10.56; (calcd for 6.21% $H_2O$: C, 54.78; H, 4.66; N, 6.61; Cl, 11.15).

EXAMPLE 136

(Scheme L: L-4 where $R_{L-1}$ is methyl, $R_{L-2}$ is phenyl, $R_5$ is 4-[(2,6-dichlorobenzoyl)amino]phenyl and stereochemistry is [2S-[1(S*),2α,4β(R*)]]).

[2S-[1(S*),2α,4β(R*)]]-4-[[[1-[[4-[(2,6-Dichlorobenzoyl)amino]phenyl]methyl]-2-methoxy-2-oxoethyl]amino]carbonyl]-1-(1-phenylethyl)-2-azetidinecarboxylic Acid Methyl Ester ($C_{31}H_{31}Cl_2N_3O_6$)

Example 136 was prepared as described in Scheme L using the product of preparation 58 as intermediate L-1. Physical properties as follows: TLC (85:15 $CHCl_2$/acetone) $R_f$=0.54; $^{13}C$ NMR ($CDCl_3$) δ 173.44, 172.62, 171.72, 162.79, 140.46, 136.69, 136.34, 133.12, 132.79, 131.29, 130.40, 129.08, 128.52, 128.45, 128.23, 120.57, 64.15, 60.51, 60.09, 53.11, 52.59, 52.19, 37.73, 26.70, 18.75; Anal. C, 60.70; H, 5.39; N, 6.62; (calcd C, 60.79; H, 5.10; N, 6.86).

EXAMPLE 137

(Scheme L: L-5 where $R_{L-1}$ is methyl, $R_{L-2}$ is phenyl, $R_5$ is 4-[(2,6-dichlorobenzoyl)amino]phenyl and stereochemistry is [2S-[1(S*),2α,4β(R*)]]).

[2S-[1(S*),2α,4β(R*)]]-4-[[[1-Carboxy-2-[4-[(2,6-dichlorobenzoyl)amino]phenyl]ethyl]-amino]carbonyl]-1-(1-phenylethyl)-2-azetidinecarboxylic Acid ($C_{29}H_{27}Cl_2N_3O_6$)

Example 137 was prepared from Example 136 by the procedure described in preparation 62. Physical properties as follows: [α]²⁵_D +2 (c 1.00, MeOH); ¹³C NMR (CD₃OD) δ 172.31, 169.43, 167.37, 163.72, 161.39, 160.93, 136.98, 136.11, 134.40, 133.20, 131.84, 130.93, 129.42, 129.39, 128.60, 127.89, 120.11, 62.68, 61.41, 53.51, 36.35, 25.00, 16.17; MS (FAB) m/z 586, 584, 482, 480, 204, 175, 173, 106, 105; Anal. C, 53.07; H, 4.52; N, 6.15; Cl, 10.46; (calcd for 0.80 equiv TFA and 2.13% H₂O: C, 53.20; H, 4.30; N, 6.08; Cl, 10.26).

EXAMPLE 138

(Scheme L: L-4 where R_{L-1} is methyl, R_{L-2} is phenyl, R₅ is 4-[(2,6-dichlorobenzoyl)amino]phenyl and stereochemistry is [1(R),2α,4α(S)], a single diastereomer having a cis relative configuration but unknown absolute configuration at C-2 and C-4 of the azetidine.)

[1(R),2α,4α(S)]-4-[[[1-[[4-[(2,6-Dichlorobenzoyl)amino]phenyl]methyl]-2-methoxy-2-oxoethyl]amino]carbonyl]-1-(1-phenylethyl)-2-azetidinecarboxylic Acid 2-Methyl Ester (C₃₁CH₃₁Cl₂N₃O₆)

Example 138 was prepared as described in Scheme L using the product of preparation 59 as intermediate L-1. Physical properties as follows: TLC R_f=0.47 (85:15 CHCl₃/acetone): ¹³C NMR (CDCl₃) δ 173.42, 172.40, 171.74, 162.46, 140.80, 136.76, 136.03, 132.64, 132.35, 130.80, 129.82, 128.38, 128.04, 127.85, 127.69, 120.39, 66.11, 61.50, 59.78, 52.83, 52.42, 51.72, 37.12, 25.03, 20.20; MS (+ESI, 200:1 MeOH/HCO₂H solution) m/z 614.2, 612.2; Anal. C, 60.66; H, 5.18; N, 6.80; Cl, 11.42; (calcd C, 60.79; H, 5.10; N, 6.86; Cl, 11.58).

EXAMPLE 139

(Scheme L: L-5 where R_{L-1} is methyl, R_{L-2} is phenyl, R₅ is 4-[(2,6-dichlorobenzoyl)amino]phenyl and stereochemistry is [1(R),2α,4α(S)], a single diastereomer having a cis relative configuration but unknown absolute configuration at C-2 and C-4 of the azetidine).

[1(R),2α,4α(S)]-4-[[[1-Carboxy-2-[4-[(2,6-dichlorobenzoyl)amino]phenyl]ethyl]amino]-carbonyl]-1-(1-phenylethyl)-2-azetidinecarboxylic Acid (C₁₉H₂₅Cl₂N₃O₆)

Example 139 was prepared from Example 138 by the procedure described in preparation 62. Physical properties as follows: [α]²⁵_D −30 (c 0.90, MeOH); ¹³C NMR (CD₃OD) δ 172.71, 172.44, 171.81, 163.71, 138.03, 136.99, 136.15, 133.31, 131.89, 130.89, 129.45, 128.33, 128.29, 128.02, 127.86, 120.23, 65.62, 61.51, 59.60, 53.47, 36.04, 24.91, 17.68; MS (FAB) m/z 586, 584, 371, 298, 204, 177, 175, 173, 133, 105, 100; Anal. C, 55.69; H, 4.49; N, 6.55; Cl, 11.81; (calcd for 0.38 equiv TFA and 2.06% H₂O: C, 55.80; H, 4.54; N, 6.56; Cl, 11.07).

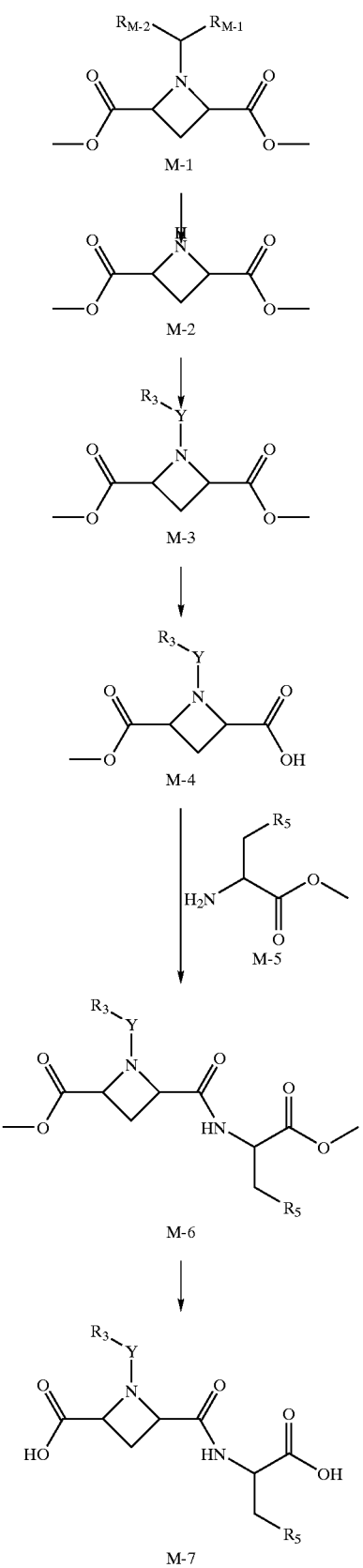

Scheme M.

141

Scheme M teaches a general method for the preparation of N-acyl azetidinedicarboxylic acid Examples M-6 and M-7, where $R_{M-1}$ is $C_{1-6}$ alkyl, $R_{M-2}$ is $C_{6-10}$ aryl, and $R_3$, $R_5$ and Y are defined as in Scheme B. Thus removal of the N-alkylaryl substituents $R_{M-1}$ and $R_{M-2}$ of M-1 gives aminodiester M-2, that is acylated to provide M-3. Partial saponification of diester M-3 gives half-acid M-4, that is coupled with reagent M-5 (as exemplified by the use of reagents A-3 and A-4 of Scheme A, and B-4 and B-5 of Scheme B) to provide Examples M-6, that are then hydrolyzed to Examples M-7 of this invention.

PREPARATION 63

(Scheme M: M-2 where stereochemistry is (2R-trans)).

(2R-trans)-2,4-Azetidinedicarboxylic Acid Dimethyl Diester ($C_7H_{11}NO_4$)

To an $N_2$-purged solution of freshly chromatographed Preparation M-1 (Scheme M where $R_{M-1}$ is methyl, $R_{M-2}$ is phenyl and stereochemistry is [2R-[1(R*),2α,4β]] prepared as described by preparation 57) (656 mg, 2.37 mmol) in MeOH (20 mL) is added 20% $Pd(OH)_2$/C (120 mg), and this mixture is hydrogenated for 19 h under an H, atmosphere (approximately 42 psi pressure). The mixture is filtered and concentrated to give the title compound as a colorless oil: TLC (4:1 Hexanes/EtOAc) $R_f$=0.04; $^1H$ NMR (CDCl$_3$) δ 4.33 (2H), 3.77 (6H), 3.38 (1H), 2.71 (2H); MS (+ESI) m/z 174.2.

PREPARATION 64

(Scheme M: M-3 where $R_3$ is ethyl, Y is $CO_2$—, and the stereochemistry is (2R-trans)).

(2R-trans)-1,2,4-Azetidinetricarboxylic Acid 1-Ethyl-2,4-dimethyl Triester ($C_{10}H_{15}NO_6$)

To a mixture of freshly prepared amine M-2 (Scheme M where stereochemistry is (2R-trans)) (14 mmol) in $CH_2Cl_2$ (20 mL) under $N_2$ at 0° C. is added $Et_3N$ (3.0 mL, 22 mmol), followed by the dropwise addition of ClCO$_2$Et (1.5 mL, 18 mmol). After 22 h the reaction is quenched with saturated NaHCO$_3$, diluted with $H_2O$, and extracted with EtOAc. The combined organic extracts are dried, filtered and concentrated to give 2.79 g of the carbamate, that is purified by silica flash chromatography: TLC (4:1 Hexanes/EtOAc) $R_f$=0.17; $[α]^{25}_D$ +183 (c 0.83, MeOH); $^1H$ NMR (CDCl$_3$) δ 4.77 (2H), 4.15 (1H), 4.10 (1H), 3.80 (6H), 2.58 (2H), 1.23 (3H); $^{13}C$ NMR (CD$_3$OD) δ 1 73.11, 173.05, 157.47, 63.30. 61.00, 60.18, 53.41, 26.43, 15.27; MS (EI) m/z 245, 186, 172, 142, 114; Anal. C, 48.90; H, 6.21; N, 5.73; (calcd C, 48.98; H, 6.16; N, 5.71).

PREPARATION 65

(Scheme M: M-4 where $R_3$ is ethyl, Y is $CO_2$—, and the stereochemistry is (2R-trans)).

(2R-trans)-1,2,4-Azetidinetricarboxylic Acid 1-Ethyl-2-Methyl Diester ($C_9H_{13}NO_6$)

A mixture of M-3 (Scheme M, where $R_3$ is ethyl, Y is $CO_2$—, and the stereochemistry is (2R-trans)) (1.68 g, 6.85 mmol) and LiOH (7.00 mmol) in 1:1 MeOH/H$_2$O (40 mL) is stirred at rt for 45 h, and then is concentrated. The residue is dissolved in half-saturated NaHCO$_3$, and the solution is extracted with Et$_2$O. The Et$_2$O solution is discarded. The aqueous solution is adjusted with concentrated HCl to pH 4,

142 and is concentrated to a yellow solid. This solid is triturated with CHCl$_3$. The CHCl$_3$ solution is filtered and concentrated to give, as a light brown oil, the title compound: TLC (600:400:1 Hexanes/Acetone/HCO$_2$H) $R_f$=0.21–0.45; $^1H$ NMR (CDCl$_3$) δ 4.87 (1H), 4.77–4.68 (1H), 4.64–4.50 (1H), 4.18–3.97 (2H), 3.76 (3H), 2.52–2.33 (2H), 1.26–1.13 (3H); MS (–ESI, MeOH solution) m/z 230.1. This material is used without purification.

PREPARATION 66 AND EXAMPLE 140

(Scheme M: M-6 where $R_3$ is ethyl, $R_5$ is 4-[(2,6-dichlorobenzoyl)amino]phenyl, Y is $CO_2$—, and the stereochemistry is [2R-(2α,4β(S*)]).

[2R-(2α,4β(S*)]-4-[[[1-[[4-[(2,6-Dichlorobenzoyl)amino]phenyl]methyl]-2-methoxy-2-oxoethyl]amino]carbonyl]-1,2-azetidinedicarboxylic Acid 1-Ethyl-2-methyl Diester ($C_{26}H_{27}Cl_2N_3O_8$)

To a mixture of Preparation M-4 (1.08 g, 4.67 mmol) and HOBt+H$_2$O (0.63 g, 4.7 mmol) in CH$_2$Cl$_2$ (10 mL) at 0° C. is added a solution of EDC (1.04 g, 5.42 mmol) in CH$_2$Cl$_2$ (15 mL). This mixture is stirred at 0° C. for 30 min. It is then treated with M-5 (Scheme M where $R_5$ is 4-[(2,6-dichlorobenzoyl)amino]phenyl and stereochemistry is (s)) (1.88 g, 4.66 mmol) and N-methylmorpholine (0.52 mL, 4.7 mmol). The resulting solution was stirred at 0° C. for 2 h and at rt for 2 h. The reaction mixture is diluted with 10% KHSO$_4$ and extracted with CH$_2$Cl$_2$. The combined CH$_2$Cl$_2$ extracts are washed with satd NaHCO$_3$ and brine, and are combined, dried, filtered and concentrated to give a yellow foam (2.58 g), that is purified by flash chromatography to give, as a white solid, the title compound: mp 97–99° C.; TLC (9:1 CHCl$_2$/acetone) $R_f$=0.30; $[α]^{25}_D$ +79 (c 1.02, MeOH); UV (MeOH) $\lambda_{max}$ 225 (ε 12200; sh), 251 (17500); $^{13}C$ NMR (CD$_3$OD) δ 171.50, 171.30, 171.08, 163.67, 156.23, 155.96, 136.92, 136.19, 133.21, 133.03, 131.87, 130.93, 129.64, 129.44, 127.92, 119.97, 61.61, 60.56, 59.82, 59.11, 58.41, 53.45, 51.58, 51.52, 36.57, 36.29, 24.91, 13.43 (22 lines expected: 28 lines observed); MS (FAB) m/z 580.1260 (calcd for [M+H]$^+$, 580.1253); Anal. C, 51.95; H, 4.56; N, 6.89; Cl, 15.18; (calcd for 0.61% H$_2$O: C, 53.48; H, 4.73; N, 7.20; Cl, 12.14).

PREPARATION 67 AND EXAMPLE 141

(Scheme M: M-7 where $R_3$ is ethyl, $R_5$ is 4-[(2,6-dichlorobenzoyl)amino]phenyl, Y is $CO_2$—, and the stereochemistry is [2R-(2α,4β(S*)]).

[2R-(2α,4β(S*)]-4-[[[1-Carboxy-2-[4-[(2,6-dichlorobenzoyl)amino]phenyl]ethyl]-amino]-carbonyl]-1,2-azetidinedicarboxylic Acid 1-Ethyl Ester ($C_{24}H_{23}Cl_2N_3O_8$)

To a suspension of M-6 (Example 140, Scheme M where $R_3$ is ethyl, $R_5$ is 4-[(2,6-dichlorobenzoyl)amino]phenyl, Y is $CO_2$—, and the stereochemistry is [2R-(2α,4β)]) (0.201 g, 0.347 mmol) in MeOH (5 mL) is added H$_2$O (4.3 mL) and 1.00 M LiOH (0.70 mL). The reaction mixture is stirred at rt for 23 h. It is concentrated in vacuo. The aqueous concentrate is diluted with H$_2$O, and the solution is adjusted to approximately pH 12 with 1N NaOH. It is extracted with Et$_2$O, and the Et$_2$O extract is discarded. The aqueous solution is adjusted to approximately pH 3 with 1N HCl. It is extracted repeatedly with Et$_2$O. The combined Et$_2$O extracts were dried, filtered and concentrated to give, as a white solid, the title compound: TLC (500:500:1 MeOH/CH$_2$Cl$_2$/

HCO$_2$H) R$_f$=0.20; $^1$H NMR (CD$_3$OD) δ 7.59 (2H), 7.50–7.37 (3H), 7.23 (2H), 4.78–4.64 (2H), 4.61–4.51 (1H), 4.22–3.89 (2H), 3.30–3.185 (1H), 3.07–2.93 (1H), 2.42–2.23 (2H), 1.21 and 1.11 (3H total); MS (FAB) m/z 552.0946 (calcd for [M+H]$^+$ 552.0940); Anal. C, 50.48; H, 4.61; N, 6.64; Cl, 12.95; (calcd for 1.60% H$_2$O: C, 51.35; H, 4.31; N, 7.49; Cl, 12.63).

Scheme N.

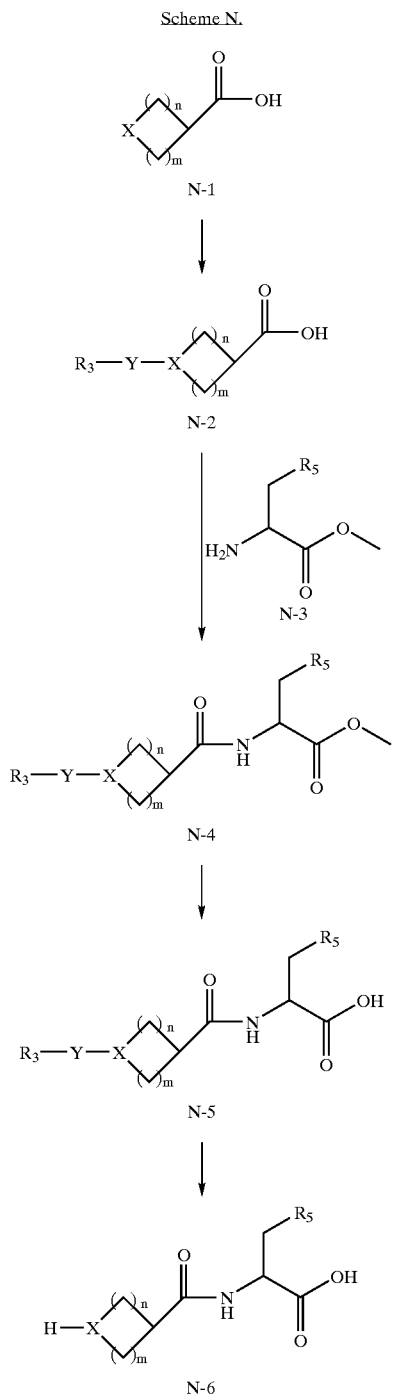

Scheme N teaches a general method for the preparation of N-acyl azetidinecarboxylic acid Examples N-5 where n equals 0, 1 or 2, m equals 0, 1 or 2, (m+n) equals 2, X is nitrogen and R$_3$, R$_5$ and Y are defined as in Scheme B, and azetidine-carboxylic acid Examples N-6 where n equals 0, 1 or 2, m equals 0, 1 or 2, (m+n) equals 2, X is nitrogen and R$_5$ is defined as in Scheme B. Thus acylation of aminoacid N-1 gives N-acylacid N-2, that is coupled with reagent N-3 (as exemplified by the use of reagents A-3 and A-4 of Scheme A, and B-4 and B-5 of Scheme B) to provide Examples N-4. Ester hydrolysis of N-4 provides Examples N-5. N-deacylation of Examples N-5 provides Examples N-6.

PREPARATION 68

(Scheme N: N-2 where n is 2, m is 0, X is N, Y is —CO$_2$—, R$_5$ is (1,1-dimethyl)ethyl, and the stereochemistry is (S)).

(S)-1,2-Azetidinedicarboxylic Acid 1-(1,1-Dimethylethyl)ester (C$_9$H$_{15}$NO$_4$)

To a mixture of (S)-(-)-2-azetidinecarboxylic acid (110 mg, 1.1 mmol), Boc$_2$O (290 mg, 1.30 mmol), and DMAP (0.017 g, 0.14 mmol) in 4:1 DMF/H$_2$O (10 mL) is added Et$_3$N (0.30 mL, 2.2 mmol). The reaction mixture is stirred at rt for 68 h, and then is concentrated. The concentrate is diluted with EtOAc, and the EtOAc solution is washed with cold 10% KHSO$_4$. The combined organic extracts are dried, filtered and concentrated to give the title compound as a colorless oil: TLC (750:250:1 Hexanes/acetone/HCO$_2$H) R$_f$=0.26; $^1$H NMR (CD$_3$OD) δ 4.97 (1H), 4.57 (1H), 3.98 (1H), 3.87 (1H), 2.57 (H), 2.13 (1H), 1.42 (9H); MS (-ESI) m/z 200.3.

PREPARATION 69 AND EXAMPLE 142

(Scheme N: N-4 where n is 2, in is 0, X is N, Y is —CO$_2$—, R$_3$ is (1,1-dimethyl)ethyl, R$_5$ is 4-[(2,6-dichlorobenzoyl)amino]phenyl and stereochemistry is (S)).

[2S-(R*,R*)]-2-[[[1-[4-[(2,6-Dichlorobenzoyl)amino]phenyl methyl]-2-methoxy-2-oxoethyl]amino]carbonyl]-1-azetidinecarboxylic Acid 1-(1,1-Dimethyl)ethyl Ester (C$_{26}$H$_{29}$Cl$_2$N$_3$O$_6$)

To a mixture of acid N-2 (Scheme N, where n is 2, m is 0, X is N, Y is —CO$_2$—, R$_3$ is (1,1-dimethyl)ethyl, and the stereochemistry is (S)) (1.04 g; 5.17 mmol) and HOBt.H$_2$O (0.71 g, 5.3 mmol) in CH$_2$Cl$_2$ (10 mL) at 0° C. is added a mixture of EDCHCl (1.00 g, 5.22 mmol) in CH$_2$Cl$_2$ (20 mL). The reaction mixture is stirred at 0° C. for 30 min, and then N-3 (Scheme N where R$_5$ is 4-[(2,6-dichlorobenzoyl)amino]phenyl and stereochemistry is (S)) (2.10 g, 5.20 mmol) and N-methylmorpholine (0.60 mL, 5.46 mmol) are added. The reaction mixture is stirred at 0° C. for 30 min and at rt for 3 h. The reaction mixture is partitioned between 10% KHSO$_4$ and CH$_2$Cl$_2$. The aqueous phase is extracted twice more with CH$_2$Cl$_2$. The combined organic extracts are washed with saturated NaHCO$_3$ and brine, and then are dried, filtered and concentrated to a yellow oil (2.54 g) that is purified by silica flash chromatography to give the title compound as a white foam: mp 106–108° C.; TLC (1:1Hexanes/EtOAc); R$_f$=0.21; [α]$^{25}_D$ –38 (c 1.01, MeOH); $^{13}$C NMR (CD$_3$OD) δ 172.37, 171.58, 163.64, 156.68, 136.98, 136.22, 133.11, 131.87, 130.90, 129.49, 127.91, 120.00, 80.42, 61.87, 53.31, 51.45, 36.40, 27.16, 20.08; MS (EI) m/z 551, 549, 478, 476, 451, 449, 396, 394, 351, 349, 280, 278, 175, 173; Anal. C, 56.33; H, 5.48; N, 7.23; Cl, 12.43; (calcd for 0.52% H$_2$O: C, 56.44; H, 5.34; N, 7.59; Cl, 12.82).

PREPARATION 70 AND EXAMPLE 143

(Scheme N: N-5 where n is 2, m is 0, X is N, Y is —CO$_2$—, R$_3$ is (1,1-dimethyl)ethyl, R$_5$ is 4-[(2,6-dichlorobenzoyl)amino]phenyl and stereochemistry is [2S-(R*,R*)]).

145

[2S-(R*,R*)]-2-[[[1-Carboxy-2-[4-[(2,6-dichlorobenzoyl)amino]phenyl]ethyl]amino]-carbonyl]-1-azetidinecarboxylic Acid 1-(1,1-Dimethylethyl)ester ($C_{25}H_{27}Cl_2N_3O_6$)

A solution of N-4 (Scheme N, where n is 2, in is 0, X is N, Y is —$CO_2$—, $R_3$ is (1,1-dimethyl)ethyl, $R_5$ is 4-[(2,6-dichlorobenzoyl)amino]phenyl and stereochemistry is (S)) (507 mg, 0.92 mmol) and LiOH (1.25 mmol) in 1:1 MeOH/$H_2O$ (10 mL) is stirred at rt for 18 h. The reaction mixture is diluted with cold 10% $KHSO_4$ and extracted with $CH_2Cl_2$. The organic extracts are dried, filtered and concentrated to a white foam (498 mg), that is purified by silica flash chromatography to give the title compound: TLC (750:250:1 hexanes/acetone/$HCO_2H$) $R_f$=0.12; $[\alpha]^{25}_D$ −27 (c 0.94, $CHCl_3$); $^{13}C$ NMR ($CD_3OD$) δ 210.05, 172.70, 172.27, 163.63, 156.75, 136.89, 136.22, 133.36, 131.88, 130.90, 129.56, 127.91, 119.95, 80.47, 61.93, 53.18, 36.47, 27.15, 20.09; MS (−ESI) m/z 533.8; MS (EI) m/z 435, 419, 417, 401, 399, 373, 371, 280, 278, 175, 173, 147, 145; Anal. C, 55.23; H, 5.25; N, 7.42; Cl, 12.87; (calcd for 1.10% $H_2O$: C, 55.36; H, 5.14; N, 7.75; Cl, 13.07).

PREPARATION 71 AND EXAMPLE 144

(Scheme N: N-6 where n is 2, m is 0, X is N, $R_5$ is 4-[(2,6-dichlorobenzoyl)amino]phenyl and stereochemistry is (2S),L).

N-[[(2S)-2-Azetidinyl]carbonyl]-4-[(2,6-dichlorobenzoyl)amino]-L-phenylalanine Trifluoroacetic acid Salt ($C_{20}H_{19}Cl_2N_3O_6 \cdot C_2HF_3O_2$)

A solution of N-5 (Scheme N, where n is 2, m is 0, X is N, Y is —$CO_2$—, $R_3$ is (1,1-dimethyl)ethyl, $R_5$ is 4-[(2,6-dichlorobenzoyl)amino]phenyl and stereochemistry is [2S-(R*,R*)]) (900 mg; 1.7 mmol) in 1:1 TFA/$CH_2Cl_2$ (5 mL) is stirred at rt for 1.5 h, and is concentrated. The residue is thrice diluted with $CHCl_3$ and re-concentrated. This residue is dissolved in MeOH and concentrated to a white foam, that is dissolved in 1:1 MeOH/$H_2O$ and then concentrated to remove most of the MeOH. The solution is frozen and lyophilized to give the product as a white powder: $[\alpha]^{25}_D$ −6 (c 0.72, MeOH); $^{13}C$ NMR ($CD_3OD$) δ 172.62, 167.54, 163.78, 136.82, 136.13, 133.43, 131.84, 130.97, 129.38, 127.93, 120.15, 58.38, 54.03, 43.73, 36.27, 23.33; MS (+ESI) m/z 436.0; MS (FAB) m/z 438, 436; Anal. C, 46.77; H, 3.75; N, 7.24; Cl, 12.44; (calcd for a 1:I TFA salt with 1.68% $H_2O$: C, 47.21; H, 3.79; N, 7.51; Cl, 12.67).

EXAMPLE 145

(Scheme N: N-4 where n is 1, in is 1, X is N, $R_3$ is (1,1-dimethyl)ethyl, $R_5$ is 4-[(2,6-dichlorobenzoyl)amino]phenyl, Y is $CO_2$— and the stereochemistry is (S)).

[S]-3-[[[1-[[4-[(2,6-Dichlorobenzoyl)amino]phenyl]methyl]-2-methoxy-2-oxoethyl]amino]-carbonyl]-1-azetidinecarboxylic Acid 1-(1,1-Dimethyl)ethyl Ester ($C_{26}H_{29}Cl_2N_3O_6$)

Example 145 was prepared as described in Scheme N from 3-azetidinecarboxylic acid. Physical properties as follows: TLC (1:1 EtOAc/hexanes) $R_f$=0.22; $[\alpha]^{25}D$ +18 (c 0.92, MeOH); $^{13}C$ NMR ($CD_3OD$) δ 172.92, 171.91, 163.68, 156.55, 136.87, 136.20, 133.27, 131.89, 130.91, 129.36, 127.90, 120.04, 79.80, 53.85, 51.45, 36.43, 32.26, 27.24; MS (EI) m/z 469, 467, 451, 359, 351, 349, 280, 278, 175, 173, 57; Anal. C, 56.82; H, 5.39; N, 7.52; Cl, 12.81; (calcd for 0.06% $H_2O$: C, 56.70; H, 5.31; N, 7.63; Cl, 12.87).

146

EXAMPLE 146

(Scheme N: N-5 where n is 1, In is 1, X is N, $R_3$ is (1,1-dimethyl)ethyl, $R_5$ is 4-[(2,6-dichlorobenzoyl)amino]phenyl, Y is $CO_2$— and the stereochemistry is (S)).

(S)-3-[[[1-Carboxy-2-[4-[(2,6-dichlorobenzoyl)amino]phenyl]ethyl]amino]carbonyl]]-1-azetidinecarboxylic Acid 1-(1,1-Dimethylethyl)ester ($C_{25}H_{27}Cl_2N_3O_6$)

Example 146 was prepared from example 145 by the procedure described in preparation 70. Physical properties as follows: TLC (600:400:1 Hexanes/Acetone/$HCO_2H$) $R_f$=0.17; $[\alpha]^{75}_D$ +33 (c 0.92, MeOH): $^{13}C$ NMR ($CD_3OD$) δ 173.05, 172.89, 16.3, 69, 156.56, 136.78, 136.19, 133.59, 131.89, 130.91, 129.40, 127.90, 120.00, 79.78, 53.67, 51.72, 36.47, 32.31, 27.24; MS (−ESI) m/z 533.9; MS (FAB) m/z 538, 536, 438, 436, 337, 335, 280, 278, 175, 173.57; Anal. C, 55.03; H, 5.21; N, 7.52; Cl, 12.81; (calcd for 1.22% $H_2O$: C, 55.30; H, 5.15; N, 7.74; Cl, 13.06).

EXAMPLE 147

(Scheme N: N-6 where n is 1, m is 1, X is NH, $R_5$ is 4-[(2,6-dichlorobenzoyl)amino]phenyl, and the stereochemistry is (L)).

N-[[3-Azetidinyl]carbonyl]-4-[(2,6-dichlorobenzoyl)amino]-L-phenylalanine, Trifluoroacetic Acid Salt ($C_{20}H_{19}Cl_2N_3O_6 \cdot C_2HF_3O_2$)

Example 147 was prepared from Example 146 by the procedure described in preparation 71. Physical properties as follows: $[\alpha]^{25}_D$ +32 (c 0.87, MeOH); $^{13}C$ NMR ($CD_3OD$) δ 173.32, 170.57, 163.80, 136.70, 136.13, 133.76, 131.84, 130.97, 129.45, 127.93, 120.17, 54.03, 36.59, 35.32); MS (FAB) m/z 438, 436, 391, 331, 175, 173, 101, 55; Anal. C, 46.85; H, 4.07; N, 7.33; Cl, 12.39; (calcd for a 1:1 TFA salt with 3.34% $H_2O$: C, 46.41; H, 3.92; N, 7.38; Cl, 12.45).

EXAMPLE 148

[S-(R*,R*)]-4-[[[1-[[4-[(2,6-Dichlorobenzoyl)amino]phenyl]methyl]-2-methoxy-2-oxoethyl]amino]carbonyl]-3-thiazolidinecarboxylic Acid 3-(2-Pyridinylmethyl)ester (Scheme A, A-7: where $R_{A-1}$ and $R_{A-2}$ are the same and equal to proton, $R_3$ is 2-pyridinylmethyl, Y is $CO_2$—, $R_5$ is 4-[(2,6-dichlorobenzoyl)amino]phenyl and stereochemistry is (S,S)).

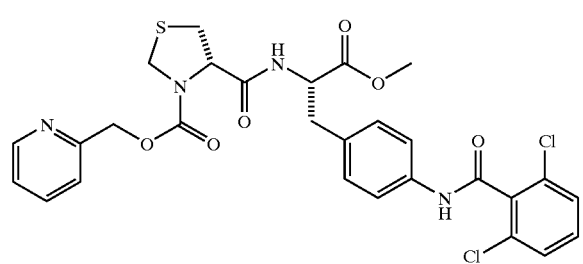

Example 148 was prepared as described in Scheme A from D-cysteine using 2-pyridinemethanol to form the requisite carbamate. Physical data as follows: $^1H$ NMR (300 $MH_2$, $CDCl_3$) δ 8.37 (1H), 7.70 (1H), 7.51 (2H), 7.27 (6H), 7.08 (2H), 6.92 (1H), 5.24 (2H), 4.77 (3H), 4.40 (1H), 3.74 (3H), 3.37 (1H), 3.15 (3H); $^{13}C$ NMR (75 MHz, $CDCl_3$) δ

171.4, 162.5, 155.2, 149.0, 137.1, 136.5, 136.0, 132.4, 130.7, 129.9, 128.0, 123.1, 120.6, 63.0, 53.4, 52.5, 36.8; MS (ESI+) for $C_{28}H_{26}Cl_2N_4O_6S$ m/z 616.8 (M+H)$^+$; HRMS (EI) calcd for $C_{28}H_{26}Cl_2N_4O_6S$ 616.0950, found 616.0946, Anal. Calcd for $C_{28}H_{26}Cl_2N_4O_6S$: C, 54.46; H, 4.24; N, 9.07. Found: C, 54.61; H, 4.32; N, 8.97.

EXAMPLE 149

[S-(R*,R*)]-4-[[[-Carboxy-2-[4-[(2,6-dichlorobenzoyl)amino]phenyl]ethyl]amino]carbonyl]-3-thiazolidinecarboxylic Acid 3-(2-pyridinylmethyl)ester (Scheme A, A-8: where $R_{A-1}$ and $R_{A-2}$ are the same and equal to proton, $R_3$ is 2-pyridinylmethyl, Y is $CO_2$—, $R_5$ is 4-[(2,6-dichlorobenzoyl)amino]phenyl and stereochemistry is (S,S)).

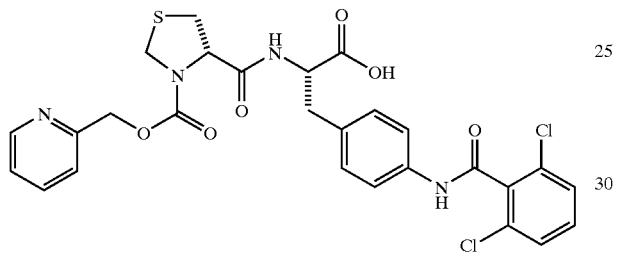

Example 149 was prepared from example 148 by the procedure described in preparation 6. Physical data as follows: IR (mull) 1713, 1666, 1605, 1576, 1561, 1539, 1515, 1442, 1431, 1413, 1351, 1325, 1271, 1194, 766 cm$^{-1}$; $^1$H NMR (300 MHz, CD$_3$OD) δ 8.80 (1H), 8.56 (1H), 7.99 (2H), 7.58 (2H), 7.45 (3H), 7.25 (2H), 5.43 (2H), 4.60 (3H), 3.30 (3H), 2.93 (2H); $^{13}$C NMR (75 MHz, CD$_3$OD) δ 172.7, 171.5, 163.7, 152.8, 151.3, 146.6, 141.9, 136.8, 136.1, 113.6, 131.8, 130.9, 129.6, 127.9, 126.1, 125.4, 120.1, 63.2, 62.8, 59.4, 53.5, 36.4, 35.1; MS (ESI+) for $C_{27}H_{24}Cl_2N_4O_6S$ m/z 602.9 (M+H)$^+$; MS (FAB) m/z (rel. intensity) 603 (MH+, 59), 605 (43), 603 (59), 154 (51), 139 (99), 137 (46), 136 (47), 123 (67), 105 (5 8), 103)(61), 93 (38); HRMS (FAB) calcd for $C_{27}H_{24}Cl_2N_4O_6S+H_1$ 603.0872, found 603.0876; Anal. Calcd for $C_{27}H_{24}Cl_2N_4O_6S\cdot0.3H_2O$: C, 53.26; H, 4.07; N, 9.20. Found: C, 52.97; H, 4.23; N, 9.04.

EXAMPLE 150

[S-(R*,R*)]-4-[[[1-[[4-[(2,6-Dichlorobenzoyl)amino]phenyl]methyl]-2-methoxy-2-oxoethyl]amino]carbonyl]-δ-oxo-3-thiazoidinepentanoic Acid (Scheme A, A-7: where $R_{A-1}$ and $R_{A-2}$ are the same and equal to proton, $R_3$ is $(CH_2)_3CO_2H$, Y is CO—, $R_5$ is 4-[(2,6-dichlorobenzoyl)amino]phenyl and stereochemistry is (S,S)).

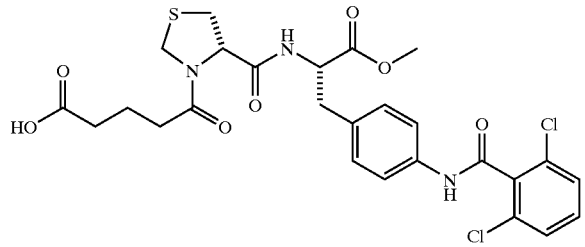

Example 150 was prepared as described in Scheme A from D-cysteine using glutaric anhydride to form the requisite amide. Physical data as follows: IR (mull) 3077, 3053, 3040, 1738, 1728, 1696, 1682, 1641, 1557, 1437, 1430, 1414, 1307, 1232, 1209 cm$^{-1}$; $^1$H NMR (300 MHz, CDCl$_3$) δ 7.56 (2H), 7.30 (3H), 7.08 (2H), 4.96 (1H), 4.62 (3H), 3.72 (3H), 3.28 (4H), 2.37 (4H), 1.90 (2H); $^{13}$C NMR (75 MHz, CDCl$_3$) δ 179.5, 176.0, 175.6, 173.6, 167.2, 140.6, 140.0, 136.1, 134.5, 133.7, 133.4, 131.8, 124.4, 66.7, 65.9, 57.2, 56.3, 40.3, 39.3, 37.3, 36.7, 36.2, 33.5, 23.6; MS (FAB) m/z (rel. intensity) 596 (MH$^+$, 90), 598 (63), 597 (40), 596 (90), 341 (25), 263 (25), 230 (32), 225 (31), 193 (31), 141 (99), 88 (36); HRMS (FAB) calcd for $C_{26}H_{27}Cl_2N_3O_7S+H_1$ 596.1025, found 596.1036, Anal. Calcd for $C_{26}H_{27}Cl_2N_3O_7S\cdot0.3H_2O$: C, 51.88; H, 4.62; N, 6.98. Found: C, 51.69; H, 4.69; N, 6.59.

EXAMPLE 151

[S-(R*,R*)]-4-[[[1-Carboxy-2-[4-[(2,6-dichlorobenzoyl)amino]phenyl]ethyl]amino]carbonyl]-δ-oxo-3-thiazoidinepentanoic Acid Methyl Ester (Scheme A, A-8: where $R_{A-1}$ and $R_{A-2}$ are the same and equal to proton, $R_3$ is $(CH_2)_3CO_2CH_3$, Y is CO—, $R_5$ is 4-[(2,6-dichlorobenzoyl)amino]phenyl and stereochemistry is (S,S)).

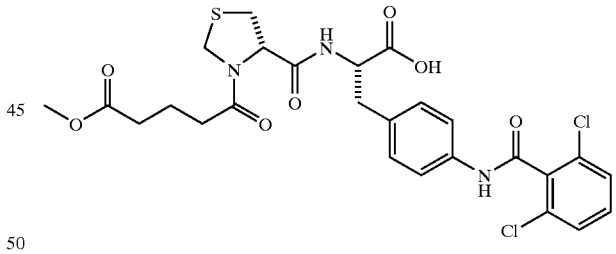

Example 151 was prepared as described in Scheme A from D-cysteine using methyl glutaryl chloride to form the requisite amide. Physical data as follows: IR (mull) 3287, 3196, 1724, 1662, 1607, 1562, 1540, 1516, 1431, 1414, 1326, 1268, 1217, 1195, 799 cm$^{-1}$; MS (FAB) m/z (rel. intensity) 596 (MH$^+$, 72), 598 (52), 596 (72), 229 (37), 193 (37), 167 (34), 133 (44), 129 (69), 121 (48), 103 (83), 89 (99); $^1$H NMR (300 MHz, CDCl$_3$) δ 7.56 (2H), 7.43 (3H), 7.23 (2H), 4.53 (3H), 3.63 (3H), 2.96 (4H), 2.45 (3H), 2.24 (2H), 1.93 (2H); $^{13}$C NMR (75 MHz, CDCl$_3$) δ 174.0, 172.1, 169.9, 162.9, 162.8, 136.1, 132.2, 130.6, 130.0, 127.9, 120.3, 62.9, 54.5, 51.6, 49.8, 36.8, 33.5, 33.0, 32.7, 29.6, 19.6; HRMS (FAB) calcd for $C_{26}H_{27}Cl_2N_3O_7S+H_1$ 596.1025, found 596.1047, MS (FAB) m/z (rel. intensity) 596 (MH$^+$, 72), 598 (52), 596 (72), 229 (37), 167 (34), 133 (44), 129 (69), 121 (48), 103 (83), 89 (99).

EXAMPLE 152

[S-(R*,R*)]-4-[[[1-Carboxy-2-[4-[(2,6-dichlorophenyl)methoxy]phenyl]ethyl]amino]carbonyl]-3-thiazolidinecarboxylic Acid 3-[2-(1-Piperidinyl)ethyl]ester (Scheme A, A-8: where $R_{A-1}$ and $R_{A-2}$ are the same and equal to proton, $R_3$ is 2-(1-piperidinyl)ethyl, Y is $CO_2$—, $R_5$ is 4-[(2,6-dichlorophenyl)methoxy]phenyl and stereochemistry is (S,S)).

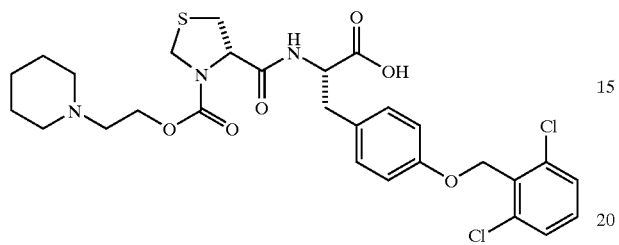

Example 152 was prepared from example 5 by the procedure described in preparation 6. Physical data as follows: IR (mull) 3254, 2654, 1711, 1565, 1547, 1512, 1438, 1344, 1300, 1240, 1196, 1179, 1119, 1014, 767 cm$^{-1}$; $^1$H NMR (300 MHz, CD$_3$OD) δ 7.45 (2H), 7.36 (1H), 7.19 (2H), 6.97 (2H), 5.26 (2H), 4.50 (5H), 3.60 (11H), 1.83 (6H); MS (ESI+) for $C_{38}H_{33}Cl_2N_3O_6S$ m/z 610.0 (M+H)$^+$; Anal. Calcd for $C_{38}H_{33}Cl_2N_3O_6S \cdot 1.5H_2O \cdot HCl$: C, 49.90; H, 5.53; N, 6.24; Cl, 15.78. Found: C, 49.86; H, 5.43; N, 6.29; Cl, 15.65. % Water (KF): 3.99.

EXAMPLE 153

[S-(R*,R*)]-4-[[[1-Carboxy-2-[4-[(2,6-dichlorophenyl)methoxy]phenyl]ethyl]amino]-carbonyl]-N-methyl-N-[2-(2-pyridinyl)ethyl]-3-thiazolidinecarboxamide (Scheme A, A-8: where $R_{A-1}$ and $R_{A-2}$ are the same and equal to proton, $R_3$ is 2-(2-pyridyl)ethyl, Y is CON(CH$_3$)—, $R_5$ is 4-[(2,6-dichlorophenyl)methoxy]phenyl and stereochemistry is (S,S)).

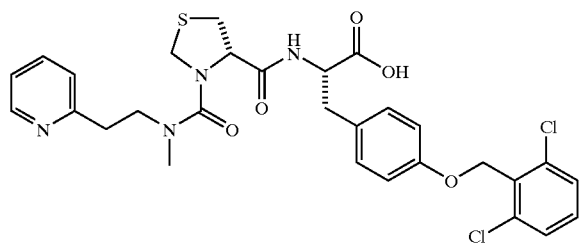

Example 153 was prepared as described in Scheme A using 2-(2-methylaminoethyl)pyridine to form the requisite urea and hydrolysis according to the procedure described in preparation 6. Physical data as follows: mp 80° C. (softens), 125° C. IR (mull) 1661, 1611, 1585, 1565, 1511, 1489, 1439, 1394, 1300, 1240, 1196, 1179, 1017, 779, 768 cm$^{-1}$; $^1$H NMR (300 MHz, CD$_3$OD) δ 8.44 (1H), 7.75 (1H), 7.35 (5H), 7.12 (2H), 6.93 (2H), 5.22 (2H), 4.83 (1H), 4.65 (1H), 4.32 (2H), 3.77 (1H), 3.45 (1H), 3.20 (1H), 3.00 (5H), 2.84 (3H); $^{13}$C NMR (75 MHz, CD$_3$OD) δ 173.0, 170.8, 162.4, 158.4, 157.9, 147.9, 138.0, 136.6, 132.2, 130.6, 130.1, 129.3, 128.3, 124.2, 122.0, 114.5, 64.8, 64.7, 53.3, 52.5, 49.7, 35.7, 34.8, 32.8; MS (ESI+) for $C_{29}H_{30}Cl_2N_4O_5S$ m/z 617.0 (M+H)$^+$; Anal. Calcd for $C_{29}H_{30}Cl_2N_4O_5S$: C, 56.40; H, 4.90; N, 9.07. Found: C, 56.31; H, 5.07; N, 8.98.

PREPARATION 72 AND EXAMPLE 154

[S-(R*,R*) 4-[[[1-[4-[(2,6-Dichlorobenzoyl)amino]phenyl]methyl]-2-[(4-pyridinyl)methoxy]-2-oxoethyl]amino]carbonyl]-3-thiazolidinecarboxylic Acid 3-Ethyl Ester

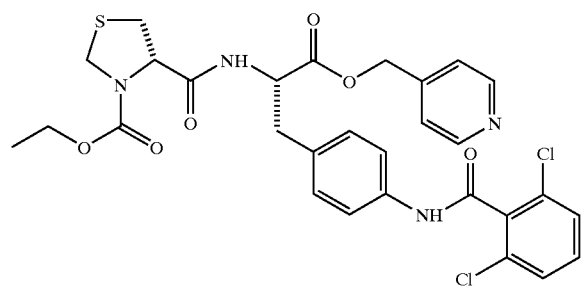

To a solution of Example 12 (Scheme A, A-8: where $R_{A-1}$ and $R_{A-2}$ are the same and equal to H, $R_3$ is ethyl, Y is $CO_2$, $R_5$ is 4-[(2,6-dichlorobenzoyl)amino]phenyl and stereochemistry is (S,S)) (400 mg, 0.74 mmol) in dimethylformamide (4 mL) was added tetramethylguanidine (204 µL, 1.63 mmol) followed by 4-picolyl chloride (138 mg, 0.81 mmol). The solution was heated to 65° C. for 3 h and volatiles removed in vacuo. Purification of the residue by flash chromatography using methylene chloride/methanol (2%) as eluant afforded the title compound (320 mg) as an amorphous solid: IR (mull) 3275, 1748, 1677, 1608, 1561, 1539, 1515, 1431, 1415, 1344, 1325, 1271, 1222, 1194, 799 cm$^{-1}$; $^1$H NMR (300 MHz, CDCl$_3$) δ 8.87 (1H), 8.48 (2H), 7.50 (2H), 7.25 (3H), 7.10 (2H), 6.93 (2H), 5.08 (2H), 4.79 (2H), 4.61 (1H), 4.28 (1H), 4.13 (2H), 3.16 (4H), 1.21 (3H); $^{13}$C NMR (75 MHz, CDCl$_3$) δ 174.6, 170.7, 170.6, 162.6, 149.2, 144.5, 136.9, 136.0, 132.3, 131.7, 130.7, 129.8, 128.0, 122.5, 120.3, 65.0, 63.0, 62.7, 53.3, 37.3, 20.9, 14.5; MS (ESI+) for $C_{29}H_{28}Cl_2N_4O_6S$ m/z 630.8 (M+H)$^+$; Anal. Calcd for $C_{29}H_{28}Cl_2N_4O_6S$: C, 55.15; H, 4.47; N, 8.87. Found: C, 54.85; H, 4.58; N, 8.74. Anal. Calcd for $C_{29}H_{28}Cl_2N_4O_6S$: C, 55.15; H, 4.47; N, 8.87; Cl, 11.23; S, 5.08. Found: C, 54.85; H, 4.58; N, 8.74.

PREPARATION 73 AND EXAMPLE 155

[S-(R*,R*)]-3-[[[1-Carboxy-2-[4-[(2,6-dichlorophenyl)methoxy]phenyl]ethyl]amino]carbonyl]-8-methyl-1-thia-4,8-diazaspiro[4.5]decane-4-carboxylic Acid 4-Ethyl Ester (Scheme B, B-7: where $R_{B-1}$ and $R_{B-2}$ are the same and equal to H, $R_{B-3}$ and $R_{B-4}$ together form a cyclic ring of 6 atoms of the formula —CH$_2$CH$_2$N(CH$_3$)CH$_2$CH$_2$—, Y is $CO_2$, $R_3$ is ethyl, $R_5$ is 4-[(2,6-dichlorophenyl)methoxy]phenyl and stereochemistry is (S,S)).

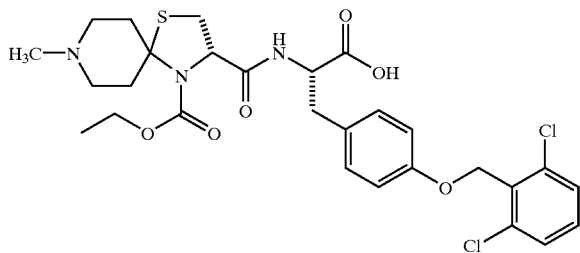

t-Butyl ester B-6 (Scheme B where $R_{B-1}$ and $R_{B-2}$ are the same and equal to H, $R_{B-3}$ and $R_{B-4}$ together form a cyclic ring of 6 atoms of the formula —$CH_2CH_2N(CH_3)$ $CH_2CH_2$—, Y is $CO_2$, $R_3$ is ethyl, $R_{B-5}$ is O-i-butyl, $R_5$ is 4-[(2,6-dichlorophenyl)methoxy]phenyl and stereochemistry is (S,S), prepared according to Scheme B from 1-methyl-4-piperidone and D-cysteine) (681 mg, 1.02 mmol) was dissolved in a solution of HCl in dioxane (4 M, 28 mL) at ambient temperature. After 18 h, volatiles were removed in vacuo to afford a residue (650 mg) which was lyophilized from water. Further purification of a portion of this product (200 mg) was effected by chromatography on a Biotage Flash 40™ system using a 40 g KP-C18-HS (35–70 μm) silica gel cartridge using aqueous acetonitrile (40%) as eluant to afford the title compound (94 mg) as an amorphous powder: IR (mull) 1696, 1611, 1585, 1565, 1511, 1439, 1404, 1335, 1303, 1271, 1239, 1196, 1178, 1017, 769 cm$^{-1}$; $^1$H NMR (DMSO-d$_6$, 300 MHz) δ 8.25 (1H), 7.54 (2H), 7.43 (1H), 7.13 (2H), 6.94 (2H), 5.16 (2H), 4.84 (1H), 4.41 (1H), 4.00 (2H), 3.07 (4H), 2.73 (4H), 2.53 (3H), 1.96 (1H), 1.69 (1H), 1.11 (3H); $^{13}$C NMR (CDCl$_3$, 75 MHz) δ 173.9, 169.2, 157.7, 153.2, 136.9, 132.1, 130.7, 130.5, 129.3, 128.5, 114.7, 73.2, 66.7, 65.2, 62.8, 54.0, 43.5, 36.5, 14.6; MS (ESI+) for $C_{28}H_{33}Cl_2N_3O_6S$ m/z 610.0 (M+H)$^+$; MS (ESI−) for $C_{28}H_{33}Cl_2N_3O_6S$ m/z 607.9 (M−H)$^-$; HRMS (FAB) calcd for $C_{28}H_{33}Cl_2N_3O_6S+H_1$ 610.1545, found 610.1561, Anal. Calcd for $C_{28}H_{33}Cl_2N_3O_6S \cdot 0.6HCl \cdot H_2O$: C, 51.70; H, 5.52; N, 6.46; Cl, 14.71. Found: C, 51.28; H, 5.49; N, 6.50; Cl, 14.57. % Water (KF): 2.72.

EXAMPLE 156

[S-(R*,R*)]-4-[[[1-[[4-[(2,6-Dichlorophenyl) methoxy]phenyl]methyl]-2-methoxy-2-oxoethyl] amino]carbonyl]-3-thiazolidinecarboxylic Acid 3-(3-Tetrahydrofuranyl)ester (Scheme A, A-7: where $R_{A-1}$ and $R_{A-2}$ are the same and equal to proton, $R_3$ is 3-tetrahydrofuranyl, Y is $CO_2$—, $R_5$ is 4-[(2,6-dichlorobenzoyl)amino]phenyl and stereochemistry is (S,S)).

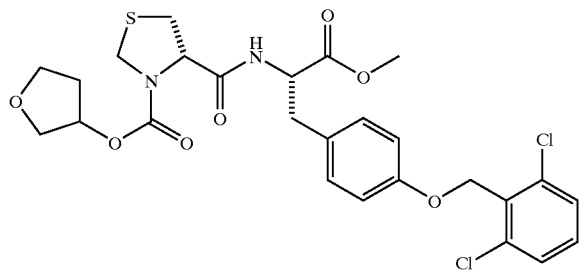

Example 156 was prepared as described in Scheme A from D-cysteine using 3-hydroxytetrahydrofuran to form the requisite carbamate. Physical properties as follows: mp 125–126.5° C. IR (mull) 3311, 1750, 1744, 1708, 1661, 1549, 1515, 1439, 1408, 1307, 1243, 1227, 1212, 1173, 1019 cm$^{-1}$, $^1$H NMR (300 MHz, CD$_3$OD) δ 7.38 (3H), 7.14 (2H), 7.96 (2H), 5.20 (1H), 5.25 (2H), 4.61 (4H), 3.79 (4H), 3.74 (3H), 3.19 (2H), 2.84 (2H), 2.29 (2H); $^{13}$C NMR (75 MHz, CDCl$_3$, spectra complicated via the presence of diastereomers) δ 171.7, 171.6, 158.1, 137.0, 132.1, 130.5, 130.4, 130.3, 128.5, 128.2, 115.1, 77.2, 77.2, 73.2, 67.0, 65.2, 63.1, 63.0, 53.3, 52.5, 52.4, 36.9, 32.9; MS (ESI+) for $C_{26}H_{28}Cl_2N_2O_7S$ m/z 582.8 (M+H)$^+$; Anal. Calcd for $C_{26}H_{28}Cl_2N_2O_7S$: C, 53.52; H, 4.84; N, 4.80. Found: C, 53.34; H, 4.87; N, 4.86.

EXAMPLE 157

[S-(R*,R*)]-2-[[[1-Carboxy-2-[4-[(2,6-dichlorobenzoyl)amino]phenyl]ethyl]amino] carbonyl]-hexahydro-γ-oxo-1H-azepine-1-butanoic Acid

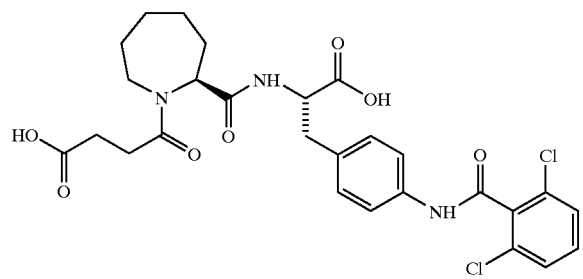

Example 157 was prepared as described for the preparation of Example 167. Physical properties as follows: IR (mull) 1781, 1709, 1651, 1625, 1612, 1550, 1537, 1515, 1444, 1431, 1418, 1398, 1331, 1193, 798 cm$^{-1}$; $^1$H NMR (300 MHz, DMSO-d$_6$) δ 1.45 (8H), 2.30 (4H), 2.90 (3H), 3.80 (1H), 4.50 (2H), 7.16 (2H), 7.50 (5H), 7.94 (1H), 10.62 (1H), 7.71 (1H); MS (FAB) m/z (rel. intensity) 578 (M+H, 43), 581 (9), 580 (29), 579 (19), 578 (43), 577 (10), 227 (11), 226 (99), 198 (18), 173 (9), 98 (46).

PREPARATION 74 AND EXAMPLE 158

(Scheme N, N-6: where n is 2, m is 0, X is N, $R_5$ is 4-[(2,6-dichlorobenzoyl)amino]phenyl and stereochemistry is 2S-(R*,R*)).

[2S-(R*,R*)]-2-[[[1-[[4-[(2,6-Dichlorobenzoyl) amino]phenyl]methyl]-2-methoxy-2-oxoethyl] amino]carbonyl]azetidine ($C_{21}H_{21}Cl_2N_3O_4$)

A solution of the product of example 142 (Scheme N: N-4 where n is 2, m is 0, X is N, Y is —$CO_2$—, $R_3$ is (1,1-dimethyl)ethyl, $R_5$ is 4-[(2,6-dichlorobenzoyl)amino] phenyl and stereochemistry is (S)) (512 mg; 0.93 mmol) in 1:1 TFA/CH$_2$Cl$_2$ (10 mL) is stirred at rt for 1 h. The reaction mixture is concentrated under reduced pressure. The residue is taken up in a mixture of CH$_2$Cl$_2$ and satd aqueous NaHCO. The aqueous phase I extracted twice additionally with CH$_2$Cl$_2$. The combined CH$_2$Cl$_2$ portions are dried, filtered and concentrated to give a yellow oil (440 mg), that is purified by silica flash chromatography (95:5 CH$_2$Cl$_2$/MeOH) to afford the title compound (324 mg) as a white foam: mp 113–115° C.; TLC (95:5 CH$_2$Cl$_2$/MeOH) R$_f$=0.10; [α]$^{25}_D$ −34 (c 0.96, MeOH); UV (MeOH) λ$_{max}$ 224 (sh, ε 12100), 251 (17700), 284 (sh, 2880); IR (mineral oil mull)

3260, 1744, 1664, 1606, 1561, 1537, 1515, 1431, 1414, 1323, 1270, 1223, 1195, 799, 782 cm$^{-1}$; $^1$H NMR (CD$_3$OD) δ 7.61 (2H), 7.50–7.38 (3H), 7.25 (2H), 4.86 (1H), 4.75 (1H), 4.21 (1H), 3.73 (3H), 3.61 (2H), 3.39–3.28 (1H), 3.23 (1H), 3.05 (1H), 2.63–2.50 (1H), 2.21–2.08 (1H); MS (+ESI) m/z 450.0; MS (EI) m/z 451, 449, 396, 394, 351, 349, 278, 211, 175, 173, 96, 70, 56; Anal. C, 55.68; H, 4.79; N, 8.96; Cl, 15.43; (calcd for+1.08% H$_2$O: C, 55.41; H, 4.77; N, 9.23; Cl, 15.58).

EXAMPLE 159

O-[(2,6-Dichlorophenyl)methyl]-N-[[(4S)-3-methylsulfonyl)-4-thiazolidinyl]carbonyl]-L-tyrosinamide (Scheme C, C-10: where R$_{C-1}$, R$_{C-2}$, R$_{C-3}$ and R$_{C-4}$ are the same and equal to proton, R$_3$ is methyl, Y is SO$_2$—, R$_5$ is 4-[(2,6-dichlorophenyl)methoxy]phenyl and stereochemistry is (S,S)).

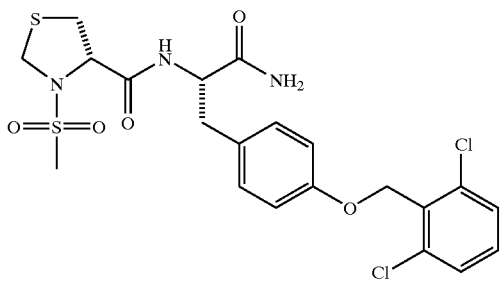

Example 159 was prepared as described in Scheme C using methanesulfonyl chloride to form the requisite sulfonamide. Physical properties as follows: mp 228–230° C.; $^1$H NMR (300 MHz, DMSO-d$_6$) δ 8.03 (1H), 7.54 (2H), 7.44 (2H), 7.14 (3H), 6.92 (2H), 5.16 (2H), 4.69 (2H), 4.41 (1H), 4.31 (1H), 3.21 (1H), 3.01 (3H), 2.87 (3H); $^{13}$C NMR (75 MHz, DMSO-d$_6$) δ 172.9, 169.1, 157.5, 136.5, 132.3, 132.0, 130.8, 130.6, 129.2, 114.6, 65.3, 64.4, 54.3, 52.0, 37.3, 35.0; MS (ESI–) for C$_{21}$H$_{23}$Cl$_2$N$_3$O$_5$S$_2$ m/z 530.2 (M–H)$^-$; Anal. Calcd for C$_{21}$H$_{23}$Cl$_2$N$_3$O$_5$S$_2$: C, 47.37; H, 4.35; N, 7.89. Found: C, 47.43; H, 4.46; N, 7.81.

EXAMPLE 160

[S-(R*,R*)]-3-[[[1-[[4-[(2,6-Dichlorophenyl)methoxy]phenyl]methyl]-2-methoxy-2-oxoethyl]amino]carbonyl]-1-thiacazaspiro[4.4]nonanecarboxylic Acid 4-Ethyl Ester (Scheme B, B-6: where R$_{B-1}$ and R$_{B-2}$ are the same and equal to H, R$_{B-3}$ and R$_{B-4}$ together form a carbocyclic ring of 5 atoms, R$_{B-5}$ is OCH$_3$, Y is CO$_2$, R$_3$ is ethyl, R$_5$ is 4-[(2,6-dichlorophenyl)methoxy]phenyl and stereochemistry is (S,S)).

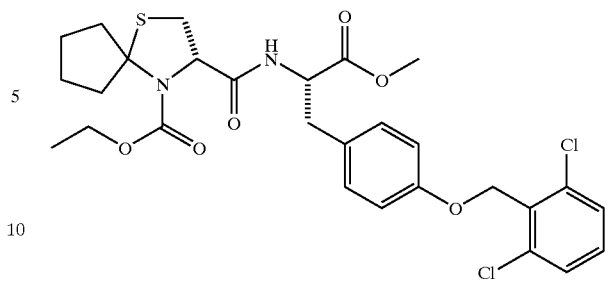

Example 160 was prepared as described in Scheme B. Physical properties as follows: IR (mull) 1746, 1705, 1681, 1510, 1439, 1399, 1336, 1301, 1276, 1241, 1203, 1178, 1110, 1017, 769 cm$^{-1}$; $^1$H NMR (CDCl$_3$) δ 7.36 (2H), 7.25 (1H), 7.03 (2H), 6.93 (2H), 6.64 (1H), 5.22 (2H), 4.85S(2H), 4.15 (2H), 3.73 (3H), 3.15 (4H), 2.69 (1H), 2.48 (1H), 1.76 (6H), 1.23 (3H); $^{13}$C NMR (CDCl$_3$) δ 171.5, 170.7, 158.0, 152.5, 137.0, 132.0, 130.5, 130.3, 128.5, 128.2, 115.0, 66.4, 65.2, 61.9, 53.1, 52.4, 37.1, 32.3, 25.1, 24.6, 14.5; MS (ESI+) for C$_{28}$H$_{32}$Cl$_2$N$_2$O$_6$S m/z 594.9 (M+H)$^+$, MS (ESI–) for C$_{28}$H$_{32}$Cl$_2$N$_2$O$_6$S m/z 592.8 (M–H)$^-$; Anal. Calcd for C$_{28}$H$_{32}$Cl$_2$N$_2$O$_6$S.0.10H$_2$O: C, 56.30; H, 5.43; N, 4.69. Found: C, 56.20; H, 5.24; N, 4.69. % Water (KF): 0.31.

EXAMPLE 161

[S-(R*,R*)]-3-[[[1Carboxy-2-[4-[(2,6-dichlorophenyl)methoxy]phenyl ethyl]amino]carbonyl]-1-thia-4-azapiro[4.4]nonane-4-carboxylic Acid 4-Ethyl Ester (Scheme B, B-7: where R$_{B-1}$ and R$_{B-2}$ are the same and equal to H, R$_{B-3}$ and R$_{B-4}$ together form a carbocyclic ring of 5 atoms, Y is CO$_2$, R$_3$ is ethyl, R$_5$ is 4-[(2,6-dichlorophenyl)methoxy]phenyl and stereochemistry is (S,S)).

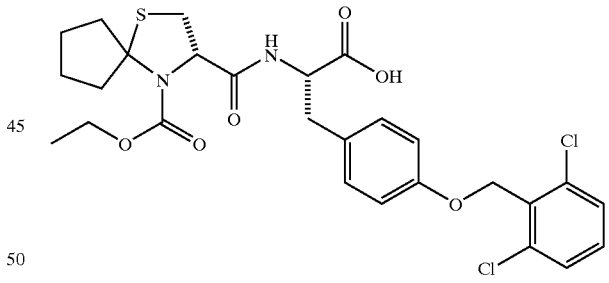

Example 161 was prepared from example 160 by the procedure described in preparation 6. Physical properties as follows: IR (mull) 1737, 1708, 1675, 1612, 1511, 1439, 1402, 1338, 1301, 1241, 1197, 1179, 1115, 1018, 769 cm$^{-1}$; $^1$H NMR (DMSO-d$_6$) δ 8.07 (1H), 7.54 (2H), 7.45 (1H), 7.12 (2H), 6.94 (2H), 5.15 (2H), 4.63 (1H), 4.33 (1H), 3.91 (2H), 3.05 (2H), 2.79 (1H), 2.60 (1H), 1.60 (6H), 1.07 (3H); $^{13}$C NMR (DMSO-d) δ 172.7, 169.4, 157.1, 155.7, 135.9, 131.6, 131.4, 130.3, 129.6, 128.7, 114.1, 83.9, 64.7, 60.5, 53.1, 38.0, 36.2, 31.8, 24.2, 24.1, 14.1; MS (ESI+) for C$_{27}$H$_{30}$Cl$_2$N$_2$O$_6$S m/z 580.8 (M+H)$^+$; MS (ESI–) for C$_{27}$H$_{30}$Cl$_2$N$_2$O$_6$S m/z 578.8 (M–H)$^-$; HRMS (EI) calcd for C$_{27}$H$_{30}$Cl$_2$N$_2$O$_6$S 580.1202, found 580.1172; Anal. Calcd for C$_{27}$H$_{30}$Cl$_2$N$_2$O$_6$S.0.19H$_2$O: C, 55.44; H, 5.24; N, 4.79. Found: C, 55.24; H, 5.32; N, 4.79. % Water (KF): 0.59.

PREPARATION 75

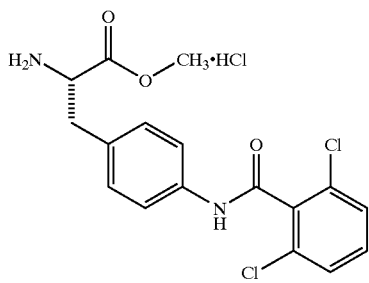

The aminoester product of preparation 75 is useful as a synthetic intermediate (for example, reagent A-4 of Scheme A).

To a cold (0–5° C.) solution of anhydrous methanolic HCl was added 100 g of L-4-nitrophenylalanine (Advanced ChemTech) portionwise over 15 min. The mechanically stirred mixture was heated to gentle reflux for 48 h. The mixture was allowed to cool and then filtered through a sintered glass filter funnel, washing the collected solids with hot MeOH until only insoluble residues remained. The filtrate was concentrated in vacuo to afford the methyl ester (120 g) as waxy off white solid which was used without further purification.

To a suspension of methyl ester described above (87 g, 0.33 mole) in $CH_2Cl_2$ (1500 mL) at ambient temperature was added di-t-butyldicarbonate (109 g, 0.50 mole) followed by the dropwise addition of $Et_3N$ (51 mL, 0.37 mole). After 15 min additional $Et_3N$ (40 mL, 0.29 mol) was added to maintain a slightly basic mixture (ca. pH 8). The reaction mixture was stirred 18 h and additional $CH_2Cl_2$ (1400 mL) and $Et_3N$ (15 mL, 0.11 mol) were added. After an additional 2 h the reaction mixture was quenched by the slow addition of MeOH (100 mL), stirred for 1 h and then partitioned between $CH_2Cl_2$ and cold 10% aqueous $KHSO_4$. The organic layer was washed with saturated $NaHCO_3$ and brine, dried ($Na_2SO_4$), filtered and concentrated in vacuo. Flash chromatography of the residue using hexane and a gradient of a 1:1 mixture of $EtOA_c/CH_2Cl_2$ (25–33%) afforded the Boc-methyl ester (69 g) as a white solid. Physical properties as follows: $^1$H NMR (300 MHz; $CDCl_3$) δ 8.16 (2H), 7.31 (2H), 5.04 (1H), 4.63 (1H), 3.73 (3H), 3.18 (2H), 1.41 (9H); MS (ES+) for $C_{15}H_{20}N_2O_6$ m/z 325.2 (M+H)$^+$.

Palladium on carbon (10% w/w. 1.25 g) was added to a Parr hydrogenation flask under a $N_2$ atmosphere and carefully wetted with 100 mL of MeOH/THF (1:1). A solution of the Boc-methyl ester described above (25 g, 77 mmol) in 400 mL of MeOH/THF (1:1) was added and the mixture shaken on a hydrogenation apparatus under a hydrogen atmosphere (20 psi) for 1 h at ambient temperature. The reaction mixture was filtered through a pad of Celite and the solids washed several times with MeOH. The combined filtrates were concentrated in vacuo to afford the 4-aminophenylalanyl derivative (22.7 g) which was used without further purification. Physical properties as follows: $^1$H NMR (300 MHz, $CDCl_3$) δ 6.89 (2H), 6.61 (2H), 4.96 (1H), 4.50 (1H), 3.69 (3H), 2.95 (2H), 1.41 (9H); MS (ES+) for $C_{15}H_{22}N_2O_4$ m/z 295.2 (M+H)$^+$.

A cold (0–5° C.) solution of 2,6-dichlorobenzoyl chloride (11.1 mL, 77.5 mmol) in 125 mL of THF was treated dropwise with a solution of the 4-aminophenylalanyl derivative described above (22.7 g, 77.1 mmol) and $Et_2N$ (16 mL, 115 mmol) in 125 mL of THF. The reaction mixture was allowed to warm to temperature and stir an additional 18 h. The mixture was diluted with EtOAc (2 L) and then washed with 1N HCl, $H_2O$, 1N NaOH and brine. The organic extract was dried ($Na_2SO_4$), filtered, and concentrated in vacuo to give the crude product as a pale yellow solid. This material was recrystallized from acetone/hexanes (ca. 1:1) to afford the amide (30.8 g) as a crystalline solid. Physical properties as follows: mp 192.2–193.1° C.; IR (mull) 3305, 1747, 1736, 1690, 1665, 1609, 1548, 1512, 1433, 1414, 1325, 1277, 1219, 1171, 781 cm$^{-1}$; $^1$H NMR (300 MHz; $CDCl_3$) δ 7.57 (2H), 7.34 (4H), 7.14 (2H), 4.98 (1H), 4.60 (1H), 3.74 (3H), 3.11 (2H), 1.42 (9H); MS (ES+) for $C_{22}H_{24}Cl_2N_2O_5$ m/z 467.0 (M+H)$^+$.

To 650 mL of anhydrous 4M HCl in dioxane at ambient temperature was added the amide described above (30.6 g, 65.5 mmol) portionwise and the resulting mixture was stirred until all the solids had dissolved (ca. 1 h). Volatiles were removed in vacuo to give a light yellow solid which was partitioned between water (500 mL) and ether (1 L). The water layer was separated and concentrated in vacuo to approximately 200 mL. The aqueous solution was then frozen and lyophilized to afford the aminoester product (25.6 g) as a light yellow solid. Physical properties as follows: $[\alpha]^{25}_D$=+5 (c 1, MeOH); IR (mull) 3244, 3186, 3112, 1747, 1660, 1604, 1562, 1539, 1516, 1431, 1416, 1327, 1273, 1243, 799 cm$^{-1}$; $^1$H NMR (300 MHz; $CD_3OD$) δ 7.69 (2H), 7.45 (3H), 7.29 (2H), 4.34 (1H), 3.83 (3H), 3.21 (2H); $^{13}$C NMR (300 MHz; $CD_3OD$) δ 169.0, 163.9, 137.8, 136.08, 131.8, 131.0, 130.3, 129.7, 127.9, 120.6, 53.8, 52.3,.35.4; MS (ES+) for $C_{17}H_{16}Cl_2N_2O_3$ m/z 367.1 (M+H)$^+$.

PREPARATION 76

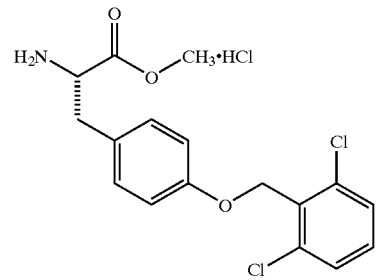

The aminoester product of preparation 75 is useful as a synthetic intermediate (for example, reagent A-4 of Scheme A).

To a cold (0–5° C.) solution of anhydrous methanolic HCl (200 mL) was added 25 g of N-α-t-Boc-O-2,6-dichlorobenzyl-L-tyrosine (Sigma) portionwise over 15 min. After 30 minutes at 0–5° C., the mixture was heated to 50° C. for 2 h. The solution was cooled to room temperature and the volatiles removed in vacuo. The solid was suspended in ethyl ether and collected by filtration to afford the title compound (21.4 g) which was used without further purifi

EXAMPLE 162 cation. Physical properties as follows: $[\alpha]^{25}{}_D$=+16 (c 1.00, ethanol); $^1$H NMR (300 MHz, CD$_3$OD) δ 7.44 (2H), 7.35 (1H), 7.21 (2H), 7.02 (2H), 5.28 (2H), 4.29 (1H), 3.81 (3H), 3.18 (2H); MS (ESI+) for C$_{17}$H$_{17}$Cl$_2$NO$_3$ m/z 354.1 (M+H)$^+$; Anal. Calcd for C$_{17}$H$_{17}$Cl$_2$NO$_3$.HCl: C, 52.26; H, 4.64; N, 3.59. Found: C, 52.17; H, 4.74; N, 3.61.

EXAMPLE 162

2-[[[(1S)-1-[[4-[(2,6-Dichlorobenzoyl)amino]phenyl]methyl]-2-methoxy-2-oxoethyl]amino]carbonyl]-1-piperidinecarboxylic Acid 1-[(1,1-Dimethyl)ethyl]ester

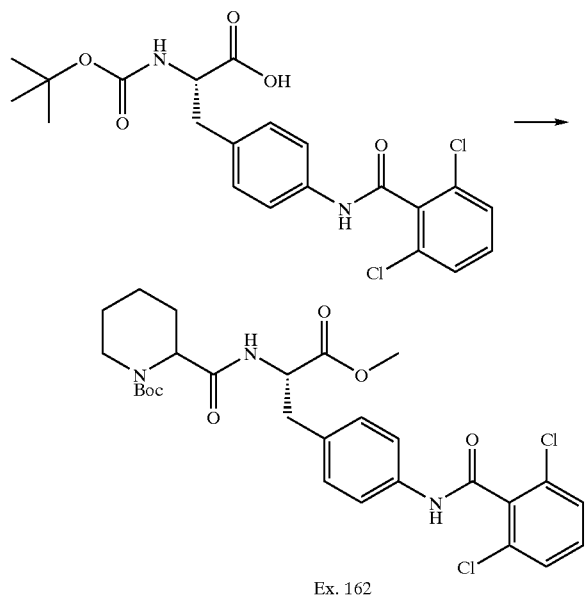

Ex. 162

Example 162: HCl gas was bubbled through a solution of N-(tert-butoxycarbonyl)-4-(2,6-dichlorobenzoylamino)-L-phenylalanine (2.51 g, 5.53 mmol) in MeOH (20 mL) for 10 minutes. The solution was stirred for additional 2 hours at room temperature. The solvent was removed in vacuo and the excess HCl was removed by the addition of Et$_2$O (3×15 mL) and evaporation under reduced pressure. The resultant gum was dissolved in THF (10 mL) and N-tert-butoxycarbonyl-pipecolinic acid (1.28 gm, 5.59 mmol), BOP-reagent (2.69 gm, 6.09 mmol) and DIEA (2.9 mL, 16.6 mmol) were added and the reaction mixture was stirred overnight. EtOAc (25 mL) was added and the mixture was extracted with 1N HCl (20 mL). The organic phase was washed with saturated LiCl (20 mL) then saturated NaHCO$_3$ (30 mL). The organic layer was dried over Na$_2$SO$_4$, filtered and evaporated. Chromatography of the residue (silica gel, Hexanes→50% EtOAc/Hexanes gradient elution) provided Example 162 as a solid (1.45 gm, 45%): ESMS (m/z) 578, 580 (MH$^+$).

EXAMPLE 163

2-[[[(1S)-1-[[4-[(2,6-Dichlorobenzoyl)amino]phenyl]methyl]-2-methoxy-2-oxoethyl]amino]carbonyl]-γ-oxo-1-piperidinebutanoic Acid

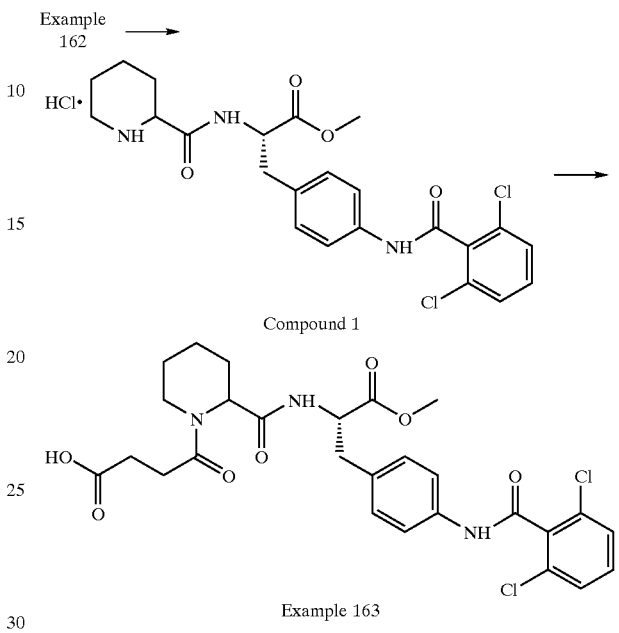

HCl gas was bubbled through a MeOH (20 mL) solution of Example 162 (1.27 gm, 2.20 mmol) for 10 min. Stirring was continued overnight at room temperature. The solvent was removed in vacuo and the excess HCl was removed by washing with Et$_2$O (3×10 mL) on a vacuum filter. The HCl salt was completely dried under high vacuum to provide Compound 1 (1.09 gm, 97%) as a solid: ESMS (m/z) 478, 480 (MH$^+$).

Example 163: Compound 1 (147 mg, 0.285 mmol) was dissolved in DMF (5 mL) containing DIEA (150 μL, 0.88 mmol). To this solution was added succinic anhydride (59 mg, 0.59 mmol) and the mixture was stirred at 50° C. for 5 hr under dry nitrogen. The solvent was evaporated and the residue was purified by column chromatography (silica gel, Hexanes→EtOAc gradient elution) to provide Example 163 as a solid (164 mg): ESMS (m/z) 578, 580 (MH$^+$).

EXAMPLES 164–166

The following mono methyl esters were prepared in a similar manner as Example 163

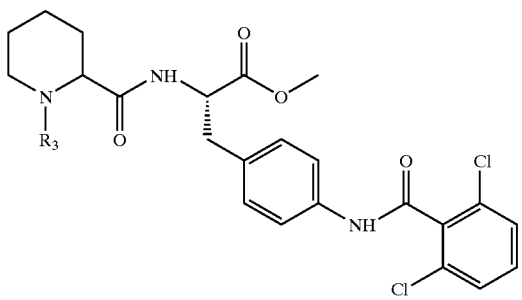

159
-continued

| ex# | R₃ | MS |
|---|---|---|
| 164 | | (m/z) 646 |
| 165 | | (MH⁺) 620 |
| 166 | | (MH⁺) 574 ([M-H]⁻) |

EXAMPLE 167

2-[[[(1S)-1-[(2,6-Dichlorobenzoyl)amino]phenyl]ethyl]amino]carbonyl]-γ-oxo-1-piperidinebutanoic Acid

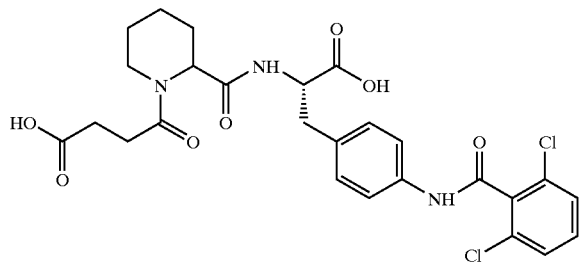

EXAMPLE 167

Example 163 (154 mg, 0.266 mmol) was treated with LiOH (26 mg, 1.07 mmol) in H₂O (5 mL) for hours. The product was then precipitated by the addition of 3 N HCl.

The product was collected by vacuum filtration and washed with cold H₂O (2×3 mL). Drying under high vacuum provided Example 167 as a solid (109 mg): ESMS (m/z) 562 ([M−H]⁻).

The following compounds were prepared in a similar manner as 167.

160
EXAMPLE 168–170

| ex# | R₃ | MS |
|---|---|---|
| 168 | | (m/z) 630 |
| 169 | | ([M-H]⁻) 604 |
| 170 | | ([M-H]⁻) 560 ([M-H]⁻) |

PREPARATION 77

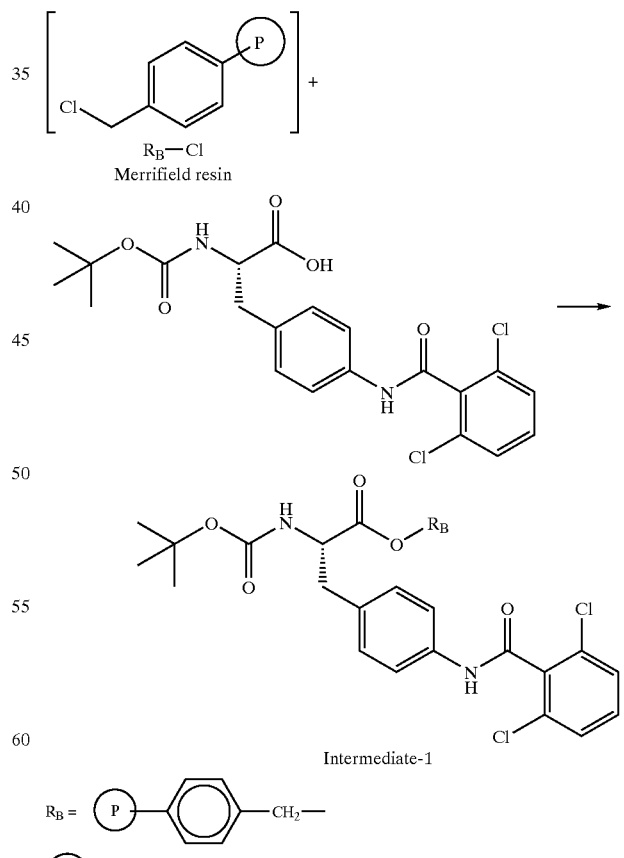

Intermediate-1: Attachment of N-tert-butoxycarbonyl-[4-(2,6-dichlorobenzoylamino)]-L-phenylalanine to Merrifield resin was done using Horiki's method (Horiki et al. *Chem. Lett.* 1978 (2) 165–168). In a 250 mL round bottom flask fitted with a drying tube, Merrifield resin (Biorad. 10.0 g, 13.5 mmol/g) and anhydrous potassium fluoride (Aldrich, 1.57 g, 27.0 mmol) were added to a solution of N-tert-butoxycarbonyl-[4-(2,6-dichlorobenzoylamino)]-L-phenylalanine (Bachem California, 6.13 g, 13.5 mmol) in dry DMF (100 mL). The reaction mixture was stirred at 80° C. in an oil bath for 24 hr. The cooled resin was then filtered and washed thoroughly with DMF (2×250 mL), 50% aqueous DMF (3×250 mL), methanol (3×250 mL), dichloromethane (3×250 mL), and finally methanol (3×250 mL). The resin was then dried under reduced pressure to constant weight to give Intermediate-1. Incorporation of N-tert-butoxycarbonyl-[4-(2,6-dichlorobenzoylamino)]-L-phenylalanine onto the resin was estimated to be 0.045 mmol/g from the increase in resin mass.

EXAMPLE 171

N-[[2-(1,3-Benzodioxol-5-yl)-1-methyl-5-oxo-3-pyrrolidinyl]carbonyl]-4-[(2,6-dichlorobenzoyl)amino]-L-phenylalanine

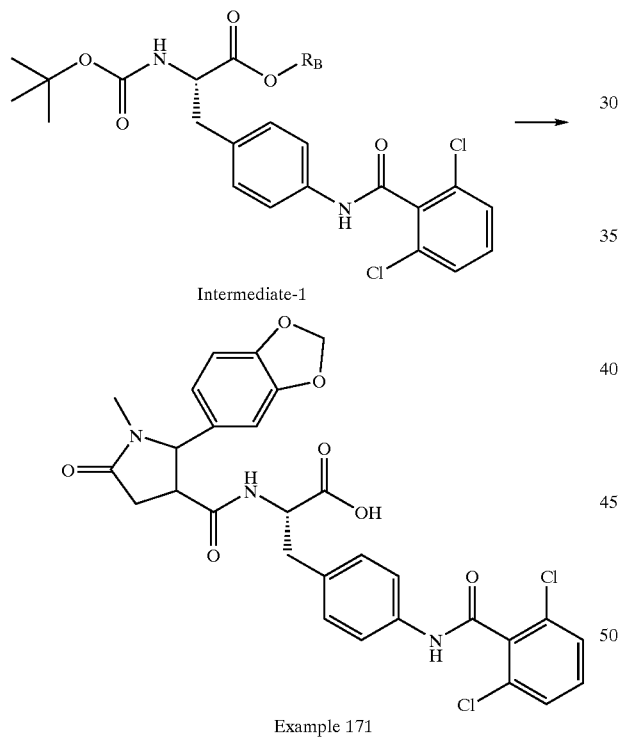

Example 171

Example 171: The Intermediate-1 (0.15 g, 0.1065 mmol/g) was pretreated with $CH_2Cl_2$ (2×3 mL). The swollen resin was then deprotected with 50% $TFA/CH_2Cl_2$ (3 mL, 30 min). The resin was rinsed in the following order: $CH_2Cl_2$ (2×3 mL), $CH_3OH$ (2×3 mL). $CH_2Cl_2$ (2×3 mL). The resin was swollen with DMF (2×3 mL). 2-(3,4-methylenedioxyphenyl)-1-methyl-5-oxo-3-pyrrolidine carboxylic acid (84 mg, 0.32 mmol) in DMF (1.0 mL) was activated with 0.5 M HBTU/HOBT in DMF (0.7 mL) and DIEA (0.139 mL, 0.799 mmol), and then added to the swollen resin. The mixture was vortexed for 2 hr at room temperature. The resin was filtered and washed in the following order: DMF (2×3 mL), $CH_2Cl_2$ (2×3 mL), $CH_3OH$ (2×3 mL), $CH_2Cl_2$ (2×3 mL), respectively. If a Kaiser test on a small quantity of the resin is positive (blue) then repeat the coupling procedure until a negative result is obtained. The resulting resin was then dried in vacuo to constant weight. The resin was placed in the polypropylene column and pretreated with 3 mL of THF. Then to the preswollen resin 1.6 mL of THF, 0.48 mL of $CH_3OH$, and 0.160 mL of 2N LiOH were added. The mixture was vortexed for 15 min and filtered to a clean and preweighed test tube. The resin was next washed with 2 mL of THF/5% $CH_3OH$ (2×) and the combined filtrates were evaporated. The resulting gum was dissolved in 1 mL of water. The solution was then acidified with 1N HCl to pH 2.0. The precipitate was centrifuged, washed with water (5 mL, 2×) and dried in vacuo to furnish 15.4 mg of Example 171 as a solid. ESMS (m/z): 596, ([M–H]⁻).

PREPARATION 78

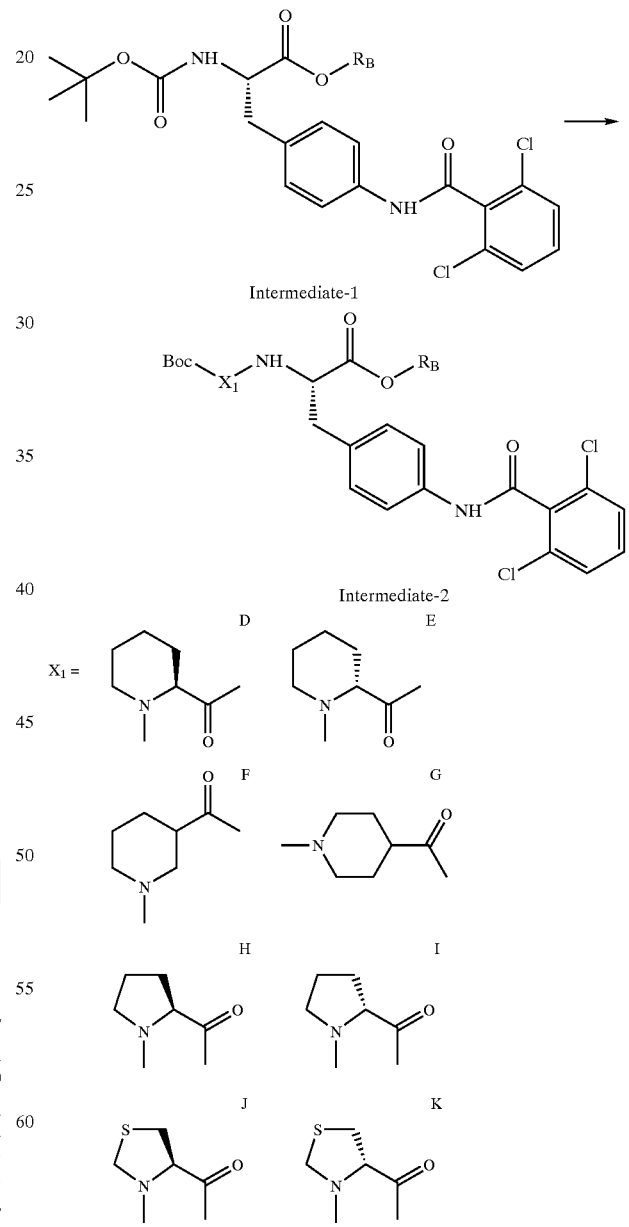

Intermediate-2F: The resin bound N-tert-butoxycarbonyl-[4-(2,6-dichlorobenzoylamino)]-L-phenylalanine (Intermediate-1), (250 mg, 0.1, 125 mmol/g) was placed in a 8.0 mL, polypropylene filter column fitted with a 2-way polypropylene stopcock. The resin was pretreated with $CH_2Cl_2$ (2×3 mL). The swollen resin was then deprotected with 50% $TFA/CH_2Cl_2$ (3–4 mL, 30 min) with shaking. The resin was rinsed in the following order: $CH_2Cl_2$ (2×3 mL), $CH_3OH$ (2×3 mL), $CH_2Cl_2$ (2×3 mL). The resin was swollen with DMF (2×3 mL). N-Tert-butoxycarbonyl-nipecotic acid (103 mg, 0.45 mmol) in DMF (1.0 mL) was activated with 0.5 M HBTU/HOBT in DMF (0.910 mL) and DIEA (0.195 mL), then added to the swollen resin. The mixture was vortexed for 2 hr at room temperature. The resin was washed in the following order: DMF (2×3 mL), $CH_2Cl_2$ (2×3 mL), $CH_3OH$ (2×3 mL), $CH_2Cl_2$ (2×3 mL) and dried (Intermediate-2F). If a Kaiser test on a small quantity of the resin is positive (blue) then repeat the coupling procedure until a negative result is obtained.

The intermediate resins Intermediate-2D, 2E, 2G, 2H, 2I, 2J & 2K were each produced following this procedure.

EXAMPLE 172

5-[[(2S)-2-[[[(1S)-1-Carboxy-2-[4-[(2,6-dichlorobenzoyl)amino]phenyl]ethyl]amino] carbonyl]-1-piperidinyl]carbonyl]-3-pyridinecarboxylic Acid

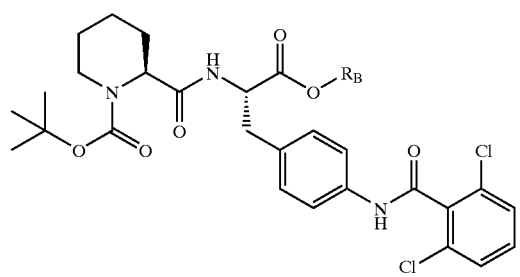

Intermediate-2D

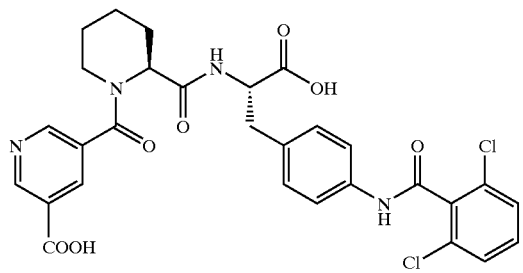

Example 172

Example 172: Resin bound Intermediate-2D (2.0 g, 1.3 mmol/g) was pretreated with $CH_2Cl_2$ (2×20 mL). The swollen resin was then deprotected with 50% $TFA/CH_2Cl_2$ (20 mL, 30 min). The resin was rinsed in the following order: $CH_2Cl_2$ (2×20 mL), $CH_3OH$ (2×20 mL), $CH_2Cl_2$ (2×20 mL). The resin was swollen with DMF (2×20 mL). 3,5-Pyridine dicarboxylic acid (652 mg, 3.9 mmol) in 20 mL of DMF was activated with 0.5 M HBTU/HOBT in DMF (8.0 mL) and DIEA (1.7 mL, 9.75 mmol), then added to the swollen resin. The mixture was vortexed for 2 hr at room temperature. The resin was filtered and washed in the following order: DMF (2×20 mL), $CH_2Cl_2$ (2×20 mL), $CH_3OH$ (2×20 mL), $CH_2Cl_2$ (2×20 mL), respectively. If a Kaiser test (Kaiser et al., *Anal. Biochem.* 1970, 34, 594–598) on a small quantity of the resin is positive (blue) then repeat the coupling procedure until a negative result is obtained. The resulting resin was then dried in vacuo to constant weight (2.2 g). The resin was treated with 25 mL of liquid HF by stirring for 60 min at 0° C. in an HF-reaction apparatus (Peninsula Laboratories Inc., Belmont, Calif.). The HF was rapidly evaporated off by vacuum aspiration at 0° C. Then 100 mL of dry ethyl ether was added. The resin and the resulting precipitates were filtered off and washed three times with 50 mL of ethyl ether, and dried in vacuo. The mixture was then treated with 25 mL of 1N NaOH (4×), and the combined solutions were lyophilized. The crude product was purified by HPLC using a C-18 column and a linear acetonitrile/0.1% HCl gradient. The gradient was run from 60% solvent A (0.1% HCl) to 80% solvent B (80% acetonitrile in 0.1% HCl) in 20 min. Lyophilization furnished 20 mg (2.5%) of Example 172. ESMS (m/z): 612 ([M–H]⁻).

EXAMPLES 173–267

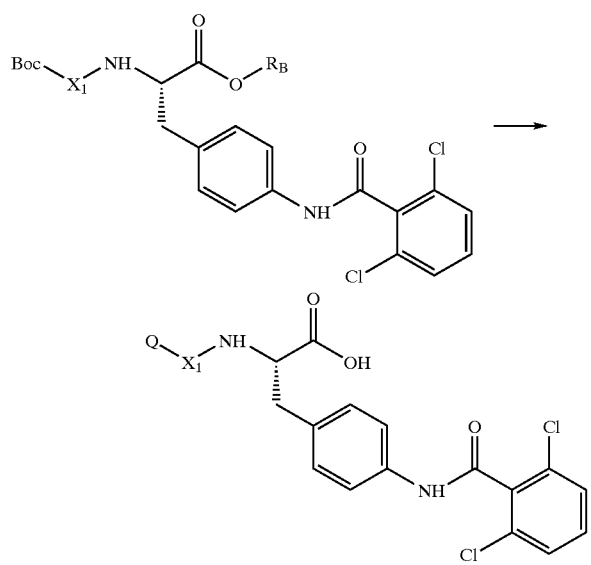

METHOD-A (EXAMPLE 173)

4-[(2,6-Dichlorobenzoyl)amino]-N-[[1-(3-methoxy-1-oxopropyl)-3-piperidinyl]carbonyl]-L-phenylalanine

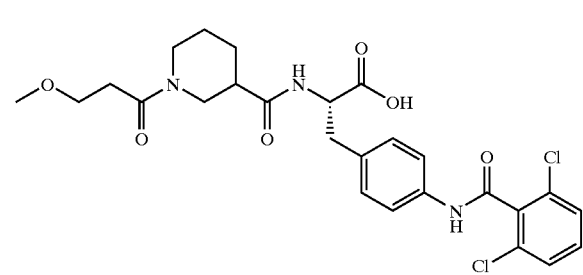

EXAMPLE 173

The Intermediate-2F (0.25 g, 0.1125 mmol/g) was pretreated with $CH_2Cl_2$ (2×3 mL). The swollen resin was then deprotected with 50% $TFA/CH_2Cl_2$ (3 mL, 30 min). Theresin was rinsed in the following order: $CH_2Cl_2$ (2×3 mL), $CH_3OH$ (2×3 mL), $CH_2Cl_2$ (2×3 mL). The resin was swollen with DMF (2×3 mL). 3-methoxypropionic acid (53 mg, 0.45 mmol) in DMF (1.0 mL) was activated with 0.5 M HBTU/HOBT in DMF (0.910 mL) and DIEA (0.195 mL), then added to the swollen resin. The mixture was vortexed for 2 hr at room temperature. The resin was filtered and washed in the following order: DMF (2×3 mL), CH₂Cl₂ (2×3 mL), CH₃OH (2×3 mL), CH₂Cl₂ (2×3 mL), respectively. If a Kaiser test on a small quantity of the resin is positive (blue) then repeat the coupling procedure until a negative result is obtained. The resulting resin was then dried in vacuo to constant weight. The resin was placed in the polypropylene column and pretreated with THF (3 mL). Then THF (3.5 mL), CH₃OH (1.0 mL) and 2N LiOH (0.175 mL) were added. The mixture was vortexed for 15 mm and filtered to a clean and preweighed test tube. The resin was next washed with THF/5% CH₃OH (2 mL) and the combined filtrates were evaporated. The resulting gum was dissolved in H₂O (1 mL). The solution was then acidified with 1 N HCl to pH 2.0. The precipitate was centrifuged, washed with water (2×5 mL) and dried in vacuo to furnish 38.3 mg of Example 173 as a solid: ESMS (m/z) 548 ([M−H])⁻.

METHOD-B (EXAMPLE 174)

3-[[[(1S)-1-Carboxy-2-[4-[(2,6-dichlorobenzoyl)amino]phenyl]ethyl]amino]carbonyl]-γ-oxo-1-piperidinebutanoic Acid

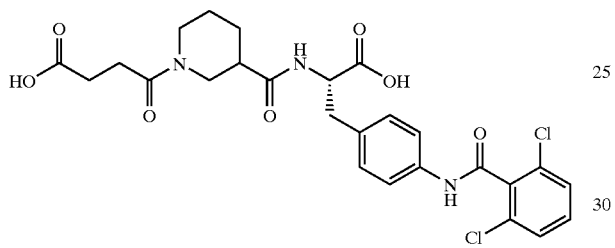

EXAMPLE 174

The Intermediate-2F (0.25 g, 0, 1125 mmol/g) was pretreated with CH₂Cl) (2×3 mL). The swollen resin was then deprotected with 50% TFA/CH₂Cl₂ (3 mL, 30 min). The resin was rinsed in the following order: CH₂Cl₂ (2×3 mL), CH₃OH (2×3 mL). CH₂Cl₂ (2×3 mL). The resin was then swollen with DMF (3 mL). Succinic anhydride (45 mg, 0.45 mmol) dissolved in DMF (4 mL) was added to the swollen resin and stirred at 50° C. for 2 hr. The resin was filtered and washed in the following order: DMF (2×3 mL), CH₂Cl₂ (2×3 mL), CH₃OH (2×3 mL), CH₂Cl₂ (2×3 mL), respectively. If a Kaiser test on a small quantity of the resin is positive (blue) then repeat the coupling procedure until a negative result is obtained. The resulting resin was then dried in vacuo to constant weight. The resin was placed in the polypropylene column and pretreated with THF (3 mL). Then to the swollen resin THF (3.5 mL), CH₃OH (1.0 mL) and 2N LiOH (0.175 mL) were added. The mixture was vortexed for 15 min and filtered to a clean and preweighed test tube. The resin was next washed with THF/5% CH₃OH (2×2 mL) and the combined filtrates were evaporated. The resulting gum was dissolved in H₂O (1 mL). The solution was then acidified with 1N HCl to pH 2.0. The precipitate was centrifuged, washed with H₂O (2×5 mL) and dried in vacuo to furnish 30.5 mg of Example 174 as a solid: ESMS (m/z) 562 ([M−H]⁻).

METHOD-C (EXAMPLE 175)

N-[[1-[[(4-Carboxyphenyl)amino]carbonyl]-4-piperidinyl]carbonyl]-4-[(2,6-dichlorobenzoyl)amino]-L-phenylalanine

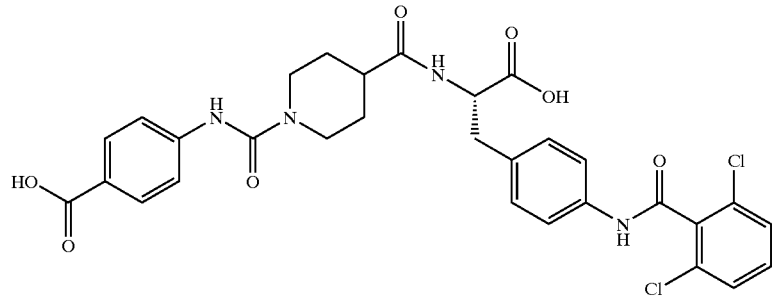

EXAMPLE 175

The Intermediate-2G (0.25 g, 0.1125 mmol/g) was pretreated with CH₂Cl₂ (2×3 mL). The swollen resin was then deprotected with 50% TFA/CH₂Cl₂ (3 mL, 30 min). The resin was rinsed in the following order: CH₂Cl₂ (2×3 mL), CH₃OH (2×3 mL), CH₂Cl₂ (2×3 mL). The resin was then swollen with DMF (3 mL). Ethyl 4-isocyanatobenzoate (22 mg, 0.108 mmol) dissolved in DMF (3 mL) and DIEA (47 μL 0.27 mmol) were added to the swollen resin. This reaction mixture was vortexed for 6–8 hr at room temperature. The resin was filtered and washed in the following order: DMF (2×3 mL), CH₂Cl₂ (2×3 mL), CH₃OH (2×3 mL), CH₂Cl₂ (2×3 mL), respectively. If a Kaiser test on a small quantity of the resin is positive (blue) then repeat the coupling procedure until a negative result is obtained. The resulting resin was then dried in vacuo to constant. The resin was placed in the polypropylene column and pretreated with THF (3 mL). Then to the swollen resin THF (3.5 mL), $CH_3OH$ (1.0 mL) and 2N LiOH (0.175 mL) were added respectively. The mixture was vortexed for 15 min and filtered to a clean and preweighed test tube. The resin was next washed with THF/5% $CH_3OH$ (2 mL) and the combined filtrates were evaporated. The resulting gum was dissolved in $H_2O$ (1 mL). The solution was then acidified with 1N HCl to pH 2.0. The precipitate was centrifuged, washed with $H_2O$ (2×5 mL) and dried in vacuo to furnish 18 mg of Example 175 as a solid: ESMS (m/z) 625, ([M–H]$^-$).

EXAMPLES 176–266

The following compounds were prepared in a similar manner as described above.

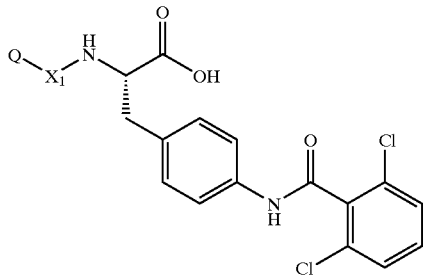

| ex# | Method | Q | $X_1$ | MS (m/z) |
|---|---|---|---|---|
| 176 | A | HOOC-CH=CH-C(O)-CH$_3$ | N-methylpiperidin-2-yl-C(O)- | 560 ([M – H]$^-$) |
| 177 | A | H$_3$CO-CH$_2$CH$_2$-C(O)-CH$_3$ | N-methylpiperidin-2-yl-C(O)- | 548 ([M – H]$^-$) |
| 178 | A | 3-COOH-cyclohexyl-C(O)-CH$_3$ | N-methylpiperidin-2-yl-C(O)- | 616 ([M – H]$^-$) |
| 179 | A | CH$_3$-C(O)-CH$_2$CH$_2$-C(O)-CH$_3$ | N-methylpiperidin-2-yl-C(O)- | 560 ([M – H]$^-$) |
| 180 | A | 3,4-dimethoxyphenyl-C(O)-CH$_3$ | N-methylpiperidin-2-yl-C(O)- | 626 ([M – H]$^-$) |
| 181 | A | 2-COOH-phenyl-C(O)-CH$_3$ | N-methylpiperidin-2-yl-C(O)- | 610 ([M – H]$^-$) |

-continued
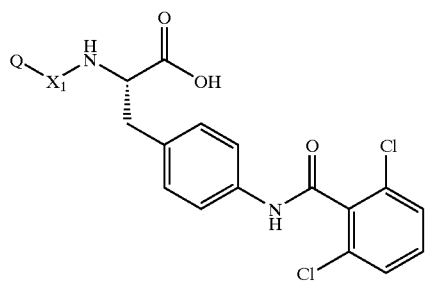
| ex# | Method | Q | X₁ | MS (m/z) |
|---|---|---|---|---|
| 182 | A | 3-acetyl-benzoic acid | 1-methyl-2-acetyl-piperidine | 610 ([M − H]⁻) |
| 183 | A | 6-acetyl-2-naphthoic acid | 1-methyl-2-acetyl-piperidine | 660 ([M − H]⁻) |
| 184 | A | 5-acetyl-nicotinic acid | 1-methyl-2-acetyl-piperidine | 611 ([M − H]⁻) |
| 185 | A | 3-acetyl-pyridine | 1-methyl-2-acetyl-piperidine | 567 ([M − H]⁻) |
| 186 | A | 6-acetyl-picolinic acid | 1-methyl-2-acetyl-piperidine | 611 ([M − H]⁻) |
| 187 | A | 6-acetyl-nicotinic acid | 1-methyl-2-acetyl-piperidine | 611 ([M − H]⁻) |

-continued

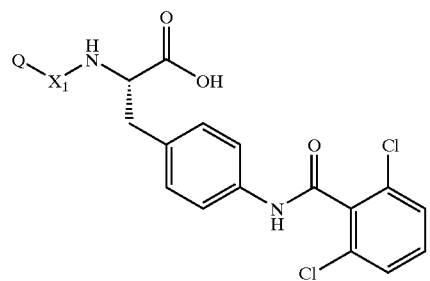

| ex# | Method | Q | X₁ | MS (m/z) |
|---|---|---|---|---|
| 188 | A | 4-hydroxyquinolin-2-yl-carbonyl | 1-methylpiperidin-2-yl-carbonyl | 633 ([M − H]⁻) |
| 189 | A | 5-(HOOC)-1H-pyrazol-3-yl-carbonyl | 1-methylpiperidin-2-yl-carbonyl | 600 ([M − H]⁻) |
| 190 | A | 4-(HOOC)-thiazolidin-2-yl-carbonyl | 1-methylpiperidin-2-yl-carbonyl | 621 ([M − H]⁻) |
| 191 | A | 5-nitrofuran-2-yl-carbonyl | 1-methylpiperidin-2-yl-carbonyl | 603 ([M − H]⁻) |
| 192 | A | tetrahydrofuran-2-yl-carbonyl | 1-methylpiperidin-2-yl-carbonyl | 560 ([M − H]⁻) |
| 193 | A | tetrahydrofuran-3-yl-carbonyl | 1-methylpiperidin-2-yl-carbonyl | 560 ([M − H]⁻) |
| 194 | B | HOOC-CH₂CH₂-C(O)- | 1-methylpiperidin-3-yl-carbonyl | 562 ([M − H]⁻) |

-continued

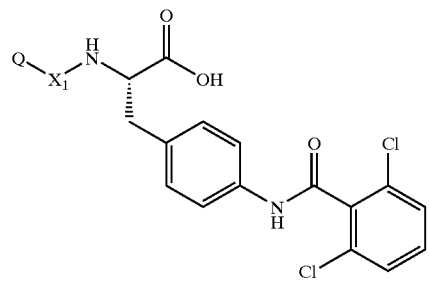

| ex# | Method | Q | X₁ | MS (m/z) |
|---|---|---|---|---|
| 195 | B | cyclopentane-1,1-diyl with CH₂COOH and CH₂C(O)CH₃ | 1-methylpiperidin-3-yl carbonyl | 630 ([M − H]⁻) |
| 196 | B | HOOC-CH₂-C(CH₃)₂-CH₂-C(O)CH₃ | 1-methylpiperidin-3-yl carbonyl | 604 ([M − H]⁻) |
| 197 | B | HOOC-CH=CH-C(O)CH₃ (cis) | 1-methylpiperidin-3-yl carbonyl | 560 ([M − H]⁻) |
| 198 | A | HOOC-CH=CH-C(O)CH₃ (trans) | 1-methylpiperidin-3-yl carbonyl | 560 ([M − H]⁻) |
| 199 | A | H₃CO-CH₂CH₂-C(O)CH₃ | 1-methylpiperidin-3-yl carbonyl | 548 ([M − H]⁻) |
| 200 | A | 3-acetylcyclohexane-1-carboxylic acid | 1-methylpiperidin-3-yl carbonyl | 616 ([M − H]⁻) |
| 201 | A | CH₃C(O)-CH₂CH₂-C(O)CH₃ | 1-methylpiperidin-3-yl carbonyl | 560 ([M − H]⁻) |
| 202 | C | HOOC-CH₂-NH-C(O)CH₃ | 1-methylpiperidin-3-yl carbonyl | 563 ([M − H]⁻) |

-continued

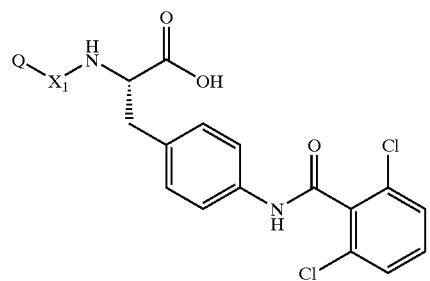

| ex# | Method | Q | X₁ | MS (m/z) |
|---|---|---|---|---|
| 203 | A | 3,4-dimethoxyphenyl C(O) (H₃CO, H₃CO substituents) | 1-methylpiperidin-3-yl C(O) | 626 ([M − H]⁻) |
| 204 | A | 2-carboxyphenyl C(O) (COOH) | 1-methylpiperidin-3-yl C(O) | 610 ([M − H]⁻) |
| 205 | A | 3-carboxyphenyl C(O) (COOH) | 1-methylpiperidin-3-yl C(O) | 610 ([M − H]⁻) |
| 206 | A | 6-carboxynaphth-2-yl C(O) (HOOC) | 1-methylpiperidin-3-yl C(O) | 660 ([M − H]⁻) |
| 207 | A | 5-carboxypyridin-3-yl C(O) (HOOC) | 1-methylpiperidin-3-yl C(O) | 611 ([M − H]⁻) |
| 208 | C | 4-carboxyphenyl-NH-C(O)- (HOOC) | 1-methylpiperidin-3-yl C(O) | 625 ([M − H]⁻) |
| 209 | B | HOOC-CH₂CH₂-C(O)- | 1-methylpiperidin-4-yl C(O) | 562 ([M − H]⁻) |

-continued

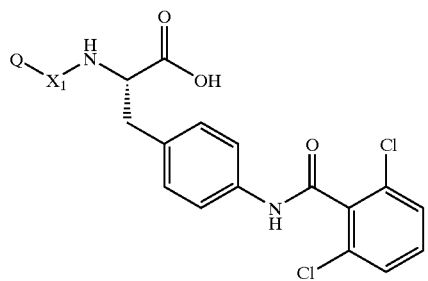

| ex# | Method | Q | X₁ | MS (m/z) |
|---|---|---|---|---|
| 210 | B | cyclopentane-1,1-diyl with CH₂COOH and CH₂C(O)CH₃ | 1-methylpiperidin-4-yl C(O)CH₃ | 630 ([M − H]⁻) |
| 211 | B | HOOC-CH₂-C(CH₃)₂-CH₂-C(O)-CH₃ | 1-methylpiperidin-4-yl C(O)CH₃ | 604 ([M − H]⁻) |
| 212 | B | HOOC-CH=CH-C(O)-CH₃ (cis) | 1-methylpiperidin-4-yl C(O)CH₃ | 560 ([M − H]⁻) |
| 213 | A | HOOC-CH=CH-C(O)-CH₃ (trans) | 1-methylpiperidin-4-yl C(O)CH₃ | 560 ([M − H]⁻) |
| 214 | A | H₃CO-CH₂-CH₂-C(O)- | 1-methylpiperidin-4-yl C(O)CH₃ | 548 ([M − H]⁻) |
| 215 | A | 3-acetylcyclohexane-1-carboxylic acid | 1-methylpiperidin-4-yl C(O)CH₃ | 616 ([M − H]⁻) |
| 216 | A | CH₃-C(O)-CH₂-CH₂-C(O)-CH₃ | 1-methylpiperidin-4-yl C(O)CH₃ | 560 ([M − H]⁻) |
| 217 | C | HOOC-CH₂-NH-C(O)-CH₃ | 1-methylpiperidin-4-yl C(O)CH₃ | 563 ([M − H]⁻) |
| 218 | A | 3,4-dimethoxyphenyl-C(O)-CH₃ | 1-methylpiperidin-4-yl C(O)CH₃ | 626 ([M − H]⁻) |

-continued

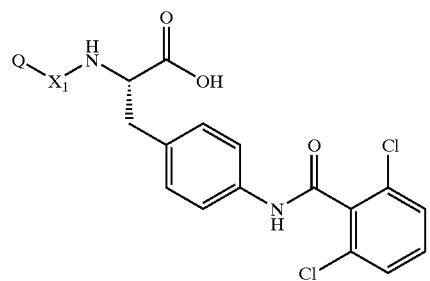

| ex# | Method | Q | X₁ | MS (m/z) |
|---|---|---|---|---|
| 219 | A | 2-acetyl-benzoic acid | 1-methylpiperidin-4-yl carbonyl | 610 ([M − H]⁻) |
| 220 | A | 3-acetyl-benzoic acid | 1-methylpiperidin-4-yl carbonyl | 610 ([M − H]⁻) |
| 221 | A | 6-acetyl-2-naphthoic acid | 1-methylpiperidin-4-yl carbonyl | 660 ([M − H]⁻) |
| 222 | A | 5-acetyl-nicotinic acid | 1-methylpiperidin-4-yl carbonyl | 611 ([M − H]⁻) |
| 223 | C | 4-(acetylamino)benzoic acid | 1-methylpiperidin-4-yl carbonyl | 625 ([M − H]⁻) |
| 224 | B | 4-oxopentanoic acid | 1-methylpyrrolidin-2-yl carbonyl | 548 ([M − H]⁻) |
| 225 | B | 1-(2-oxopropyl)cyclopentane-1-acetic acid | 1-methylpyrrolidin-2-yl carbonyl | 616 ([M − H]⁻) |

-continued

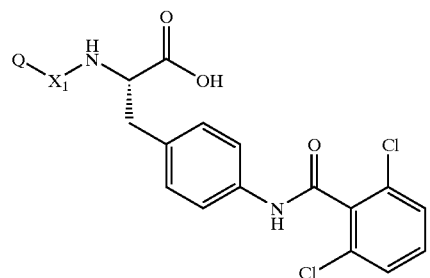

| ex# | Method | Q | X₁ | MS (m/z) |
|---|---|---|---|---|
| 226 | B | (CH₃)₂C(CH₂COOH)CH₂C(O)CH₃ | N-methylpyrrolidine-2-carbonyl | 590 ([M − H]⁻) |
| 227 | B | (Z)-HOOC-CH=CH-C(O)CH₃ | N-methylpyrrolidine-2-carbonyl | 546 ([M − H]⁻) |
| 228 | A | (E)-HOOC-CH=CH-C(O)CH₃ | N-methylpyrrolidine-2-carbonyl | 546 ([M − H]⁻) |
| 229 | A | H₃CO-CH₂CH₂-C(O)CH₃ | N-methylpyrrolidine-2-carbonyl | 534 ([M − H]⁻) |
| 230 | A | 3-acetyl-cyclohexane-1-carboxylic acid | N-methylpyrrolidine-2-carbonyl | 602 ([M − H]⁻) |
| 231 | A | CH₃C(O)CH₂CH₂C(O)CH₃ | N-methylpyrrolidine-2-carbonyl | 546 ([M − H]⁻) |
| 232 | C | HOOC-CH₂-NH-C(O)CH₃ | N-methylpyrrolidine-2-carbonyl | 549 ([M − H]⁻) |
| 233 | A | 3,4-dimethoxyphenyl-C(O)CH₃ | N-methylpyrrolidine-2-carbonyl | 612 ([M − H]⁻) |

-continued
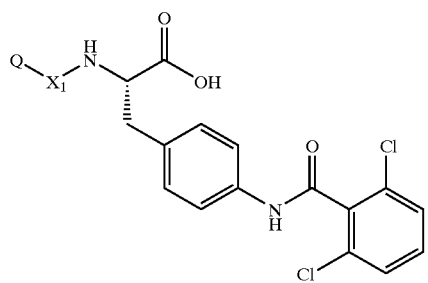
| ex# | Method | Q | X₁ | MS (m/z) |
|---|---|---|---|---|
| 234 | A | 2-acetyl-benzoic acid | N-methyl-prolyl | 596 ([M − H]⁻) |
| 235 | A | 3-acetyl-benzoic acid | N-methyl-prolyl | 596 ([M − H]⁻) |
| 236 | A | 6-acetyl-2-naphthoic acid | N-methyl-prolyl | 646 ([M − H]⁻) |
| 237 | A | 3-acetyl-5-carboxy-pyridine | N-methyl-prolyl | 597 ([M − H]⁻) |
| 238 | C | 4-(acetylamino)benzoic acid | N-methyl-prolyl | 611 ([M − H]⁻) |
| 239 | A | 3-acetyl-pyridine | N-methyl-thiazolidinyl | 571 ([M − H]⁻) |
| 240 | A | 6-acetyl-2-carboxy-pyridine | N-methyl-thiazolidinyl | 615 ([M − H]⁻) |

-continued

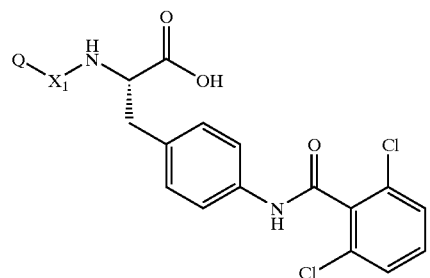

| ex# | Method | Q | X₁ | MS (m/z) |
|---|---|---|---|---|
| 241 | A | 6-acetyl-nicotinic acid (HOOC-pyridine-C(O)CH₃) | N-methyl-thiazolidine-C(O)- | 615 ([M − H]⁻) |
| 242 | A | 4-hydroxy-2-acetyl-quinoline | N-methyl-thiazolidine-C(O)- | 637 ([M − H]⁻) |
| 243 | A | 3-carboxy-5-acetyl-pyrazole | N-methyl-thiazolidine-C(O)- | 604 ([M − H]⁻) |
| 244 | A | 4-carboxy-2-acetyl-thiazolidine | N-methyl-thiazolidine-C(O)- | 625 ([M − H]⁻) |
| 245 | A | 2-acetyl-tetrahydrofuran | N-methyl-thiazolidine-C(O)- | 564 ([M − H]⁻) |
| 246 | A | 3-acetyl-tetrahydrofuran | N-methyl-thiazolidine-C(O)- | 564 ([M − H]⁻) |
| 247 | A | HOOC-CH₂CH₂-C(O)CH₃ | N-methyl-piperidine-C(O)- | 562 ([M − H]⁻) |

-continued

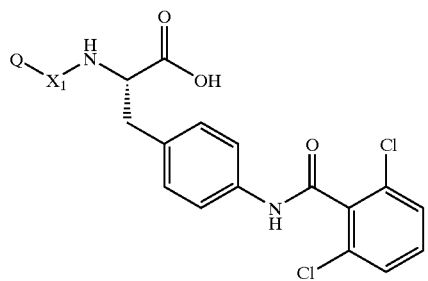

| ex# | Method | Q | X₁ | MS (m/z) |
|---|---|---|---|---|
| 248 | A | HOOC-CH=CH-C(O)-CH₃ | N-methyl piperidine-2-C(O)- | 560 ([M − H]⁻) |
| 249 | A | H₃CO-CH₂-CH₂-C(O)-CH₃ | N-methyl piperidine-2-C(O)- | 548 ([M − H]⁻) |
| 250 | A | HOOC-(pyridin-3,5-diyl)-C(O)- | N-methyl piperidine-2-C(O)- | 611 ([M − H]⁻) |
| 251 | A | HOOC-(pyridin-2,6-diyl)-C(O)- | N-methyl piperidine-2-C(O)- | 611 ([M − H]⁻) |
| 252 | A | (pyridin-3-yl)-C(O)- | N-methyl piperidine-2-C(O)- | 567 ([M − H]⁻) |
| 253 | A | (tetrahydrofuran-2-yl)-C(O)- | N-methyl piperidine-2-C(O)- | 560 ([M − H]⁻) |
| 254 | A | HOOC-CH₂-CH₂-C(O)-CH₃ | N-methyl pyrrolidine-2-C(O)- | 548 ([M − H]⁻) |
| 255 | A | HOOC-CH=CH-C(O)-CH₃ | N-methyl pyrrolidine-2-C(O)- | 546 ([M − H]⁻) |

-continued

| ex# | Method | Q | X₁ | MS (m/z) |
|---|---|---|---|---|
| 256 | A | H₃CO-CH₂CH₂-C(=O)-CH₃ | N-methylpyrrolidine-2-carbonyl | 534 ([M − H]⁻) |
| 257 | A | 5-(HOOC)-pyridin-3-yl-C(=O)-CH₃ | N-methylpyrrolidine-2-carbonyl | 597 ([M − H]⁻) |
| 258 | A | 6-(HOOC)-pyridin-2-yl-C(=O)-CH₃ | N-methylpyrrolidine-2-carbonyl | 597 ([M − H]⁻) |
| 259 | A | pyridin-3-yl-C(=O)-CH₃ | N-methylpyrrolidine-2-carbonyl | 553 ([M − H]⁻) |
| 260 | A | tetrahydrofuran-2-yl-C(=O)-CH₃ | N-methylpyrrolidine-2-carbonyl | 546 ([M − H]⁻) |
| 261 | A | HOOC-CH=CH-C(=O)-CH₃ | N-methylthiazolidine-4-carbonyl | 564 ([M − H]⁻) |
| 262 | A | H₃CO-CH₂CH₂-C(=O)-CH₃ | N-methylthiazolidine-4-carbonyl | 552 ([M − H]⁻) |
| 263 | A | 5-(HOOC)-pyridin-3-yl-C(=O)-CH₃ | N-methylthiazolidine-4-carbonyl | 615 ([M − H]⁻) |

-continued

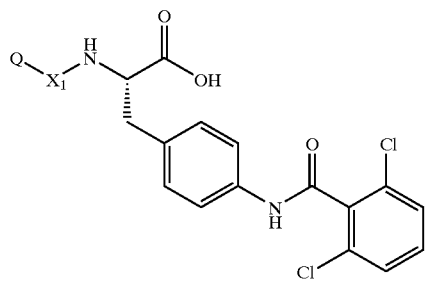

| ex# | Method | Q | X₁ | MS (m/z) |
|---|---|---|---|---|
| 264 | A | HOOC-pyridine-C(=O)- | thiazolidine-C(=O)- | 615 ([M − H]⁻) |
| 265 | A | pyridin-3-yl-C(=O)- | thiazolidine-C(=O)- | 571 ([M − H]⁻) |
| 266 | A | tetrahydrofuran-2-yl-C(=O)- | thiazolidine-C(=O)- | 564 ([M − H]⁻) |

EXAMPLE 267

5-[[[(1S)-1-Carboxy-2-[4-[(2,6-dichlorobenzoyl)amino]phenyl]ethyl]amino]carbonyl]-tetrahydro-γ-oxo-1,4-thiazepine-4(5H)-butanoic Acid

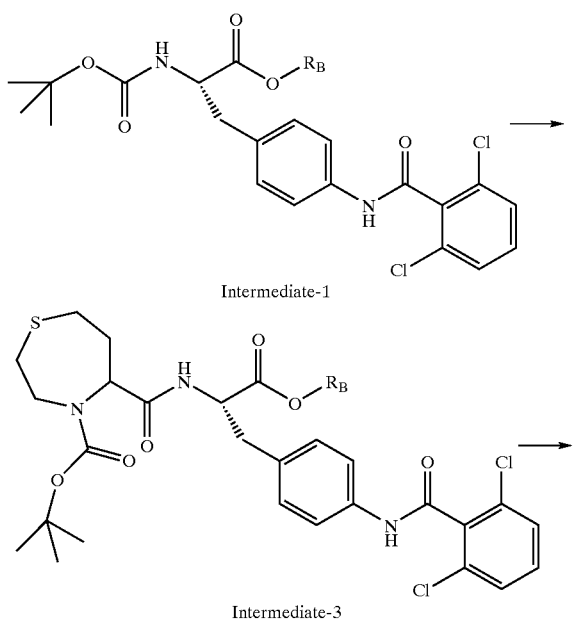

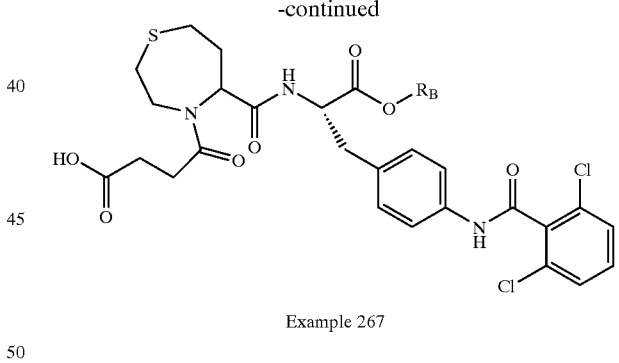

Example 267

The Intermediate-1 (0.3 g, 0.1 95 mmol/g) was pretreated with CH₂Cl₂ (2×3 mL). The swollen resin was then deprotected with 50% TFA/CH₂Cl₂ (3 mL, 30 min). The resin was rinsed in the following order: CH₂Cl₂ (2×3 mL), CH₃OH (2×3 mL), CH₂Cl₂ (2×3 mL). The resin was swollen with DMF (2×3 mL). N-Tert-butoxycarbonyl-1,4-thiazoline-5-carboxylic acid (204 mg, 0.78 mmol) in DMF (2.0 mL) was activated with 0.5 M HBTU/HOBT in DMF (1.6 mL) and DIEA (0.340 mL, 1.95 mmol), then added to the swollen resin. The mixture was vortexed for 2 hr at room temperature. The resin was filtered and washed in the following order: DMF (2×3 mL). CH₂Cl₂ (2×3 mL), CH₃OH (2×3 mL), CH₂Cl₂ (2×3 mL), respectively. If a Kaiser test on a small quantity of the resin is positive (blue) then repeat the coupling procedure until a negative result is obtained. The resin (intermediate-3. 0.2 g, 0.13 mmol/g) was pretreated with CH₂Cl₂ (2×3 mL). The swollen resin was then deprotected with 50% TPA/CH$_2$Cl$_2$ (3 mL, 30 min). The resin was rinsed in the following order: CH$_2$Cl$_2$ (2×3 mL), CH$_3$OH (2×3 mL), CH$_2$Cl$_2$(2×3 mL). The resin was then swollen with DMF (3 mL). Succinic anhydride (78 mg, 0.78 mmol) dissolved in DMF (4 mL) was added to the swollen resin and stirred at 50° C. for 2 hr. Then the resin was filtered and washed in the following order: DMF (2×3 mL), CH$_2$Cl$_2$ (2×3 mL), CH$_3$OH (2×3 mL), CH$_2$Cl$_2$ (2×3 mL) respectively. If a Kaiser test on a small quantity of the resin is positive (blue) then repeat the coupling procedure until a negative result is obtained. The resulting resin was then dried in vacuo to constant weight. The resin was placed in the polypropylene column and pretreated with THF (3 mL). Then THF (3.9 mL), CH$_2$OH (1.2 mL) and 2N LiOH (0.195 mL) were added to the swollen resin. The mixture was vortexed for 15 min and filtered to a clean and preweighed test tube. The resin was next washed with THF/5% CH$_3$OH (2×2 mL) and the combined filtrates were evaporated. The resulting gum was dissolved in H$_2$O (1 mL). The solution was then acidified with 1N HCl to pH 2.0. The precipitate was centrifuged, washed with H$_2$O (2×5 mL) and dried in vacuo to furnish 80 mg of Example 267 as a solid: ESMS (m/z) 594 ([M−H]$^-$).

Scheme O

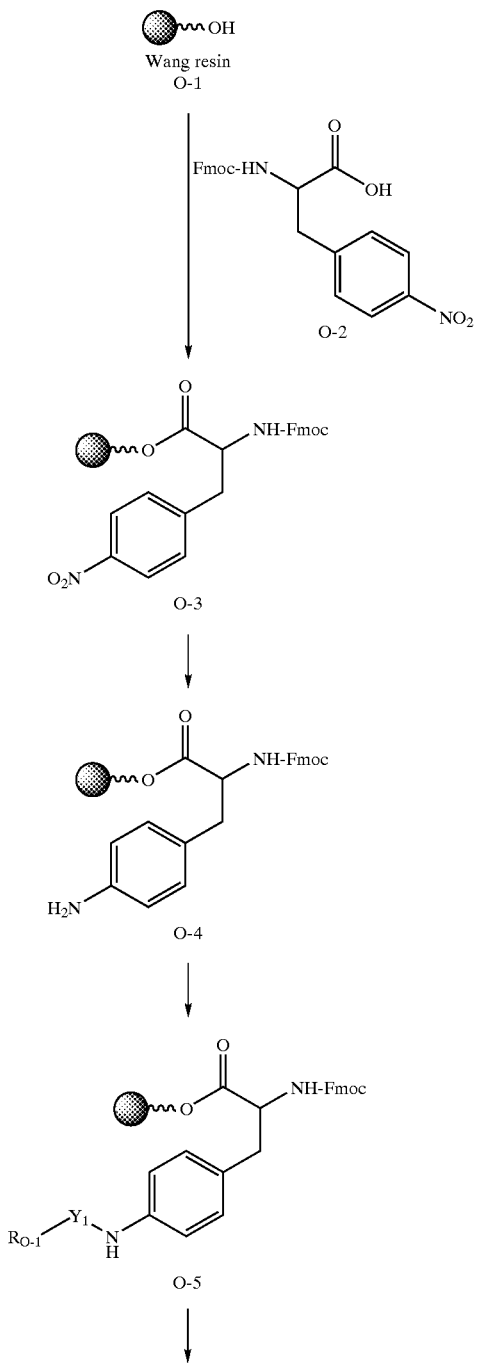

-continued
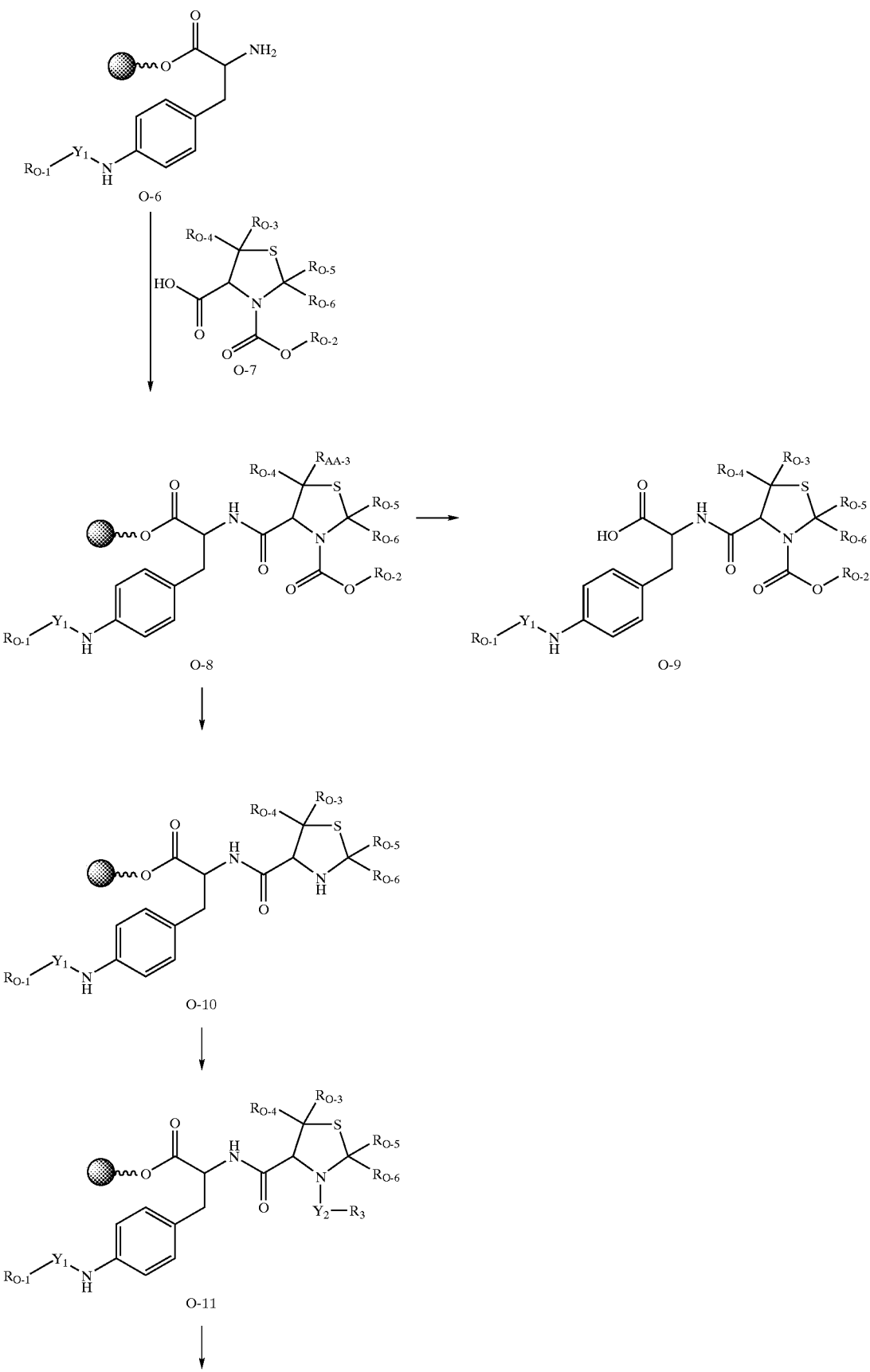

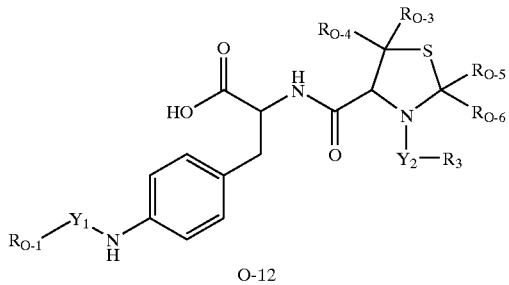

O-12

Where: $R_{O-1}$ is defined as $R_{12}$; $R_{O-2}$ is defined as $C_{1-6}$ alkyl or $C_{7-17}$ arylalkyl; $R_{O-3}$, $R_{O-4}$, and $R_{O-5}$ are defined independently as $R_1$. $R_{O-6}$ is defined as $R_2$. $Y_1$ and $Y_2$ are defined independently as Y.

Scheme O describes a method for the preparation of examples of the formula O-9 and O-12. Commercially available Wang resin (O-1) is acylated with commercially available N-α-Fmoc-Phe(NO$_2$)—OH (O-2) under standard conditions to afford the resin of formula O-3. Reduction of the aromatic nitro group (Meyer et al., *Mol. Diversity* 1995, 1, 13–20) affords the resin bound aniline (O-4) which may be reacted with a variety of electrophilic reagents to afford resin bound amides (O-5 where Y, is C(=O)), ureas (O-5 where $Y_1$ is C(=O)NH), sulfonamides (O-5 where $Y_1$ is SO$_2$), and carbamates (O-5 where $Y_1$ is C(=O)O). Removal of the Fmoc group under standard conditions provides amine of general structure O-6 which is acylated using standard solid-phase peptide synthesis conditions (Atherton, E.; Sheppard R. C. *Solid Phase Peptide Synthesis: A Practical Approach*; IRL Press at Oxford University Press: Oxford, 1989) with a commercially available or readily prepared thiazolidine-4-carboxylic acid of general formula O-7 to afford the resin bound intermediate O-8. Mild cleavage under standard conditions (Atherton, E.; Sheppard R. C. *Solid Phase Peptide Synthesis: A Practical Approach*; IRL Press at Oxford University Press: Oxford, 1989) affords the acid of general structure O-9. In those cases where $R_{O-2}$ is a 9-fluorenylmethyl group, standard Fmoc group removal affords the amine of general structure O-10, which may be reacted with a variety of electrophilic reagents as described in Scheme A to afford resin bound amides, ureas, sulfonamides and carbamates of general structure O-11. Mild cleavage under standard conditions affords the acid of general structure O-12.

PREPARATION 79 AND EXAMPLE 268

(4S)-4-[[[(1S)-1-Carboxy-2-[4-[(benzoyl)amino]phenyl]ethyl]amino]carbonyl]-3-thiazolidinecarboxylic Acid 3-Ethyl Ester

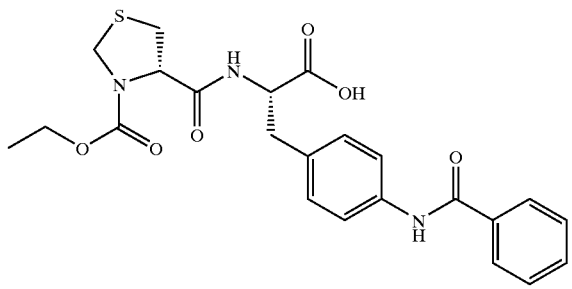

To a mixture of Wang resin (1% DVB, Advanced Chemtech, 2.75 g, 2.20 mmol based on manufacture's loading of 0.8 mmol/g resin) in DMF (12 mL) was added N-α-Fmoc-Phe(NO$_2$)—OH, O-2 (Advanced Chemtech, 1.90 g, 4.40 mmol) at room temperature. After mixing for 10 min (by passing a slow stream of nitrogen through the mixture) pyridine (587 μL, 7.26 mmol) and 2,6-dichlorobenzoyl chloride (630 μL, 4.40 mmol) were added. The mixture was agitated overnight via nitrogen bubbling, filtered, washed with DMF, methylene chloride and methanol and dried in vacuo. In order to cap any unreacted hydroxymethyl groups, the resin was suspended in dichloroethane (5 mL) and to this mixture was added benzoyl chloride (0.75 mL) and pyridine (0.75 mL). The mixture was agitated for 2 h, filtered, washed with DMF, methylene chloride, methanol, methylene chloride and methanol, and dried in vacuo to afford the resin O-3 (3.30 g). IR (diamond anvil) 1733, 1606 (resin), 1520 (resin), 1494 (resin), 1452 (resin), 1347, 1247, 1174, 1029 cm$^{-1}$.

To the prewashed (2×20 mL DMF) resin O-3 (1.0 g, ca. 0.6 mmol based on an adjusted loading of 0.6 mmol/g) was added SnCl$_2$.2H$_2$O (6 mL of a 2M solution in DMF, 12 mmol). The viscous suspension was agitated for 4 hours by nitrogen bubbling, filtered and washed with DMF (2×20 mL). The resin was resuspended with SnCl$_2$.2H$_2$O (6 mL of a 2M solution in DMF, 12 mmol), agitated overnight via nitrogen bubbling, filtered, washed extensively with DMF, water, 2-propanol, methylene chloride and methanol and dried in vacuo to afford the resin O-4. Examination of the FTIR spectra of a small sample of resin O-4 failed to exhibit an absorption at 1347 cm$^{-1}$.

To a mixture of prewashed (2×20 mL CH$_2$Cl$_2$) resin O-4 (0.30 g, ca. 0.18 mmol based on an adjusted loading of 0.6 mmol/g) in 1,2-dichloroethane (3 mL) was added benzoyl chloride (174 μL, 1.50 mmol) and DIEA (313 μL, 1.80 mmol). The mixture was agitated overnight via nitrogen bubbling, filtered, washed with methylene chloride, DMF, methanol, and methylene chloride and dried in vacuo to afford resin O-5. To a mixture of resin O-5 in methylene chloride (5 mL) was added a solution of piperidine in DMF (30%, 5 mL). A slow stream of nitrogen was bubbled through the mixture to effect mixing for 20 min. The resin was filtered, washed with DMF and resuspended in a solution of piperidine in DMF (30%, 10 ml). After gentle mixing for 40 min, the resin was filtered and washed with DMF, methylene chloride, methanol and methylene chloride and diluted with DMF (40 mL). To this mixture was added N-ethoxycarbonyl-D-thiazolidine-4-carboxylic acid (O-7, 0.15 g, 0.72 mmol), HOBt (0.11 g, 0.72 mmol), PyBOP (0.37 g, 0.72 mmol) and DIEA (313 μL, 1.80 mmol). The reaction was mixed for 4 h at which point the qualitative Kaiser test was negative. The resin was filtered and washed with DMF, methylene chloride and MeOH and dried in vacuo to afford resin O-8. After swelling with a minimum of

EXAMPLE 269

(4S)-4-[[[(1S)-1-Carboxy-2-[4-[(acetyl)amino]phenyl]ethyl]amino]carbonyl]-3-thiazolidinecarboxylic Acid 3-Ethyl Ester

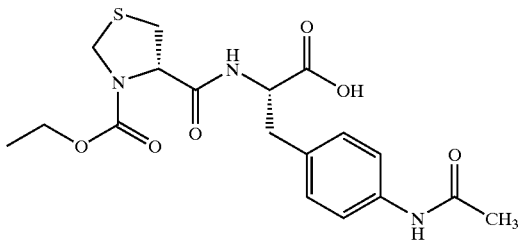

The title compound was prepared as described in Scheme O using acetyl chloride to form the requisite amide. Physical data as follows: IR (drift) 3311, 1709, 1667, 1602, 1536, 1517, 1412, 1378, 1344, 1321, 1266, 1218, 1185, 1116, 769 cm$^{-1}$; $^1$H NMR (300 MHz, DMSO-d$_6$) δ 9.79 (1H), 8.15 (1H), 7.37 (2H), 7.02 (2H), 4.54 (2H), 4.31 (1H), 4.19 (1H), 3.95 (2H), 3.12 (1H), 2.93 (1H), 2.75 (1H), 1.82 (3H), 1.09 (3H); $^{13}$C NMR (75 MHz, DMSO-d$_6$) δ 173.2, 169.8, 168.5, 154.0, 138.2, 132.4, 129.8, 119.1, 62.1, 61.7, 53.9, 36.7, 24.4, 21.5, 14.8; MS (ESI+) for C$_{18}$H$_{23}$N$_3$O$_6$S m/z 410.0 (M+H)$^+$; MS (ESI−) for C$_{18}$H$_{23}$N$_3$O$_6$S m/z 408.0 (M−H)$^-$; MS (FAB) m/z (rel. intensity) 410 (MH$^+$, 99), 486 (20), 411 (22), 410 (99), 409 (9), 205 (22), 188 (9), 177 (9), 160 (35), 148 (9), 88 (14); HRMS (FAB) calcd for C$_{18}$H$_{23}$N$_3$O$_6$S+H$_1$ 410.1385, found 410.1379, Anal. Calcd for C$_{18}$H$_{23}$N$_3$O$_6$S.0.3H$_2$O: C, 52.11; H, 5.73; N, 10.13. Found: C, 51.73; H, 5.73; N, 9.82.

EXAMPLE 270

(4S)-4-[[[(1S)-1-Carboxy-2-[4-[(3-phenylpropanoyl)amino]phenyl]ethyl]amino]carbonyl]-3-thiazolidinecarboxylic Acid 3-Ethyl ester

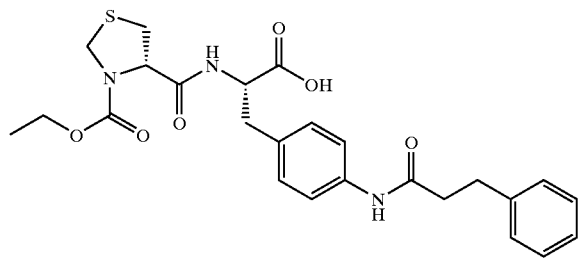

The title compound was prepared as described in Scheme O using hydrocinnamoyl chloride to form the requisite amide. Physical data as follows: IR (drift) 3311, 2978, 2930, 1665, 1601, 1534, 1517, 1413, 1379, 1344, 1252, 1216, 1187, 1115, 700 cm$^{-1}$; $^1$H NMR (300 MHz, CDCl$_3$/CD$_3$OD (10%)) δ 7.34 (2H), 7.21 (5H), 7.02 (2H), 4.67 (3H), 4.30 (1H), 4.09 (2H), 3.11 (4H), 2.97 (2H), 2.58 (2H), 1.19 (3H); $^{13}$C NMR (75 MHz, CDCl$_3$) δ 172.7, 171.3, 170.0, 154.8, 140.7, 137.0, 131.6, 129.7, 128.4, 128.2, 126.2, 119.9, 63.0, 62.6, 53.1, 38.9, 36.7, 31.5, 29.6, 14.2; MS (ESI+) for C$_{25}$H$_{29}$N$_3$O$_6$S m/z 500.2 (M+H)$^+$; MS (ESI−) for C$_{25}$H$_{29}$N$_3$O$_6$S m/z 498.3 (M−H)$^-$; Anal. Calcd for C$_{25}$H$_{29}$N$_3$O$_6$S: C, 60.10; H, 5.85; N, 8.41. Found: C, 59.85; H, 6.07; N, 8.09.

EXAMPLE 271

(4S)-4-[[[(1S)-1-Carboxy-2-[4-[(3-pyridinylcarbonyl)amino]phenyl]ethyl]amino]carbonyl]-3-thiazolidinecarboxylic Acid 3-Ethyl Ester

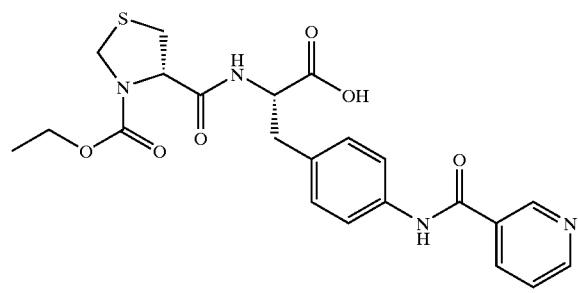

The title compound was prepared as described in Scheme O using nicotinoyl chloride to form the requisite amide. Physical data as follows: IR (drift) 3301, 3061, 2983, 2935, 1709, 1675, 1603, 1535, 1517, 1415, 1380, 1345, 1326, 1204, 1140 cm$^{-1}$; $^1$H NMR (300 MHz, DMSO-d$_6$) δ 12.74 (1H), 10.42 (1H), 9.11 (1H), 8.76 (1H), 8.29 (2H), 7.67 (2H), 7.55 (1H), 7.19 (2H), 4.62 (2H), 4.44 (1H), 4.29 (1H), 4.05 (2H), 3.24 (1H), 3.04 (1H), 2.88 (2H), 1.15 (3H); $^{13}$C NMR (75 MHz, DMSO-d$_6$) δ 173.1, 170.0, 164.3, 154.0, 152.4, 149.0, 137.7, 135.9, 133.5, 131.1, 129.8, 123.9, 120.5, 62.4, 61.8, 15 53.8, 36.7, 14.8; MS (ESI+) for C$_{22}$H$_{24}$N$_4$O$_6$S m/z 473.3 (M+H)$^+$; MS (ESI−) for C$_{22}$H$_{24}$N$_4$O$_6$S m/z 471.3 (M−H)$^-$; HRMS (FAB) calcd for C$_{22}$H$_{24}$N$_4$O$_6$S+H$_1$ 473.1494, found 473.1509.

--- methylene chloride (ca. 0.5 mL), the resin O-8 was suspended with 95% aqueous TFA (5 mL). The mixture was mixed by magnetic stirring for 1 h, filtered and washed with TFA (2×3 mL) and methylene chloride. The combined filtrates were evaporated in vacuo to afford a residue that was purified by flash chromatography using methylene chloride/methanol (2%) containing glacial acetic acid (0.1%) as eluant to afford the title compound (80 mg). Lyophilization from glacial acetic acid afforded an amorphous powder: IR (drift) 3311, 3298, 1670, 1601, 1579, 1531, 1487, 1412, 1380, 1345, 1324, 1265, 1205, 1190, 709 cm$^{-1}$; $^1$H NMR (300 MHz, DMSO-d$_6$) δ 10.39 (1H), 8.39 (1H), 8.14 (2H), 7.86 (2H), 7.74 (3H), 7.36 (2H), 4.83 (2H), 4.59 (1H), 4.48 (1H), 4.22 (2H), 3.48 (2H), 3.26 (1H), 3.06 (2H), 1.35 (3H); $^{13}$C NMR (75 MHz, DMSO-d$_6$) δ 173.4, 169.8, 165.8, 154.0, 138.0, 135.4, 133.3, 131.9, 129.8, 128.8, 128.0, 120.4, 61.8, 54.2, 48.8, 36.7, 14.8; MS (ESI+) for C$_{23}$H$_{25}$N$_3$O$_6$S m/z 472.0 (M+H)$^+$; MS (ESI−) for C$_{23}$H$_{25}$N$_3$O$_6$S m/z 470.1 (M−H)$^-$; MS (FAB) m/z (rel. intensity) 472 (MH$^+$, 99), 472 (99), 472 (99), 371 (31), 160 (31), 81 (31), 71 (45), 69 (46), 57 (71), 55 (58), 43 (47), 41 (42); HRMS (FAB) calcd for C$_{23}$H$_{25}$N$_3$O$_6$S+H$_1$ 472.1542, found 472.1563; Anal. Calcd for C$_{23}$H$_{25}$N$_3$O$_6$S.1.5H$_2$O: C, 55.41; H, 5.66; N, 8.43. Found: C, 55.47; H, 5.21; N, 8.00.

EXAMPLE 272

(4S)-4-[[[(1S)-1-Carboxy-2-[4-[(4-methoxybenzoyl)amino]phenyl]ethyl]amino]carbonyl]-3-thiazolidinecarboxylic Acid 3-Ethyl Ester

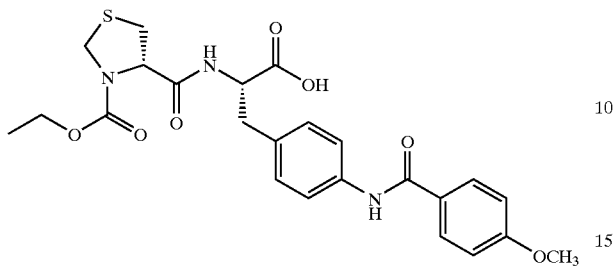

The title compound was prepared as described in Scheme O using p-anisoyl chloride to form the requisite amide. Physical data as follows: IR (drift) 1709, 1667, 1604, 1532, 1514, 1439, 1412, 1379, 1343, 1323, 1255, 1221, 1178, 1027, 763 cm$^{-1}$; $^1$H NMR (300 MHz, CDCl$_3$/CD$_3$OD (10%)) δ 7.79 (2H), 7.47 (2H), 7.05 (2H), 6.87 (2H), 4.68 (2H), 4.58 (1H), 4.28 (1H), 4.07 (2H), 3.79 (3H), 3.66 (2H), 3.04 (4H), 1.17 (3H); $^{13}$C NMR (75 MHz, CDCl$_3$) δ 177.9, 174.0, 170.1, 166.3, 158.8, 141.1, 135.8, 133.7, 133.0, 130.8, 124.6, 117.7, 66.9, 66.6, 59.3, 40.7, 33.5, 24.5, 18.2; MS (ESI+) for C$_{24}$H$_{27}$N$_3$O$_7$S m/z 502.0 (M+H)$^+$; MS (ESI−) for C$_{24}$H$_{27}$N$_3$O$_7$S m/z 500.1 (M−H)$^−$; MS (FAB) m/z (rel. intensity) 502 (MH$^+$, 52), 503 (17), 502 (52), 297 (12), 240 (12), 160 (21), 135 (99), 88 (12), 73 (20), 69 (13), 57 (12); HRMS (FAB) calcd for C$_{24}$H$_{27}$N$_3$O$_7$S+H$_1$ 502.1648, found 502.1657, Anal. Calcd for C$_{24}$H$_{27}$N$_3$O$_7$S.0.3H$_2$O: C, 56.86; H, 5.49; N, 10 8.29. Found: C, 56.65; H, 5.34; N, 7.92.

EXAMPLE 273

(4S)-4-[[[(1S)-1-Carboxy-2-[4-[(4-methylbenzoyl)amino]phenyl]ethyl]amino]carbonyl]-3-thiazolidinecarboxylic Acid 3-Ethyl Ester

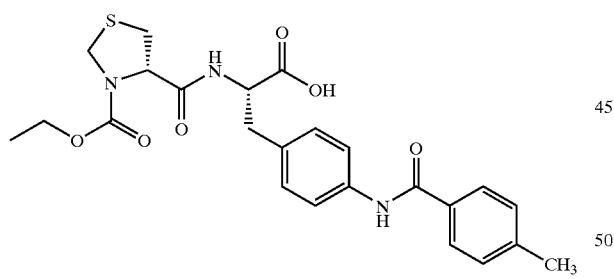

The title compound was prepared as described in Scheme O using p-tolouyl chloride to form the requisite amide. Physical data as follows: IR (drift) 3310, 2981, 2929, 1671, 1608, 1599, 1531, 1517, 1413, 1379, 1344, 1324, 1265, 1210, 1188 cm$^{-1}$; $^1$H NMR (300 MHz, DMSO-d$_6$) δ 10.10 (1H), 8.24 (1H), 7.85 (2H), 7.67 (2H), 7.33 (2H), 7.17 (2H), 4.62 (2H), 4.41 (1H), 3.28 (2H), 4.02 (2H), 3.23 (1H), 3.04 (1H), 2.87 (2H), 2.38 (3H), 1.15 (3H); $^{13}$C NMR (75 MHz, DMSO-d$_6$) δ 173.2, 169.8, 165.6, 154.0, 141.9, 138.1, 133.1, 132.5, 129.7, 129.7, 128.1, 120.4, 62.4, 61.8, 54.0, 36.7, 21.4, 14.8; MS (ESI+) for C$_{24}$H$_{27}$N$_3$O$_6$S m/z 486.2 (M+H)$^+$; HRMS (FAB) calcd for C$_{24}$H$_{27}$N$_3$O$_6$S+H$_1$ 486.1699, found 486.1713; Anal. Calcd for C$_{24}$H$_{27}$N$_3$O$_6$S.0.3H$_2$O: C, 58.71; H, 5.67; N, 8.56. Found: C, 58.37; H, 5.67; N, 8.35.

EXAMPLE 274

(4S)-4-[[[(1S)-1-Carboxy-2-[4-[[2-(trifluoromethyl)benzoyl]amino]phenyl]ethyl]amino]carbonyl]-3-thiazolidinecarboxylic Acid 3-Ethyl Ester

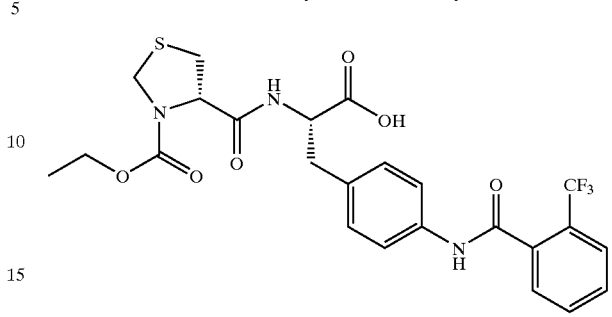

The title compound was prepared as described in Scheme O using (2-trifluoromethyl)benzoyl chloride to form the requisite amide. Physical data as follows: IR (drift) 3295, 1709, 1663, 1603, 1533, 1518, 1414, 1380, 1344, 1316, 1269, 1176, 1132, 1108, 769 cm$^{-1}$; $^1$H NMR (300 MHz, DMSO-d$_6$) δ 10.48 (1H), 8.23 (1H), 7.77 (2H), 7.58 (2H), 7.17 (2H), 4.64 (2H), 4.44 (1H), 4.29 (1H), 3.99 (2H), 3.24 (1H), 3.05 (2H), 1.09 (3H); $^{13}$C NMR (75 MHz, DMSO-d$_6$) δ 173.2, 169.2, 165.8, 154.1, 137.8, 136.7, 133.0, 130.4, 129.9, 128.9, 126.7, 126.4, 126.0, 119.8, 62.2, 61.8, 54.0, 37.1, 14.7; MS (ESI+) for C$_{24}$H$_{25}$F$_3$N$_3$O$_6$S m/z 540.0 (M+H)$^+$; MS (ESI−) for C$_{24}$H$_{25}$F$_3$N$_3$O$_6$S m/z 540.0 (M−H)$^−$; HRMS (FAB) calcd for C$_{24}$H$_{24}$F$_3$N$_3$O$_6$S+H$_1$ 540.1416, found 540.1423; Anal. Calcd for C$_{24}$H$_{24}$F$_3$N$_3$O$_6$S.0.5H$_2$O: C, 51.49; H, 4.70; N, 7.83. Found: C, 51.42; H, 4.42; N, 7.45.

EXAMPLE 275

(4S)-4-[[[(1S)-1-Carboxy-2-[4-[(2,4,6-trichlorobenzoyl)amino]phenyl]ethyl]amino]-carbonyl]-3-thiazolidinecarboxylic Acid 3-Ethyl Ester

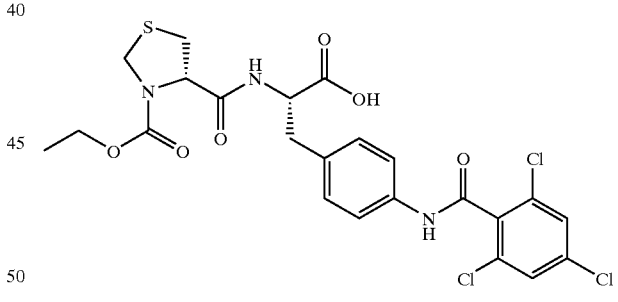

The title compound was prepared as described in Scheme O using 2,4,6-trichlorobenzoyl chloride to form the requisite amide. Physical data as follows: IR (drift) 3286, 2926, 1709, 1664, 1604, 1578, 1542, 1517, 1413, 1379, 1345, 1325, 1269, 1218, 1187 cm$^{-1}$; $^1$H NMR (300 MHz, CDCl$_3$/CD$_3$OD (10%)) δ 7.58 (2H), 7.41 (2H), 7.20 (2H), 4.84 (2H), 4.69 (1H), 4.41 (1H), 4.19 (2H), 3.27 (4H), 1.26 (3H); $^{13}$C NMR (75 MHz, DMSO-d$_6$) δ 173.0, 169.8, 161.5, 154.0, 137.2, 135.9, 135.1, 133.9, 132.6, 130.1, 128.5, 119.6, 62.2, 61.7, 54.0, 36.7, 14.8; MS (FAB) m/z (rel. intensity) 574 (MH$^+$, 95), 576 (96), 574 (95), 160 (99), 91 (79), 88 (40), 69 (64), 57 (59), 55 (59), 43 (56), 41 (39); HRMS (FAB) calcd for C$_{23}$H$_{22}$Cl$_3$N$_3$O$_6$S+H$_1$ 574.0373, found 574.0364, Anal. Calcd for C$_{23}$H$_{22}$Cl$_3$N$_3$O$_6$S: C, 48.06; H, 3.86; N, 7.31; Cl, 18.50. Found: C, 48.52; H, 4.13; N, 7.08.

EXAMPLE 276

(4S)-4-[[[(1S)-1-Carboxy-2-[4-[[(2,5-dichlorophenyl)sulfonyl]amino]phenyl]ethyl]amino]carbonyl]-3-thiazolidinecarboxylic Acid 3-Ethyl Ester

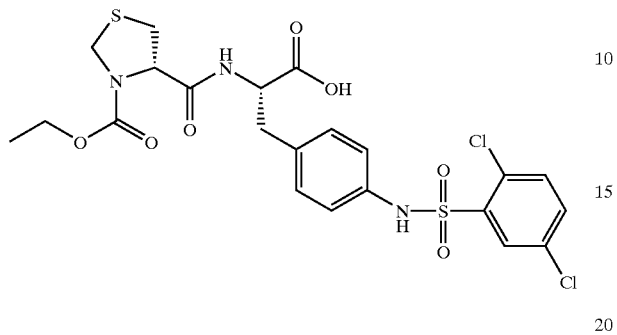

The title compound was prepared as described in Scheme O using 2,5-dichlorobenzene sulfonyl chloride to form the requisite sulfonamide. Physical data as follows: IR (drift) 1709, 1676, 1531, 1512, 1450, 1428, 1409, 1378, 1344, 1221, 1167, 1143, 1113, 1101, 1041 cm$^{-1}$; $^1$H NMR (300 MHz, DMSO-d$_6$) δ 8.36 (1H), 7.90 (3H), 7.20 (2H), 7.12 (2H), 4.70 (2H), 4.47 (1H), 4.34 (1H), 4.10 (2H), 3.19 (4H), 1.27 (3H); $^{13}$C NMR (75 MHz, DMSO-d$_6$) δ 173.0, 169.8, 153.9, 138.7, 135.5, 134.8, 134.1, 132.6, 131.0, 130.5, 130.0, 120.0, 62.4, 61.7, 53.5, 36.3, 14.8; MS (FAB) m/z (rel. intensity) 576 (MH$^+$, 99), 652 (27), 578 (83), 577 (31), 576 (99), 160 (98), 106 (47), 88 (40), 81 (32), 69 (31), 57 (28); HRMS (FAB) calcd for C$_{22}$H$_{23}$Cl$_2$N$_3$O$_7$S+H$_1$ 576.0433, found 576.0400, Anal. Calcd for C$_{22}$H$_{23}$Cl$_2$N$_3$O$_7$S$_2$·0.1H$_2$O: C, 45.70; H, 4.04; N, 7.27. Found: C, 45.94; H, 4.04; N, 6.87.

EXAMPLE 277

(4S)-4-[[[(1S)-1-Carboxy-2-[4-[[[(2,6-dichlorophenyl)amino]carbonyl]amino]phenyl]ethyl]amino]carbonyl]-3-thiazolidinecarboxylic Acid 3-Ethyl Ester

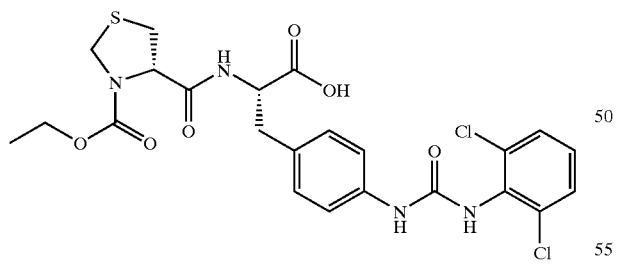

The title compound was prepared as described in Scheme O using 2,6-dichlorophenyl isocyanate to form the requisite urea. Physical data as follows: IR (drift) 3284, 3277, 1709, 1655, 1600, 1569, 1544, 1452, 1431, 1415, 1347, 1238, 1217, 1195, 771 cm$^{-1}$; $^1$H NMR (300 MHz, DMSO-d$_6$) δ 9.09 (1H), 8.41 (1H), 8.09 (1H), 7.52 (2H), 7.31 (3H), 7.08 (2H), 4.62 (2H), 4.35 (1H), 4.28 (1H), 3.27 (1H), 3.02 (1H), 2.85 (2H), 1.10 (3H); $^{13}$C NMR (75 MHz, DMSO-d$_6$) δ 173.6, 169.8, 154.0, 152.8, 138.7, 134.4, 133.9, 131.3, 130.0, 128.8, 128.7, 118.1, 62.4, 61.8, 54.3, 36.7, 14.8;

HRMS (FAB) calcd for C$_{23}$H$_{24}$Cl$_2$N$_4$O$_6$S+H$_1$ 555.0872, found 555.0877, Anal. Calcd for C$_{23}$H$_{24}$Cl$_2$N$_4$O$_6$S·2H$_2$O: C, 46.71; H, 4.77; N, 9.47. Found: C, 47.08; H, 4.53; N, 9.06.

Scheme P

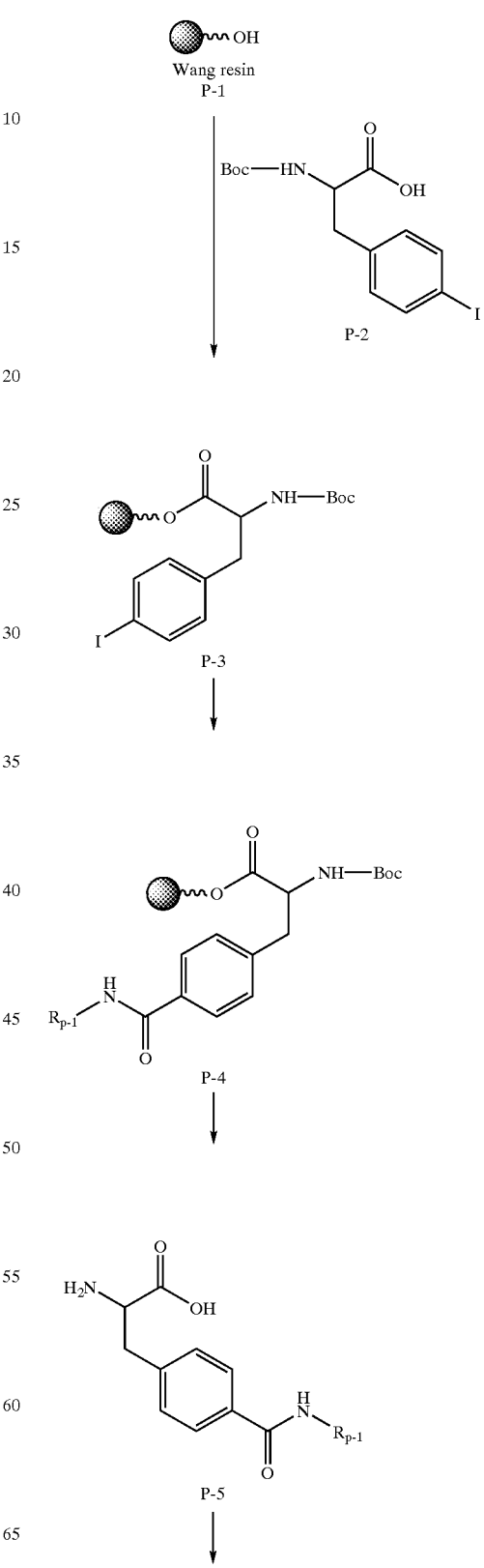

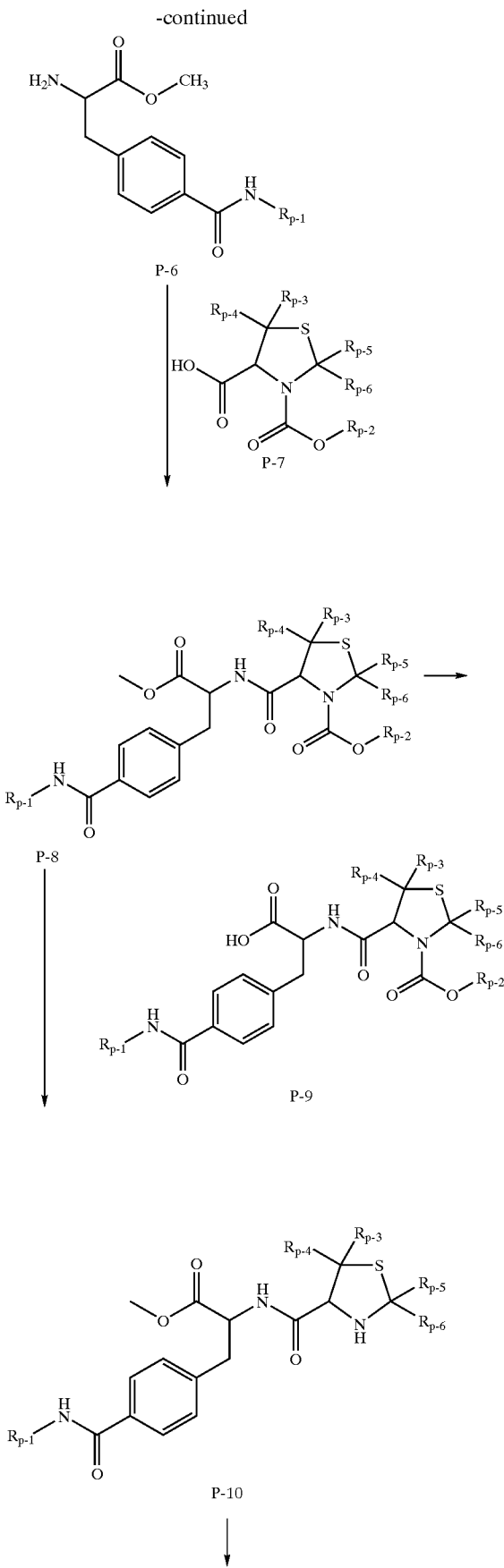

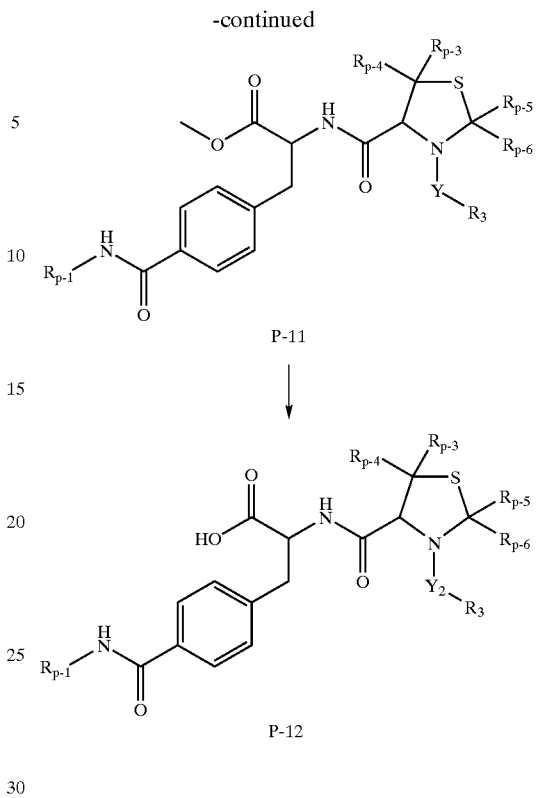

Where: $R_{P-1}$ is defined as $R_{12}$; $R_{P-2}$ is defined as $C_{1-6}$ alkyl or $C_{7-17}$ arylalkyl; $R_{P-3}$, $R_{P-4}$, and $R_{P-5}$ are defined independently as $R_1$. $R_{P-6}$ is defined as $R_2$.

Scheme P describes a method for the preparation of examples of the formula P-9 and P-12. Commercially available Wang resin (P-1) is acylated with commercially available N-α-Boc-Phe(I)—OH (P-2) under standard conditions to afford the resin of formula P-3. Carbonylation of the resin bound aryl iodide with carbon monoxide and an amine in the presence of a source of palladium(0) affords the resin bound amide of general formula P-5 (for a general review of carbonylation chemistry, see: Colquhoun, H. M.; Thompson, D. J.; Twigg, M. V. *Carbonylation* Plenum Press: New York, 1991). Mild cleavage under standard conditions affords the amino acid of general structure P-5 which is esterified under mild acid catalysis to afford the amino ester of general structure P-6. Condensation with a commercially available or readily prepared thiazolidine-4-carboxylic acid of general formula P-7 under conditions described in Scheme A affords the pseudodipeptide of general structure P-8. Mild base hydrolysis of the ester of general structure P-8 affords the acid of general structure P-9. In the case where $R_{P-2}$ is a 9-fluorenylmethyl group, standard Fmoc group removal (Atherton, E.; Sheppard R. C. *Solid Phase Peptide Synthesis: A Practical Approach*; IRL Press at Oxford University Press: Oxford, 1989) affords the amine of general structure P-10, which may be reacted with a variety of electrophilic reagents as described in Scheme A to afford amides, ureas, sulfonamides and carbamates of general structure P-11. Mild base hydrolysis of the ester in general structure P-11 affords the acid of general structure P-12.

PREPARATION 80 AND EXAMPLE 278

(4S)-4-[[[(1S)-1-Carboxy-2-[4-[[(2,4,6-trichlorophenyl)amino]carbonyl]phenyl]ethyl]amino]carbonyl]-3-thiazolidinecarboxylic Acid 3-Ethyl Ester

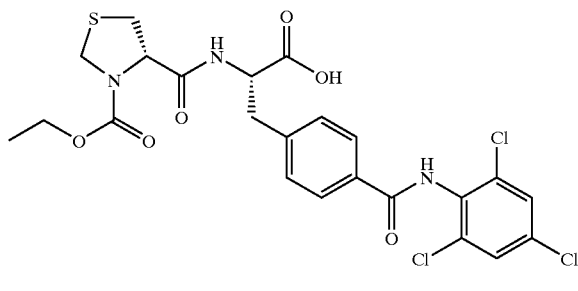

To a cooled (0–50° C.) mixture of Wang polystyrene resin P-1 (Advanced Chemtech, 2.0 g, ca. 1.5 mmol), N-Boc-4-iodo-L-phenylalanine P-2 (Bachem, 4.00 g, 10 mmol), and $PPh_3$ (1.30 g, 5.0 mmol) in THF (20 mL) was added diethyl azodicarboxylate (0.80 mL, 5.0 mmol) in 4 approximately equal portions at 5 min intervals. When the orange color had discharged, the mixture was warmed to ambient temperature and stirred for 5 h. The mixture was diluted with THF (30 mL) and filtered. The resin was washed with DMF, THF and MeOH and dried in vacuo to afford the esterified resin P-3 (2.68 g) as a colorless powder: $^{13}C$ NMR (100 MHz, $CD_2Cl_2$, 4 mm MAS probe) δ 171.86, 155.33, 137.85, 136.40, 131.87, 128.00, 92.74, 80.09, 54.05, 38.05, 28.51.

$N_2$ was bubbled through a mixture of N-Boc4-iodo-L-phenylalanine functionalized Wang resin P-3 (500 mg, ca. 0.3 mmol), $PPh_3$ (0.21 g, 0.8 mmol), 2,4,6-trichloroaniline (0.98 g, 5.0 mmol) and DIEA (3.48 mL, 20 mmol) in NMP (20 mL) for 10 min. $Pd_2dba_3$ (0.18 g, 0.2 mmol) was added and the reaction mixture was placed under a CO atmosphere and heated (bath temp. 70° C.) for 18 h. Upon cooling to ambient temperature, the mixture was diluted with 3% (w/v) sodium diethyldithiocarbamate in 95:5 NMP:DIEA (10 mL). After an additional 10 min, the mixture was filtered and the resin washed with NMP, THF and MeOH and dried in vacuo to afford the functionalized resin P-4 as a colorless powder.

Resin P-4 was swollen with methylene chloride (0.5 mL) and diluted with 95:5 TFA:$H_2O$ (10 mL). After 90 min the mixture was filtered and the resin washed with TFA (3×5 mL) and $CH_2Cl_2$. The combined filtrates were concentrated in vacuo and the residue lyophilized from glacial acetic acid to provide the amino acid P-5 (152 mg) as a powder which was used without purification. Physical data as follows: MS (FAB) m/z (rel. intensity) 387 (M+H, 42), 427 (26), 426 (80), 389 (46), 387 (42), 366 (33), 279 (99), 177 (54), 146 (18), 119 (26), 23 (26); HRMS (FAB) calcd for $C_{16}H_{13}Cl_3N_2O_3+H_1$ 387.0070, found 387.0084.

The amino acid P-5 was dissolved in methanolic HCl (20 mL) and stirred at room temperature for 18 h. Concentration in vacuo afforded the methyl ester P-6 which was used without purification. Physical data as follows: MS (ES+) for $C_{17}H_{15}Cl_3N_2O_3$ m/z 400.9 (M+H)$^+$.

To a cooled (0–5° C.) solution of N-ethoxycarbonyl-D-thiazolidine-4-carboxylic acid P-7 (82 mg, 0.4 mmol) and HOAt (54 mg, 0.4 mmol) in $CH_2Cl_2$/DMF (1:1, 4 mL) was added EDC (76 mg, 0.4 mmol). After stirring for 10 min, the solution was added to the amino ester P-6 described above at 0–5° C. followed by DIEA (208 μL, 1.2 mmol). After an additional 30 min at 0–5° C., the solution was allowed to warm to room temperature and stirred an additional hour. Volatiles were removed in vacuo and the residue partitioned between ethyl acetate and 0.1 N aqueous HCl. The organic layer was separated, washed with 0.1 N aqueous HCl, saturated aqueous $NaHCO_3$, brine, dried ($MgSO_4$), filtered and concentrated in vacuo. Purification of the residue by flash chromatography using $CH_2Cl_2$/ethyl acetate/hexanes (1:1:2) containing 2-propanol (0.1%) as eluant afforded the ester P-8 as a powder: $^1H$ NMR (300 MHz, $CDCl_3$) δ 7.99 (1H), 7.87 (2H), 7.40 (2H), 7.24 (2H), 4.92 (1H), 4.70 (2H), 4.34 (1H), 4.10 (2H), 3.74 (3H), 3.20 (4H), 1.25 (3H); $^{13}C$ NMR (75 MHz, $CDCl_3$) δ 171.2, 169.7, 165.4, 154.9, 140.6, 134.3, 133.4, 132.2, 131.3, 129.7, 128.4, 127.9, 63.1, 62.7, 60.4, 53.0, 52.6, 37.6, 21.0, 14.5; MS (ESI+) for $C_{24}H_{24}Cl_3N_3O_6S$ m/z 589.9 (M+H)$^+$; MS (ESI−) for $C_{24}H_{24}Cl_3N_3O_6S$ m/z 588.0 (M−H)$^-$.

To a cooled (0–5° C.) solution of the ester P-8 (72 mg, 0.12 mmol) in THF (5 mL) and water (0.5 mL) was added an 0.1 N aqueous solution of NaOH (1.3 mL, 0.13 mmol) via a syringe pump over 1 h. After an additional 45 min at 0–5° C., the reaction mixture was diluted with ethyl acetate and acidified with 0.25 N HCl to a pH of ca. 3. The organic layer was separated, washed with water and concentrated in vacuo. Purification of the residue by flash chromatography using methylene chloride and methanol (0–5%) as eluant provided a solid which was crystallized from ethyl acetate/$CH_2Cl_2$/hexanes to afford the title compound (45 mg) as colorless solid: IR (drift) 1743, 1726, 1709, 1691, 1675, 1663, 1553, 1521, 1490, 1428, 1415, 1379, 1345, 1290, 1189 cm$^{-1}$; $^1H$ NMR (300 MHz, DMSO-$d_6$) δ 10.27 (1H), 8.35 (1H), 7.92 (2H), 7.81 (2H), 7.37 (2H), 4.62 (2H), 4.53 (1H), 4.29 (2H), 4.00 (2H), 3.11 (3H), 2.77 (1H), 1.12 (3H); $^{13}C$ NMR (75 MHz, DMSO-$d_6$) δ 172.9, 170.0, 165.4, 154.0, 142.5, 135.5, 133.9, 133.0, 131.6, 129.8, 128.7, 128.0, 62.0, 61.7, 53.4, 37.0, 14.8; MS (FAB) m/z (rel. intensity) 574 (MH$^+$, 80), 576 (80), 574 (80), 379 (99), 160 (82), 91 (95), 81 (72), 69 (93), 57 (86), 55 (86), 43 (90); HRMS (FAB) calcd for $C_{23}H_{22}Cl_3N_3O_6S+H_1$ 574.0373, found 574.0358.

Scheme Q

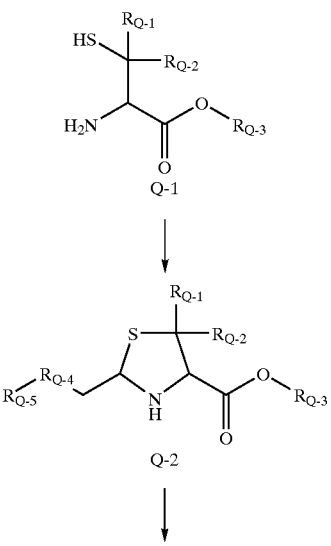

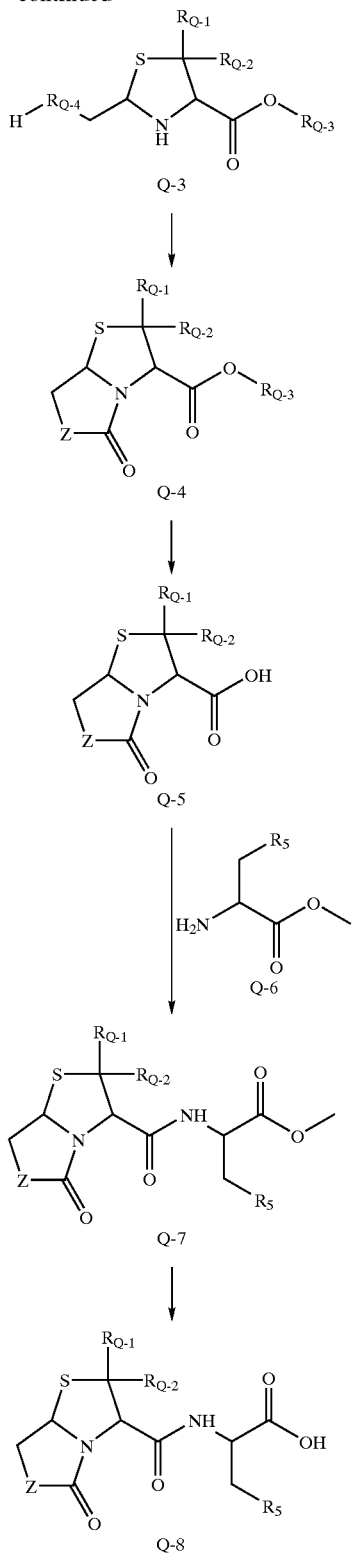

$R_{Q-1}$ and $R_{Q-2}$ are defined independently as $R_1$. $R_{Q-3}$ is defined as $C_{1-6}$ alkyl or $C_{7-17}$ arylalkyl, $R_{Q-4}$ is defined as oxygen or $N-R_{11}$. $R_{Q-5}$ is defined as a suitable protecting group for a nitrogen (such as Boc or Fmoc) or oxygen (such as t-butyldimethylsilyl) (Greene, T. W.; Wuts, P. G. M. *Protective Groups in Organic Synthesis*, John Wiley and Sons, New York, 1991).

Scheme Q describes a general method for the preparation of examples of the formula Q-7. A commercially available or readily prepared sulfur containing amino acid of structure Q-1 is condensed with a suitably protected aldehyde to afford the thiazolidine-4-carboxylic acid of general formula Q-2. Standard deprotection (Greene, T. W.; Wuts, P. G. M. *Protective Groups in Organic Synthesis*, John Wiley and Sons, New York, 1991) affords intermediate Q-3 which is readily cyclized to the bicycle Q-4 using 1,1'-carbonyldiimidazole or phosgene or a suitable equivalent. For the preparation of bicycles of general structure Q-4 in which Z is $CH_2$, see as examples: (a) Aszodi, J.; Bonnet, A.; Teutsch, G. *Tetrahedron* 1990, 46, 1579. (b) Baldwin, J. E.; Lee, V.; Schofield, C. J. *Heterocycles* 1992, 34, 903. (c) Genin, M. J.; Johnson, R. L. *J. Am. Chem. Soc.* 1992, 114, 8778. (d) Siddiqui, M. A.; Preville, P.; Tarazi, M.; Warder, S. E.; Eby, P.; Gorseth, E.; Puumala, K.; DiMaio, J. *Tetrahedron Lett.* 1997, 38, 8807. (e) Subasinghe, M. L.; Bontems, R. J.; McIntee, E.; Mishra, R. K.; Johnson, R. L. *J. Med. Chem.* 1993, 36, 2356. Removal of the ester protecting group affords the acid of general structure Q-5 which is condensed with amino acyl derivative Q-6 under standard peptide synthesis conditions to provide Q-7 (for a review of procedures of peptide synthesis see: Bodansky, M.; Bodansky, A. *The Practice of Peptide Synthesis*; Springer-Verlag: Berlin, 1984). Mild base hydrolysis of the ester of general structure Q-7 provides acid Q-8.

PREPARATION 81

(Scheme Q, Q-2: where $R_{Q-1}$ and $R_{Q-1}$ are equal to hydrogen, $R_{Q-3}$ is ethyl, $R_{Q-4}$ is NH, $R_{Q-5}$ is Boc and stereochemistry is (S)).

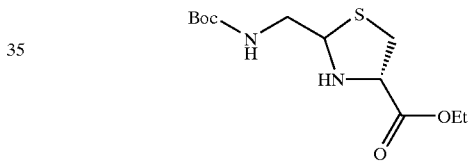

To a suspension of D-cysteine 1.5 hydrate hydrochloride (Q-1, Scheme Q where $R_{Q-1}$ and $R_{Q-1}$ are equal to hydrogen, $R_{Q-3}$ is hydrogen and stereochemistry is (S)) (5 g, 27.1 mmol) in absolute ethyl alcohol (50 mL) was added triethylorthoformate (13.5 mL, 81.2 mmol) at ambient temperature. A stream of anhydrous HCl gas was bubbled through the solution for 30 min. The stream of anhydrous HCl gas was maintained as the mixture heated to 70° C. for 2 h. The reaction mixture was concentrated in vacuo and the resulting residue triturated with diethyl ether to afford D-cysteine ethyl ester (4.43 g) as a white solid which was used without further purification. Physical data as follows: $^1$H NMR (300 MHz, $D_2O$) 4.36 (1H), 4.27 (2H), 3.12 (2H), 1.25 (3H); MS (ESI+) for $C_5H_{11}NO_2S$ m/z 150.0 (M+H)$^+$.

To a solution of D-cysteine ethyl ester (1.89 g, 10.2 mmol) in $H_2O$ (46 mL) was added potassium acetate (1.22 g, 12.4 mmol) and t-butyl N-(2-oxoethyl)carbamate (Aldrich, 2.38 g, 12.0 mmol based on 80% purity as determined by $^1$H NMR) in ethyl alcohol (46 mL) at ambient temperature. After 8 h, the reaction mixture was concentrated in vacuo and the residue purified by flash chromatography using methylene chloride/methanol (1%) as eluant to afford the title compound (1.9 g) as an oil: $^1$H NMR (300 MHz, $CDCl_3$) δ 5.01 (1H), 4.75 (1H), 4.26 (2H), 3.93 (1H), 3.37 (2H), 3.12 (1H), 2.91 (1H), 1.47 (9H), 1.32 (3H); MS (ESI+) for $C_{12}H_{22}N_2O_4S$ m/z 291.1 (M+H)$^+$, MS (ESI−) for $C_{12}H_{22}N_2O_4S$ m/z 288.9 (M−H)$^-$.

PREPARATION 82

(Scheme Q, Q-3: where $R_{Q-1}$ and $R_{Q-1}$ are equal to hydrogen, $R_{Q-3}$ is ethyl, $R_{Q-4}$ is NH, and stereochemistry is (S)).

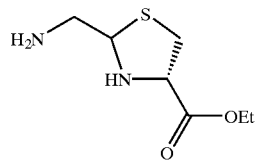

To a cooled (10–15° C.) solution of Q-2 (Scheme Q where $R_{Q-1}$ and $R_{Q-1}$ are equal to hydrogen, $R_{Q-3}$ is ethyl, $R_{Q-4}$ is NH, $R_{Q-5}$ is Boc and stereochemistry is (S)) (1.9 g) in dioxane (38 mL) was added dropwise anhydrous 4 M HCl in dioxane (156 mL). The solution was allowed to warm to ambient temperature and stirred for 2 h. The reaction mixture was concentrated in vacuo and azeotroped three times with methanol which afforded the title compound (1.72 g) as a tacky yellow solid: $^1$H NMR (300 MHz, CDCl$_3$) δ 8.57 (2H), 5.80 (1H), 5.25 (1H), 4.39 (2H), 4.17 (1H), 3.79 (4H), 1.37 (3H); MS (ESI+) for $C_7H_{14}N_2O_2S$ m/z 191.1 (M+H)$^+$, MS (ESI−) for $C_7H_{14}N_2O_2S$·2HCl m/z 261.0 (M−H)$^−$.

PREPARATION 83

(Scheme Q, Q-4: where $R_{Q-1}$ and $R_{Q-1}$ are equal to hydrogen, $R_{Q-3}$ is ethyl, Z is NH, and stereochemistry is (S)).

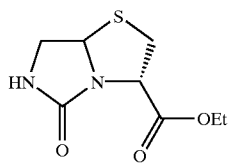

To a cooled (0–5° C.) solution of Q-3 (Scheme Q where $R_{Q-1}$ and $R_{Q-1}$ are equal to hydrogen, $R_{Q-3}$ is ethyl, $R_{Q-4}$ is NH, and stereochemistry is (S)) (1.72 g, 6.54 mmol) in THF (650 mL) was added triethylamine (2.83 mL, 20.3 mmol) and 1,1'-carbonyldiimidazole (1.11 g, 6.87 mmol). After 3 d at ambient temperature, the mixture was recooled (0–5° C.), treated with additional 1,1'-carbonyldiimidazole (530 mg, 3.27 mmol) and allowed to warm to ambient temperature. After 18 h, the reaction mixture was concentrated in vacuo and the resulting residue was partitioned between ethyl acetate and 0.25 N HCl. The organic layer was separated, washed with brine, dried (MgSO$_4$), filtered and concentrated in vacuo. The diastereomeric mixture was separated by chiral chromatography [5×25 cm (R,R) Whelk-O I, 50 mL/min 40% Isopropanol/heptane, 210 nm,]. Further purification of each isolated diastereomer by flash chromatography using methylene chloride/ethyl acetate (25%) as eluant afforded the diastereomers (255 mg, 464 mg) as oils. Physical data for the faster eluting diastereomer (analytical column conditions 0.46×25 cm (R,R) Whelk-O I, 0.5 mL/min 40% IPA/heptane, 210 nm) as follows: $^1$H NMR (300 MHz, CDCl$_3$) δ 5.51 (1H), 5.15 (1H), 4.32 (2H), 3.96 (1H), 3.86 (1H), 3.53 (1H), 3.26 (1H), 3.13 (1H), 1.34 (3H); MS (ESI+) for $C_8H_{12}N_2O_3S$ m/z 217.1 (M+H)$^+$, MS (ESI+) for $C_8H_{12}N_2O_3S$ m/z 239.0 (M+Na)$^+$, MS (ESI−) for $C_8H_{12}N_2O_3S$ m/z 215.1 (M−H)$^−$.).

PREPARATION 84

(Scheme Q, Q-5: where $R_{Q-1}$ and $R_{Q-1}$ are equal to hydrogen, and Z is NH).

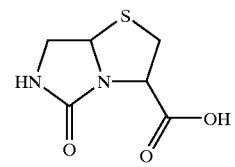

To a cooled (0–5° C.) solution of the faster eluting diastereomer of general structure Q-4 (Scheme Q where $R_{Q-1}$ and $R_{Q-1}$ are equal to hydrogen, $R_{Q-3}$ is ethyl, Z is NH, and stereochemistry is (S)) (100 mg, 0.46 mmol) in THF (13 mL) and H$_2$O (1.5 mL) was added via syringe pump over 1 h 0.1 N NaOH (9.7 mL, 0.97 mmol). The reaction mixture was stirred for 2 h at 0° C., acidified with 1.0 N HCl (0.97 mL) and concentrated in vacuo. The resulting residue was dried over P$_2$O$_5$ in a vacuum desiccator to afford the title compound (87 mg) as a glassy solid which was used without further purification: MS (ESI+) for $C_6H_8N_2O_3S$ m/z 189.0 (M+H)$^+$, MS (ESI+) for $C_6H_8N_2O_3S$ m/z 211.0 (M+Na)$^+$, MS (ESI−) for $C_6H_8N_2O_3S$ m/z 187.0 (M−H)$^−$.

PREPARATION 85

(Scheme Q, Q-7: where $R_{Q-1}$ and $R_{Q-1}$ are equal to hydrogen, Z is NH, $R_5$ is 4-[(2,6-dichlorobenzoyl)amino]phenyl, and stereochemistry of the C-terminal amino acid is (S)).

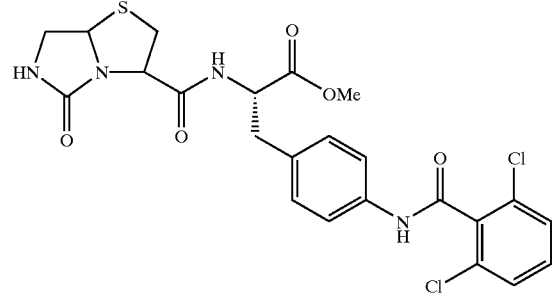

To a cooled (0–5° C.) suspension of Q-5 (Scheme Q where $R_{Q-1}$ and $R_{Q-1}$ are equal to hydrogen, and Z is NH) (87 mg, 0.46 mmol) in methylene chloride (10 mL) was added O-(7-azabenzotriaol-1-yl)-N,N,N',N'-tetramethyluronium hexafluorophosphate (HATU) (175 mg, 0.46 mmol), Q-6 (Scheme Q where $R_5$ is 4-[(2,6-dichlorobenzoyl)amino]phenyl, and stereochemistry is (S)) (204 mg, 0.51 mmol) and N,N-diisopropylethylamine (0.24 mL, 1.38 mmol). After 7 h, the reaction mixture was diluted with methylene chloride, washed with 0.1 N HCl and brine, dried (MgSO$_4$), filtered and concentrated in vacuo. Purification of the residue by flash chromatography using methylene chloride/ethyl acetate (25%) as eluant afforded the title compound (89 mg) as a white solid: $^1$H NMR (300 MHz, CDCl$_3$) δ 7.57 (2H), 7.31 (3H), 7.13 (2H), 4.97 (1H), 4.82 (1H), 4.47 (1H), 3.80 (4H), 3.55 (1H), 3.46 (1H), 3.34 (1H), 3.08 (2H); MS (ESI+) for C$_{23}$H$_{22}$Cl$_2$N$_4$O$_5$S m/z 537.0 (M+H)$^+$, MS (ESI+) for C$_{23}$H$_{22}$Cl$_2$N$_4$O$_5$S m/z 558.9 (M+Na)$^+$.

PREPARATION 86 AND EXAMPLE 279

4-[(2,6-Dichlorobenzoyl)amino]-N-[[(7aS)-hexahydro-5-oxoimidazo[5,1-b]thiazol-3-yl]carbonyl]-L-phenylalanine (Scheme Q, Q-8: where R$_{Q-1}$ and R$_{Q-1}$ are equal to hydrogen, Z is NH, R$_5$ is 4-[(2,6-dichlorobenzoyl)amino]phenyl, and stereochemistry of the C-terminal amino acid is (S)).

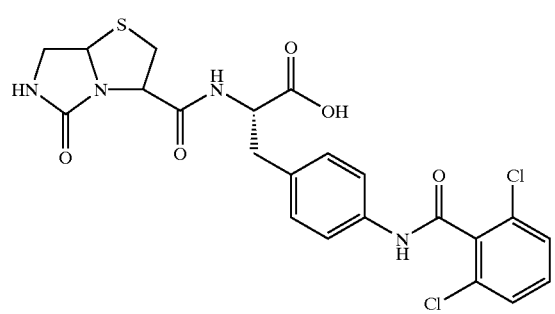

To a cooled (0–5° C.) solution of Q-7 (Scheme Q where R$_{Q-1}$ and R$_{Q-1}$ are equal to hydrogen, Z is NH, R$_5$ is 4-[(2,6-dichlorobenzoyl)amino]phenyl, and stereochemistry of the C-terminal amino acid is (S)) (88 mg, 0.16 mmol) in THF (5 mL) and H$_2$O (0.5 mL) was added via syringe pump over 1 h 0.1 N NaOH (3.4 mL, 0.34 mmol). After 2 h, the reaction mixture was partitioned between ethyl acetate and 0.1 N HCl (7 mL) and diluted with H$_2$O (20 mL). The organic layer was separated, washed with H$_2$O, dried (MgSO$_4$), filtered and concentrated in vacuo. The resulting white solid was lyophilized from glacial acetic acid to afford the title compound (22 mg) as white solid: IR (drift) 2924, 1726, 1720, 1663, 1657, 1608, 1515, 1456, 1431, 1402, 1398, 1243, 1194, 797, 780 cm$^{-1}$; $^1$H NMR (300 MHz, CD$_3$OD) δ 8.05 (1H), 7.61 (2H), 7.46 (3H), 7.25 (2H), 4.93 (2H), 4.74 (2H), 4.47 (1H), 3.77 (1H), 3.39 (2H), 3.25 (1H), 3.04 (2H); $^{13}$C NMR (75 MHz, CD$_3$OD) δ 171.8, 165.2, 164.7, 138.2, 137.7, 135.1, 133.4, 132.4, 130.9, 129.4, 121.7, 66.3, 64.4, 54.5, 44.9, 37.4, 33.9; HRMS (FAB) calcd for C$_{22}$H$_{20}$Cl$_2$N$_4$O$_5$S+H$_1$ 523.0610, found 523.0629, MS (ESI+) for C$_{22}$H$_{20}$Cl$_2$N$_4$O$_5$S m/z 523.0 (M+H)$^+$, MS (ESI−) for C$_{22}$H$_{20}$Cl$_2$N$_4$O$_5$S m/z 521.1 (M−H)$^-$.

EXAMPLE 280

4-[(2,6-Dichlorobenzoyl)amino]-N-[[(7aR)-hexahydro-5-oxoimidazo[5,1-b]thiazol-3-yl]carbonyl]-L-phenylalanine (Scheme Q, Q-8: where R$_{Q-1}$ and R$_{Q-1}$ are equal to hydrogen, Z is NH, R$_5$ is 4-[(2,6-dichlorobenzoyl)amino]phenyl, and stereochemistry of the C-terminal amino acid is (S)).

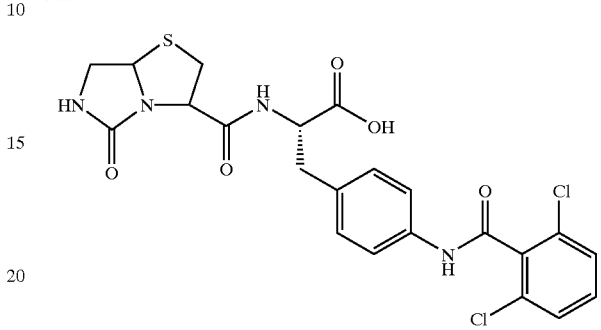

Example 280 was prepared as described in Scheme Q from the slower eluting diastereomer of general structure Q-4 (Scheme Q where R$_{Q-1}$ and R$_{Q-1}$ are equal to hydrogen, R$_{Q-3}$ is ethyl, and Z is NH). Physical data as follows: IR (drift) 3251, 3079, 1730, 1662, 1611, 1549, 1516, 1482, 1431, 1333, 1306, 1269, 1229, 1196, 792 cm$^{-1}$; $^1$H NMR (300 MHz, CD$_3$OD) δ 7.59 (2H), 7.44 (3H), 7.24 (2H), 4.65 (1H), 3.81 (1H), 3.44 (1H), 3.23 (2H), 3.08 (2H); $^{13}$C NMR (75 MHz, CD$_3$OD) δ 175.3, 172.22, 164.6, 155.3, 139.7, 139.1, 136.1, 134.1, 133.9, 132.3, 131.8, 130.9, 122.0, 68.4, 64.6, 45,6, 44.0, 36.3; HRMS (FAB) calcd for C$_{22}$H$_{20}$Cl$_2$N$_4$O$_5$S+H$_1$ 523.0610, found 523.0629, MS (ESI+) for C$_{22}$H$_{20}$Cl$_2$N$_4$O$_5$S m/z 523.0 (M+H)$^+$, MS (ESI−) for C$_{22}$H$_{20}$Cl$_2$N$_4$O$_5$S m/z 521.0 (M−H)$^-$, Anal. Calcd for C$_{22}$H$_{20}$Cl$_2$N$_4$O$_5$.0.13H$_2$O: C, 50.26; H, 3.88; N, 10.66. Found: C, 50.72; H, 3.96; N, 10.13. % Water (KF): 0.45.

EXAMPLE 281

4-[(2,6-Dichlorobenzoyl)amino]-N-[(tetrahydro-5-oxo-5H-thiazolo[3,2-c]oxazol-3-yl)carbonyl]-L-phenylalanine (Less Polar Diastereomer)

(Scheme Q, Q-8: where R$_{Q-1}$ and R$_{Q-1}$ are equal to hydrogen, Z is O, R$_5$ is 4-[(2,6-dichlorobenzoyl)amino]phenyl, and stereochemistry of the C-terminal amino acid is (S)).

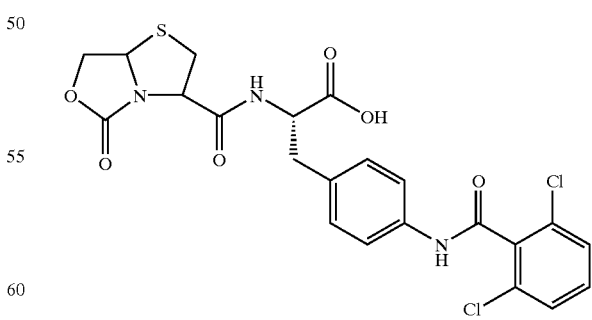

Example 281 was prepared as described in Scheme Q using commercially available (t-butyldimethylsilyloxy)acetaldehyde to form the requisite thiazolidine-4-carboxylic acid. Physical data as follows: IR (drift) 3293, 3194, 1754, 1667, 1603, 1533, 1517, 1431, 1411, 1392, 1324, 1266, 1206, 798, 781 cm$^{-1}$; $^1$H NMR (300 MHz, DMSO-d$_6$) δ 8.44 (1H), 7.53 (5H), 7.21 (2H), 5.00 (1H), 4.84 (1H), 4.65 (1H), 4.42 (2H), 3.08 (2H), 2.91 (1H); $^{13}$C NMR (75 MHz, CD$_3$OD) δ 169.4, 163.8, 160.6, 136.7, 136.2, 133.9, 131.9, 130.9, 129.5, 127.9, 120.4, 68.1, 64.4, 63.2, 53.4, 36.1, 33.7; MS (ESI+) for C$_{22}$H$_{19}$Cl$_2$N$_3$O$_6$S m/z 524.0 (M+H)$^+$, MS (ESI−) for C$_{22}$H$_{19}$Cl$_2$N$_3$O$_6$S m/z 522.0 (M−H)$^-$, Anal. Calcd for C$_{22}$H$_{19}$Cl$_2$N$_3$O$_6$S.0.31H$_2$O: C, 49.86; H, 3.73; N, 7.93. Found: C, 49.61; H, 3.82; N, 7.54. % Water (KF): 1.06.

EXAMPLE 282

4-[(2,6-Dichlorobenzoyl)amino]-N-[(tetrahydro-5-oxo-5H-thiazolo[3,2-c]oxazol-3-yl)carbonyl]-L-phenylalanine (More Polar Diastereomer)

(Scheme Q, Q-8: where R$_{Q-1}$ and R$_{Q-1}$ are equal to hydrogen, Z is O, R$_5$ is 4-[(2,6-dichlorobenzoyl)amino] phenyl, and stereochemistry of the C-terminal amino acid is (S)).

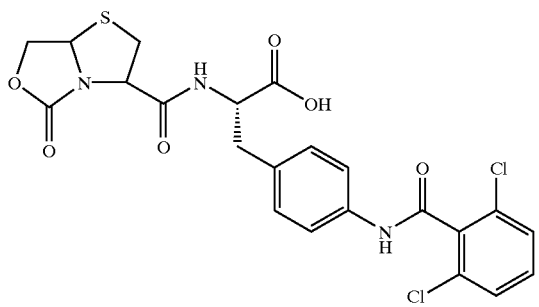

Example 282 (diastereomer of Example 281) was prepared as described in Scheme Q. Physical data as follows: IR (drift) 3296, 1753, 1666, 1603, 1579, 1535, 1517, 1431, 1411, 1390, 1324, 1267, 1207, 798, 781 cm$^{-1}$; $^1$H NMR (300 MHz, DMSO-d$_6$) δ 8.57 (1H), 7.54 (5H), 7.20 (2H), 5.23 (1H), 4.86 (1H), 4.66 (1H), 4.45 (2H), 3.22 (1H), 3.09 (1H), 2.93 (m, 2H); $^{13}$C NMR (75 MHz, CD$_3$OD) δ 172.8, 169.7, 163.8, 160.6, 136.8, 136.2, 133.7, 131.9, 130.9, 129.5, 127.9, 120.2, 68.1, 64.9, 63.1, 53.6, 37.5, 36.2, 34.2; MS (ESI+) for C$_{22}$H$_{19}$Cl$_2$N$_3$O$_6$S m/z 523.9 (M+H)$^+$, MS (ESI−) for C$_{22}$H$_{19}$Cl$_2$N$_3$O$_6$S m/z 521.9 (M−H)$^-$; HRMS (EI) calcd for C$_{22}$H$_{19}$Cl$_2$N$_3$O$_6$S 523.0372, found 523.0366. Anal. Calcd for C$_{22}$H$_{19}$Cl$_2$N$_3$O$_6$S.0.35H$_2$O: C, 49.79; H, 3.74; N, 7.92. Found: C, 50.14; H, 4.08; N, 8.13. % Water (KF): 1.19.

EXAMPLE 283

(4S)-4-[[[(1S)-1-Carboxy-2-[4-[(2,6-dichlorobenzoyl)amino]phenyl]ethyl]amino]carbonyl]-2-(4-pyridinyl)-3-thiazolidinecarboxylic Acid 3-Ethyl Ester

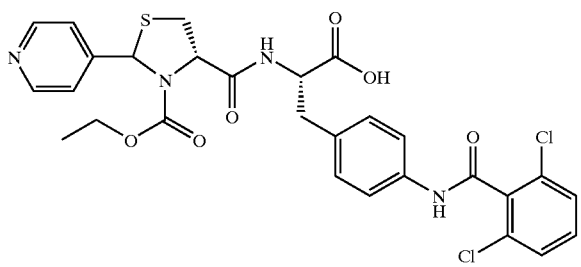

Example 283 was prepared as described in Scheme B using D-cysteine and 4-pyridinecarboxaldehyde to from the requisite thiazolidine carboxylic acid. Physical data as follows: IR (drift) 3055, 2981, 2928, 1679, 1604, 1535, 1515, 1450, 1431, 1406, 1378, 1331, 1194, 797, 778 cm$^{-1}$; $^1$H NMR (300 MHz, CD$_3$OD) δ 8.68 (2H), 8.28 (2H), 7.55 (2H), 7.42 (4H), 7.25 (2H), 6.28 (1H), 4.70 (1H), 4.09 (2H), 3.46 (1H), 3.16 (1H), 2.94 (1H), 2.73 (1H), 1.17 (3H); $^{13}$C NMR (75 MHz, CD$_3$OD) δ 190.2, 171.1, 162.1, 153.8, 141.4, 135.3, 134.6, 131.9, 130.3, 129.4, 128.2, 126.4, 122.4, 118.5, 61.0, 51.7, 35.5, 26.6, 11.7; MS (FAB) m/z (rel. intensity) 617 (MH$^+$, 99), 621 (35), 620 (72), 619 (99), 618 (91), 617 (99), 371 (22), 179 (23), 173 (28), 124 (27), 57 (24); HRMS (EI) calcd for C$_{28}$H$_{26}$Cl$_2$N$_4$O$_6$S+H$_1$ 617.1028, found 617.1019, Anal. Calcd for C$_{28}$H$_{26}$Cl$_2$N$_4$O$_6$S.0.9HCl.1.1H$_2$O: C, 50.19; H, 4.38; N, 8.36; Cl, 15.34. Found: C, 49.79; H, 4.49; N, 8.11; Cl, 15.05. % Water (KF): 2.96.

EXAMPLE 284

4-[[[(1S)-2-Amino-1-[4-[(2,6-dichlorophenyl)methoxy]phenyl]methyl]-2-oxoethyl]amino]-carbonyl]-3-thiazolidinecarboxylic Acid 3-[2-(1-Pyrrolidinyl)ethyl]ester

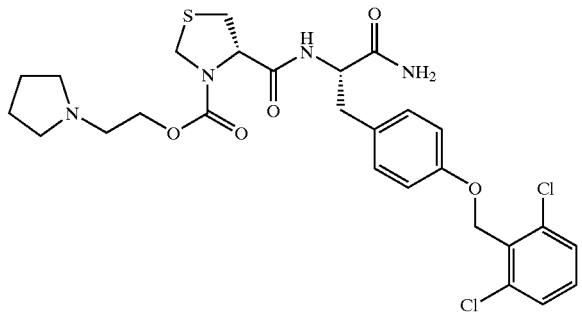

Example 284 was prepared as described in Scheme C. Physical data as follows: IR (drift) 1709, 1675, 1511, 1458, 1435, 1421, 1390, 1380, 1354, 1299, 1240, 1195, 1179, 1114, 765 cm$^{-1}$; $^1$H NMR (300 MHz, CD$_3$OD) δ 8.40 (1H), 7.41 (3H), 7.22 (2H), 6.99 (2H), 5.29 (2H), 4.46 (6H), 3.77 (2H), 3.50 (2H), 3.19 (4H), 2.89 (1H), 2.04 (1H), 2.12 (4H); $^{13}$C NMR (75 MHz, CD$_3$OD) δ 174.5, 171.6, 171.1, 157.9, 153.3, 136.6, 132.2, 130.6, 130.0, 129.7, 128.3, 114.5, 64.9, 63.2, 62.1, 60.9, 54.4, 53.6, 50.0, 49.0, 37.0, 36.5, 35.2, 22.6; MS (ESI+) for C$_{27}$H$_{32}$Cl$_2$N$_4$O$_5$S m/z 595.1 (M+H)$^+$; HRMS (FAB) calcd for C$_{27}$H$_{32}$Cl$_2$N$_4$O$_5$S+H$_1$ 595.1548, found 595.1531.

EXAMPLE 285

(4S)-4-[[[(1S)-1-Carboxy-2-[4-[(2,6-dichlorophenyl)methoxy]phenyl]ethyl]amino]carbonyl]-3-thiazolidinecarboxylic Acid 3-(3-Tetrahydrofuranyl) ester

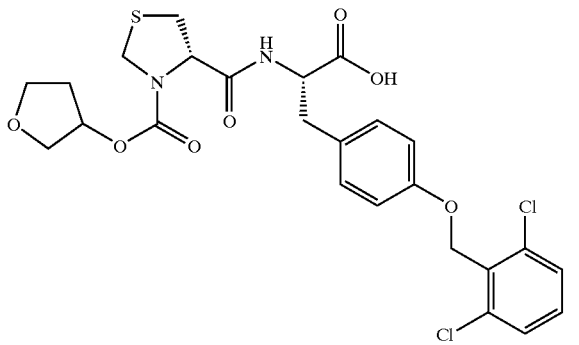

Example 285 was prepared as described in Scheme A. Physical data as follows: $^1$H NMR (300 MHz, CD$_3$OD) δ 7.41 (3H), 7.18 (2H), 6.98 (2H), 5.28 (2H), 5.15 (1H), 4.69 (2H), 4.44 (1H), 3.82 (4H); $^{13}$C NMR (75 MHz, DMSO-d$_6$) δ 172.8, 157.9, 136.7, 132.2, 130.6, 130.1, 129.5, 128.3, 114.5, 76.8, 72.7, 66.5, 64.9, 62.4, 53.5, 36.3, 34.9, 32.4; MS (FAB) m/z (rel. intensity) 569 (MH$^+$, 75), 571 (51), 570 (29), 569 (75), 322 (22), 161 (20), 159 (30), 89 (25), 73 (31), 71 (99), 43 (41); HRMS (FAB) calcd for C$_{25}$H$_{26}$Cl$_2$N$_2$O$_7$S+H$_1$ 569.0916, found 569.0939, Anal. Calcd for C$_{25}$H$_{26}$Cl$_2$N$_2$O$_7$S: C, 52.73; H, 4.60; N, 4.92;. Found: C, 52.41; H, 4.80; N, 4.62.

EXAMPLE 286

(4S)-4-[[[(1S)-2-Amino-1-[[4-[(2,6-dichlorophenyl)methoxy]phenyl]methyl]-2-oxoethyl]amino]carbonyl]-3-thiazolidinecarboxylic Acid 3-[2-(1-Piperidinyl)ethyl]ester

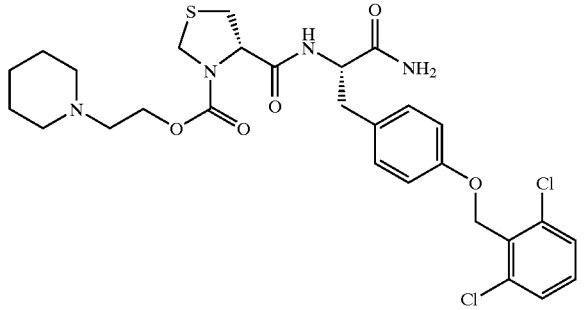

Example 286 was prepared as described in Scheme C. Physical data as follows: $^1$H NMR (300 MHz, CD$_3$OD) δ 7.43 (3H), 7.22 (2H), 6.98 (2H), 5.28 (2H), 4.66 (2H), 4.59 (1H), 4.47 (1H), 4.47 (2H), 3.05 (10H), 1.78 (4H), 1.62 (2H); $^{13}$C NMR (75 MHz, CD$_3$OD) δ 175.9, 172.9, 159.3, 138.1, 133.6, 132.0, 131.4, 131.1, 129.7, 120.1, 115.9, 66.3, 64.6, 63.7, 62.3, 61.9, 57.8, 55.8, 55.1, 51.3, 50.3, 38.5, 37.8, 36.6, 25.0, 23.5; MS (ESI+) for C$_{28}$H$_{34}$Cl$_2$N$_4$O$_5$S m/z 609.0 (M+H)$^+$.

EXAMPLE 287

(4S)-4-[[[(1S)-2-Amino-1-[[4-[(2,6-dichlorophenyl)methoxy]phenyl]methyl]-2-oxoethyl]amino]carbonyl]-3-thiazolidinecarboxylic Acid 3-[2-(4-Methyl-1-piperazinyl)ethyl]ester

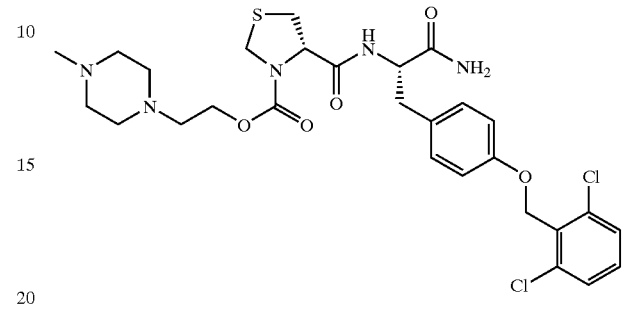

Example 287 was prepared as described in Scheme C. Physical data as follows: $^1$H NMR (300 MHz, CD$_3$OD) δ 7.41 (3H), 7.21 (2H), 6.98 (2H), 5.28 (2H), 4.67 (1H), 4.58 (1H), 4.46 (1H), 4.23 (2H), 3.20 (2H), 2.71 (13H), 2.50 (3H); MS (ESI+) for C$_{28}$H$_{35}$Cl$_2$N$_5$O$_5$S m/z 624.0 (M+H)$^+$; Anal. Calcd for C$_{28}$H$_{35}$Cl$_2$N$_5$O$_5$S.0.5C$_2$H$_4$O$_2$.0.5H$_2$O: C, 49.82; H, 5.54; N, 10.02. Found: C, 49.82; H, 5.77; N, 9.65.

EXAMPLE 288

(4S)-4-[[[(1S)-2-Amino-1-[[4-[(2,6-dichlorobenzoyl)amino]phenyl]methyl]-2-oxoethyl]amino]carbonyl]-3-thiazolidinecarboxylic Acid 3-[2-(4-Morpholinyl)ethyl]ester

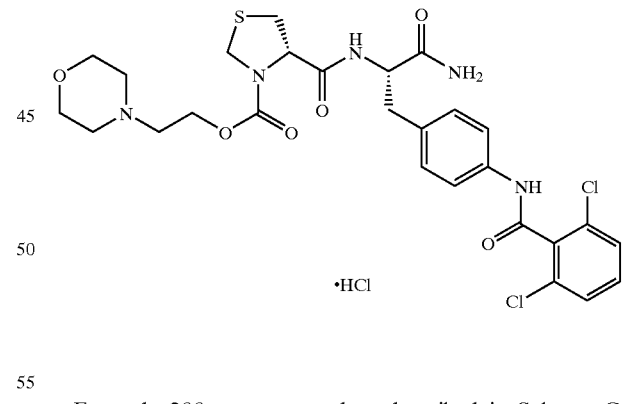

Example 288 was prepared as described in Scheme C. Physical data as follows: IR (drift) 1671, 1603, 1536, 1518, 1430, 1415, 1361, 1349, 1324, 1269, 1194, 1134, 1118, 1104, 799 cm$^{-1}$; $^1$H NMR (300 MHz, CD$_3$OD) δ 7.62 (1H), 7.46 (3H), 7.31 (2H), 4.68 (3H), 4.41 (3H), 3.95 (4H), 3.48 (5H), 3.22 (3H), 2.90 (2H); $^{13}$C NMR (75 MHz, CD$_3$OD) δ 175.8, 173.1, 165.3, 154.7, 138.2, 137.6, 135.2, 133.3, 132.4, 130.9, 129.4, 121.7, 121.5, 65.0, 64.8, 63.7, 60.6, 57.4, 55.8, 53.6, 51.4, 50.4, 38.6, 38.1, 36.6, 35.0; MS (ESI+) for C$_{27}$H$_{31}$Cl$_2$N$_5$O$_6$S m/z 623.9 (M+H)$^+$; HRMS (FAB) calcd for C$_{27}$H$_{31}$Cl$_2$N$_5$O$_6$S+H$_1$ 624.1450, found 624.1452.

Scheme R

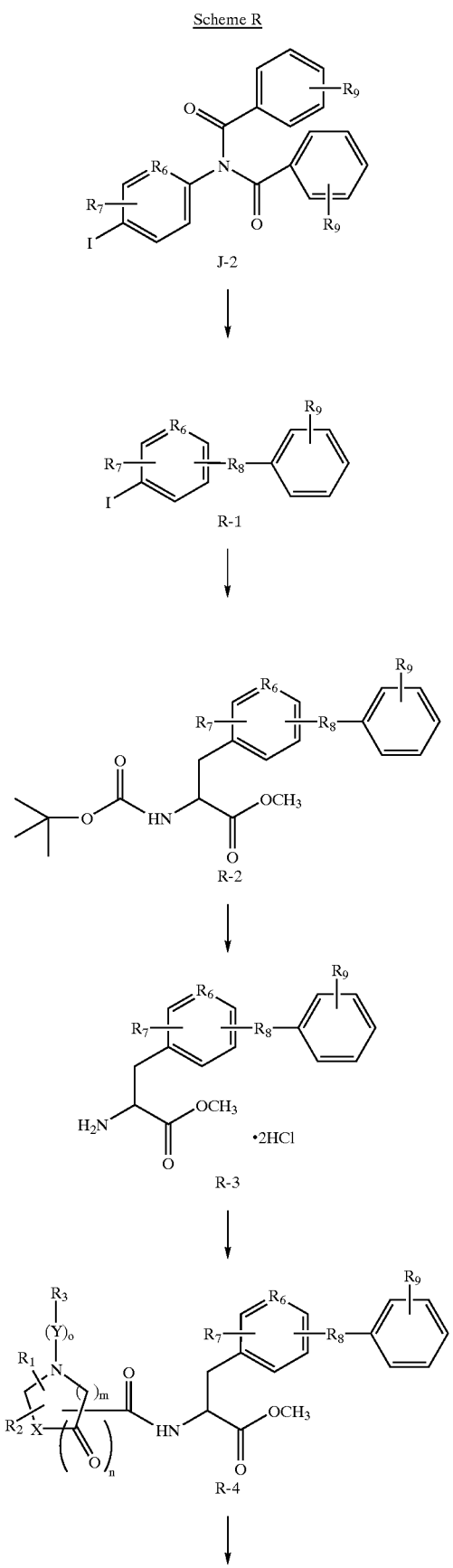

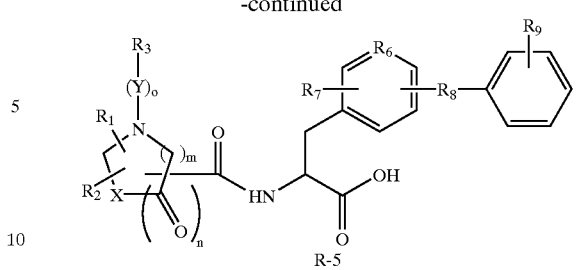

SCHEME R

Scheme R teaches a general method for the preparation of Examples corresponding to structures R-4 and R-5, where R₆ is nitrogen. Thus reaction of the amide R-1 (obtained from the imide J-2), with the organozinc derived from a suitable protected β-iodoalanine, provides the acylamino azaphenylalanine R-2. N-deprotection of R-2 gives the aminoester R-3, that is used (as exemplified by reagent A-4 of Scheme A, and by reagent B-5 of Scheme B) for the synthesis of Examples R-4 and R-5 of this invention.

PREPARATION 87

(Scheme R: R-1 where $R_6$ is N, $R_7$ is H, $R_8$ is —NHC(O)—, and $R_9$ is 2,6-dichloro).

2,6-Dichloro-N-(5-iodo-2-pyridinyl)benzamide ($C_{12}H_7Cl_2IN_2O$)

A mixture of J-2 and $NH_2NH_2 \cdot H_2O$ in MeOH is refluxed for 6 h under Ar. The reaction mixture is cooled, and the MeOH is removed in vacuo. The residue is partitioned between $H_2O$ and EtOAc. The EtOAc extracts are dried, filtered and concentrated to give a brown-colored solid, that is purified by silica flash chromatography (99:1 toluene/EtOAc) to provide Preparation 87: TLC (98:2 toluene/EtOAc) $R_f$ 0.43; $^1$H NMR (CDCl₃, 300 MHz) δ 10.23 (1H), 8.26 (1H), 7.99 (1H), 7.57 (1H), 7.41–7.31 (3H); $^{13}$C NMR (CDCl₃, 75 MHz) δ 163.40, 153.22, 150.95, 147.16, 135.83, 132.72, 131.90, 130.34, 128.65, 128.50, 117.09, 86.55; MS (ESI) 393, 391.

PREPARATION 88

(Scheme R: R-2 where $R_6$ is N, $R_7$ is H, $R_8$ is —NHC(O)—, $R_9$ is 2,6-dichloro and the stereochemistry is S).

(S)-6[(2,6-Dichlorobenzoyl)amino]-α-1[(1,1-dimethylethoxy)carbonyl]amino]-3-pyridinepropanoic Acid Methyl Ester ($C_{21}H_{23}Cl_2N_3O_5$)

To an amberized flask containing activated Zn dust (0.0.802 g, 12.27 mmol) under Ar is added dry THF (6 mL) and 1,2-dibromoethane (0.045 mL). This suspension is brought briefly to a gentle reflux, and then is cooled to rt. A solution of TMSCl (1 M in THF, 0.39 mL) is added. The reaction mixture is stirred at 45±5° C. for 30 min. and then is cooled to rt. To this mixture is added a degassed solution of N-[(1,1-dimethylethoxy)carbonyl]-3-iodo-L-alanine methyl ester (4.04 g, 12.27 mmol) in 2:1 N,N-dimethylacetamide/THF (18 mL). The reaction mixture is stirred at 45±5° C. for 5 h, and then is cooled to 0° C. To this mixture is added $PdCl_2(PPh_3)_2$ (0.428 g) followed immediately by a degassed solution of Preparation 87 in 1:1

N,N-dimethylacetamide/THF (19 mL). This reaction mixture is stirred at 45±5 °C. for 44 h. It is cooled to 0° C., and is quenched with cold aqueous satd $NH_4Cl$. This mixture is extracted with EtOAc. The combined EtOAc extracts are washed with aqueous satd $NH_4Cl$ and brine. The EtOAc extracts are dried, filtered and concentrated to provide a green-brown colored oil, that is purified by silica flash chromatography (steps of 750:250:1, 700:300:1 and 650:350:1 heptane/EtOAc/iPrOH) to provide Preparation 88: TLC $R_f$=0.28 (7:3 hexanes/EtOAc).

PREPARATION 89

(Scheme R: R-3 where $R_6$ is N, $R_7$ is H, $R_8$ is —NHC(O)—, $R_9$ is 2,6-dichloro and the stereochemistry is S).

(S)-α-Amino-6-[(2,6-dichlorobenzoyl)amino]-3-pyridinepropanoic Acid Methyl Ester Dihydrochloride Salt ($C_{16}H_{15}Cl_2N_3O_3 \cdot 2HCl$, R-3)

A solution of Preparation 88 (0.812 g, 1.73 mmol) in 4 M HCl in dioxane (20 mL) is stirred under Ar at rt for 20 h. The reaction mixture is concentrated in vacuo, and the residue is taken up in $H_2O$ (60 mL). This aqueous mixture is extracted with $Et_2O$ (3 60 mL), and the $Et_2O$ extracts are discarded. The aqueous solution is frozen and lyophilized to provide Preparation 89: IR (diffuse reflectance) 3021, 2995, 2953, 2893, 2884, 2866, 2853, 2844, 2341, 2015, 1916, 1749, 1646, 1569, 1252 $cm^{-1}$; MS (EI) 367 ($M^+$), 282, 280, 262, 175, 173, 147, 145, 109, 107, 88.

PREPARATION 90 & EXAMPLE 289

[S-(R*,R*)]-4-[[[1-[[2-[(2,6-Dichlorobenzoyl)amino]-5-pyridinyl]methyl]-2-methoxy-2-oxoethyl]amino]carbonyl]-3-thiazolidinecarboxylic Acid Ethyl Ester ($C_{23}H_{24}Cl_2N_4O_6S$)

(Scheme R: R-4 where $R_1$ is H, $R_2$ is H, $R_3$ is -Et, X is S, (Y) is —C(O)O, m is 2, n is 0, o is 1, $R_6$ is N, $R_7$ is H, $R_8$ is —NHC(O)—, $R_1$ is 2,6-dichloro and the stereochemistry is [S-(R*,R*)]).

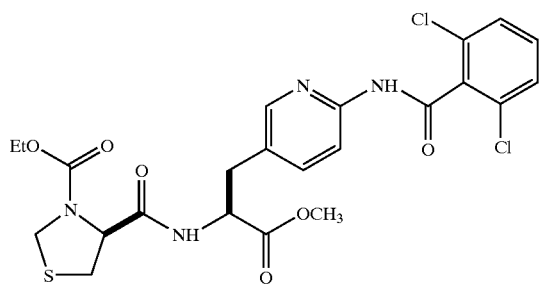

To a mixture of the N-acylthiazolidinecarboxylic acid (0.292 g, 1.42 mmol), HOAt (0.193 g, 1.42 mmol) in 4:1 $CH_2Cl_2$/DMF (5.25 mL) at 0° C. is added EDC (0.272 g, 1.42 mmol). This reaction mixture is stirred at 0° C. for 20 min. Solid Preparation 89 (0.568 g, 1.29 mmol) and NMM (0.316 mL, 3.27 mmol) are added. The resulting reaction mixture is stirred at 0° C. for 4 h, and then is kept at 4° C. for 40 h. The mixture is concentrated in vacuo, and the residue is taken up in $CH_2Cl_2$. The $CH_2Cl_2$ mixture is extracted with $H_2O$, aq satd $NaHCO_3$, and $H_2O$. The combined aqueous washes are back-extracted with $CH_2Cl_2$. The combined $CH_2Cl_2$ extracts are dried, filtered and concentrated to a pale yellow-colored foam, that is purified by silica flash chromatgraphy (600:400:1 EtOAc/heptane/iPrOH) to give Preparation 90 (Example 289): IR (diffuse reflectance) 3275, 1742, 1697, 1665, 1586, 1559, 1532, 1476, 1427, 1398, 1382, 1351, 1344, 1311, 1284, 1279, 1242, 1223, 1196, 1100, 1023, 802, 787, 770, 697 $cm^{-1}$; MS (EI) 554 ($M^+$), 495, 422, 395, 352, 315, 293, 280, 172, 160, 144, 116, 107, 88, 60.

EXAMPLE 290

[S-(R*,R*)]-4-[[[1-Carboxy-2-[2-[(2,6-dichlorobenzoyl)amino]-5-pyridinyl]ethyl]amino]carbonyl]-3-thiazolidinecarboxylic Acid Ethyl Ester ($C_{22}H_{22}Cl_2N_4O_6S$, Example 290)

(Scheme R: R-4 where $R_1$ is H, $R_2$ is H, $R_3$ is -Et, X is S, (Y) is —C(O)O, m is 2, n is 0, o is 1, $R_6$ is N, $R_7$ is H, $R_8$ is —NHC(O)—, $R_9$ is 2,6-dichloro and the stereochemistry is [S-(R*,R*)]).

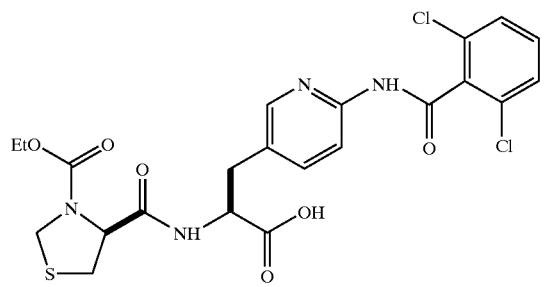

To a solution of Preparation 289 (0.400 g, 0.72 mmol) in 6:1 THF/$H_2O$ (25.6 mL) at 0° C. under Ar is added slowly over 4 h (via syringe pump) an aqueous solution of NaOH (1 M, 7.92 mL). The reaction mixture is stirred an additional 1.5 h. The reaction mixture is partitioned between aqueous HCl and EtOAc. The aqueous solution is separated, and is extracted further with EtOAc. The combined EtOAc extracts are dried, filtered and concentrated to a beige-colored foam. This foam is taken up in 1:1 MeCN/$H_2O$. This solution is frozen and lyophilized to give Example 290 as a beige-colored solid: mp 142–144° C.; IR (diffuse reflectance) 3169, 3094, 3031, 2980, 2964, 2935, 1735, 1691, 1591, 1556, 1531, 1480, 1431, 1400, 1379, 1344, 1308, 1288, 1266, 1216, 1194, 1148, 799, 782, 772 $cm^{-1}$; Anal. C, 48.72; H, 4.29; Cl, 12.26; N, 9.95; S, 5.62; (calcd C, 48.81; H, 4.10; Cl, 13.10; N, 10.35; S, 5.92).

Biological Assays

Jurkat-endothelial Cell Adhesion Assay:

The following assay established the activity of the present compounds in inhibiting $\beta_1$-mediated cell adhesion in a representative in vitro system. This assay measures the adhesive interactions of a T-cell line, Jurkat, known to express the $\alpha_4\beta_1$ integrin, to endothelial monolayers in the presence of test compounds. The test compounds were added in increasing concentrations to T-cells and then the T-cell compound mixture was added to IL-1 stimulated endothelial cell monolayers. The plates were incubated, washed and the percentage of attached cells was quantitated. The present assay directly demonstrates the cell adhesion inhibitory activity and adhesion modulatory activity of the compounds.

Human umbilical vein endothelial cells were purchased from Clonetics (San Diego, Calif.) at passage number 2. The cells were grown on 0.5% porcine skin gelatin pre-coated flasks (Sigma, St. Louis Mo.) in EGM-UV media (Clonetics, San Diego, Calif.) supplemented with 10% fetal bovine serum. Cells are refed every 2–3 days reaching confluence by day 4 to 6. The cells are monitored for factor VIII antigen and results show that at passage 12, the cells are positive for this antigen. The endothelial cells are not used following passage 6.

The T-cell line Jurkat was obtained from American Type Tissue Culture Collection (Rockville, Md.) and the cells were cultured in RPMI containing 10% fetal calf serum. The cells were washed twice in Hank's Balanced Salt Solution (HBSS) and resuspended in Dulbecco's Minimal Eagle's Media (DMEM) containing 2.5 mg/ml Human Serum Albumin (HSA). Jurkat cells ($1 \times 10^6$ cells/ml) were stained with 10 ng/ml BCECF-AM (Molecular Probes, Eugene, Oreg.)) in HBSS without phenol red. The cells were loaded with BCECF for 60 minutes in the dark at 370C, washed 2 times, and resuspended in DMEM-HSA solution.

Confluent endothelial monolayers, grown in 96-well tissue culture plates, were stimulated for 4 hr. at 37° C. with 0.1 ng/ml (~50 U/ml) recombinant IL-1 (Amgen, Thousand Oaks, Calif.). Following this incubation, the monolayers were washed twice with HBSS and 0.1 ml of DMEM–HSA solution was added. Jurkat cells ($5 \times 10^5$ cells) were combined with the appropriate concentration of the test compound and 0.1 ml of the Jurkat cell-compound mixture was added to the endothelial cell monolayers. Generally, 100, 20, 5 and 1.25 $\mu$M compound concentrations were tested. These concentrations are adjusted downward for analogs found or thought to be more potent. The plates were placed on ice for 5 minutes to allow for Jurkat cell settling and the plates were incubated at 37° C. for 20 minutes. Following this incubation, the monolayers were washed twice with PBS containing 1 mM calcium chloride and 1 mM magnesium chloride and the plates were read using a Millipore Cytofluor 2300 (Marlboro, Mass.). Fluorescence in each well was measured as Arbitrary Fluorescence Units and percent adhesion in the absence of compound was adjusted to 100% and the % adhesion in the presence of compound was calculated. Monolayers were also fixed in 3% paraformaldehyde and evaluated microscopically to verify the adhesion. This procedure is a modification of a previously published method (Cardarelli et al., *J. Biol. Chem.* 269:18668–18673 (1994)).

Jurkat-CS-1 Assay

The CS-1 derived peptide, CLHPGEILDVPST, and the scrambled control peptide, CLHGPIELVSDPT, were synthesized on a Beckman 990 synthesizer using t-Boc methodology. The peptides were immobilized onto microtiter plates using the heterobifunctional crosslinker 3-(2-pyridyldithio)propionic acid N-hydroxysuccinimide ester (SPDP) as reported by Pierschbacher et al., *Proc. Natl. Acad. USA*, 80:1224–1227 (1983). Microtiter plates were coated with 20 $\mu$g/ml HSA for 2 hr. at room temperature, washed once with PBS and derivatized with 10 $\mu$g/ml SPDP for 1 hr. After washing, 100 $\mu$l of a 100 $\mu$g/ml cysteine containing peptide solution which had been recently dissolved was added to the wells and allowed to crosslink to the plates overnight at 4° C. Unbound peptide was removed from plates by washing with PBS. To block non-reacted sites, the plates are coated with 100 $\mu$l of a 2.5 mg/ml BSA solution in PBS for 1 hr. at 37° C. 100 $\mu$l of Jurkat cells ($2.5 \times 10^6$ cells/ml) in DMEM plus BSA (2.5 mg/ml) was mixed with an appropriate concentration of the compound to be tested and the mixture was added to peptide coated dishes and incubated for 1 hr. at 37° C. Generally 100, 20, 5 and 1.25 $\mu$M concentrations of the compound were tested. The concentrations of the compound were adjusted downward for compounds thought or found to be more potent.

Following this incubation the plates were washed once with PBS and the attached cells were fixed with 3% paraformaldehyde in PBS and stained with 0.5% toluidine blue in 3.7% formaldehyde. The cells were stained overnight at room temperature and the optical density at 590 nm of toluidine blue stained cells was determined using a vertical pathway spectrophotometer to quantitate attachment (VMAX Kinetic Microplate Reader, Molecular Devices, Menlo Park, Calif.). This procedure is a modification of a previously published method (Cardarelli et al, J. Biol. Chem., 269:18668–18673 (1994) and Cardarelli et al, Proc. Natl. Acad. Sci. USA, 83:2647–2651 (1986)).

The preferred compounds are those which have low $IC_{50}$ values in the Jurkat EC assay or the Jurkat-CS-1 assay described above or which have at least moderate activity in both assays. All of the compounds of the present invention have an activity of less than 50 $\mu$M in the Jurkat CS-1 assay or less than 500 $\mu$M in the Jurkat EC assay. Compounds with activity in the Jurkat CS-1 assay preferably have $IC_{50}$ values of less than 1 $\mu$M, more preferably less than 0.5 $\mu$M, most preferably less than or equal to 0.08 $\mu$M. Compounds with activity in the Jurkat EC assay preferably have $IC_{50}$ values of less than 10 $\mu$M, more preferably less than 5 $\mu$M, most preferably less than or equal to 0.8 $\mu$M.

In the Jurkat EC Assay, $IC_{50}$ value ranges ($\mu$M) are depicted by A, B, and C and in the Jurkat CS-1 Assay, $IC_{50}$ value ranges are depicted by D, E, and F. These ranges are as follows:

In Vitro Data:

EC: A$\geq$1 $\mu$M; 1 $\mu$M>B>0.25 $\mu$M; C$\leq$0.25 $\mu$M
CS-1 D$\geq$0.75 $\mu$M; 0.75 $\mu$M>E>0.05 $\mu$M; F$\leq$0.05 $\mu$M.

| Ex. | JK/EC | JK/CS-1 |
|---|---|---|
| 1 | A | E |
| 2 | C | E |
| 3 | C | F |
| 4 | C | F |
| 5 | B | E |
| 6 | A | D |
| 7 | A | E |
| 8 | B | E |
| 9 | C | F |
| 10 | C | F |
| 11 | A | E |
| 12 | C | F |
| 13 | A | D |
| 14 | B | E |
| 15 | A | D |
| 16 | C | E |
| 17 | A | D |
| 18 | A | D |
| 19 | C | E |
| 20 | A | D |
| 21 | C | E |
| 22 | A | D |
| 23 | C | F |
| 24 | B | E |
| 25 | C | F |
| 26 | A | D |
| 27 | A | D |
| 28 | A | D |
| 29 | B | E |
| 30 | A | E |
| 31 | C | F |
| 32 | A | D |
| 33 | C | E |
| 34 | A | E |
| 35 | B | E |
| 36 | C | F |
| 37 | C | F |
| 38 | A | D |
| 39 | C | E |
| 41 | A | D |
| 42 | B | E |
| 43 | C | F |
| 44 | A | D |
| 45 | B | E |
| 46 | A | D |
| 47 | C | F |
| 48 | A | D |
| 49 | A | D |
| 50 | A | E |
| 51 | B | E |
| 52 | C | E |

-continued

| Ex. | JK/EC | JK/CS-1 |
|---|---|---|
| 53 | C | F |
| 54 | A | E |
| 55 | C | F |
| 56 | A | E |
| 57 | A | D |
| 58 | C | F |
| 59 | A | E |
| 60 | C | F |
| 61 | B | E |
| 62 | C | F |
| 63 | C | F |
| 64 | C | F |
| 65 | A | E |
| 66 | C | E |
| 67 | A | E |
| 68 | A | E |
| 69 | A | D |
| 70 | B | F |
| 71 | A | D |
| 72 | A | D |
| 73 | A | E |
| 74 | B | E |
| 75 | A | D |
| 76 | C | E |
| 77 | A | D |
| 78 | A | E |
| 79 | A | D |
| 80 | A | D |
| 82 | B | E |
| 83 | A | E |
| 84 | C | F |
| 85 | C | F |
| 86 | A | D |
| 87 | A | D |
| 88 | A | E |
| 89 | A | E |
| 90 | A | |
| 91 | A | D |
| 92 | A | D |
| 93 | A | D |
| 94 | A | |
| 95 | A | |
| 96 | A | D |
| 97 | A | D |
| 99 | C | F |
| 100 | B | E |
| 101 | B | E |
| 102 | A | D |
| 103 | B | F |
| 104 | A | E |
| 105 | A | E |
| 107 | A | E |
| 109 | A | D |
| 110 | A | |
| 111 | B | E |
| 112 | A | |
| 113 | A | E |
| 114 | A | D |
| 115 | A | E |
| 116 | A | D |
| 117 | A | E |
| 119 | A | D |
| 121 | A | E |
| 123 | A | D |
| 124 | A | D |
| 125 | B | E |
| 126 | A | D |
| 127 | C | E |
| 129 | B | E |
| 131 | B | E |
| 133 | A | D |
| 135 | B | E |
| 137 | B | E |
| 139 | A | E |
| 140 | A | D |
| 141 | A | E |
| 142 | A | D |
| 143 | A | E |
| 144 | A | E |
| 145 | A | D |
| 146 | A | D |
| 147 | A | D |
| 148 | C | F |
| 149 | C | F |
| 150 | B | E |
| 151 | C | F |
| 152 | C | F |
| 153 | A | D |
| 154 | B | F |
| 155 | A | D |
| 156 | A | E |
| 157 | C | E |
| 158 | A | D |
| 159 | A | D |
| 161 | A | D |
| 163 | A | |
| 164 | A | |
| 165 | C | |
| 166 | A | |
| 167 | B | E |
| 168 | A | |
| 169 | A | |
| 170 | A | |
| 171 | A | E |
| 172 | C | F |
| 173 | C | E |
| 174 | B | |
| 175 | A | |
| 176 | A | E |
| 177 | A | F |
| 178 | A | F |
| 179 | B | |
| 180 | A | |
| 181 | A | E |
| 182 | B | E |
| 183 | A | |
| 184 | C | F |
| 185 | C | F |
| 186 | C | F |
| 187 | A | E |
| 188 | A | E |
| 189 | A | E |
| 190 | B | E |
| 191 | A | E |
| 192 | C | F |
| 193 | C | E |
| 195 | A | E |
| 196 | A | E |
| 197 | A | D |
| 298 | B | |
| 200 | A | E |
| 201 | A | E |
| 202 | A | |
| 203 | A | E |
| 204 | B | E |
| 205 | B | |
| 206 | B | E |
| 207 | A | E |
| 208 | A | |
| 209 | A | |
| 210 | A | |
| 211 | A | |
| 212 | A | |
| 213 | A | |
| 214 | A | |
| 215 | A | |
| 216 | A | E |
| 217 | A | |
| 218 | A | |
| 219 | A | |
| 220 | A | E |
| 221 | A | |
| 222 | A | E |
| 224 | A | E |

-continued

| Ex. | JK/EC | JK/CS-1 |
|---|---|---|
| 225 | A | E |
| 226 | A | E |
| 227 | A | E |
| 228 | A | E |
| 229 | A | E |
| 230 | A | E |
| 231 | A | E |
| 232 | A | D |
| 233 | A | E |
| 234 | A | E |
| 235 | A | E |
| 236 | A | D |
| 237 | A | E |
| 238 | A | E |
| 239 | A | E |
| 240 | A | E |
| 241 | A | E |
| 242 | A | E |
| 243 | B | E |
| 244 | B | E |
| 245 | C | E |
| 246 | B | E |
| 247 | B | E |
| 248 | B | E |
| 249 | B | E |
| 250 | C | E |
| 251 | C | F |
| 252 | C | F |
| 253 | C | E |
| 254 | B | E |
| 255 | A | E |
| 256 | C | F |
| 257 | B | E |
| 258 | C | F |
| 259 | C | E |
| 260 | B | E |
| 261 | B | E |
| 262 | C | F |
| 263 | B | E |
| 264 | C | F |
| 265 | C | F |
| 266 | C | F |
| 267 | A | E |
| 268 |  | D |
| 269 |  | D |
| 270 |  | E |
| 271 |  | E |
| 272 |  | E |
| 273 |  | D |
| 274 |  | E |
| 275 |  | F |
| 276 |  | D |
| 277 |  | D |
| 278 |  | E |
| 279 |  | E |
| 280 |  | E |
| 281 |  | E |
| 282 |  | F |
| 283 |  | E |
| 284 |  | E |
| 285 |  | E |
| 286 |  | E |
| 287 |  | E |
| 288 |  | D |
| 290 |  | F |

Biological Activity in Dextran Pleurisy Model

Certian compounds of the present invention were tested in a Dextran® pleurisy model.

Rational for Developing an $\alpha_4\beta_1$ Integrin Antaeonist to Treat Inflammatory Diseases VLA-4, a member of the β1 integrin family of adhesion molecules, is thought to play a critical role in several types of inflammatory disease processes by promoting leukocyte adhesion to vascular cell adhesion molecule (VCAM-1) and the CS-1 domain of fibronectin in extracellular tissue matrix (Elices M J, Osborn L, Takada Y, Crouse C, Luhowskyj S, Hemler M, Lobb R R. VCAM-1 on activated endothelium interacts with the leukocyte integrin VLA-4 at asite distinct from the VLA-4-fibronectin binding site. Cell; 60; 577–584, 1990, Humphries M J, Akiyama S K, Komoriya A, Olden K, Yamada K M. Identification of an alternatively-spliced site in human plasma fibronectin that mediates cell type-specific adhesion. J Cell Biol; 103: 2637–2647. 1986. Wayner E A, Garcia-Pardo A, Humphries M J, McDonald J A, Carter W G. Identification and characterization of the T lymphocyte adhesion receptor for an alternative cell attachment domain (CS-1) in plasma fibronectin. J Cell Biol; 109: 1321–1330, 1989, Guan J-L. Hynes R O. Lymphoid cells recognize an alternatively-spliced segment of fibronectin via the integrin $\alpha_4\beta_1$. Cell; 60: 53–61, 1990). Of the cell types expressing VLA-4, the major emphasis has been on eosinophils, lymphocytes, and monocytes. Validation of the role of VLA-4 has relied predominantly on the use of anti-VLA-4 antibodies which have been shown to suppress delayed-type hypersensitivity responses (Issekutz T B. Dual inhibition of VLA-4 and LFA-1 maximally inhibits cutaneous delayed-type hytersensitivity-induced inflammation. Am J Pathol; 143: 1286–1293, 1993, Scheynius A, Camp R L, Puré E. Reduced contact sensitivity reactions in mice treated with monoclonal antibodies to leukocyte function-associated molecule-1 and intercellular adhesion molecule-1. J Immunol; 150: 655–663, 1993, Ferguson T A, Kupper T S. Antigen-independent processes in antigen-specific immunity. J Immunol; 150:1172–1182, 1993, Chisholm P L, Williams C A, Lobb R R. Monoclonal antibodies to the integrin α-4 subunit inhibit the murine contact hypersensitivity restonse. Eur J Immunol; 23: 682–688. 1993. Elices M J, Tamraz S, Tollefson V, Vollger L W. The integrin VLA-4 mediates leukocyte recruitment to skin inflammatory sites in vivo. Clin Exp Rheumatol; 11 (Suppl 8) S77–80), 1993, experimental allergic encephalomyelitis (Yednock T A, Cannon C, Fritz L C, Sanchez-Madrid F, Steinman L M, Karin N. Prevention of experimental autoimmune encephalomyelitis by antibodies against $\alpha_4\beta_1$ integrin. Nature: 356: 63–66, 1992, Canella B, Raine C S. The VCAM-1/VLA-4 pathway is involved in chronic lesion expression in multiple sclerosis (MS). J Neuropathol Exp Neurol; 52: 3 11. 1993), HIV-induced encephalitis (Sasseville V G, Newman W, Brodie S J, Hesterberg P, Pauley D, Ringler D J. Monocyte adhesion to endothelium in simian immunodeficiency virus-induced AIDS encephalitis is mediated by vascular cell adhesion molecule-1/$\alpha_4\beta_1$ integrin reactions. Am J Pathol: 144: 27–40, 1994), pulmonary inflammation and airway hyperreactvity in asthma (Abraham W M, Sieiczak M W, Ahmed A, Cortes A, Lauredo I T, Kim J, Pepinsky, B, et al. $\alpha_1$-integins mediate antigen-induced late bronchial responses and prolonged airway hyperresponsiveness in sheep. J Clin Invest. 93: 776–787. 1994. Pretolani M. Ruffié C, Roberto LapaeSilva A, Joseph D, Lobb R R, Vargaftig B B. Antibody to very late activation antigen 4 prevents antigen-induced bronchial hyperreactivity and cellular infiltration in the guinea-pig airways. J Exp Med. 180: 795–805. 1994), experimental models of autoimmune-mediated diabetes (Yang X-D. Karin N, Tisch R, Steinman L, McDevitt H O. Inhibition of insulitis and prevention of diabetes in non-obese diabetic mice by blocking, L-selectin and very late antigen 4 adhesion receptors. Proc Natl Acad Sci USA; 90: 10494–10498, 1993, Burkly L C, Jakubowski A, Hattori M. Protection against adoptive transfer of autoimmune diabetes medicated through very late antigen-4 integin. Diabetes; 43: 529–534. 1994), and experimental colitis (Podolsky D K, Lobb R, King N, Benjamin C D, Pepinsky B, Sehgal P, et al. Attentuation of colitis in the cotton-top Tamarin by anti-4 integrin monoclonal antibody. J Clin Invest. 92: 372–380, 1993). Since eosinophils represent a major component of the inflammatory cell influx in asthmatic lung tissue we developed a simple acute inflammatory model of VLA-4 integrin-dependent eosinophil infiltration which could be used to identify VLA-4 antagonists; such compounds would be of potential value in the treatment of asthma as well as other diseases in which VLA-4 played a role.

Materials and Methods

Animals, Housing and Viral Testing:

C57BL/6 mice (Jackson, Bar Harbor, Me.), 6–8 weeks old, weighing 20–25 g were used throughout. All mice were acclimated for at least 7–14 days after arrival and maintained under controlled temperature (20–22° C.) and a 12 hr daily light cycle (6.00 A.M.–6.00 P.M.). Mice were housed in laminar flow racks and checked biweekly for viral infections (mouse hepatitis virus, minute virus of mice, rodent orphan parvovirus, Sendai) with kits obtained from Oreganon Teknika (Durham, N.C.) using established enzyme-linked immunoabsorbent assays. Mice testing positive for any of the above were omitted from the study. All mice were fed standard laboratory chow (Upjohn Lab Rodent Irradiated Mouse Chow, #5011-3, PMI Feeds, St. Louis, Mo.) and acidified drinking water (pH 5.0) ad libitum.

Induction of Inflammation by Intrapleural Injection of Dextran:

Intrapleural injections were made using a 27G needle cut to 3–4 mm and blunted by filing. Injections were made by inserting the needle between the mid-intercostal ribs on the right side of the thoracic cavity.

Dextran (MW 5–40×10$^6$, St Louis, Mo.) was injected as a 10% solution in saline in a volume of 100 $\mu$l/mouse. Care was taken to avoid bleeding at the site of injection at which the intercostal muscles were cut to facilitate smooth insertion of the needle.

Quantitation of Pleural Inflammatory Leukocyte Responses:

Pleural leukocytes were collected as follows: 4 h post-induction, pleural inflammatory exudate was removed by washing with 2×1.0 ml Ca$^{++}$/Mg$^{++}$ free HBSS (Gibco, Grand Island, N.Y.) containing 45 mg EDTA/100 ml HBSS, 4° C. Total leukocyte counts were made by hemocytometer following erythrocyte lysis in 2% acetic acid in PBS buffer; exudate leukocyte pellets were resuspended in serum for cytospin preparations and stained (Diff Quik, Baxter Healthcare, McGraw Park, Ill.) for differential leukocyte counts (neutrophils, eosinophils, and mononuclear leukocytes).

The pleural cavities of mice receiving either no intrapleural injection, or saline were washed and the cells counted in the same way to estimate baseline or saline-induced pleural leukocyte counts respectively.

Administration of Compounds:

All drugs were dissolved in PBS and the pH adjusted to 7.5 with NaOH. Each compound was administered intravenously through the retroorbital sinus at hourly intervals (0–3 h) starting from time "0" as indicated. Mice were carefully monitored for side effects; none were noted for the series of compounds reported herein.

The following compounds were tested for their inhibitory effects on dextran-induced leukocyte infiltration: Examples 3, 8, 9, 10, 12, 16, 37, 62, 66, 67, 99, 100, 111, 113, 115, 127, 131, 141, 184, 185, 192, PBS (saline) was administered iv. as a control. Inhibition of eosinophil infiltration, which was suppressed by anti-alpha-4 Mab (PS/2, 50%), was used as a readout of VLA-4 antagonist activity of the compounds tested. Data for neutrophils are also reported.

Results:

Dextran pleural leukocyte response. The total pleural leukocyte counts were 255×10$^4$(+/−16 SEM) cells in the normal pleural cavity; of the normal pleural leukocyte population, all cells were mononuclear (a similar response was observed following intrapleural saline injection). Four hours after intrapleural injection of dextran total pleural leukocyte counts increased to 719×10$^4$(+/−67 SEM) and comprised 36.8×10$^4$(+/−4.1 SEM) eosinophils, 292×10$^4$(+/−25 SEM) neutrophils and 391×10$^4$ (+/−48 SEM) mononuclear leukocytes.

% Inhibition of Eosinophil infiltration

A>40; B: 20–39; C<19

| Example | Dose | Eos |
| --- | --- | --- |
| 3 | 50 × 2 iv | A |
| 8 | 100 × 1 po | C |
| 9 | 50 × 2 iv | A |
| 10 | 100 × 1 po | B |
| 12 | 50 × 2 iv | A |
| 16 | 50 × 2 iv | A |
| 37 | 50 × 2 iv | A |
| 62 | 50 × 2 iv | B |
| 66 | 50 × 2 iv | A |
| 67 | 50 × 2 iv | A |
| 99 | 50 × 2 iv | A |
| 100 | 50 × 2 iv | B |
| 111 | 50 × 2 iv | C |
| 113 | 50 × 2 iv | C |
| 115 | 50 × 2 iv | B |
| 127 | 50 × 2 iv | B |
| 131 | 50 × 2 iv | C |
| 141 | 50 × 2 iv | A |
| 185 | 50 × 2 iv | B |
| 184 | 50 × 2 iv | B |
| 192 | 50 × 2 iv | B |

What is claimed is:

1. A compound of the formula:

[Chemical structure showing a compound with substituents $R_1$, $R_2$, $R_3$, $R_4$, $R_5$, W, X, Y groups with indices p, m, n, and o]

wherein $R_1$ is hydrogen or $C_{1-3}$ alkyl;

$R_2$ is hydrogen or $C_{1-6}$ alkyl;

in addition, $R_1$ and $R_2$ may be attached to the same carbon atom and may form a carbocyclic ring of 5–8 atoms together with the carbon atom to which they are attached or be attached to the same atom and form a ring of 5–8 atoms of the formula:

[Chemical structure showing a ring with $(CH_2)_l$ and $NR_{11}$ groups]

together with the carbon atom to which they are attached;

$R_3$ and Y represent a) $R_3$ is $C_{7-17}$ arylalkyl, ($C_{1-6}$ alkyl)-OH, ($C_{1-6}$ alkyl)-$CO_2$—$R_{11}$, ($C_{1-6}$ alkyl)-CN, adamantyl, phenyl, or one of the following:

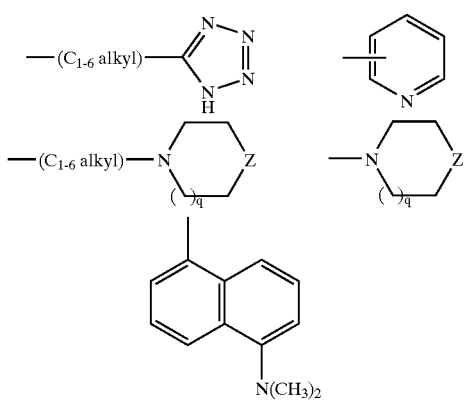

and Y is —C(=O)—, or
b) $R_3$ is $C_{1-6}$ alkyl, $C_{7-17}$ arylalkyl, $(C_{1-6}$ alkyl)-OH, $(C_{1-6}$ alkyl)-$CO_2$—$R_{11}$, $(C_{1-6}$ alkyl)-CN, adamantyl, phenyl, or one of the following:

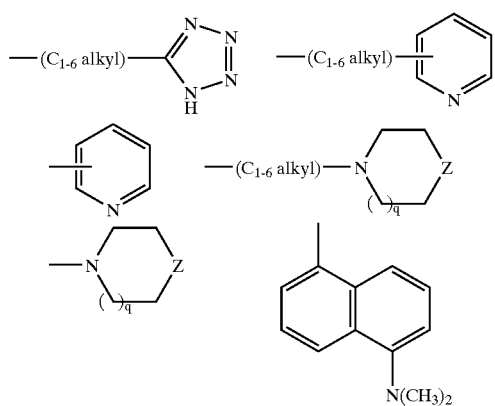

and Y is —C(=O)—, —$SO_2$—, or —C(=O)N($R_{10}$)—;
$R_4$ is —OH, $NH_2$, NHOH, or is of the formula

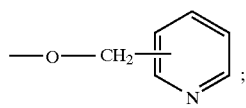

$R_5$ is a formula of the following:

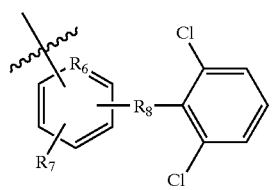

wherein $R_7$ is hydrogen or Cl;
$R_6$ is N or CH;
$R_8$ is —NH—$Y_1$—, or —CONH—;
$R_{10}$ is $C_{1-6}$ alkyl, or $(C_{1-6}$ alkyl)-OH, or hydrogen;
$R_{11}$ is hydrogen or $CH_3$;
W is $(C_{1-6}$ alkyl);
X is S;
$Y_1$ is —CO—, —C(=O)O—, —$SO_2$—, or —C(=O)N($R_{10}$)—;

Z is O, $CH_2$, or N—$R_{11}$;
l is 1 or 2;
m is 2;
n is 0;
o is 0 or 1;
p is 0; and
q is 0 or 1.

2. The compound according to claim 1, wherein
$R_8$ is —NHCO—.

3. The compound according to claim 2, wherein
$R_1$ is hydrogen;
$R_2$ is hydrogen;
$R_3$ is $(C_{1-6}$ alkyl) —$CO_2R_{11}$;
$R_4$ is OH;
$R_6$ is CH;
$R_7$ is hydrogen;
Y is —CO—; and
l is 1,
wherein $R_{11}$ is as defined above.

4. The compound according to claim 2, wherein
$R_1$ is hydrogen;
$R_2$ is hydrogen
$R_3$ is $C_{1-6}$ alkyl, adamantyl,

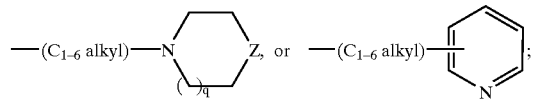

$R_4$ is OH;
$R_6$ is CH;
$R_7$ is hydrogen;
Z is O;
Y is —C(=O) O—; and
l is 1,
wherein q is as defined above.

5. The compound according to claim 1, wherein said compound is

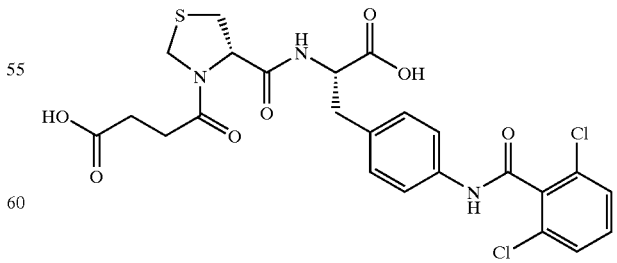

6. A pharmaceutical composition comprising:
a therapeutically effective amount of the compound as set forth in any one of claims 1; and a pharmaceutically acceptable carrier or diluent.

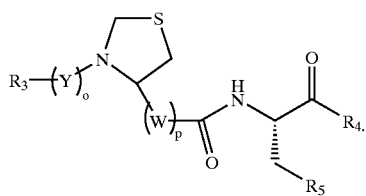

7. A method for treating or preventing $\alpha_4\beta_1$ adhesion mediated conditions in a human which comprises administering to a patient an effective amount of the compound according to any one of claims 1–5.

8. The method according to claim 7, wherein said condition is selected from the group consisting of rheumatoid arthritis, asthma, allergy conditions, allograft rejection, psoriasis, eczema, contact dermatitis and other skin inflammatory diseases, inflammatory and immunoinflammatory conditions including ophthalmic inflammatory conditions, inflammatory bowel diseases, atherosclerosis, and ulcerative colitis.

9. The method according to claim 8, wherein said condition is asthma.

* * * * *